(12) United States Patent
Pijnappel

(10) Patent No.: US 10,696,967 B2
(45) Date of Patent: Jun. 30, 2020

(54) NATURAL CRYPTIC EXON REMOVAL BY PAIRS OF ANTISENSE OLIGONUCLEOTIDES

(71) Applicant: Erasmus University Medical Center Rotterdam, Rotterdam (NL)

(72) Inventor: Wilhelmus Wenceslaus Matthias Pijnappel, Vleuten (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

(21) Appl. No.: 16/323,287

(22) PCT Filed: Aug. 4, 2017

(86) PCT No.: PCT/NL2017/050527
§ 371 (c)(1),
(2) Date: Feb. 5, 2019

(87) PCT Pub. No.: WO2018/026284
PCT Pub. Date: Feb. 8, 2018

(65) Prior Publication Data
US 2019/0194661 A1    Jun. 27, 2019

(30) Foreign Application Priority Data
Aug. 5, 2016 (NL) ...................... 2017294

(51) Int. Cl.
*A61K 48/00* (2006.01)
*C07H 21/04* (2006.01)
*C12N 15/113* (2010.01)

(52) U.S. Cl.
CPC ........ *C12N 15/113* (2013.01); *C12N 15/1137* (2013.01); *C12N 2310/11* (2013.01); *C12N 2310/315* (2013.01); *C12N 2310/346* (2013.01); *C12N 2310/351* (2013.01); *C12N 2320/31* (2013.01); *C12N 2320/33* (2013.01); *C12Y 302/0102* (2013.01)

(58) Field of Classification Search
CPC ............................ C12N 15/113; A61K 31/713
See application file for complete search history.

(56) References Cited

FOREIGN PATENT DOCUMENTS

| WO | 2015/035231 A1 | 3/2015 |
|----|----------------|--------|
| WO | 2015/190921 A2 | 12/2015 |
| WO | 2015/190922 A1 | 12/2015 |
| WO | 2016/138534 A2 | 9/2016 |
| WO | 2017/099579 A1 | 6/2017 |

OTHER PUBLICATIONS

Atze J Bergsma et al: "From Cryptic Toward Canonical Pre-mRNA Splicing in Pompe Disease: a Pipeline for the Development of Antisense Oligonucleotides", Molecular Therapy—Nucleic Acids, vol. 5, Sep. 13, 2016 (Sep. 13, 2016), p. e361, XP055370150, GB ISSN: 2162-2531, DOI: 10.1038/mtna.2016.75.

Atze J. Bergsma et al: "Identification and Characterization of Aberrant GAA Pre-mRNA Splicing in Pompe Disease Using a Generic Approach", Human Mutation, vol. 36, No. I, 2015, pp. 57-68, XP055212207, ISSN: 1059-7794, DOI: 10.1002/humu.22705 cited in the application the whole document.

Erik Van Der Wal et al: "GAA Deficiency in Pompe Disease Is Alleviated by Exon Inclusion in iPSC-Derived Skeletal Muscle Cells", Molecular Therapy—Nucleic Acids, vol. 7, 2017, pp. 101-115, XP055370418, GB ISSN: 2162-2531, DOI: 10.1016/j.omtn.2017.03.002.

Erik Van Der Wal et al: "Antisense Oligonucleotides Promote Exon Inclusion and Correct the Common c.-32-13T>G GAA Splicing Variant in Pompe Disease", Molecular Therapy—Nucleic Acids, vol. 7, 2017, pp. 90-100, XP055370420, GB ISSN: 2162-2531, DOI: 10.1016/j.omtn.2017.03.001.

Eva Pros et al: "Antisense therapeutics for neurofibromatosis type 1 caused by deep intronic mutations", Human Viutation, vol. 30, No. 3, Feb. 24, 2009 (Feb. 24, 2009), pp. 454-462, XP055370208, us ISSN: 1059-7794, DOI: 10.1002/humu.20933 the whole document.

Nlend Rachel Nlend et al: "Antisense genes to induce exon inclusion. ", Methods in Molecular Biology (Clifton, N.J.). vol. 867, 2012, pp. 325-347, XP002770049, ISSN: 1940-6029 cited in the application the whole document.

*Primary Examiner* — Amy H Bowman
(74) *Attorney, Agent, or Firm* — Banner & Witcoff, Ltd.

(57) ABSTRACT

The invention relates to a method for repairing aberrant splicing in Pompe patients that carry the IVS1 variant, wherein such aberrant splicing is caused by the expression of a natural pseudo exon present in GAA intron 1, comprising blocking of either the natural cryptic 3' splice site or the natural cryptic 5' splice site of said natural pseudo exon with an antisense oligomeric compound (AON). Further, the invention comprises an antisense oligomeric compound targeting SEQ ID NO: 1 or SEQ ID NO: 180, preferably selected from the sequences of SEQ ID NO: 91-179, sequences that are complementary to said sequences or sequences that have an identity of 80% with said sequences or the complementary sequences and a second AON from the sequences of SEQ ID NO: 346-508, sequences that are complementary to said sequences or sequences that have an identity of 80% with said sequences or the complementary sequences.

11 Claims, 61 Drawing Sheets
Specification includes a Sequence Listing.

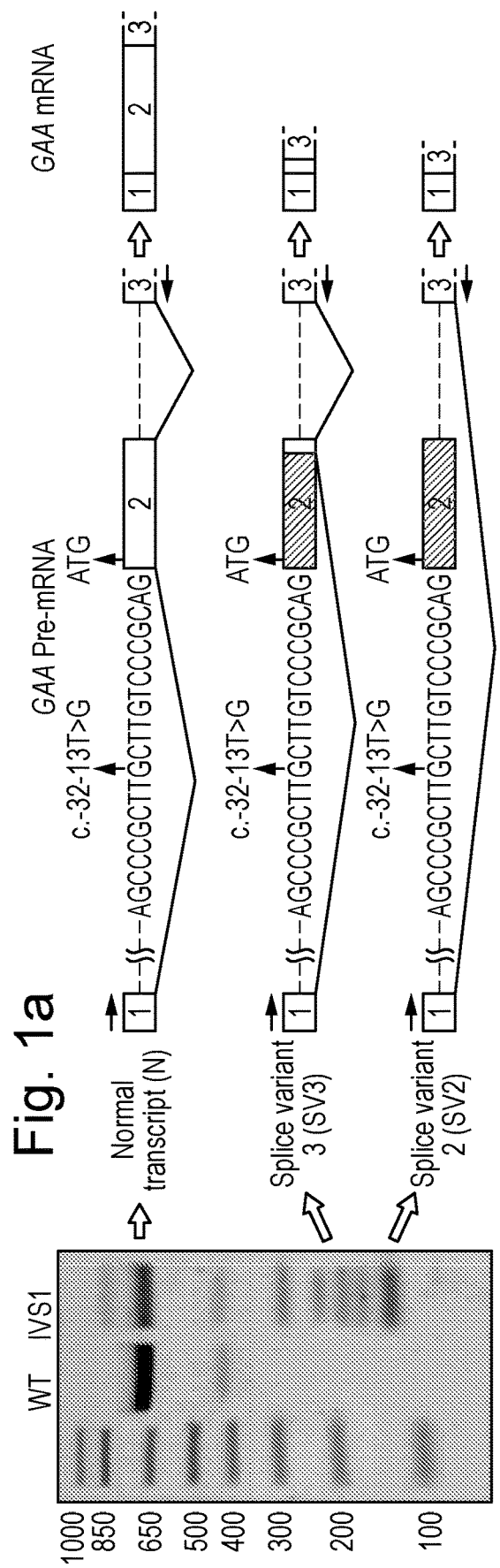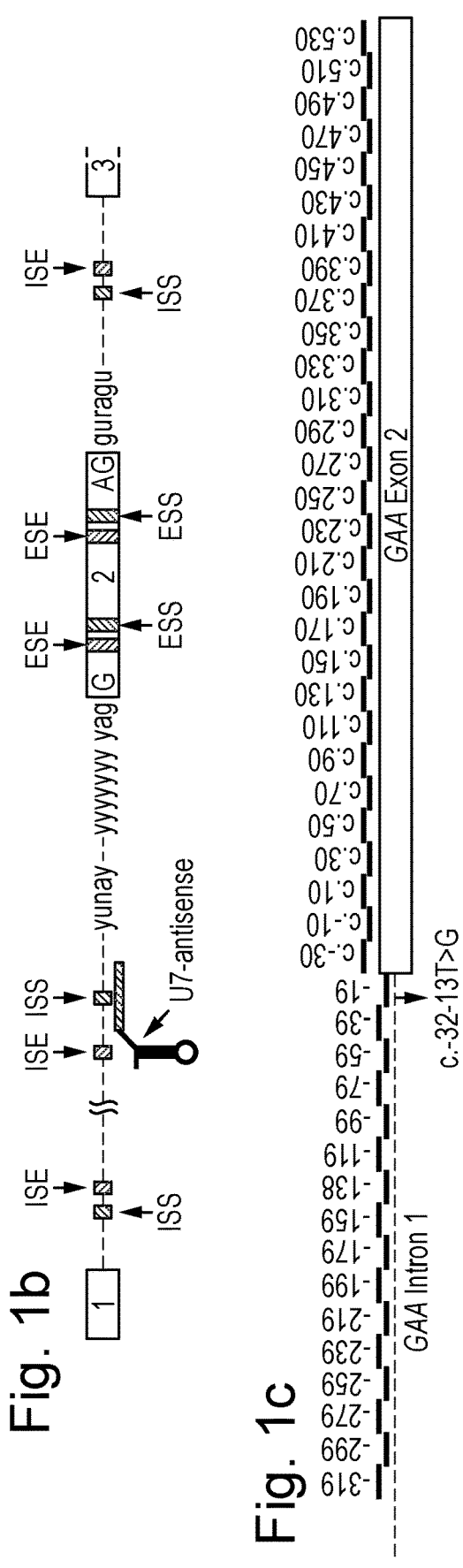

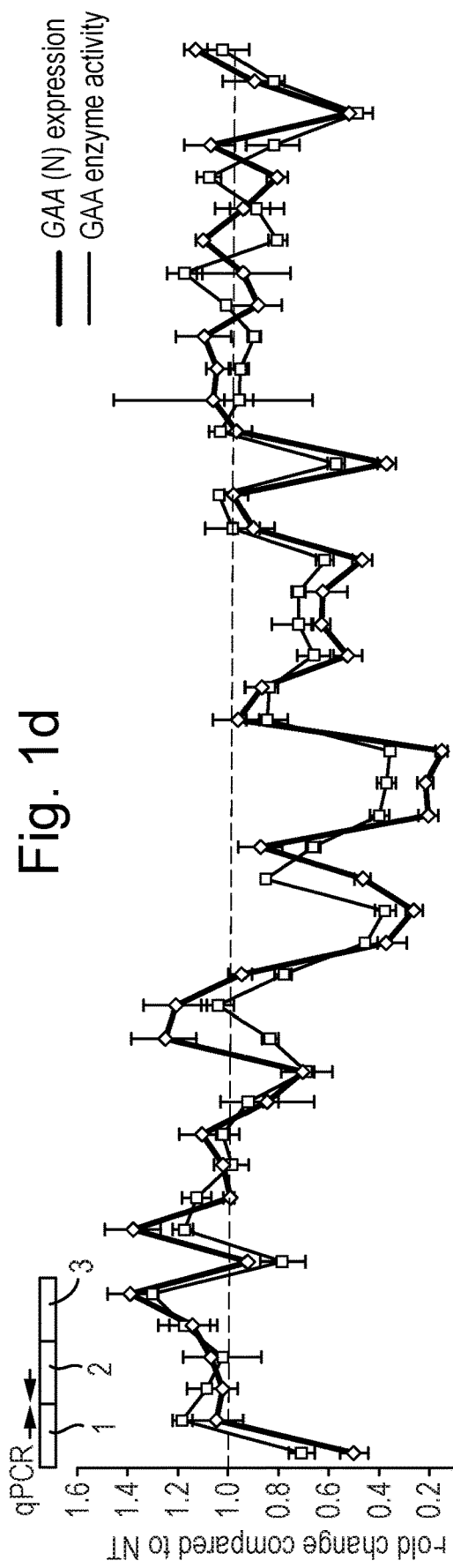
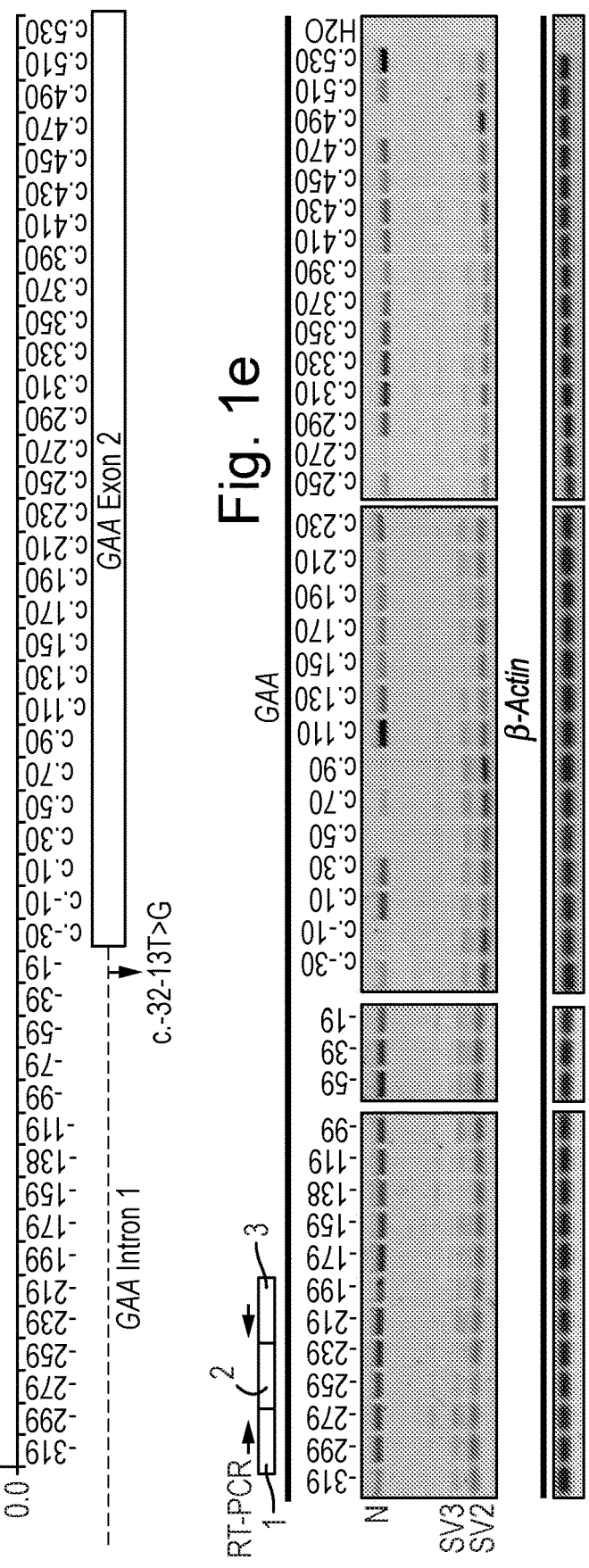
Fig. 1d
Fig. 1e

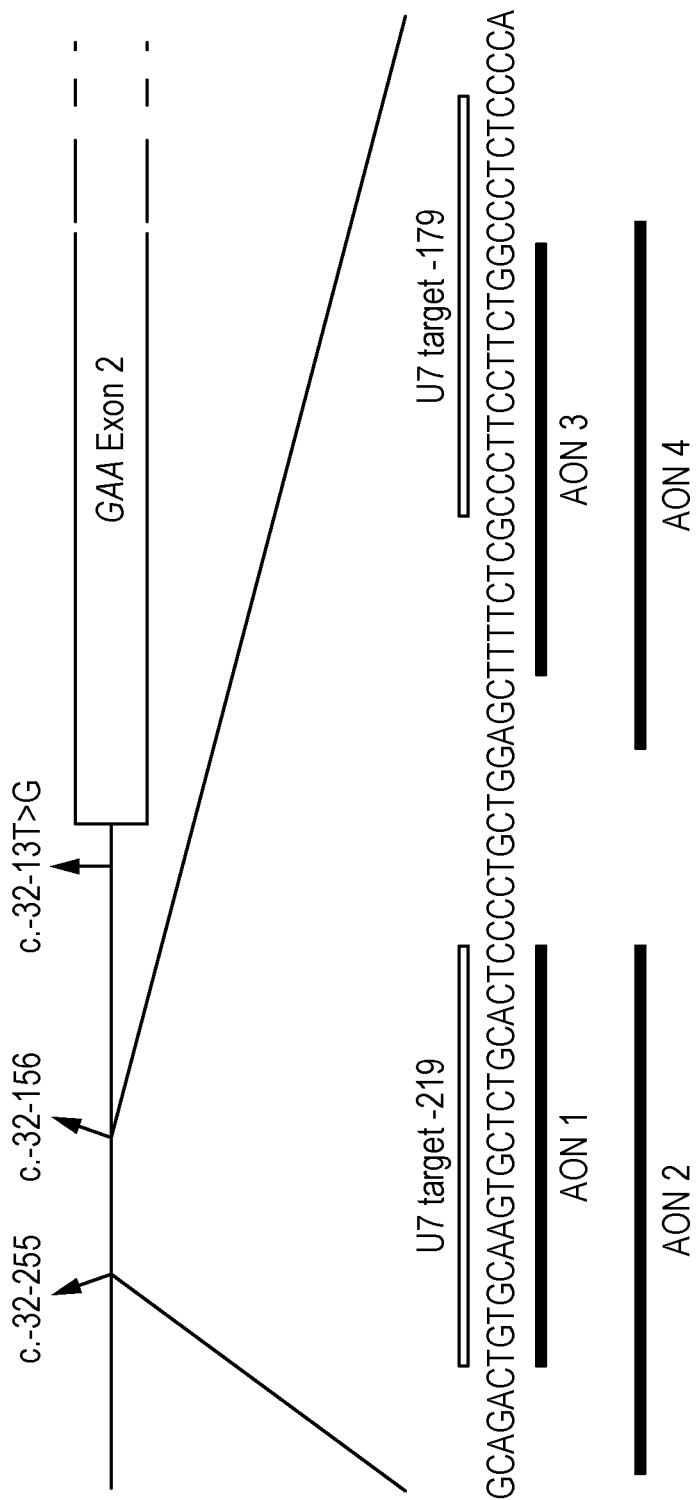

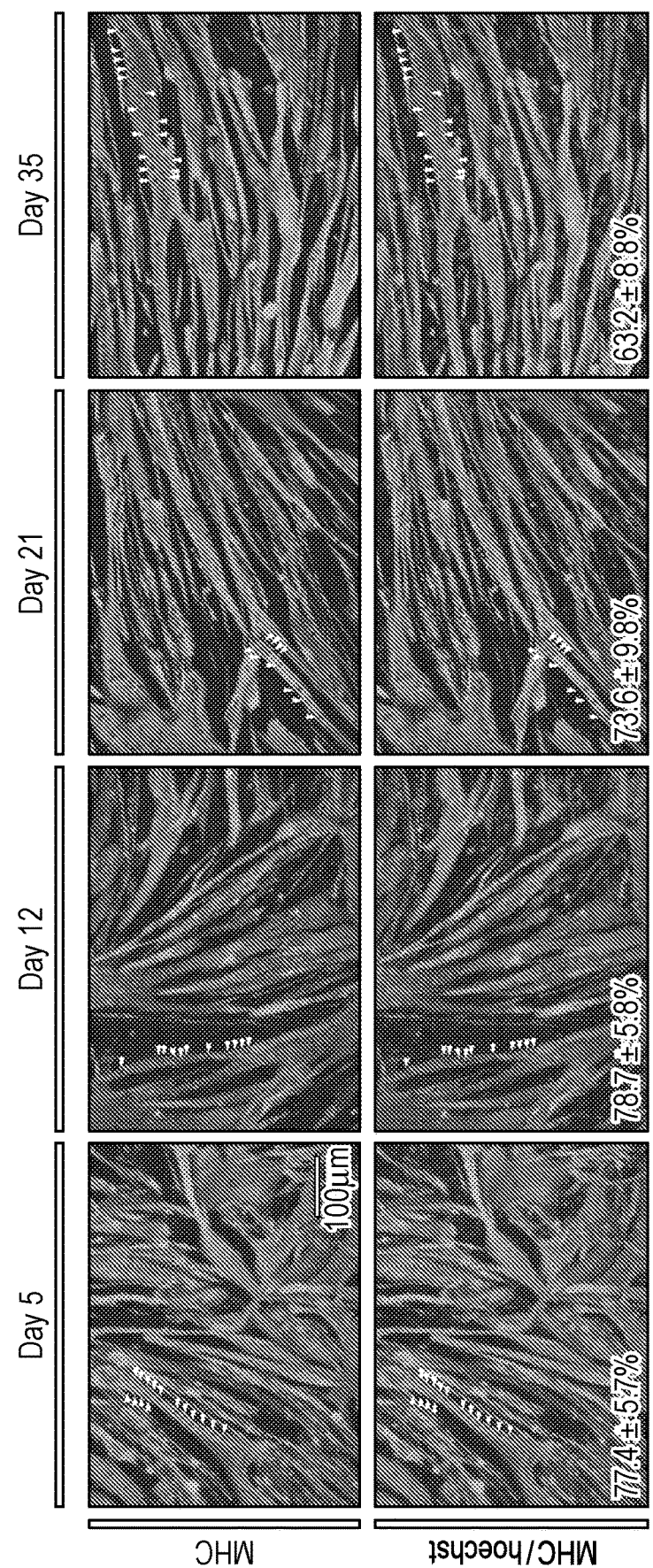

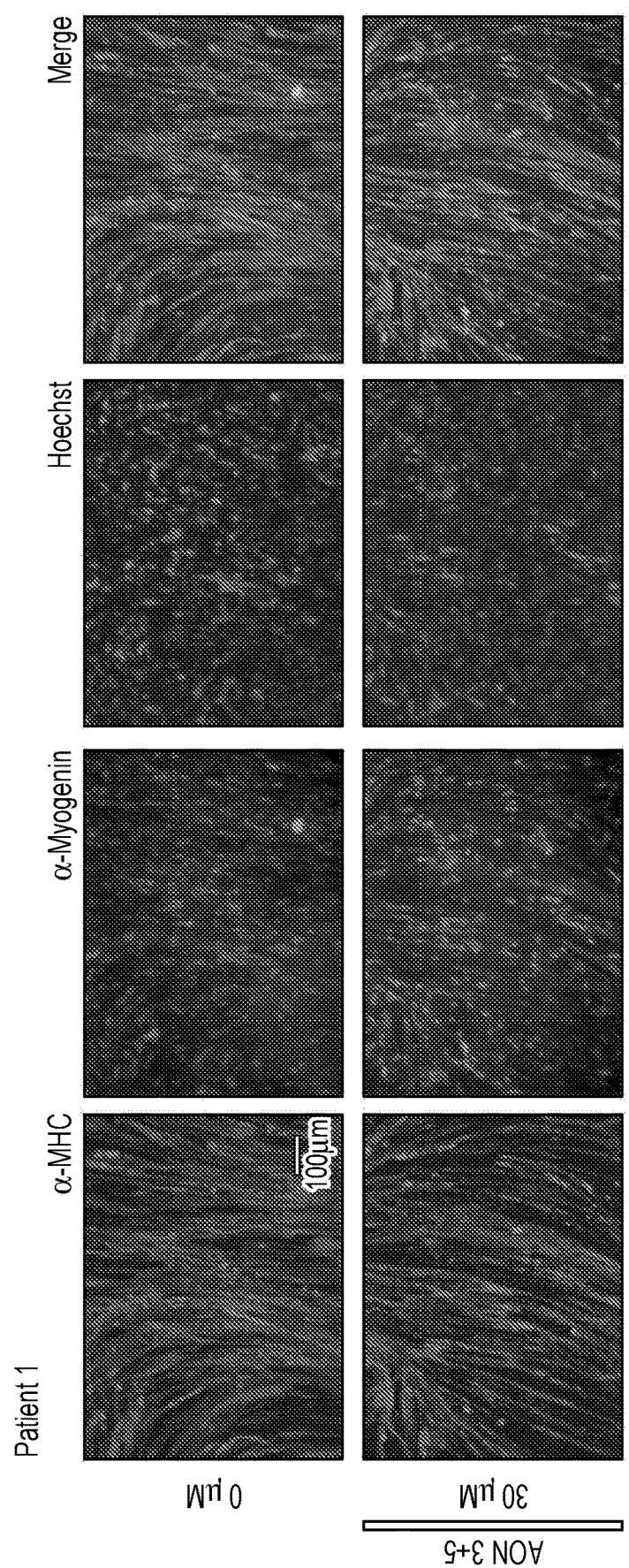

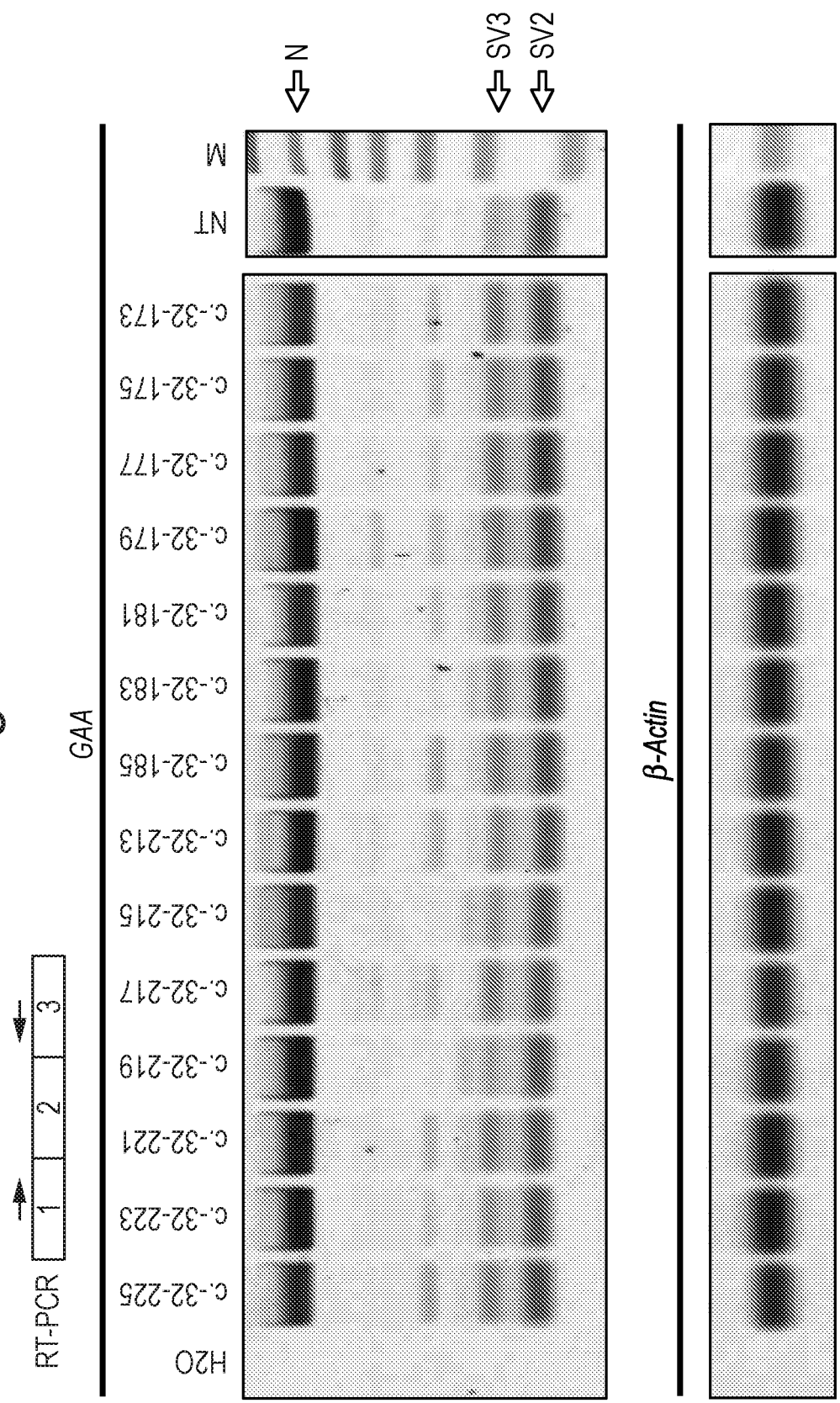

| Name: | cDNA location | sequence 5' to 3' | nucleotides |
|---|---|---|---|
| CypA 1 | CypA c.165_173+11 | TGTACCCTTACCACTCAGTC | 20 |
| CypA 2 | CypA c.165_173+16 | CATGTTGTACCCTTACCACTCAGTC | 25 |
| AON 1 | GAA c.-32-219_-200 | GAGTGCAGAGCACTTGCACA | 20 |
| AON 2 | GAA c.-32-224_-200 | GAGTGCAGAGCACTTGCACAGTCTG | 25 |
| AON 3 | GAA c.-32-187_-167 | CCAGAAGGAAGGGCGAGAAAA | 21 |
| AON 4 | GAA c.-32-190_-166 | GCCAGAAGGAAGGGCGAGAAAAGCT | 25 |
| AON 5 | GAA c.-32-64_-40 | TTTGAGAGCCCCGTGAGTGCCGCCC | 25 | reference sequence for cDNA annotation is NM_000152.3

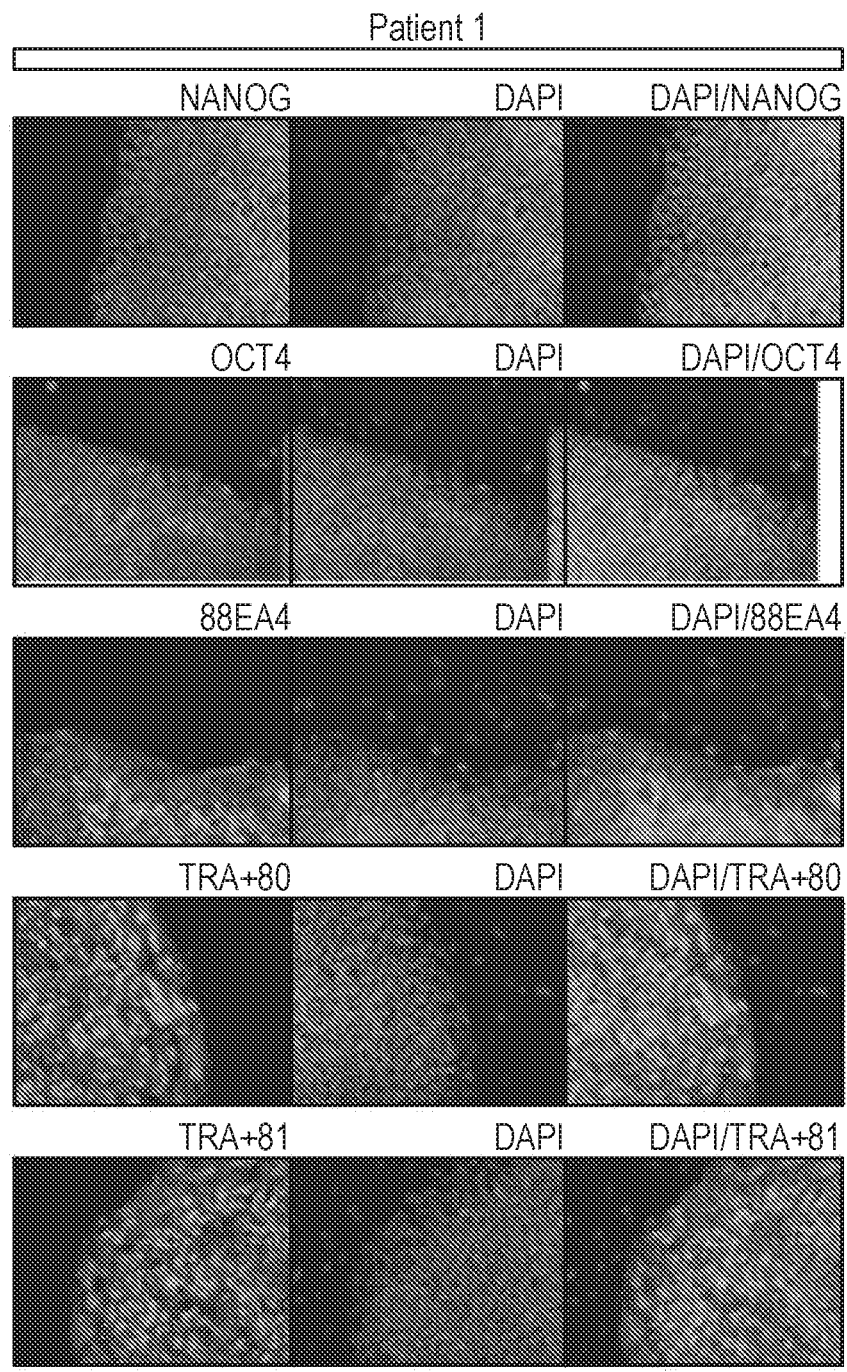
Fig. 8a(Cont. I)

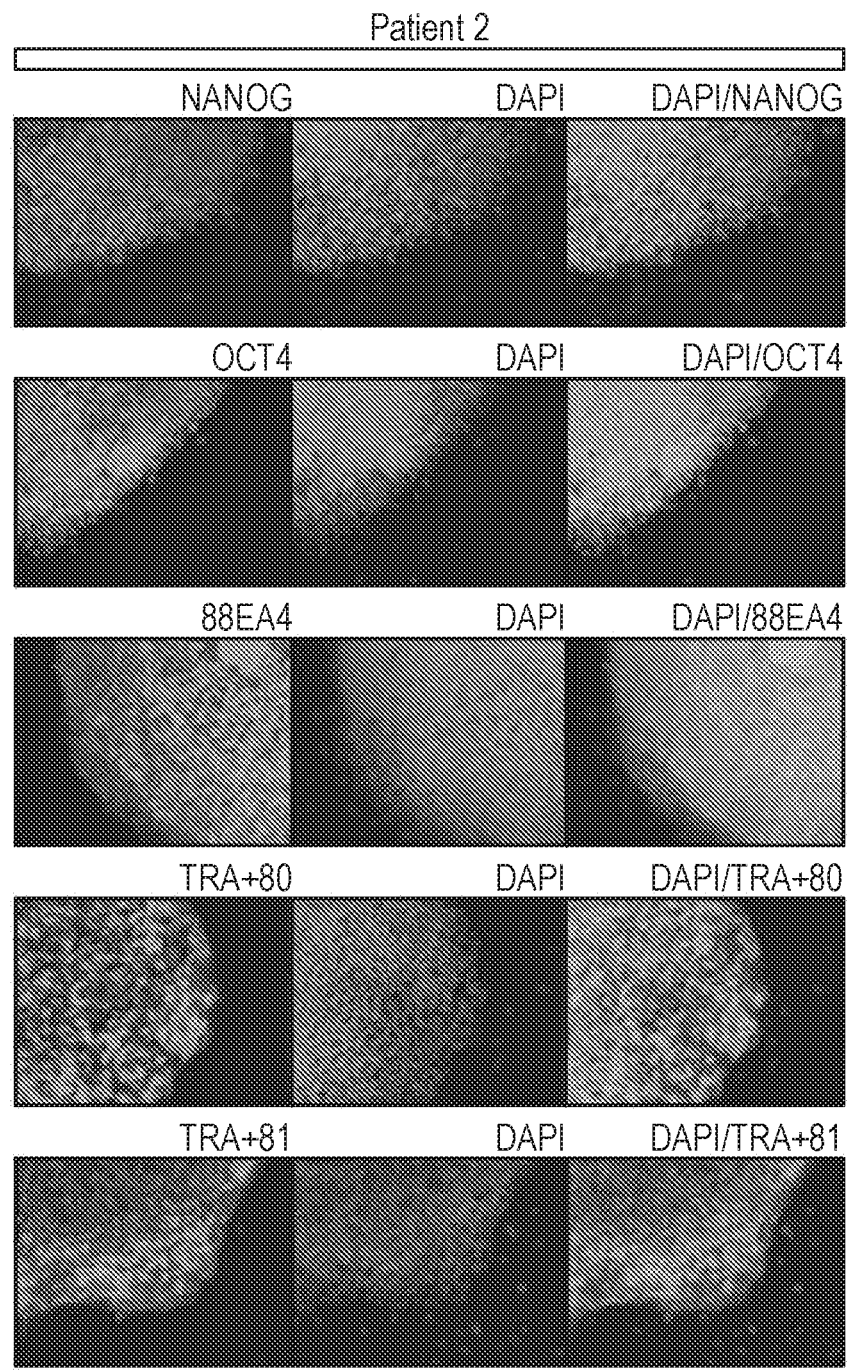
Fig. 8a(Cont. II)

Fig. 8b(Cont. I)
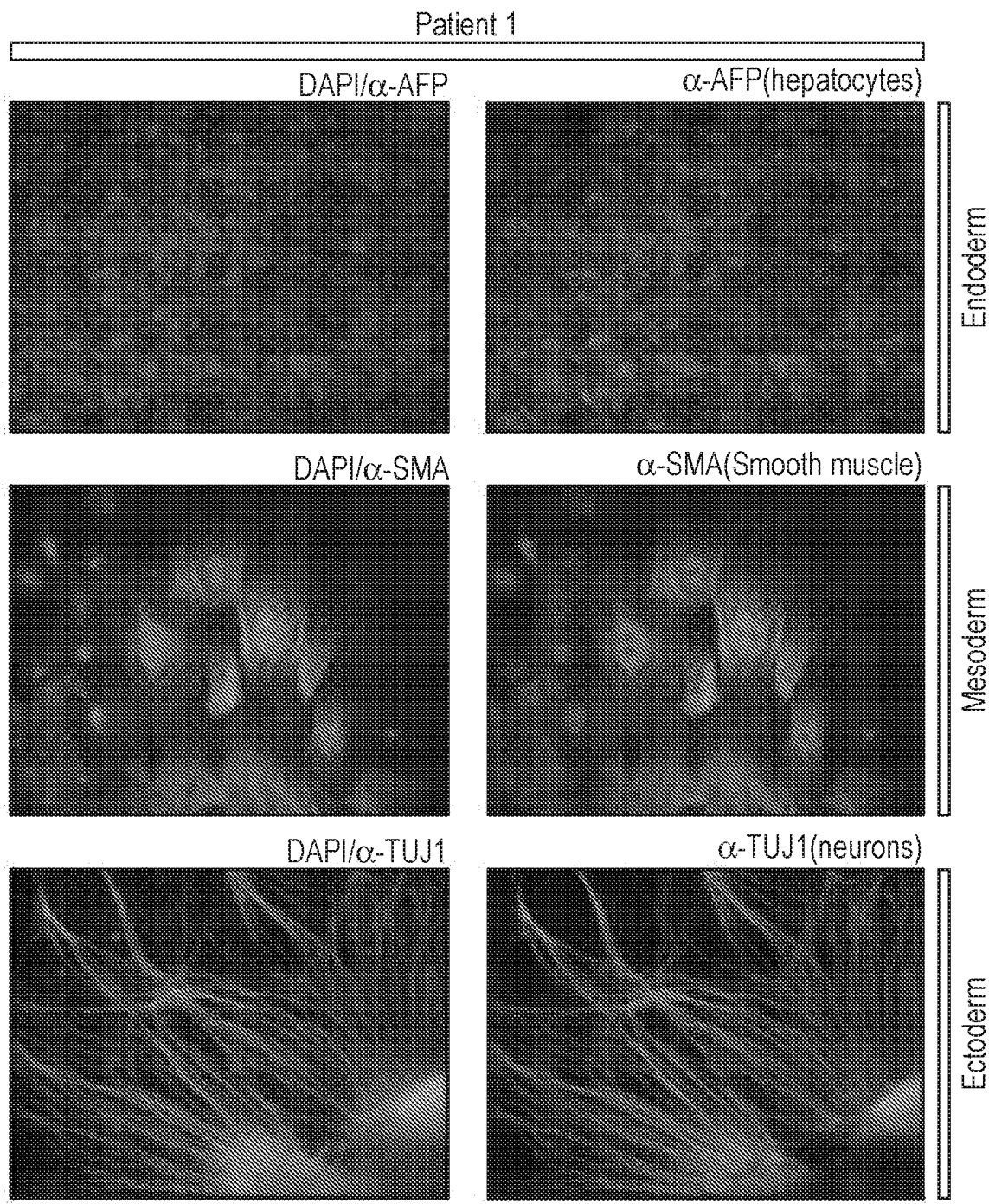

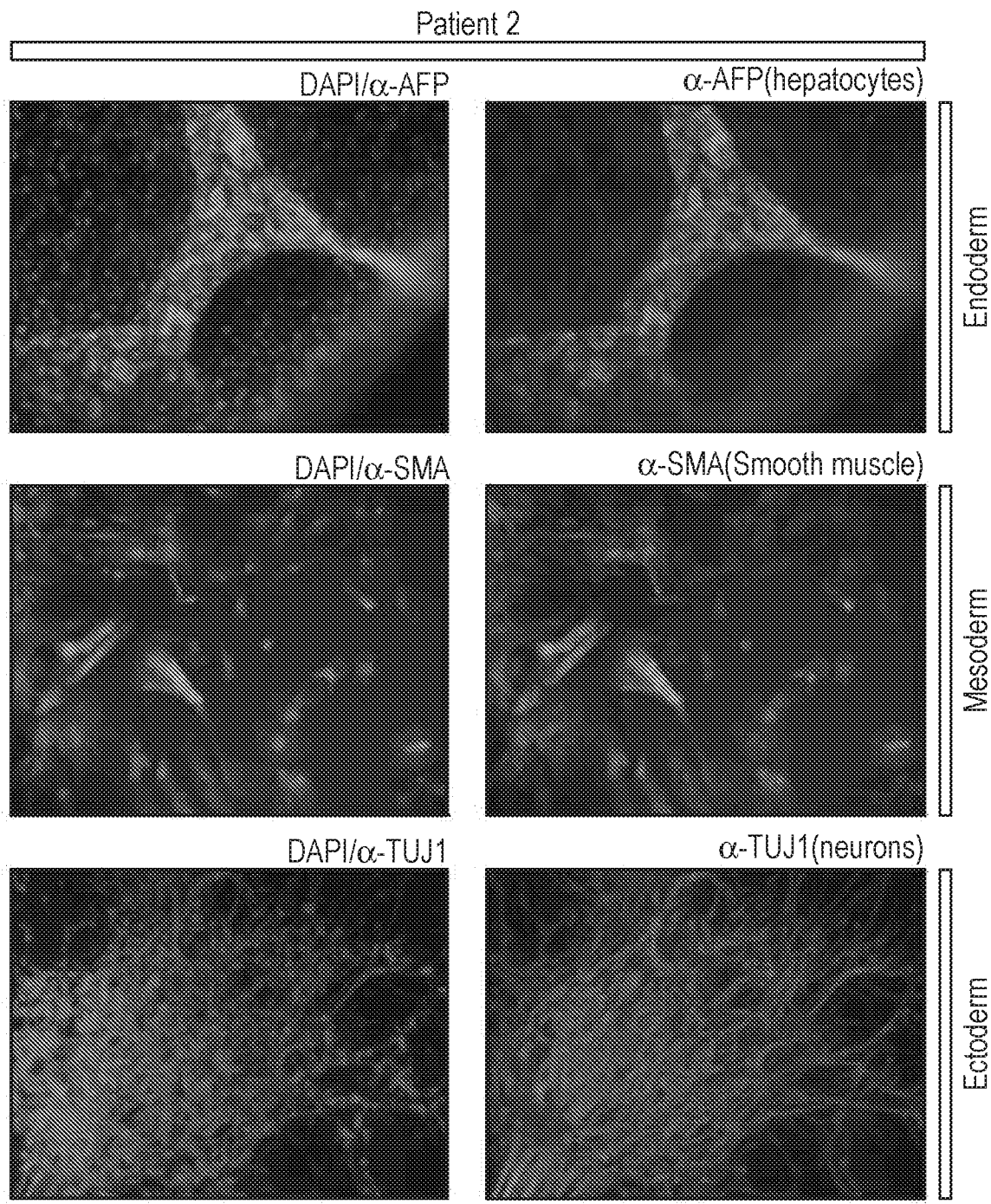
Fig. 8b(Cont. II)

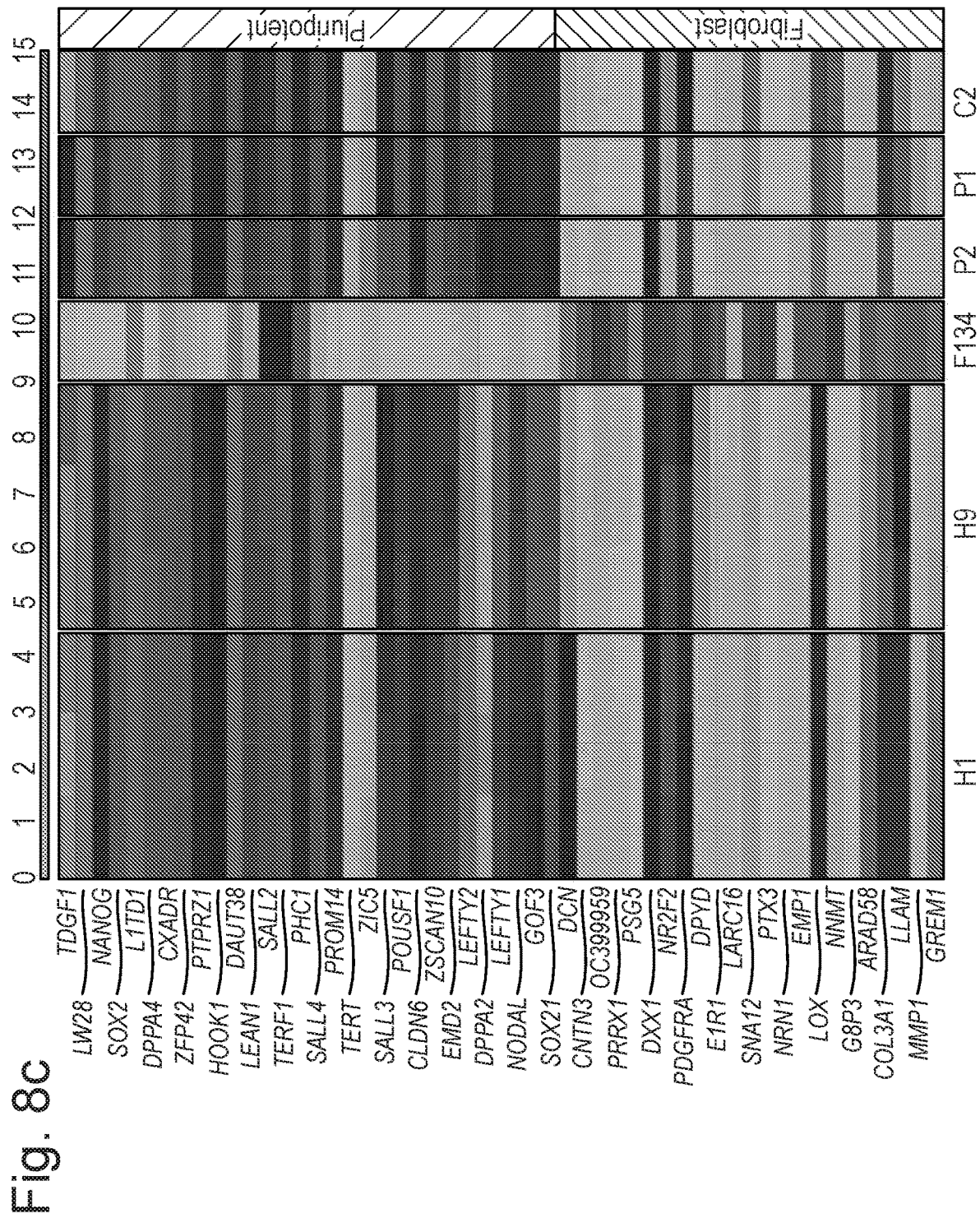

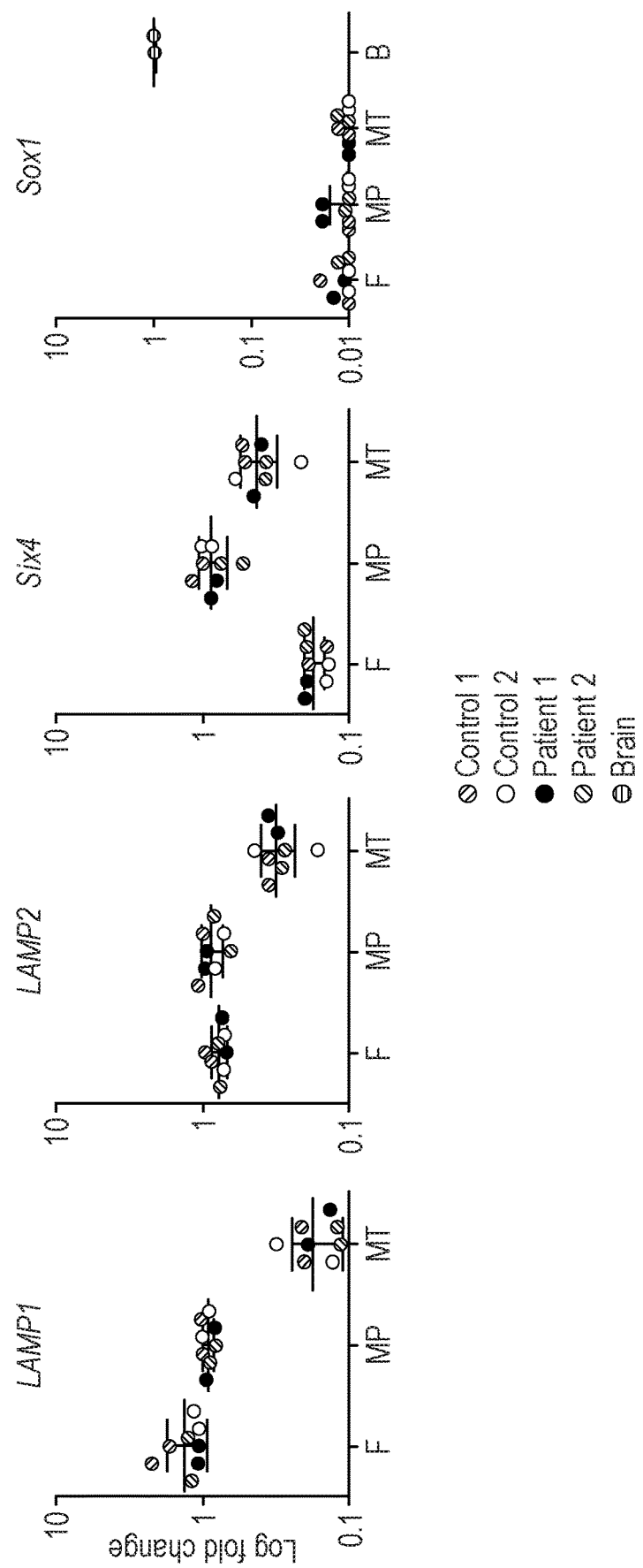

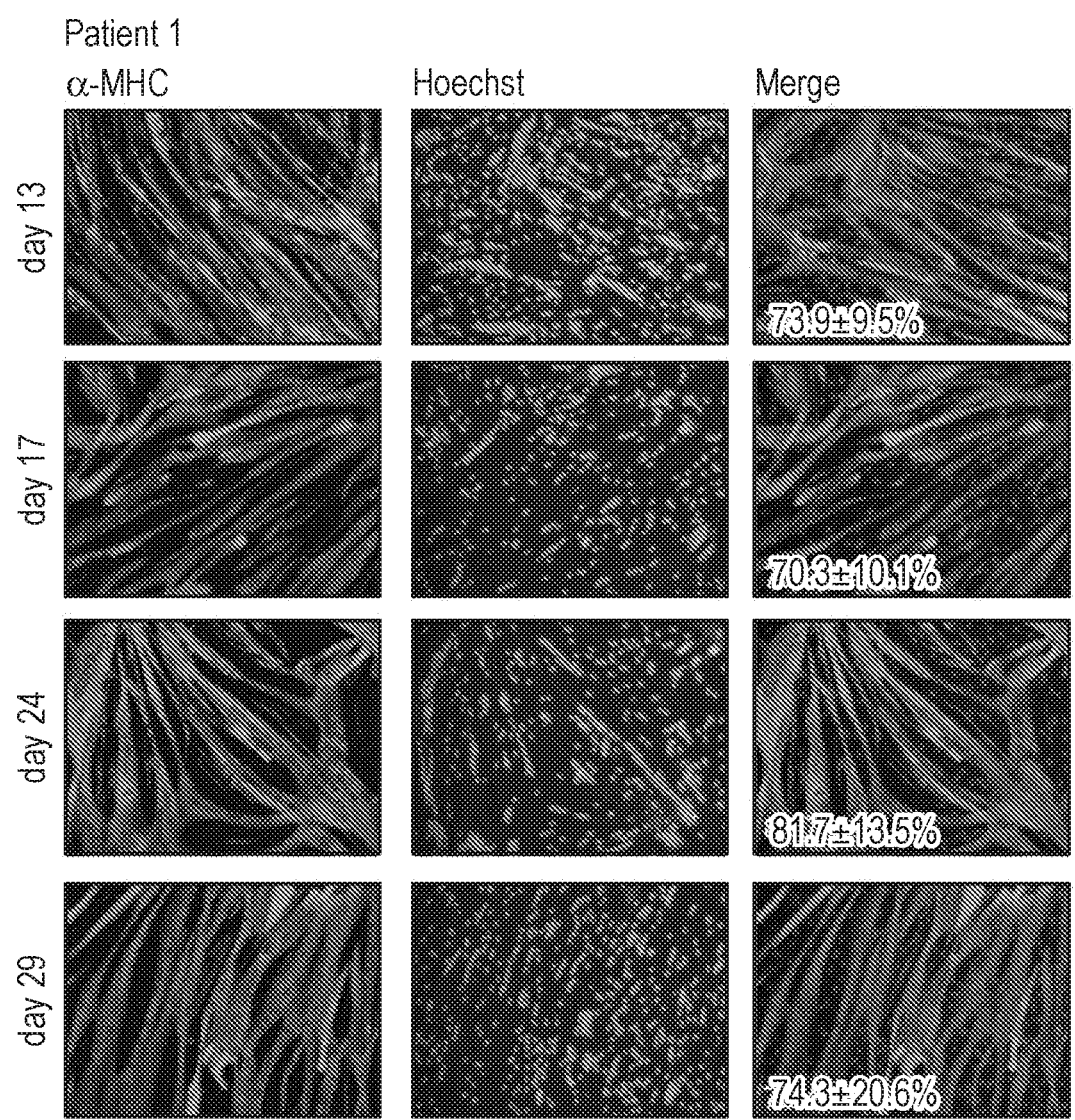
Fig. 8i(Cont. I)

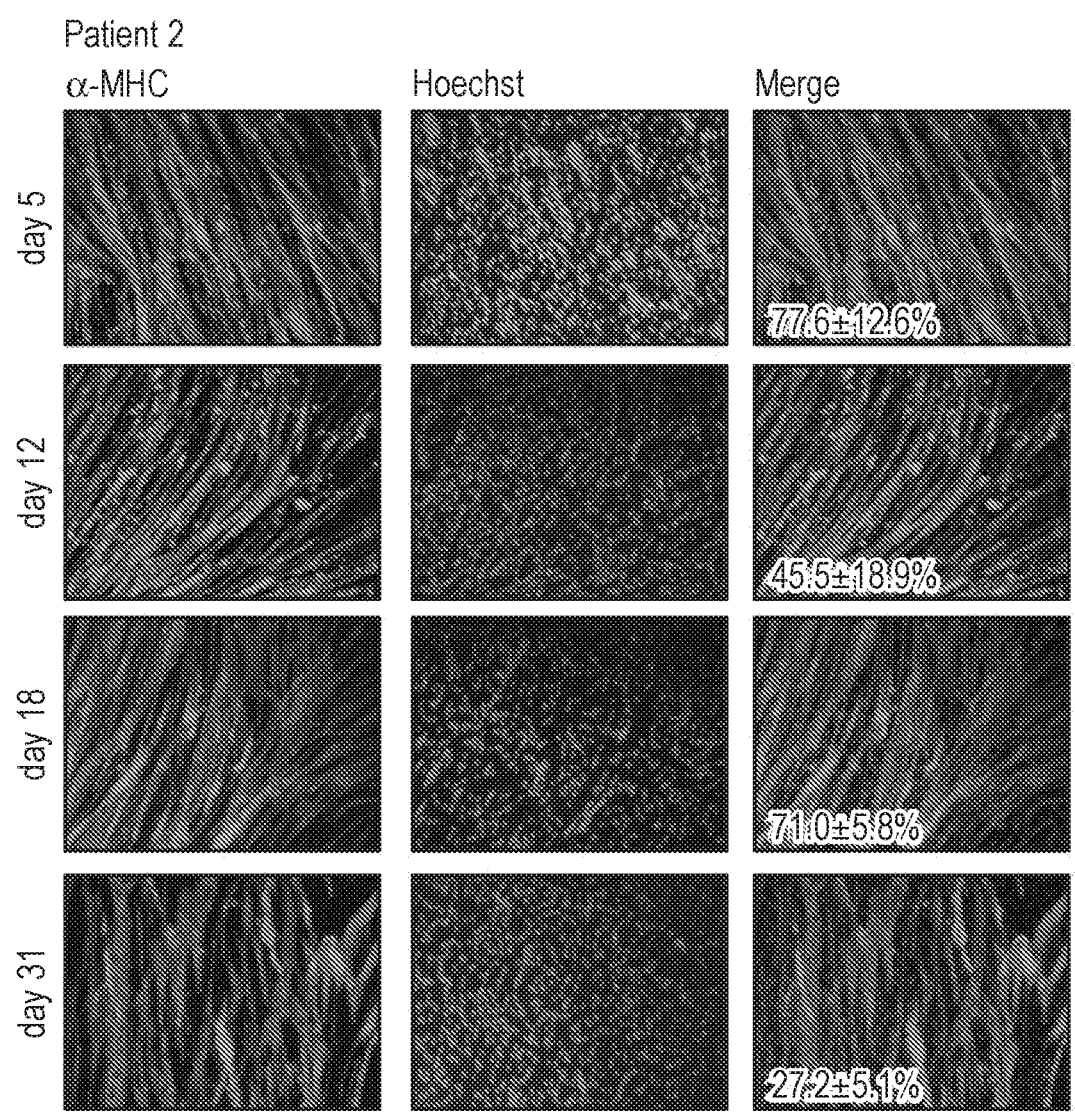
Fig. 8i(Cont. II)

Fig. 8j  Control 1 day 26
α-MHC/hoechst
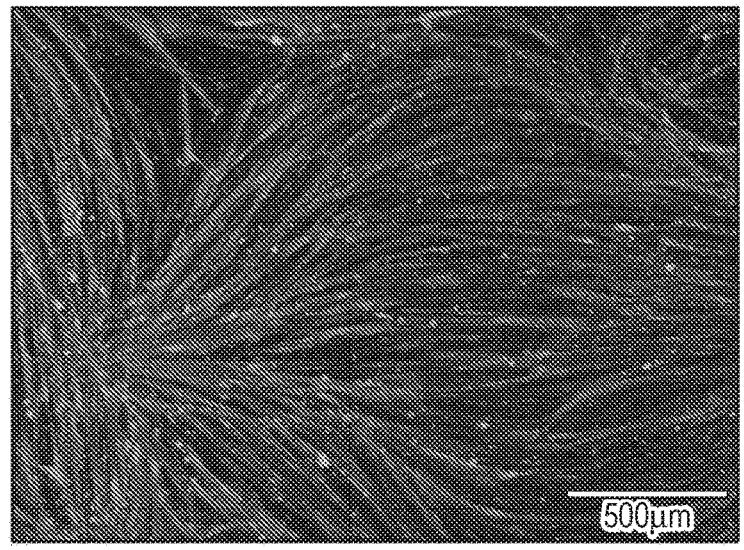
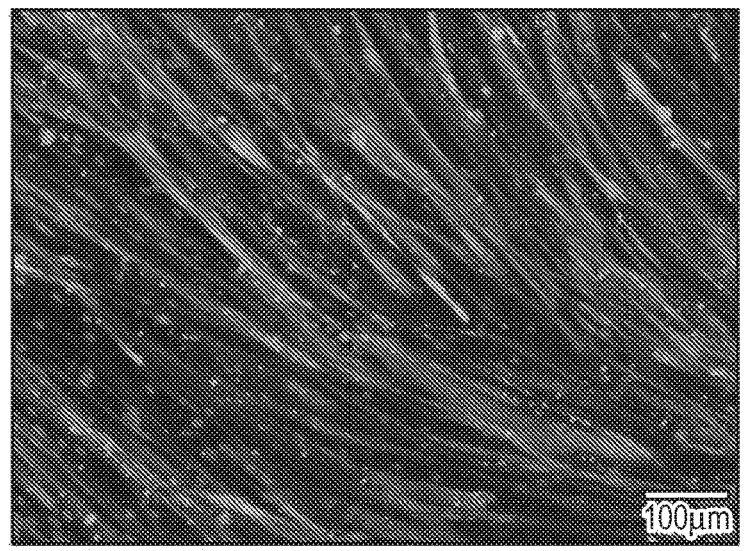
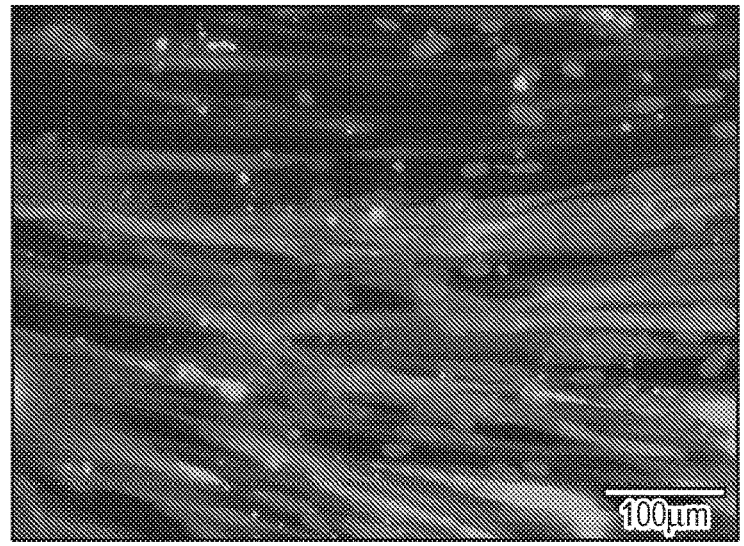

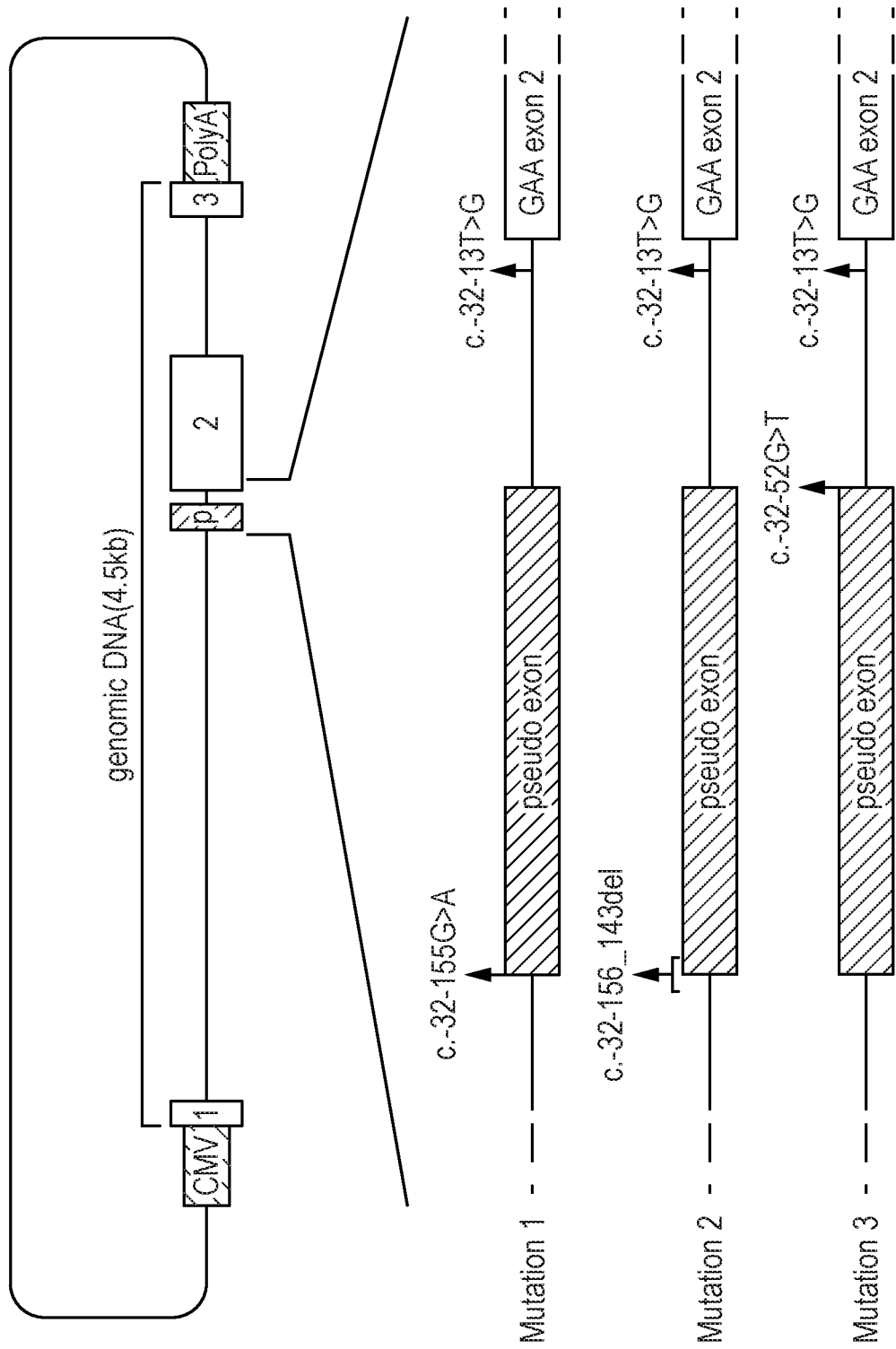

Fig. 10b

Mutation 1 (c.-32-155G>A)

| Reference sequence | CTCCCCAGCTAGACAGCAGGGCAACA |
|---|---|
| SpliceSiteFinder-like | 75% |
| MaxEntScan | 59% — 19% |
| NNSPLICE 3' | 90% 60% |
| GeneSplicer | 50% 79% |
| Human Splicing Finder | 90% 83% — 85% |
| | -32-160 -32-150 -32-140 |
| Mutated sequence | CTCCCCAATCTAGACAGCAGGGCAACA |
| SpliceSiteFinder-like | 74% |
| MaxEntScan | 46% — 4% |
| NNSPLICE 3' | 60% |
| GeneSplicer | 43% 79% |
| Human Splicing Finder | 83% — 85% |

Mutation 2 (c.-32-156_-143del)

| Reference sequence | CTCCCCAGCTAGACAGCAGGGCAACA |
|---|---|
| SpliceSiteFinder-like | 75% |
| MaxEntScan | 59% — 19% |
| NNSPLICE 3' | 90% 60% |
| GeneSplicer | 50% 79% |
| Human Splicing Finder | 90% 83% — 85% |
| | -32-160 |
| Mutated sequence | TCCCCGGCAACACCCACCCTGGCCAC |
| SpliceSiteFinder-like | |
| MaxEntScan | |
| NNSPLICE 3' | |
| GeneSplicer | |
| Human Splicing Finder | |

Mutation 3 (c.-32-52G>T)

| | |
|---|---|
| SpliceSiteFinder-like | 73% |
| MaxEntScan | 70% |
| NNSPLICE 5' | 100% |
| GeneSplicer | 68% |
| Human Splicing Finder | 83% |
| | -32-60 -32-50 |
| Reference sequence | GCTTTGAGAGCCCCGTGAGTGCCGCC |
| SpliceSiteFinder-like | |
| MaxEntScan | |
| NNSPLICE 5' | |
| GeneSplicer | |
| Human Splicing Finder | |
| | -32-60 -32-50 |
| Mutated sequence | GCTTTGAGAGCCCCTTGAGTGCCGCC |

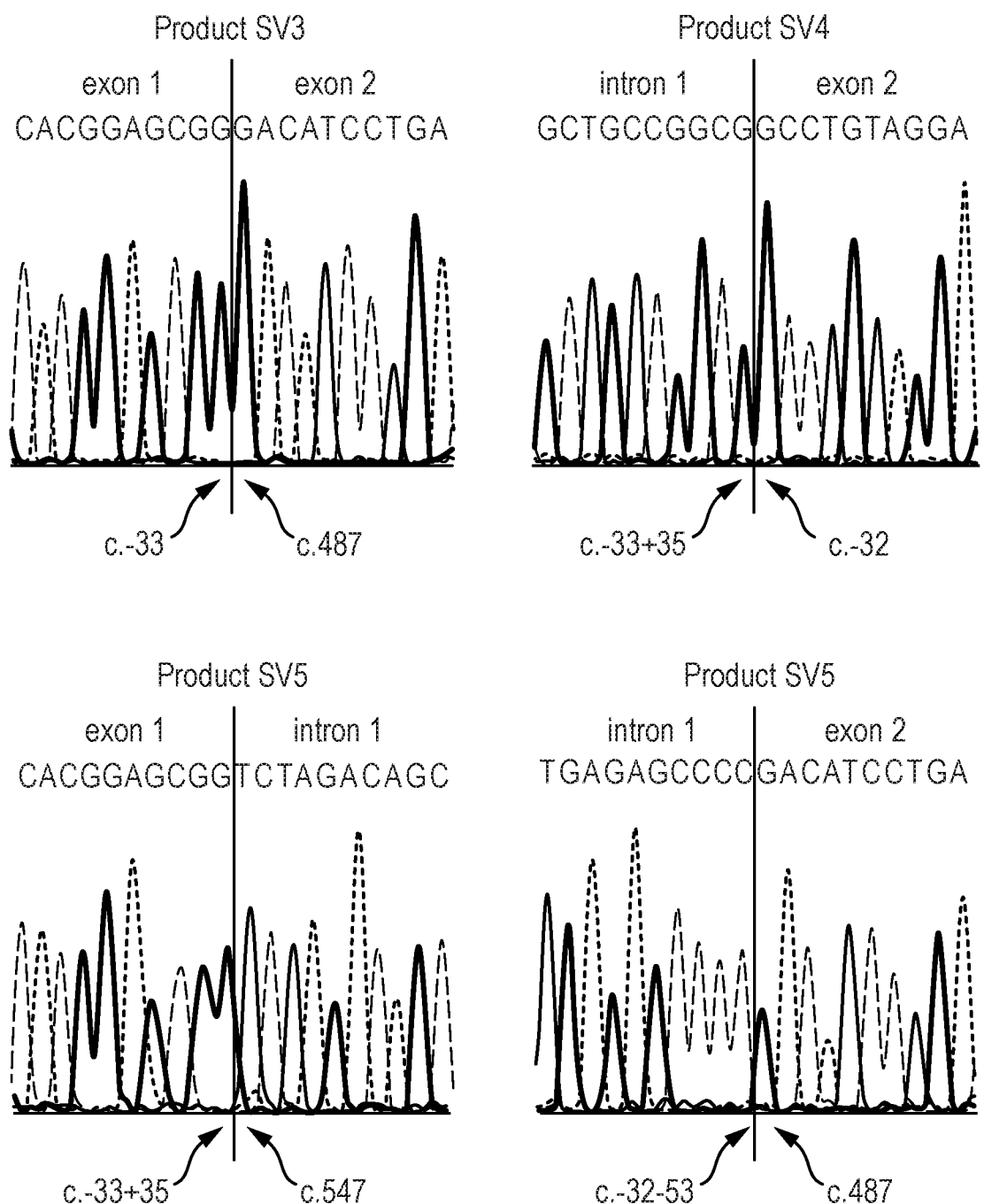
Fig. 10d(Cont. I)

Fig. 10d(Cont. II)
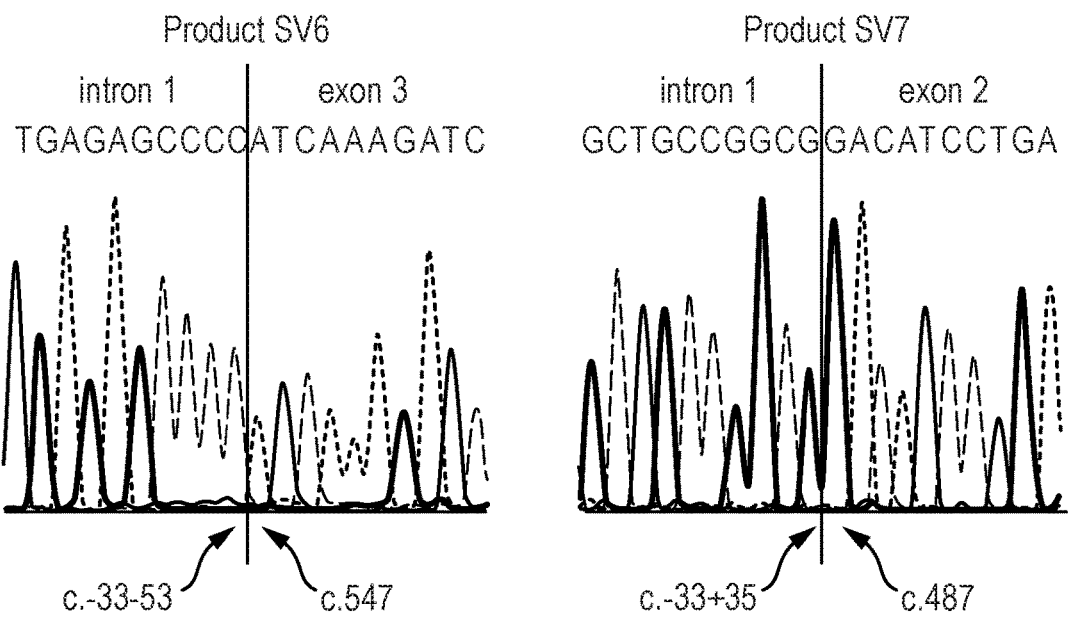
Fig. 10e
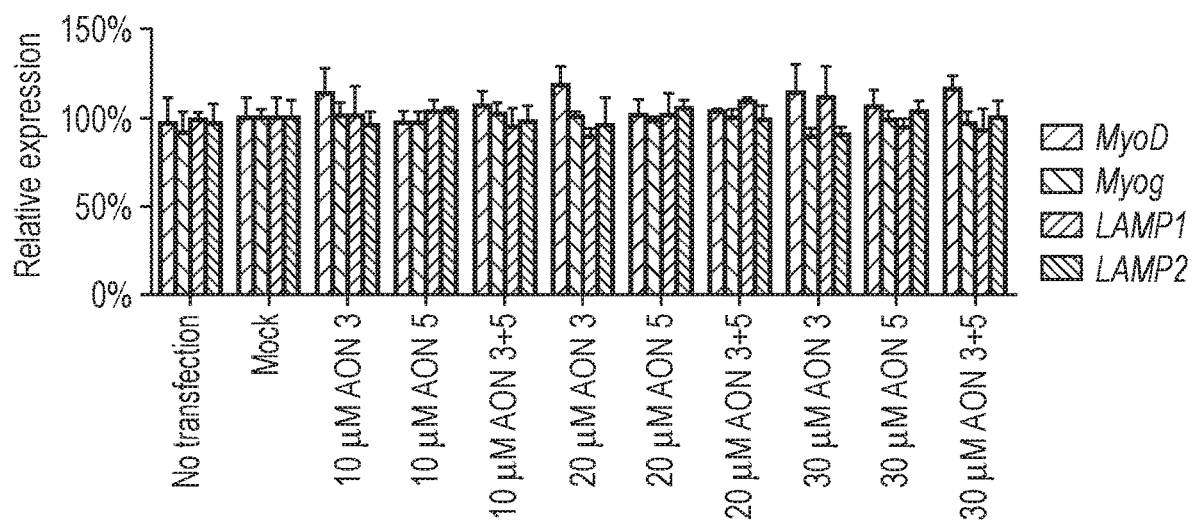

NATURAL CRYPTIC EXON REMOVAL BY PAIRS OF ANTISENSE OLIGONUCLEOTIDES

RELATED APPLICATIONS

This application is a National Stage Application under 35 U.S.C. 371 of co-pending PCT application PCT/NL2017/050527 designating the United States and filed Aug. 4, 2017; which claims the benefit of NL application number 2017294 filed on Aug. 5, 2016 each of which are hereby incorporated by reference in their entireties.

FIELD OF THE INVENTION

The invention is related to antisense oligonucleotides that are useful for the treatment of aberrant gene splicing, especially aberrant splicing in Pompe disease and to pharmaceutical compositions comprising the antisense oligonucleotides. The invention is also related to a method to modulate splicing, especially splicing of pre-mRNA of the GAA gene and to treatment of Pompe disease.

BACKGROUND OF THE INVENTION

Pompe disease, also known as acid maltase deficiency or Glycogen storage disease type II, is an autosomal recessive metabolic disorder which damages muscle and nerve cells throughout the body. It is caused by an accumulation of glycogen in the lysosome due to a deficiency of the lysosomal acid α-glucosidase enzyme. The build-up of glycogen causes progressive muscle weakness (myopathy) throughout the body and affects various body tissues, particularly in the heart, skeletal muscles, liver and nervous system.

In Pompe disease, a protein, acid α-glucosidase (EC 3.2.1.20), also known as acid maltase, which is a lysosomal hydrolase, is defective. The protein is an enzyme that normally degrades the α-1,4 and α-1,6 linkages in glycogen, maltose and isomaltose and is required for the degradation of 1-3% of cellular glycogen. The deficiency of this enzyme results in the accumulation of structurally normal glycogen in lysosomes and cytoplasm in affected individuals. Excessive glycogen storage within lysosomes may interrupt normal functioning of other organelles and lead to cellular injury. The defective protein is the result of alternative splicing which is caused by mutations in the GAA gene on long arm of chromosome 17 at 17q25.2-q25.3 (base pair chr17:80,101,526 to 80,119,882 build GRCh38/hg38). The gene spans approximately 18 kb and contains 20 exons with the first exon being noncoding.

Although over 460 GAA mutations have been described (http://cluster15.erasmusmc.nl/klgn/pompe/mutations.html), only a few splicing mutations have been characterized. Severe mutations that completely abrogate GAA enzyme activity cause a classic infantile disease course with hypertrophic cardiomyopathy, general skeletal muscle weakness, and respiratory failure and result in death within 1.5 years of life. Milder mutations leave partial GAA enzyme activity which results in a milder phenotype with onset varying from childhood to adult. In general, a higher residual enzyme activity in primary fibroblasts is associated with later onset of Pompe disease. Enzyme replacement therapy (ERT) has been developed for Pompe disease, in which recombinant human GAA protein is administered intravenously every two weeks. This treatment can rescue the lives of classic infantile patients and delay disease progression of later onset patients, but the effects are heterogeneous.

Antisense oligonucleotides (antisense oligomeric compounds, AONs) are currently being tested in clinical trials for their ability to modulate splicing. A classical example is (treatment of) Duchenne muscular dystrophy. In this disease, mutation hotspots are present in certain exons. Using antisense oligomeric compounds, the mutated exon is skipped and the mutation is bypassed. This results in a slightly shorter protein that is still partially functional. It is straightforward to induce exon skipping using antisense oligomeric compounds, because it is evident that the antisense oligomeric compound must be targeted to the relevant splice site. Also in Epidermolysis bullosa (WO2013053819) and in Leber congenital amaurosis symptoms (WO2012168435) antisense oligonucleotides are used for exon skipping.

However, for a very common mutation in Pompe Disease, the so-called c.-32-13T>G (IVS1) mutation, such a strategy does not work. The IVS1 mutation causes a skipping of exon 2 resulting in the deletion of the canonical translation start side and leads to mRNA decay and thus no protein is transcribed. For antisense therapy to work for the IVS1 mutation in Pompe disease, it needs to induce GAA exon 2 inclusion, i.e. an effect strongly contrasting with exon skipping. However, it is very difficult to induce exon inclusion, because it relies on targeting a splicing repressor sequence, which cannot be reliably predicted. Splicing repressor sequences may be present anywhere in the gene, either in an exon (termed exonic splicing silencer or ESS) or in an intron (termed intronic splicing silencer or ISS) and maybe close to the mutation or far away or maybe close to the affected splice site or far away from it.

Our earlier research (e.g. WO 2015/190922 and WO 2015/109021) has led to the discovery of sites in the genomic sequence of the GAA gene that cause aberrant splicing and in these co-pending patent applications it has been shown that antisense oligonucleotide-based compounds directed to those sites may be able to restore the aberrant splicing caused by the IVS1 mutation. There is, however, still room for improvement of the undisturbed expression of the GAA gene in Pompe patients.

SUMMARY OF THE INVENTION

The inventors now have found that the GAA IVS1 mutation causes novel aberrant splicing. Besides the already known splice products N (leaky wild type splicing), SV1 (alternative splice donor from exon 1, perfect skipping of exon 2), SV2 (full skipping of exon 2), and SV3 (partial skipping of exon 2), the inventors surprisingly found that the IVS1 mutation results in the usage of a natural pseudo exon that is present in GAA intron 1. This natural pseudo exon is by itself not affected by the IVS1 mutation. However, weakening on the canonical splice acceptor of GAA exon 2 leads to the inclusion of this natural pseudo exon. Blocking of either the natural cryptic 3' splice site or the natural cryptic 5' splice site of this natural pseudo exon with AONs restores wild type GAA splicing in cells carrying the IVS1 allele. Blocking of both natural cryptic splice sites simultaneously is more effective in restoration of splicing and GAA enzyme activity.

Therefore, the present invention relates to a method for repairing aberrant splicing in Pompe disease, wherein such aberrant splicing is caused by the expression of a natural pseudo exon, comprising blocking of either the natural cryptic 3' splice site or the natural cryptic 5' splice site of said natural pseudo exon with an antisense oligomeric compound (AON).

In a further aspect, the invention relates to a method for repairing aberrant splicing in Pompe disease, wherein such aberrant splicing is caused by the expression of a natural pseudo exon, comprising providing a pair of AONs, in which the first AON is directed to the acceptor splice site of said natural pseudo exon (i.e. 3' splice site of the natural pseudo exon) and wherein the second AON is directed to the donor splice site of said natural pseudo exon (i.e. the 5' splice site of the natural pseudo exon), wherein the application of said pair of AONs provides for a silencing of the expression of the natural pseudo exon, and promotes canonical splicing.

More preferably in the present invention the disease is Pompe disease, wherein Pompe disease is characterized by the IVS1 mutation.

In one aspect of the invention an antisense oligomeric compound (AON) is directed against the natural cryptic donor splice site chosen from the sequences SEQ ID NO: 1-90, preferably SEQ ID NO: 1, more preferably SEQ ID NO: 2-27, even more preferably SEQ ID NO: 5, 16 and 21.
In a further aspect of the present invention an AON is directed against the cryptic acceptor site chosen from the sequences SEQ ID NO: 180-345, preferably SEQ ID NO: 180, more preferably a site chosen from the sequences of SEQ ID NO: 196-216. Alternatively the AON is chosen from the sequences SEQ ID NO: 346-508, more preferably from sequences of SEQ ID NO; 360-380 and 425, or even more preferably SEQ ID NO: 363, 368, 375 and 425 or sequences that have an identity of 80% with said sequences.
In a further embodiment, the invention comprises a method according to the invention wherein a pair of AONs is formed by selecting a first AON from the sequences of SEQ ID NO: 91-179 more preferably from sequences of SEQ ID NO: 91-116 or sequences that have an identity of 80% with said sequences and a second AON from the sequences of SEQ ID NO: 346-508, more preferably from sequences of SEQ ID NO: 360-380 and 425 or sequences that have an identity of 80% with said sequences, preferably wherein the pair of AONs is SEQ ID NO: 93, 104 or 110 and one of SEQ ID NO: 363, 368, 375 and 425.

In a further aspect, the invention is related to an antisense oligomeric compound targeting SEQ ID NO:1 or SEQ ID NO: 180. In a further embodiment the antisense oligomeric compound targets any of the sequences of SEQ ID NO: 2-90, more preferably SEQ ID NO: 2-27 or SEQ ID NO: 181-345, more preferably SEQ ID NO: 196-216.

In a still further aspect the invention is related to a pair of antisense oligomeric compounds of which a first AON targets one of the sequences of SEQ ID NO: 1-90 and of which the second AON targets one of the sequences of SEQ ID NO: 180-345.

Preferably, in a further aspect of the invention, said AON is selected from the sequences of SEQ ID NO: 91-179, more preferably from sequences of SEQ ID NO: 91-116, sequences that are complementary to said sequences or sequences that have an identity of 80% with said sequences or the complementary sequences and a second AON from the sequences of SEQ ID NO: 346-508, more preferably from sequences of SEQ ID NO: 360-380 and 425, sequences that are complementary to said sequences or sequences that have an identity of 80% with said sequences or the complementary sequences, more preferably an AON selected from the group consisting of SEQ ID NO: 93, 104 or 110 and one of SEQ ID NO: 363, 368, 375 and 425, or sequences complimentary thereto or sequences having an identity of 80% with said sequences or the complementary sequences.
In a further preferred embodiment, the invention comprises a pair of AONs of which a first member is selected from the sequences of SEQ ID NO: 91-179, more preferably from sequences of SEQ ID NO: 91-116, sequences that are complementary to said sequences or sequences that have an identity of 80% with said sequences or the complementary sequences and of which a second AON is selected from the sequences of SEQ ID NO: 346-508, more preferably from sequences of SEQ ID NO: 360-380, sequences that are complementary to said sequences or sequences that have an identity of 80% with said sequences or the complementary sequences.

In a further aspect, the invention comprises an AON selected from the sequences of SEQ ID NO: 91-179, more preferably from sequences of SEQ ID NO: 91-116, sequences that are complementary to said sequences or sequences that have an identity of 80% with said sequences or the complementary sequences and a second AON from the sequences of SEQ ID NO: 346-508, more preferably from sequences of SEQ ID NO: 360-380 and 425, sequences that are complementary to said sequences or sequences that have an identity of 80% with said sequences or the complementary sequences for use in the treatment of Pompe disease, more preferably an AON selected from the group consisting of SEQ ID NO: 93, 104 and 110 and one of SEQ ID NO: 363, 368, 375 and 425, or sequences complimentary thereto or sequences having an identity of 80% with said sequences or the complementary sequences.

In a still further aspect, the invention comprises a pair of AONs according to the invention, of which a first member is selected from the sequences of SEQ ID NO: 91-179, more preferably from sequences of SEQ ID NO: 91-116, sequences that are complementary to said sequences or sequences that have an identity of 80% with said sequences or the complementary sequences and of which a second AON is selected from the sequences of SEQ ID NO: 346-508, more preferably from sequences of SEQ ID NO: 360-380 and 425, sequences that are complementary to said sequences or sequences that have an identity of 80% with said sequences or the complementary sequences for use in the treatment of Pompe disease, more preferably wherein said pair comprises SEQ ID NO: 93, 104 or 110 and one of SEQ ID NO: 363, 368, 375 and 425, or sequences complimentary thereto or sequences having an identity of 80% with said sequences or the complementary sequences.

In a preferred embodiment each of said AON or pair of AONs according to the invention, or AON or pair of AONs for use according to the invention is uniformly modified, preferably wherein the sugar of one or more nucleotides is modified, more preferably wherein the sugar modification is 2'-O-methyl or 2'-O-methoxyethyl, or alternatively or in combination wherein the base of one or more nucleotides is modified, or alternatively or in combination wherein the backbone of the oligomeric compound is modified, more preferably wherein the backbone is morpholino phosphorothioates, or morpholino phosphorodiamidate.

In a further aspect, the invention relates to a pharmaceutical composition comprising an AON or pair of AONs according to the invention, preferably wherein said pharmaceutical composition further provides a pharmaceutical acceptable excipient and/or a cell delivery agent.

DESCRIPTION OF THE FIGURES

FIG. 1. Screen to identify silencers of GAA exon 2 splicing.
(a) Outline of the three major splicing products of the GAA pre-mRNA caused by the IVS1 variant in patient-derived primary fibroblasts known to date. The gel illustrates the results of flanking exon RT-PCR analysis of exon 2 using primers that anneal to exon 1 and exon 3. WT: control fibroblasts; IVS1: fibroblasts from patient 1. Left lane: DNA size markers (in basepairs). Cartoons of pre-mRNAs illustrate splicing events as described 22, 23, 24, 25. The location of the c.-32-13C>T (IVS1) variant in the pY tract is indicated. Spliced mRNA cartoons are shown on the far right with sizes of the PCR products shown below the cartoons. Sizes of introns and exons in the cartoon are not to scale. AGCCCGCTTGCTTGTCCCGCAG: SEQ ID NO: 570.

(b) Cartoon showing hypothetical splicing regulatory elements that may be subject to modulation e.g. by a U7 snRNA 56.

(c) Locations of U7 snRNA-based AONs used in the screen in (d).

(d) Screen to identify splicing silencers of GAA exon 2. Primary fibroblasts from patient 1 (IVS1, c.525delT) were transduced with 200 ng U7 snRNA-expressing lentiviruses. The effects on GAA exon 2 expression were measured using RT-qPCR (black line; GAA (N) expression; primers indicated in the upper left cartoon). Effects on GAA enzymatic activity are indicated by the red line. The cartoon of GAA pre-mRNA below the graph indicates the positions of the AONs tested. Data are expressed relative to non-transduced (NT) fibroblasts and represent means+/−SD of three biological replicates. Samples were normalized for β-Actin expression.

(e) The experiment of (d) was also analyzed by flanking exon RT-PCR of GAA exon 2. β-Actin mRNA was used as loading control. *P<0.05 and **P<0.01 (n=3).

FIG. 2. Splicing correction of GAA exon 2 in fibroblasts using PMO-based AONs.

(a) Positions in the GAA pre-mRNA to which PMO-based AONs 1-4 anneal.

(b) Effect of AONs 1-4 in fibroblasts from patient 1. GAA exon 2 inclusion in the mRNA was measured using RT-qPCR analysis (see FIG. 2d) (GAA (N) mRNA level), and GAA enzymatic activity using 4-MU as substrate. Data are expressed relative to levels in healthy control fibroblasts and were corrected for β-Actin expression. GCAGACTGTG-CAAGTGCTCTGCACTCCCCTGCTG-GAGCTTTTCTCGCCCTTCCTTCTGGCCCTCTCCCCA: SEQ ID NO: 571

Figure 2B:
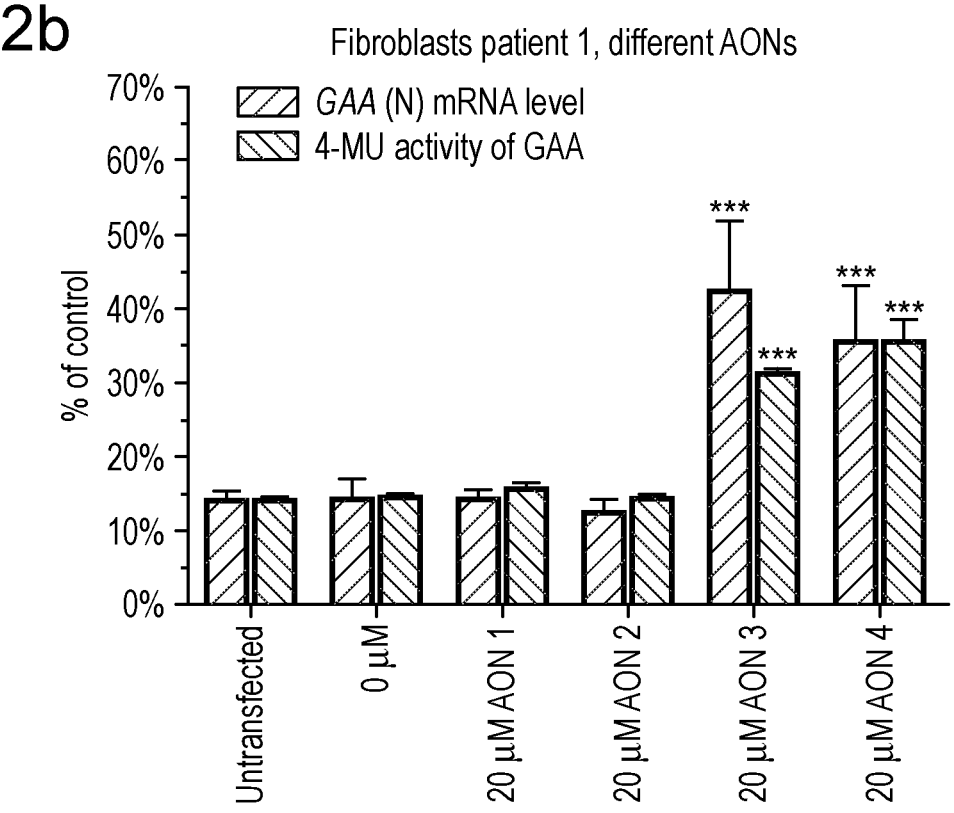
Figure 2C:
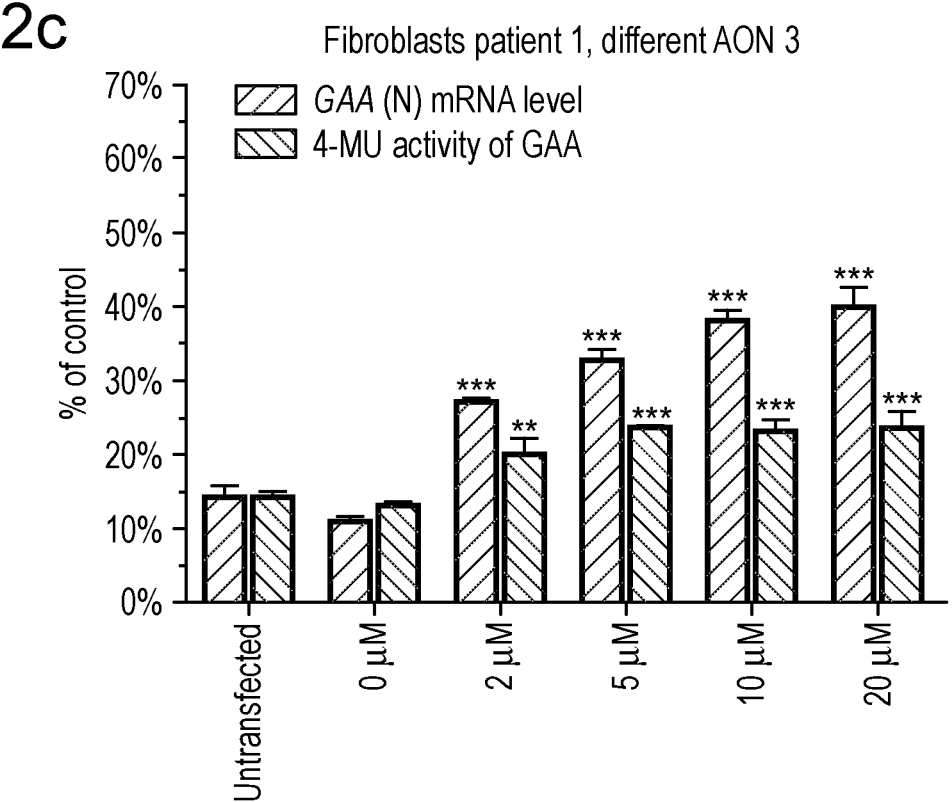

(c) As in FIG. 2b, but now using a concentration range of AON 3.

(d) As in FIG. 2b, but now using a concentration range of AON 4.

(e) Flanking exon RT-PCR analysis (as in FIG. 2a) of the effect of AON 4 on GAA exon 2 inclusion in fibroblasts from patient 1 and 2. −: 0 µM AON, +: 20 µM AON. (f) RT-qPCR analysis of individual splicing products of GAA exon 2 splicing. The N, SV2, and SV3 products were quantified using primers as outlined in the cartoon, and the effect of AON 4 on GAA exon 2 splicing was determined in fibroblasts from patients 1 and 2 and control 1. Data are corrected for ß-Actin expression and normalized per splicing variant for expression in untreated cells to visualize the effect per variant. Note that patient 2 carried a missense variant on the second allele which shows mRNA expression (partially masking effects on the IVS1 allele), whereas patient 1 has no GAA mRNA expression from the second allele due to NMD. Data are means+/−SDs of three biological replicates. *p<0.05, p<0.01, *p<0.001.

FIG. 3. Expansion of purified iPS-derived myogenic progenitors and differentiation into multinucleated myotubes.

(a) I, Scheme for differentiation of iPS cells into myogenic progenitors and FACS purification; II, Scheme for expansion of purified myogenic progenitors. The expansion medium is indicated. The average passage (P) number and fold expansion are also indicated.

(b) Linear proliferation curves for all four iPS-derived myogenic progenitor lines during expansion. The single R2 shown was calculated for all datapoints of the 4 lines, and indicates high concordance between the four lines.

(c) mRNA expression of iPS-derived myogenic progenitors and myotubes. Equal amounts of total RNA were isolated from fibroblasts (F), myogenic progenitors (MP), and myotubes (MT), and mRNA expression of the indicated genes was determined by RT-qPCR analysis. Log fold change was calculated compared to Control 1 sample 1. Symbols are as in (b). Biological duplicates are shown.

(d) Karyotype analysis after expansion of purified myogenic progenitors at day 35 (a representative example of 15 nuclei).

(e) Myogenic progenitors retain their capacity to differentiate into multinucleated myotubes during expansion. Myogenic progenitors were expanded, and at several time points during expansion a subculture was differentiated for 4 days and stained for expression of the myogenic differentiation marker MHC (MF-20 antibody; red). Nuclei were stained with Hoechst (blue). The white arrowheads point to examples of aligned nuclei present in a single myotube.

FIG. 4. Quantitative analysis of GAA exon 2 splicing in expanded iPS-derived myotubes.

(a) Comparison of aberrant GAA splicing in fibroblasts and myotubes. Equal amounts of total RNA from primary fibroblasts (F) and their corresponding iPS-derived myotubes (MT), derived from patient 1 or a healthy control, were analyzed by flanking exon RT-PCR of exon 2 as described in FIG. 1a.

(b), as (a) but now analyzed by RT-qPCR of individual splicing products. To facilitate comparison between different cell types, no normalization was used, and all products were compared to the value of average control fibroblast product N levels using the delta-Ct method. (c-i) Quantitative analysis of splicing correction in iPS-derived myotubes.

(c) Effect of AON 3 on GAA exon 2 splicing in myotubes from patient 1 as analyzed with RT-qPCR analysis of individual splicing products. Data were normalized against expression of four genes that showed no consistent changes in expression: MyoD, Myogenin, LAMP1, and LAMP2 (see FIG. 9h).

(d) As (c), but now for AON 4.

(e) Effect of AONs 3 and 4 on GAA exon 2 splicing in myotubes from control 1 as analyzed with RT-qPCR analysis of splice product N. Control cells have undetectable levels of aberrant splice products SV2 and SV3.

(f) Flanking exon RT-PCR analysis of the effect of AON 3 on GAA exon 2 splicing in myotubes from patient 1 and control 1.

(g) Effects of AON 3 and 4 on GAA enzymatic activity in myotubes from patient 1.

(h) As (g), but now in myotubes from control 1. (i) AON treatment does not affect myogenic differentiation. Immunofluorescent stainings of myotubes after treatment with AONs 3 and 4. Red: MHC (anti-MF-20); green: Myogenin; blue: nuclei (Hoechst). 0 µM: mock transfection. Representative pictures are shown. Quantitative data are means+/−SDs of three biological replicates. *p<0.05, p<0.01, *p<0.001.

FIG. 5. Blocking of a natural pseudo exon restores GAA exon 2 splicing.

(a) The splicing silencer in intron 1 is predicted to be the pY tract of a pseudo exon. Human splice finder was used to predict splice sites around the splicing silencer identified in FIG. 1. Note that predictions were independent of the IVS1 variant. A strong 3' splice site was predicted at c.-32-154, and a strong 5' splice site at c.-32-53, which suggested the presence of a natural pseudo exon, indicated by 'p' in the cartoon. The canonical 3' splice site of exon 2 at c.-32 showed strong prediction and is also indicated.
(b) Blocking of pseudo exon splicing restores GAA exon 2 splicing. AON 5 was designed to block the predicted 5' splice site, and AONs 3 and 5 were tested alone or in combination in myotubes from patient 1. Flanking RT-PCR analysis of GAA exon 2 was performed. Splicing products were identified by TOPO cloning and are indicated in the gel and in the cartoons in (c).
(d). Analysis of the experiment in (c) by RT-qPCR of individual splicing products. Splicing to the pseudo exon is represented by SV5 and SV6 and these products were quantified using a unique PCR primer.
(e) Analysis of the experiment in (c) on GAA enzyme activity.
(f) Combined treatment with AONs 3 and 5 does not interfere with myogenic differentiation to myotubes. Immunofluorescent staining results are shown for treatment of iPS-derived myotubes obtained from patient 1. Red: MHC (anti-MF-20); green: Myogenin; blue: nuclei (Hoechst). 0 μM: mock transfection. Representative pictures are shown. Quantitative data are means+/−SDs of three biological replicates. *p<0.05, p<0.01, *p<0.001.

Figure 2D:
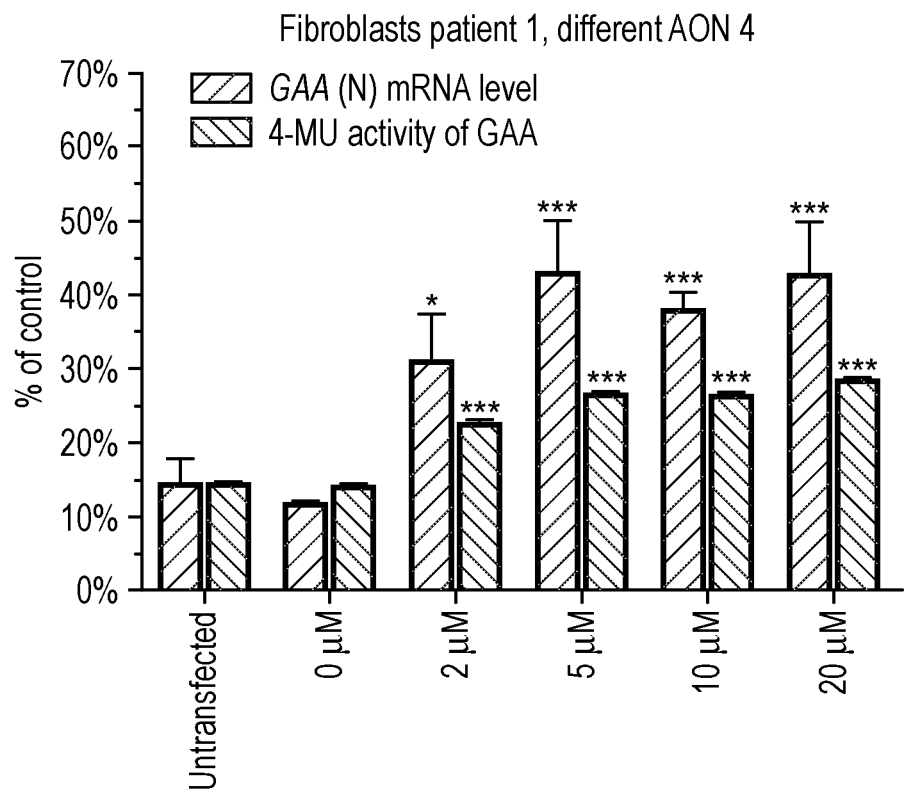

FIG. 6 A U7 snRNA screen to identify splicing repressors.
(a) In silico prediction of exonic and intronic splicing silencers around the GAA IVS1 variant. Algorithms from Human Splicing Finder 2.4.1 are indicated below the graph.
(b) One-step cloning strategy for rapid cloning of AONs in the lentiviral U7 snRNA expression vector. A unique NsiI site was introduced in the U7 snRNA. AON sequences and the NsiI site were part of a forward primer in PCR, and a unique SalI site was included in the reverse PCR primer.
(c) Cartoon of the region of the Cyclophilin A (CypA) gene that was targeted using a U7 snRNA-expressed AON (CyPA-E4) as described previously by Liu et al.[29].
(d) RT-PCR analysis of patient 1 fibroblasts in which the CypA pre-mRNA was targeted using CyPA-E4. As control, and empty, non-transducedU7 lentivirus was used (NT). The PCR strategy is shown above the gel. Sizes of spliced mRNAs are indicated to the right of the gel. ß-actin was used as loading control.
(e) RT-qPCR analysis of the samples of (d). The PCR strategy is shown above the figure.
(f) Testing of the optimal viral amount for detection of splicing modulation sequences. Patient 1 fibroblasts were infected with various lentiviruses at the amounts indicated. The optimum amount was determined to be 200 ng lentivirus per ml of medium. Data are means+/−SD of two biological replicates. Data points from 200 ng were taken from FIG. 2d (N=3). NT: non-transduced.
(g) Two hits from the screen shown in FIG. 2d were further tested in a microwalk using the U7 snRNA system. Primer locations are shown here.
(h) Results of the microwalk, as analyzed by RT-qPCR (FIG. 2d).
(i) As (h), using RT-PCR analyses. Results are expressed relative to non-transduced and represent means+/−SD of three biological replicates. **P<0.01.

FIG. 7 PMO-based AONs promote exon inclusion in primary fibroblasts from Pompe patients.
(a) Sequences of PMO-AONs used.
CypA 1: SEQ ID NO: 552;
CypA 2: SEQ ID NO: 553;
AON 1: SEQ ID NO: 554;
AON 2: SEQ ID NO: 555;
AON 3: SEQ ID NO: 556;
AON 4: SEQ ID NO: 557;
AON 5: SEQ ID NO: 558;
(b-d) Test of PMO-based AONs on positive control CypA.
(b) Location of AONs designed to block the splice donor of CypA exon 4. TTTTTCATCTGCACTGCCAAGACT-GAGTGGTAAGGGTACAACATGGCACACTAAC-CACCT: SEQ ID NO: 559
(c) Fibroblasts from patient 1 were transfected with AONs at various concentrations as indicated, and CyPA mRNAs were analyzed by RT-PCR. Cartoons at the right side of the gel indicate sizes of splicing products.
(d) RT-qPCR analysis of exon 4 skipping of the experiment in (c). The cartoon highlights the primer location. Data represent means of 3 technical replicates.
(e-f) Promotion of GAA exon 2 inclusion.
(e) Effect of AON 3 on GAA exon 2 inclusion (measured using RT-qPCR analysis as in FIG. 2d) and on GAA enzymatic activity in fibroblasts from patient 2. Note that this patient has genotype IVS1, c.923A>C, and that the c.923A>C allele causes background expression of the N form of GAA mRNA. Data are means+/−SD from three biological replicates.
(f) As (e) but with AON 4. Data for Supplementary FIG. 2e,f are means+/−SD from three biological replicates. *p<0.05, p<0.01, *p<0.001.

FIG. 8. Purification and expansion of iPS-derived myogenic progenitors.
(a-d) Generation and characterization of iPS cells.
(a) Immunofluorescent analysis of iPS cells from control 2 and patient 1 and 2 with antibodies to Nanog, Oct4, SSEA4, TRA-I-60 an TRA-I-81 (red). DAPI was used to stain nuclei (blue). Control 1 iPS cells were published previously[26].
(b) In vitro differentiation potential of iPS lines from (a) into the three germ layers. Stainings for α-Fetoprotein (AFP) show hepatocytes (endoderm; red), stainings for smooth muscle actin (SMA) show smooth muscle cells (mesoderm, red), and neuron-specific class III ß-tubulin (TUJ1) stainings show neurons (ectoderm, red). DAPI staining shows nuclei in blue.
(c) Microarray analysis of mRNA expression of pluripotency and fibroblast genes. iPS cell are marked as P2, P1 and C2 (patients 2 and 1, and control 2, respectively). For comparison, human embryonic stem cell lines H1 and H9 and fibroblast line F134 were also analyzed.
(d) Karyotype analysis of the four iPS lines used in this study. All lines have normal karyotypes. Representative karyotypes of 10 nuclei per cell line are shown.
(e-j) Expansion and differentiation of purified iPS-derived myogenic progenitors. (e) Immunofluorescent staining for Pax7 (in red) in non-purified myogenic progenitors following the 35-day differentiation protocol outlined in FIG. 3A I. Nuclei were stained with Hoechst (blue).
(f) Myogenic progenitors from (e) were purified by FACS sorting for HNK-1-/C-MET+ cells, and differentiated for 4 days into myotubes, which were stained with an MF-20 antibody to MHC (red). Nuclei were stained with Hoechst (blue). Purification yields and differentiation capacities without subsequent expansion were variable and prevented reproducible quantitative analysis.

(g-j) Characterization of expanded myogenic progenitors. Equal amounts of total RNA from fibroblasts (F), purified and expanded myogenic progenitors (MPs) and myotubes (MTs) from purified and expanded MPs were analyzed by RT-qPCR analysis. Biological duplicates are shown. Lines represent means.

(h) Immunofluorescent analysis of MyoD in expanded myogenic progenitors. Myogenic progenitors were expanded in proliferation medium and stained at the start of expansion and after expansion to ~1012 cells. Representative pictures are shown.

(i). Unchanged capacity to differentiate into multinucleated myotubes during expansion. Myogenic progenitors were expanded and at several time points during expansion, and a subculture from the expansion was differentiated for 4 days and stained for MHC expression (anti-MF20, red). Nuclei were stained with Hoechst (blue).

(j) Examples of myogenic differentiation after expansion of myogenic progenitors to ~1012 cells. Staining was as in (i). Multiple aligned myonuclei were seen in extended myotubes.

FIG. 9 Promotion of exon inclusion in patient-derived myotubes.

(a) GAA enzyme activity in iPSC-derived multinucleated myotubes. Myogenic progenitors from the cells indicated were differentiated for 4 days, and GAA enzyme activity was determined. The average activity present in the two healthy controls paralleled those present in fibroblasts (data not shown), and was used to calculate the percentage of residual activity in myotubes from the two patients.

(b) Morphology of differentiated myotubes, obtained from purified myogenic progenitors from control 1 and patient 1, with and without AON treatment. Cells were stained with antibodies against Myosin Heavy Chain (MHC) and Myogenin. Nuclei were visualized with Hoechst.

(c) Same as (a), but for control 2 and patient 2. (c-g) AONs promote exon 2 inclusion and GAA enzyme activity in patient-derived myotubes but not in myotubes from a healthy control.

(d) Effect of AON 3 on GAA pre-mRNA splicing in myotubes from patient 2, measured with RT-qPCR analysis of individual splicing products.

(e) As (c), but using AON 4.

(f) Effects of AON 3 and 4 on expression of the N form of GAA mRNA in myotubes from control 2.

(g) Effects of AON 3 and 4 on GAA enzymatic activity in myotubes from patient 2.

(h) Effects of AON 3 and 4 on GAA enzymatic activity in myotubes from control 2.

(i) Effects of AON 3 and 4 on expression of reference genes (MyoD, Myog, LAMP1, LAMP2) in myotubes from patients and controls. In all experiments, data represent means+/−SD of three biological replicates. *p<0.05, p<0.01, *p<0.001.

FIG. 10 Identification of a natural pseudo exon that competes with GAA exon inclusion.

(a) Sequence analysis of splicing products from Table 6.

(b) AON treatment does not change expression of reference genes in myotubes. The experiment of FIG. 2b-e was analyzed by RT-qPCR for expression of the reference genes shown. Equal amounts of total RNA were used.

Mutation 1 Reference sequence: SEQ ID NO: 572; Mutated sequence: SEQ ID NO: 573;
Mutation 2 Reference sequence: SEQ ID NO: 572; Mutated sequence: SEQ ID NO: 574;
Mutation 3 Reference sequence: SEQ ID NO: 575; Mutated sequence: SEQ ID NO: 576;

(c-e) Mutations in splice sites of the pseudo exon abolish pseudo exon inclusion.

(c) Cartoon of the minigene comprising the 5 kb genomic GAA sequence from exons 1-3. This sequence was obtained by PCR and cloned into pcDNA3.1. The pseudo exon is indicated along with the splice sites that were mutated by site directed mutagenesis.

(d) Splicing prediction of the effect of the mutations shown in (c). Mutation 1 generated a new predicted 3' splice site 5 nt downstream, whereas Mutations 2 and 3 completely abolished predicted 3' and 5' splice site, respectively.
Product N (exon 1-exon 2): SEQ ID NO: 560;
Product N (exon 2-exon 3): SEQ ID NO: 561;
Product SV1 (intron 1-exon 3): SEQ ID NO: 562;
Product SV2 (exon 1-exon 2): SEQ ID NO: 563;
Product SV3 (exon 1-exon 2): SEQ ID NO: 564;
Product SV4 (intron 1-exon 2): SEQ ID NO: 565;
Product SV5 (exon 1-intron 1): SEQ ID NO: 566;
Product SV5 (intron 1-exon 2): SEQ ID NO: 567;
Product SV6 (intron 1-exon 3): SEQ ID NO: 568;
Product SV7 (intron 1-exon 2): SEQ ID NO: 569;

(e) Wild type and mutated minigenes were transfected in HEK293 cells, and expression of GAA splice variants containing the pseudo exon was quantified by RT-qPCR analysis using the primers indicated. While this experiment further validates the identification of the pseudo exon, we found in an extensive set of experiments that GAA splicing regulation from the minigene does not faithfully reproduce endogenous GAA splicing. For example, abolishment of pseudo gene inclusion promotes endogenous GAA exon 2 inclusion but not in the context of the minigene. This may be caused by differences in promoters, polyadenylation, and/or chromatin organization, all of which are factors that are known to affect splicing outcome.

Figure 11:
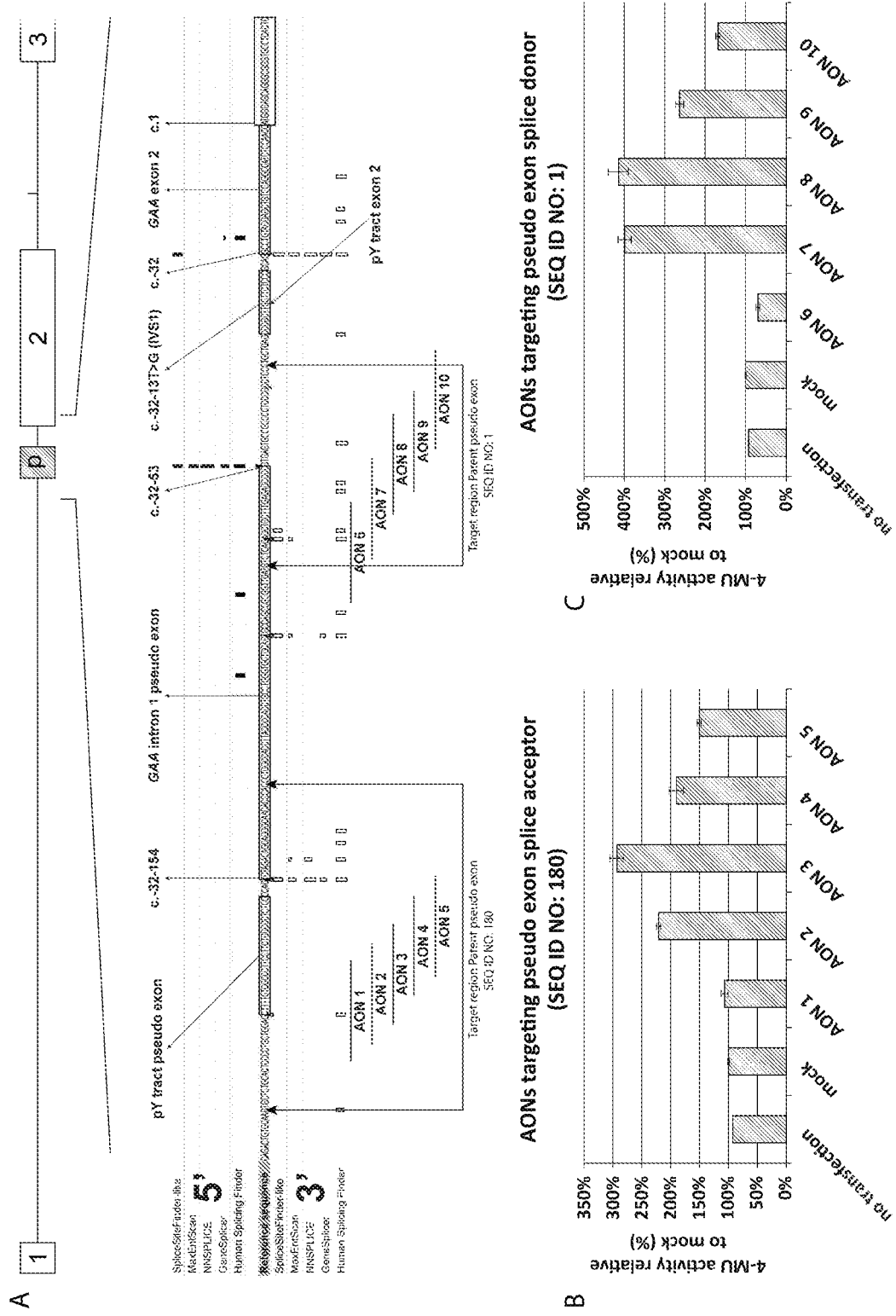

FIG. 11: AONs tested for identification of the target region.

A) cartoon depicting the region between exon 1 and exon 3 of the GAA gene. The region surrounding the canonical GAA exon 2 splice acceptor site and the pseudo exon (p) are magnified. Results of in silico prediction show that both splice acceptor (3') and donor (5') splice sites of the pseudo exon are predicted by five out of five algorithms indicated on the left. Five AONs (AONs 1-5) were generated to determine the boundaries of the acceptor splice site target region (SEQ ID NO: 180, shown with arrows) as well as five AONs (AONs 6-10) for the splice donor site. The sequences and corresponding SEQ ID NO of the AONs are shown in Table 11.

B) GAA enzymatic activity in iPSC-derived skeletal muscle cells from a Pompe patient carrying the c.-32-13T>G variant after transfection of AONs 1-5 for defining the pseudo exon splice acceptor target region. Activity is relative to mock transfection as measured with the 4MU-activity assay.

C) As in (B), but now with AONs 6-10 for definition of the pseudo exon splice donor target region.

Figure 12:
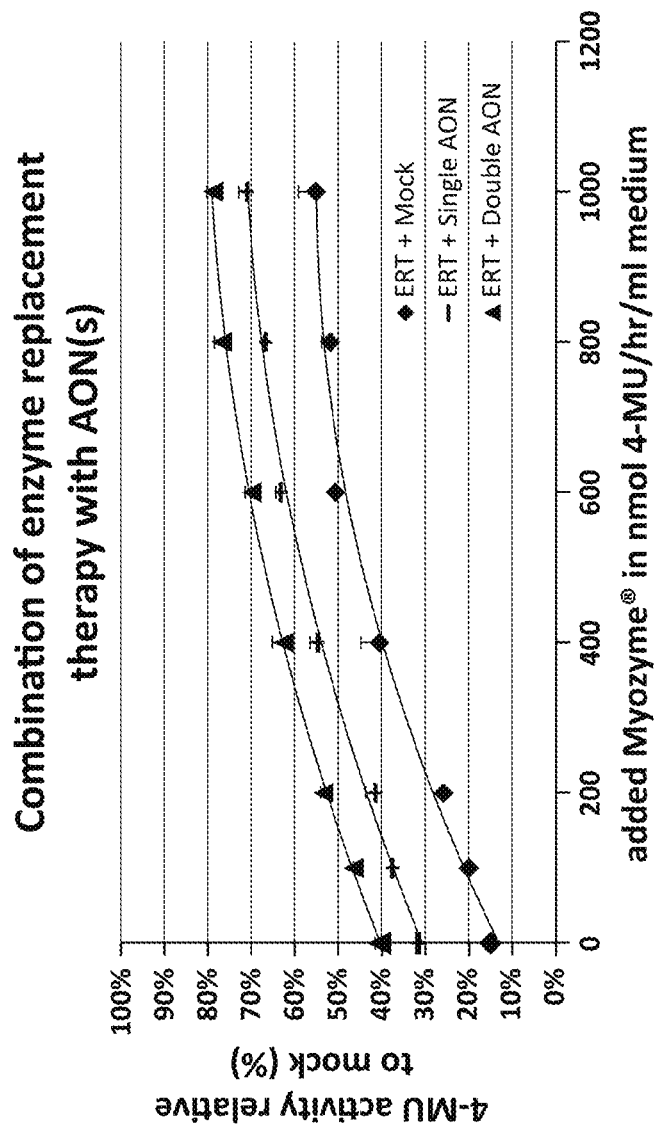

FIG. 12: Combined therapy of AONs with Enzyme Replacement Therapy.

iPSC-derived skeletal muscle cells from a Pompe patient carrying the c.-32-13T>G variant were treated with ERT and AONs. Different concentrations of Myozyme® were supplied to the cells via addition to the media. AONs were transfected using endoporter transfection reagent as described. Mock AON treatment was performed without addition of AON. Single AON treatment was performed using the AON with SEQ ID NO: 104 at a concentration of 20 μM. Double AON treatment was performed using the AONs with SEQ ID NO: 104 and SEQ ID NO: 368 at a concentration of 10 μM of each AON.

DETAILED DESCRIPTION

The principle behind antisense technology is that an antisense compound that hybridizes to a target nucleic acid modulates gene expression activities such as transcription, splicing or translation. This sequence specificity makes antisense compounds extremely attractive as tools for target validation and gene functionalization, as well as therapeutics to selectively modulate the expression of genes or gene products involved in disease.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "alternative splice transcripts." These are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA transcripts produce smaller mRNA transcripts. Consequently, mRNA alternative splice transcripts are processed pre-mRNA transcripts and each unique pre-mRNA transcript must always produce a unique mRNA transcript as a result of splicing. If no splicing of the pre-mRNA transcript occurs then the pre-mRNA transcript is identical to the mRNA transcript.

It is also known in the art that such alternative splice transcripts can be produced through the use of alternative signals to start or stop transcription and that pre-mRNAs and mRNAs can possess more than one start codon or stop codon. Alternative splice transcripts that originate from a pre-mRNA or mRNA that use alternative start codons are known as "alternative start transcripts" of that pre-mRNA or mRNA. Those transcripts that use an alternative stop codon are known as "alternative stop transcripts" of that pre-mRNA or mRNA. One specific type of alternative stop transcript is the "polyA transcript" in which the multiple transcripts produced result from the alternative selection of one of the "polyA stop signals" by the transcription machinery, thereby producing transcripts that terminate at unique polyA sites.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the subject invention. As used herein, the terms "include" and "comprise" are used synonymously.

The articles "a" and "an" are used herein to refer to one or to more than one (i.e., to at least one) of the grammatical object of the article. The use of the alternative (e.g., "or") should be understood to mean either one, both, or any combination thereof of the alternatives.

The terms "individual", "patient", and "subject" are used interchangeably herein and refer to mammals, in particular primates and preferably humans.

The term "exon" refers to a portion of a gene that is present in the mature form of mRNA. Exons include the ORF (open reading frame), i.e., the sequence which encodes protein, as well as the 5' and 3' UTRs (untranslated regions). The UTRs are important for translation of the protein. Algorithms and computer programs are available for predicting exons in DNA sequences (Grail, Grail 2 and Genscan and US 20040219522 for determining exon-intron junctions).

As used herein, the term "protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art.

As used herein, the term "internal exon" refers to an exon that is flanked on both its 5' and 3' end by another exon. For an mRNA comprising n exons, exon 2 to exon (n−1) are the internal exons. The first and last exons of an mRNA are referred to herein as "external exons".

A "natural cryptic splice site" or "natural pseudo splice site" is a site that is normally not used in pre-mRNA splicing, but can be utilized when canonical splicing has been weakened. It can be located either in an intron or an exon. The term "induced splice site" refers to an RNA sequence that is changed by an (induced) mutation, resulting in the generation of a novel splice site that is used in pre-mRNA splicing. The term "natural pseudo exon" or "natural cryptic exon" refers to a region in the pre-mRNA that is present in normal, healthy persons and that could function as an exon during splicing and is located in an intronic region of the pre-mRNA. The natural pseudo exon is often not utilized in normal, healthy cells, but is utilized in diseased cells that carry a mutation in the gene. This mutation does not affect the strength of the natural cryptic splice sites. Instead it affects the strength of a canonical splice site.

The term "intron" refers to a portion of a gene that is not translated into protein and while present in genomic DNA and pre-mRNA, it is removed in the formation of mature mRNA.

The term "messenger RNA" or "mRNA" refers to RNA that is transcribed from genomic DNA and that carries the coding sequence for protein synthesis. Pre-mRNA (precursor mRNA) is transcribed from genomic DNA. In eukaryotes, pre-mRNA is processed into mRNA, which includes removal of the introns, i.e., "splicing", and modifications to the 5' and 3' end (e.g., polyadenylation). mRNA typically comprises from 5' to 3'; a 5' cap (modified guanine nucleotide), 5' UTR (untranslated region), the coding sequence (beginning with a start codon and ending with a stop codon), the 3' UTR, and the poly(A) tail.

The terms "nucleic acid sequence" or "nucleic acid molecule" or "nucleotide sequence" or "polynucleotide" are used interchangeably and refer to a DNA or RNA molecule (or non-natural DNA or RNA variants) in single or double stranded form. An "isolated nucleic acid sequence" refers to a nucleic acid sequence which is no longer in the natural environment from which it was isolated, e.g. the nucleic acid sequence in a cell.

A "mutation" or a "variant" in a nucleic acid molecule is a change of one or more nucleotides compared to the wild type sequence, e.g. by replacement, deletion or insertion of one or more nucleotides. A "point mutation" or a "point variant" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) and share at least a certain minimal percentage of sequence identity (as defined further below). These programs use the Needleman and Wunsch global alignment algorithm to align two sequences over their entire length, maximising the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (http://www.ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences are "highly homogenous" or have "substantial sequence identity" if the percentage sequence identity is at least 70%, 75%, 80%, 85%, 90%, 95%, 98%, 99% or more, preferably at least 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'homologous sequences' herein, e.g. other variants of a pre-mRNA or homologues or derivatives of antisense oligomeric compounds. It should be understood that sequences with substantial sequence identity do not necessarily have the same length and may differ in length. For example sequences that have the same nucleotide sequence but of which one has additional nucleotides on the 3'- and/or 5'-side are 100% identical when relating to the shared sequence part.

The term "hybridisation" as used herein is generally used to mean hybridisation of nucleic acids at appropriate conditions of stringency as would be readily evident to those skilled in the art depending upon the nature of the probe sequence and target sequences. Conditions of hybridisation and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. Hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature (TM) of the duplex. The TM is known to be a function of the G-C content and duplex length as well as the ionic strength of the solution.

The term "allele(s)" means any of one or more alternative forms of a gene at a particular locus, all of which alleles relate to one trait or characteristic at a specific locus. One allele is present on each chromosome of the pair of homologous chromosomes. These may be identical alleles of the gene (homozygous) or two different alleles (heterozygous).

"Mutant allele" refers herein to an allele comprising one or more mutations in the sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different conformation, being targeted to a different sub-cellular compartment, having a modified catalytic domain, having a modified binding activity to nucleic acids or proteins, etc.; it may also lead to a different splicing event.

A "fragment" of the gene or nucleotide sequence or antisense oligomeric compound refers to any subset of the molecule, e.g., a shorter polynucleotide or oligonucleotide.

An "AON derivative" refers to a molecule substantially similar to the antisense oligomeric compound or a fragment thereof, such as a nucleotide substitution variant having one or more substituted nucleotides, but which maintains the ability to hybridize with the particular gene. Preferably the AON derivative comprises the mutations as identified by the invention. Derivatives may also include longer sequences.

An "analogue" refers to a non-natural molecule substantially similar to or functioning in relation to either the entire molecule, a variant or a fragment thereof.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is completely devoid of intron sequences. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "(pre-)mRNA processing" refer to the modification of a pre-mRNA following transcription, in which introns are removed and exons are joined. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS), exonic silencer sequences (ESS) and terminal stem loop (TSL) sequences.

As used herein, the terms "intronic silencer sequences (ISS)" and "exonic silencer sequences (ESS)" refer to sequence elements within introns and exons, respectively, that control alternative splicing by the binding of trans-acting protein factors within a pre-mRNA thereby resulting in differential use of splice sites. Typically, intronic silencer sequences are less conserved than the splice sites at exon-intron junctions.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and pre-mRNA.

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art (e.g. Leparc, G. G. and Mitra, R. D. Nucleic Acids Res. 35(21): e146, 2007).

As used herein "splice donor site" refers to a splice site found at the 5' end of an intron, or alternatively, the 3' end of an exon. Splice donor site is used interchangeably with "5' splice site." As used herein "splice acceptor site" refers to a splice site found at the 3' end of an intron, or alternatively, the 5' end of an exon. Splice acceptor site is used interchangeably with "3' splice site."

As used herein, "targeting" or "targeted to" refer to the process of designing an oligomeric compound such that the compound hybridizes with a selected nucleic acid molecule or region of a nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding GAA" encompass DNA encoding GAA, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes GAA. The GAA protein may be any mammalian enzyme, but it preferably is the human GAA.

The targeting process usually also includes determination of at least one target region, segment, or site within the target nucleic acid for the antisense interaction to occur such that the desired effect, e.g., modulation of expression, will result.

As used herein, "target mRNA" refers to the nucleic acid molecule to which the oligomeric compounds provided herein are designed to hybridize. In the context of the present disclosure, target mRNA is usually unspliced mRNA, or pre-mRNA. In the context of the present invention, the target mRNA is GAA mRNA or GAA pre-mRNA.

"Region" is defined as a portion of the target nucleic acid having at least one identifiable structure, function, or characteristic. Target regions may include, for example, a particular exon or intron, or may include only selected nucleotides within an exon or intron which are identified as appropriate target regions. Target regions may also be splicing repressor sites. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Target degradation can include (performance of) an RNase H, which is a cellular endonuclease which cleaves the RNA strand of an RNA:DNA duplex. It is known in the art that single-stranded antisense compounds which are "DNA-like" elicit cleavage by RNAse H. Occupancy-based antisense mechanisms, whereby antisense compounds hybridize yet do not elicit cleavage of the target, include inhibition of translation, modulation of splicing, modulation of poly(A) site selection and disruption of regulatory RNA structure.

For the present invention "RNA-like" antisense compounds for use in occupancy-based antisense mechanisms are preferred.

In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self-complementarity to allow for hybridization and formation of a fully or partially double-stranded compound.

The term "antisense oligonucleotide, AON, or antisense oligomeric compound" refers to an oligonucleotide that is capable of interacting with and/or hybridizing to a pre-mRNA or an mRNA having a complementary nucleotide sequence thereby modifying gene expression and/or splicing. Enzyme-dependent antisense oligonucleotides include forms that are dependent on RNase H activity to degrade target mRNA, and include single-stranded DNA, RNA, and phosphorothioate antisense. Steric blocking antisense oligonucleotides (RNase-H independent antisense) interfere with gene expression or other mRNA-dependent cellular processes by binding to a target sequence of mRNA. Steric blocking antisense includes 2'-0 alkyl antisense oligonucleotides, morpholino antisense oligonucleotides, and tricyclo-DNA antisense oligonucleotides. Steric blocking antisense oligonucleotides are preferred in the present invention.

As used herein, antisense oligonucleotides that are "RNase H-independent" are those compounds which do not elicit cleavage by RNase H when hybridized to a target nucleic acid. RNase H-independent oligomeric compounds modulate gene expression, such as splicing, by a target occupancy-based mechanism. RNase H-independent antisense oligonucleotides are preferred in the present invention.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences. One of skill in the art will be able to determine when an oligomeric compound is specifically hybridizable.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the antisense oligomeric compound of the present disclosure, the binding free energy for an antisense oligomeric compound with its complementary sequence is sufficient to allow the relevant function of the antisense oligomeric compound to proceed and there is a sufficient degree of complementarity to avoid non-specific binding of the antisense oligomeric compound to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et ah, CSH Symp. Quant. Biol. 1/7:123-133 (1987); Frier et al, Proc. Nat. Acad. Sci. USA 83:9373-77 (1986); and Turner et al, J. Am. Chem. Soc. 109:3783-3785 (1987)). Thus, "complementary" (or "specifically hybridizable") are terms that indicate a sufficient degree of complementarity or precise pairing such that stable and specific binding occurs between a antisense oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, "uniformly modified" or "fully modified" refers to an oligomeric compound, an antisense oligonucleotide, or a region of nucleotides wherein essentially each nucleoside is a sugar modified nucleoside having uniform modification.

As used herein, a "chimeric oligomeric compound", "chimeric antisense compound" or "chimeric antisense oligonucleotide compound" is a compound containing two or more chemically distinct regions, each comprising at least one monomer unit (i.e. a nucleotide in the case of an oligonucleotide compound). The term "chimeric antisense compound" specifically refers to an antisense compound, having at least one sugar, nucleobase and/or internucleoside linkage that is differentially modified as compared to the other sugars, nucleotides and internucleoside linkages within the same oligomeric compound. The remainder of the sugars, nucleotides and internucleoside linkages can be independently modified or unmodified. In general a chimeric oligomeric compound will have modified nucleosides that can be in isolated positions or grouped together in regions that will define a particular motif. Chimeric oligomeric compounds typically contain at least one region modified so as to confer increased resistance to nuclease degradation, increased cellular uptake, and/or increased binding affinity for the target nucleic acid. In the context of the present disclosure, a "chimeric RNase H-independent antisense compound" is an antisense compound with at least two chemically distinct regions, but which is not susceptible to cleavage by RNase H when hybridized to a target nucleic acid.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the ribose sugar of the nucleoside has been substituted with a chemically modified sugar moiety. In the context of the present disclosure, the chemically modified sugar moieties include, but are not limited to, 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

As used herein, compounds "resistant to RNase H degradation" are antisense compounds having a least one chemical modification that increases resistance of the compound to RNase H cleavage. Such modifications include, but are not limited to, nucleotides with sugar modifications. As used herein, a nucleotide with a modified sugar includes, but is not limited to, any nucleotide wherein the 2'-deoxyribose sugar has been substituted with a chemically modified sugar moiety. In the context of the present invention, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, locked nucleic acid (LNA) and ethylene bridged nucleic acid (ENA). Modified compounds resistant to RNase H cleavage are thoroughly described herein and are well known to those of skill in the art.

In the context of the present disclosure, "cellular uptake" refers to delivery and internalization of oligomeric compounds into cells. The oligomeric compounds can be internalized, for example, by cells grown in culture (in vitro), cells harvested from an animal (ex vivo) or by tissues following administration to an animal (in vivo).

By "subject" is meant an organism, which is a donor or recipient of explanted cells or the cells themselves. "Subject" also refers to an organism to which the nucleic acid molecules of this disclosure can be administered. In one embodiment of the invention and/or embodiments thereof, a subject is a mammal or mammalian cell. In another embodiment, a subject is a human or human cell. Preferably, the subject is a human being, suffering from Pompe disease, especially Pompe disease that is characterised by the so-called IVS1 variant. Such a subject is also referred to as 'patient'.

As used herein, the term "therapeutically effective amount" means an amount of antisense oligomeric compound that is sufficient, in the subject (e.g., human) to which it is administered, to treat or prevent the stated disease, disorder, or condition. The antisense oligomeric compound of the instant disclosure, individually, or in combination or in conjunction with other drugs, can be used to treat diseases or conditions discussed herein. For example, to treat a particular disease, disorder, or condition, the antisense oligomeric compound can be administered to a patient or can be administered to other appropriate cells evident to those skilled in the art, individually or in combination with one or more drugs, under conditions suitable for treatment. In the present invention the disease is preferably Pompe disease.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "isolated" means that the referenced material is removed from its native environment, e.g., a cell. Thus, an isolated biological material can be free of some or all cellular components, i.e. components of the cells in which the native material occurs naturally (e.g., cytoplasmic or membrane component).

The term "purified" as used herein refers to material that has been isolated under conditions that reduce or eliminate the presence of unrelated materials, i.e. contaminants, including native materials from which the material is obtained (e.g. a tissue culture). For example, a purified DNA antisense oligomeric compound is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Previous data showed aberrant splicing due to the IVS1 variant. Three major splice products were observed (N, SV2, SV3). Here we surprisingly found that a natural pseudo exon exists in intron 1. This is not used in control cells, but in the context of the IVS1 mutation it is utilized and competes with canonical splicing of exon 2. It is believed that this phenomenon is not limited to the IVS1 mutation in Pompe disease, but that this may occur also with the c.-32-3C>G and C>A mutations in the GAA gene.

As has been shown by Havens, M A et al., 2013, Wiley Interdisiciplinary Rev 4(3), 19 Mar. 2013 (see FIG. 1), the use of induced splice sites may in many cases lead to the creation of an extra exon. Expression of this extra exon then causes aberrant protein production. In the present invention the discovery was made that in hereditary diseases that are accompanied or caused by splicing aberrations natural pseudo-exons can be present and can be included in the transcript. Such a pseudo-exon was used preferentially when the pY tract of exon 2 was mutated by the IVS1 mutation in Pompe disease. The presence of a natural pseudo exon and its role here is completely unexpected. Detection of such a pseudo-exon is not trivial. Although several splice events have been described in the context of the IVS1 variant present in Pompe disease (see Bergsma et al., Human Mutation 36(1): 57-68) the presence of a pseudo exon in intron 1 of the GAA gene has not been described before. It is furthermore important to note that said pseudo exon is not generated by the IVS1 mutation. Rather, the IVS1 mutation weakens the splice acceptor site of the GAA exon 2. This leads toi a shift of inclusion of exon 2 towards inclusion of the pseudo exon. Hence, the existence of the pseudo exon would not logically follow from the existence of the IVS1 mutation.

It has now been found that the commonly known solution to repair such aberrant splicing, i.e. by blocking the cryptic splice site is greatly improved if both cryptic splice sites of the pseudo-exon, i.e. both the donor and acceptor splice sites, are blocked. As is commonly known in the prior art, blocking splice sites can advantageously be achieved by antisense oligonucleotides (AONs).

As such, the present invention provides a method for repairing aberrant splicing, wherein such aberrant splicing is caused by the expression of a natural pseudo exon, by providing a pair of AONs, in which the first AON is directed to the natural cryptic acceptor splice site of said natural pseudo exon (i.e. the 3' splice site of the natural pseudo exon) and wherein the second AON is directed to the natural cryptic donor splice site of said natural pseudo exon (i.e. the 5' splice site of the natural pseudo exon), wherein the application of said pair of AONs provides for a silencing of the expression of the natural pseudo exon. This also means that the target sites are relatively close; they normally will not be separated by more than 200, preferably 500 nucleotides, i.e. the cryptic exon will normally be less than 200 or 500 nucleotides, respectively. However, larger exons may occasionally occur.

Such a method can be used for any aberrant splicing resulting in the expression of a cryptic exon whether or not this aberrant splicing would cause a disease.

Preferably, the disease is Pompe disease and the aberrant splicing is caused by the so-called IVS1 mutation. In the case of this mutation a natural pseudo-exon is recognized in the region of the first intron which is spliced at the cryptic splice sites c-32-154 (natural cryptic acceptor splice site), and c.-32-52 (natural cryptic donor splice site). These sites can be blocked by using AONs that are targeted to the following regions: SEQ ID NO: 180 for the natural cryptic acceptor splice site and SEQ ID NO: 1 for the natural cryptic donor splice site.

Suitably the sequences targeting the region around c.-32-52 (the natural cryptic donor splice site) GTCTCAGAGCTGCTTTGAGAGCCCCGTGAGTGCCGCCCCTCCCGC-CTCCC-3' (SEQ ID NO:1) hybridize with at least a part of SEQ ID NO: 1. Sequences that hybridize may be shorter or longer than the target sequence.

In one aspect or embodiment of aspects and/or embodiments thereof, the invention is directed to an antisense oligomeric compound targeted to a donor splice site sequence of the natural pseudo-exon selected from the group comprising SEQ ID NO: 2-27 as shown in Table 1 and derivatives and fragments having at least 80% identity thereof.

TABLE 1

| | 25 bp TARGET sequence 5' → 3' | |
|---|---|---|
| SEQ ID NO: 3 | c.-32-77_-53 | GTCTCAGAGCTGCTTTGAGAGCCCC |
| SEQ ID NO: 4 | c.-32-76_-52 | TCTCAGAGCTGCTTTGAGAGCCCCG |
| SEQ ID NO: 5 | c.-32-75_-51 | CTCAGAGCTGCTTTGAGAGCCCCGT |
| SEQ ID NO: 6 | c.-32-74_-50 | TCAGAGCTGCTTTGAGAGCCCCGTG |
| SEQ ID NO: 7 | c.-32-73_-49 | CAGAGCTGCTTTGAGAGCCCCGTGA |
| SEQ ID NO: 8 | c.-32-72_-48 | AGAGCTGCTTTGAGAGCCCCGTGAG |
| SEQ ID NO: 9 | c.-32-71_-47 | GAGCTGCTTTGAGAGCCCCGTGAGT |
| SEQ ID NO: 10 | c.-32-70_-46 | AGCTGCTTTGAGAGCCCCGTGAGTG |
| SEQ ID NO: 11 | c.-32-69_-45 | GCTGCTTTGAGAGCCCCGTGAGTGC |
| SEQ ID NO: 12 | c.-32-68_-44 | CTGCTTTGAGAGCCCCGTGAGTGCC |
| SEQ ID NO: 13 | c.-32-67_-43 | TGCTTTGAGAGCCCCGTGAGTGCCG |
| SEQ ID NO: 14 | c.-32-66_-42 | GCTTTGAGAGCCCCGTGAGTGCCGC |
| SEQ ID NO: 15 | c.-32-65_-41 | CTTTGAGAGCCCCGTGAGTGCCGCC |
| SEQ ID NO: 16 | c.-32-64_-40 | TTTGAGAGCCCCGTGAGTGCCGCCC |
| SEQ ID NO: 17 | c.-32-63_-39 | TTGAGAGCCCCGTGAGTGCCGCCCC |
| SEQ ID NO: 2 | c.-32-62_-38 | TGAGAGCCCCGTGAGTGCCGCCCCT |
| SEQ ID NO: 18 | c.-32-61_-37 | GAGAGCCCCGTGAGTGCCGCCCCTC |
| SEQ ID NO: 19 | c.-32-60_-36 | AGAGCCCCGTGAGTGCCGCCCCTCC |
| SEQ ID NO: 20 | c.-32-59_-35 | GAGCCCCGTGAGTGCCGCCCCTCCC |
| SEQ ID NO: 21 | c.-32-58_-34 | AGCCCCGTGAGTGCCGCCCCTCCCG |
| SEQ ID NO: 22 | c.-32-57_-33 | GCCCCGTGAGTGCCGCCCCTCCCGC |
| SEQ ID NO: 23 | c.-32-56_-32 | CCCCGTGAGTGCCGCCCCTCCCGCC |
| SEQ ID NO: 24 | c.-32-55_-31 | CCCGTGAGTGCCGCCCCTCCCGCCT |
| SEQ ID NO: 25 | c.-32-54_-30 | CCGTGAGTGCCGCCCCTCCCGCCTC |
| SEQ ID NO: 26 | c.-32-53_-29 | CGTGAGTGCCGCCCCTCCCGCCTCC |
| SEQ ID NO: 27 | c.-32-52_-28 | GTGAGTGCCGCCCCTCCCGCCTCCC |

It should be noted that it may not be necessary to target the full length of SEQ ID NO: 2-27, target fragments having a shorter or longer sequence are also envisioned. In particular shorter fragments such as fragments with 18, 19, 20, 21, 22, 23, or 24 nucleotides of SEQ ID NO: 2-27 are envisioned, such as depicted in below Tables 2 and 3.

TABLE 2

21 bp TARGET sequence 5' → 3'.

| | | |
|---|---|---|
| SEQ ID NO: 28 | c.-32-77_-57 | GTCTCAGAGCTGCTTTGAGAG |
| SEQ ID NO: 29 | c.-32-76_-56 | TCTCAGAGCTGCTTTGAGAGC |
| SEQ ID NO: 30 | c.-32-75_-55 | CTCAGAGCTGCTTTGAGAGCC |
| SEQ ID NO: 31 | c.-32-74_-54 | TCAGAGCTGCTTTGAGAGCCC |
| SEQ ID NO: 32 | c.-32-73_-53 | CAGAGCTGCTTTGAGAGCCCC |
| SEQ ID NO: 33 | c.-32-72_-52 | AGAGCTGCTTTGAGAGCCCCG |
| SEQ ID NO: 34 | c.-32-71_-51 | GAGCTGCTTTGAGAGCCCCGT |
| SEQ ID NO: 35 | c.-32-70_-50 | AGCTGCTTTGAGAGCCCCGTG |
| SEQ ID NO: 36 | c.-32-69_-49 | GCTGCTTTGAGAGCCCCGTGA |
| SEQ ID NO: 37 | c.-32-68_-48 | CTGCTTTGAGAGCCCCGTGAG |
| SEQ ID NO: 38 | c.-32-67_-47 | TGCTTTGAGAGCCCCGTGAGT |
| SEQ ID NO: 39 | c.-32-66_-46 | GCTTTGAGAGCCCCGTGAGTG |
| SEQ ID NO: 40 | c.-32-65_-45 | CTTTGAGAGCCCCGTGAGTGC |
| SEQ ID NO: 41 | c.-32-64_-44 | TTTGAGAGCCCCGTGAGTGCC |
| SEQ ID NO: 42 | c.-32-63_-43 | TTGAGAGCCCCGTGAGTGCCG |
| SEQ ID NO: 43 | c.-32-62_-42 | TGAGAGCCCCGTGAGTGCCGC |
| SEQ ID NO: 44 | c.-32-61_-41 | GAGAGCCCCGTGAGTGCCGCC |
| SEQ ID NO: 45 | c.-32-60_-40 | AGAGCCCCGTGAGTGCCGCCC |
| SEQ ID NO: 46 | c.-32-59_-39 | GAGCCCCGTGAGTGCCGCCCC |
| SEQ ID NO: 47 | c.-32-58_-38 | AGCCCCGTGAGTGCCGCCCCT |
| SEQ ID NO: 48 | c.-32-57_-37 | GCCCCGTGAGTGCCGCCCCTC |
| SEQ ID NO: 49 | c.-32-56_-36 | CCCCGTGAGTGCCGCCCCTCC |
| SEQ ID NO: 50 | c.-32-55_-35 | CCCGTGAGTGCCGCCCCTCCC |
| SEQ ID NO: 51 | c.-32-54_-34 | CCGTGAGTGCCGCCCCTCCCG |
| SEQ ID NO: 52 | c.-32-53_-33 | CGTGAGTGCCGCCCCTCCCGC |
| SEQ ID NO: 53 | c.-32-52_-32 | GTGAGTGCCGCCCCTCCCGCC |
| SEQ ID NO: 54 | c.-32-51_-31 | TGAGTGCCGCCCCTCCCGCCT |
| SEQ ID NO: 55 | c.-32-50_-30 | GAGTGCCGCCCCTCCCGCCTC |
| SEQ ID NO: 56 | c.-32-49_-29 | AGTGCCGCCCCTCCCGCCTCC |
| SEQ ID NO: 57 | c.-32-48_-28 | GTGCCGCCCCTCCCGCCTCCC |

TABLE 3

18 bp TARGET sequence 5' → 3'.

| | | |
|---|---|---|
| SEQ ID NO: 58 | c.-32-77_-60 | GTCTCAGAGCTGCTTTGA |
| SEQ ID NO: 59 | c.-32-76_-59 | TCTCAGAGCTGCTTTGAG |
| SEQ ID NO: 60 | c.-32-75_-58 | CTCAGAGCTGCTTTGAGA |
| SEQ ID NO: 61 | c.-32-74_-57 | TCAGAGCTGCTTTGAGAG |
| SEQ ID NO: 62 | c.-32-73_-56 | CAGAGCTGCTTTGAGAGC |
| SEQ ID NO: 63 | c.-32-72_-55 | AGAGCTGCTTTGAGAGCC |
| SEQ ID NO: 64 | c.-32-71_-54 | GAGCTGCTTTGAGAGCCC |
| SEQ ID NO: 65 | c.-32-70_-53 | AGCTGCTTTGAGAGCCCC |
| SEQ ID NO: 66 | c.-32-69_-52 | GCTGCTTTGAGAGCCCCG |
| SEQ ID NO: 67 | c.-32-68_-51 | CTGCTTTGAGAGCCCCGT |
| SEQ ID NO: 68 | c.-32-67_-50 | TGCTTTGAGAGCCCCGTG |
| SEQ ID NO: 69 | c.-32-66_-49 | GCTTTGAGAGCCCCGTGA |
| SEQ ID NO: 70 | c.-32-65_-48 | CTTTGAGAGCCCCGTGAG |
| SEQ ID NO: 71 | c.-32-64_-47 | TTTGAGAGCCCCGTGAGT |
| SEQ ID NO: 72 | c.-32-63_-46 | TTGAGAGCCCCGTGAGTG |
| SEQ ID NO: 73 | c.-32-62_-45 | TGAGAGCCCCGTGAGTGC |
| SEQ ID NO: 74 | c.-32-61_-44 | GAGAGCCCCGTGAGTGCC |
| SEQ ID NO: 75 | c.-32-60_-43 | AGAGCCCCGTGAGTGCCG |
| SEQ ID NO: 76 | c.-32-59_-42 | GAGCCCCGTGAGTGCCGC |
| SEQ ID NO: 77 | c.-32-58_-41 | AGCCCCGTGAGTGCCGCC |
| SEQ ID NO: 78 | c.-32-57_-40 | GCCCCGTGAGTGCCGCCC |
| SEQ ID NO: 79 | c.-32-56_-39 | CCCCGTGAGTGCCGCCCC |
| SEQ ID NO: 80 | c.-32-55_-38 | CCCGTGAGTGCCGCCCCT |
| SEQ ID NO: 81 | c.-32-54_-37 | CCGTGAGTGCCGCCCCTC |
| SEQ ID NO: 82 | c.-32-53_-36 | CGTGAGTGCCGCCCCTCC |
| SEQ ID NO: 83 | c.-32-52_-35 | GTGAGTGCCGCCCCTCCC |
| SEQ ID NO: 84 | c.-32-51_-34 | TGAGTGCCGCCCCTCCCG |
| SEQ ID NO: 85 | c.-32-50_-33 | GAGTGCCGCCCCTCCCGC |
| SEQ ID NO: 86 | c.-32-49_-32 | AGTGCCGCCCCTCCCGCC |
| SEQ ID NO: 87 | c.-32-48_-31 | GTGCCGCCCCTCCCGCCT |
| SEQ ID NO: 88 | c.-32-47_-30 | TGCCGCCCCTCCCGCCTC |
| SEQ ID NO: 89 | c.-32-46_-29 | GCCGCCCCTCCCGCCTCC |
| SEQ ID NO: 90 | c.-32-45_-28 | CCGCCCCTCCCGCCTCCC |

As indicated above these targets are relevant for the (c.-32-52) cryptic splice site.

For the acceptor splice site suitably the sequences targeting the region around c.-32-154 (the natural cryptic acceptor splice site) 5'GTGCTCTGCACTCCCCTGCTG-GAGCTTTTCTCGCCCTTCCTTCTGGCCCTCTC-CCCCAGTCTAGACAGCAGGGCAACACCCAC3' (SEQ ID NO: 180) hybridize with at least a part of SEQ ID NO: 180, wherein said part that is targeted may be CTTTTCTCTCGCCCTTCCTTCTGGCCCCTCCCC (SEQ ID NO: 181). Sequences that hybridize may be shorter or longer than the target sequence.

In one aspect, the invention is directed to an antisense oligomeric compound targeted to an acceptor splice site sequence of the natural pseudo-exon such as a sequence selected from the group comprising SEQ ID NO: 182-239 as shown in Table 4 and derivatives and fragments having at least 80% identity thereof.

TABLE 4

| | 25 bp TARGET sequence 5' → 3' | |
|---|---|---|
| SEQ ID NO: 182 | c.-32-212_-188 | GTGCTCTGCACTC CCCTGCTGGAGC |
| SEQ ID NO: 183 | c.-32-211_-187 | TGCTCTGCACTCC CCTGCTGGAGCT |
| SEQ ID NO: 184 | c.-32-210_-186 | GCTCTGCACTCCC CTGCTGGAGCTT |
| SEQ ID NO: 185 | c.-32-209_-185 | CTCTGCACTCCCC TGCTGGAGCTTT |
| SEQ ID NO: 186 | c.-32-208_-184 | TCTGCACTCCCCT GCTGGAGCTTTT |
| SEQ ID NO: 187 | c.-32-207_-183 | CTGCACTCCCCTG CTGGAGCTTTTC |
| SEQ ID NO: 188 | c.-32-206_-182 | TGCACTCCCCTGC TGGAGCTTTTCT |
| SEQ ID NO: 189 | c.-32-205_-181 | GCACTCCCCTGCT GGAGCTTTTCTC |
| SEQ ID NO: 190 | c.-32-204_-180 | CACTCCCCTGCTG GAGCTTTTCTCG |
| SEQ ID NO: 191 | c.-32-203_-179 | ACTCCCCTGCTGG AGCTTTTCTCGC |
| SEQ ID NO: 192 | c.-32-202_-178 | CTCCCCTGCTGGA GCTTTTCTCGCC |
| SEQ ID NO: 193 | c.-32-201_-177 | TCCCCTGCTGGAG CTTTTCTCGCCC |
| SEQ ID NO: 194 | c.-32-200_-176 | CCCCTGCTGGAGC TTTTCTCGCCCT |
| SEQ ID NO: 195 | c.-32-199_-175 | CCCTGCTGGAGCT TTTCTCGCCCTT |
| SEQ ID NO: 196 | c.-32-198_-174 | CCTGCTGGAGCTT TTCTCGCCCTTC |
| SEQ ID NO: 197 | c.-32-197_-173 | CTGCTGGAGCTTT TCTCGCCCTTCC |
| SEQ ID NO: 198 | c.-32-196_-172 | TGCTGGAGCTTTT CTCGCCCTTCCT |
| SEQ ID NO: 199 | c.-32-195_-171 | GCTGGAGCTTTTC TCGCCCTTCCTT |
| SEQ ID NO: 200 | c.-32-194_-170 | CTGGAGCTTTTCT CGCCCTTCCTTC |
| SEQ ID NO: 201 | c.-32-193_-169 | TGGAGCTTTTCTC GCCCTTCCTTCT |
| SEQ ID NO: 202 | c.-32-192_-168 | GGAGCTTTTCTCG CCCTTCCTTCTG |
| SEQ ID NO: 203 | c.-32-191_-167 | GAGCTTTTCTCGC CCTTCCTTCTGG |
| SEQ ID NO: 204 | c.-32-190_-166 | AGCTTTTCTCGCC CTTCCTTCTGGC |

TABLE 4-continued

| | 25 bp TARGET sequence 5' → 3' | |
|---|---|---|
| SEQ ID NO: 205 | c.-32-189_-165 | GCTTTTCTCGCCC TTCCTTCTGGCC |
| SEQ ID NO: 206 | c.-32-188_-164 | CTTTTCTCGCCCT TCCTTCTGGCCC |
| SEQ ID NO: 207 | c.-32-187_-163 | TTTTCTCGCCCTT CCTTCTGGCCCT |
| SEQ ID NO: 208 | c.-32-186_-162 | TTTCTCGCCCTTC CTTCTGGCCCTC |
| SEQ ID NO: 209 | c.-32-185_-161 | TTCTCGCCCTTCC TTCTGGCCCTCT |
| SEQ ID NO: 210 | c.-32-184_-160 | TCTCGCCCTTCCT TCTGGCCCTCTC |
| SEQ ID NO: 211 | c.-32-183_-159 | CTCGCCCTTCCTT CTGGCCCTCTCC |
| SEQ ID NO: 212 | c.-32-182_-158 | TCGCCCTTCCTTC TGGCCCTCTCCC |
| SEQ ID NO: 213 | c.-32-181_-157 | CGCCCTTCCTTCT GGCCCTCTCCCC |
| SEQ ID NO: 214 | c.-32-180_-156 | GCCCTTCCTTCTG GCCCTCTCCCCA |
| SEQ ID NO: 215 | c.-32-179_-155 | CCCTTCCTTCTGG CCCTCTCCCCAG |
| SEQ ID NO: 216 | c.-32-178_-154 | CCTTCCTTCTGGC CCTCTCCCCAGT |
| SEQ ID NO: 217 | c.-32-177_-153 | CTTCCTTCTGGCC CTCTCCCCAGTC |
| SEQ ID NO: 218 | c.-32-176_-152 | TTCCTTCTGGCCC TCTCCCCAGTCT |
| SEQ ID NO: 219 | c.-32-175_-151 | TCCTTCTGGCCCT CTCCCCAGTCTA |
| SEQ ID NO: 220 | c.-32-174_-150 | CCTTCTGGCCCTC TCCCCAGTCTAG |
| SEQ ID NO: 221 | c.-32-173_-149 | CTTCTGGCCCTCT CCCCAGTCTAGA |
| SEQ ID NO: 222 | c.-32-172_-148 | TTCTGGCCCTCTC CCCAGTCTAGAC |
| SEQ ID NO: 223 | c.-32-171_-147 | TCTGGCCCTCTCC CCAGTCTAGACA |
| SEQ ID NO: 224 | c.-32-170_-146 | CTGGCCCTCTCCC CAGTCTAGACAG |
| SEQ ID NO: 225 | c.-32-169_-145 | TGGCCCTCTCCCC AGTCTAGACAGC |
| SEQ ID NO: 226 | c.-32-168_-144 | GGCCCTCTCCCCA GTCTAGACAGCA |
| SEQ ID NO: 227 | c.-32-167_-143 | GCCCTCTCCCCAG TCTAGACAGCAG |
| SEQ ID NO: 228 | c.-32-166_-142 | CCCTCTCCCCAGT CTAGACAGCAGG |
| SEQ ID NO: 229 | c.-32-165_-141 | CCTCTCCCCAGTC TAGACAGCAGGG |
| SEQ ID NO: 230 | c.-32-164_-140 | CTCTCCCCAGTCT AGACAGCAGGGC |

TABLE 4-continued

| | | 25 bp TARGET sequence 5' → 3' |
|---|---|---|
| SEQ ID NO: 231 | c.-32-163_-139 | TCTCCCCAGTCTAGACAGCAGGGCA |
| SEQ ID NO: 232 | c.-32-162_-138 | CTCCCCAGTCTAGACAGCAGGGCAA |
| SEQ ID NO: 233 | c.-32-161_-137 | TCCCCAGTCTAGACAGCAGGGCAAC |
| SEQ ID NO: 234 | c.-32-160_-136 | CCCCAGTCTAGACAGCAGGGCAACA |
| SEQ ID NO: 235 | c.-32-159_-135 | CCCAGTCTAGACAGCAGGGCAACAC |
| SEQ ID NO: 236 | c.-32-158_-134 | CCAGTCTAGACAGCAGGGCAACACC |
| SEQ ID NO: 237 | c.-32-157_-133 | CAGTCTAGACAGCAGGGCAACACCC |
| SEQ ID NO: 238 | c.-32-156_-132 | AGTCTAGACAGCAGGGCAACACCCA |
| SEQ ID NO: 239 | c.-32-155_-131 | GTCTAGACAGCAGGGCAACACCCAC |

It should be noted that it may not be necessary to target the full length of SEQ ID NO: 182-239, target fragments having a shorter or longer sequence are also envisioned. In particular shorter fragments such as fragments with 18, 19, 20, 21, 22, 23, or 24 nucleotides of SEQ ID NO: 182-239 are envisioned, such as depicted in below Tables 5 and 6.

TABLE 5

| | | 21 bp TARGET sequence 5' → 3'. |
|---|---|---|
| SEQ ID NO: 240 | c.-32-208_-188 | TCTGCACTCCCCTGCTGGAGC |
| SEQ ID NO: 241 | c.-32-207_-187 | CTGCACTCCCCTGCTGGAGCT |
| SEQ ID NO: 242 | c.-32-206_-186 | TGCACTCCCCTGCTGGAGCTT |
| SEQ ID NO: 243 | c.-32-205_-185 | GCACTCCCCTGCTGGAGCTTT |
| SEQ ID NO: 244 | c.-32-204_-184 | CACTCCCCTGCTGGAGCTTTT |
| SEQ ID NO: 245 | c.-32-203_-183 | ACTCCCCTGCTGGAGCTTTTC |
| SEQ ID NO: 246 | c.-32-202_-182 | CTCCCCTGCTGGAGCTTTTCT |
| SEQ ID NO: 247 | c.-32-201_-181 | TCCCCTGCTGGAGCTTTTCTC |
| SEQ ID NO: 248 | c.-32-200_-180 | CCCCTGCTGGAGCTTTTCTCG |
| SEQ ID NO: 249 | c.-32-199_-179 | CCCTGCTGGAGCTTTTCTCGC |
| SEQ ID NO: 250 | c.-32-198_-178 | CCTGCTGGAGCTTTTCTCGCC |
| SEQ ID NO: 251 | c.-32-197_-177 | CTGCTGGAGCTTTTCTCGCCC |
| SEQ ID NO: 252 | c.-32-196_-176 | TGCTGGAGCTTTTCTCGCCCT |
| SEQ ID NO: 253 | c.-32-195_-175 | GCTGGAGCTTTTCTCGCCCTT |
| SEQ ID NO: 254 | c.-32-194_-174 | CTGGAGCTTTTCTCGCCCTTC |
| SEQ ID NO: 255 | c.-32-193_-173 | TGGAGCTTTTCTCGCCCTTCC |
| SEQ ID NO: 256 | c.-32-192_-172 | GGAGCTTTTCTCGCCCTTCCT |
| SEQ ID NO: 257 | c.-32-191_-171 | GAGCTTTTCTCGCCCTTCCTT |
| SEQ ID NO: 258 | c.-32-190_-170 | AGCTTTTCTCGCCCTTCCTTC |

TABLE 5-continued

| | | 21 bp TARGET sequence 5' → 3'. |
|---|---|---|
| SEQ ID NO: 259 | c.-32-189_-169 | GCTTTTCTCGCCCTTCCTTCT |
| SEQ ID NO: 260 | c.-32-188_-168 | CTTTTCTCGCCCTTCCTTCTG |
| SEQ ID NO: 262 | c.-32-187_-167 | TTTTCTCGCCCTTCCTTCTGG |
| SEQ ID NO: 263 | c.-32-186_-166 | TTTCTCGCCCTTCCTTCTGGC |
| SEQ ID NO: 264 | c.-32-185_-165 | TTCTCGCCCTTCCTTCTGGCC |
| SEQ ID NO: 265 | c.-32-184_-164 | TCTCGCCCTTCCTTCTGGCCC |
| SEQ ID NO: 266 | c.-32-183_-163 | CTCGCCCTTCCTTCTGGCCCT |
| SEQ ID NO: 267 | c.-32-182_-162 | TCGCCCTTCCTTCTGGCCCTC |
| SEQ ID NO: 268 | c.-32-181_-161 | CGCCCTTCCTTCTGGCCCTCT |
| SEQ ID NO: 269 | c.-32-180_-160 | GCCCTTCCTTCTGGCCCTCTC |
| SEQ ID NO: 270 | c.-32-179_-159 | CCCTTCCTTCTGGCCCTCTCC |
| SEQ ID NO: 271 | c.-32-178_-158 | CCTTCCTTCTGGCCCTCTCCC |
| SEQ ID NO: 272 | c.-32-177_-157 | CTTCCTTCTGGCCCTCTCCCC |
| SEQ ID NO: 273 | c.-32-176_-156 | TTCCTTCTGGCCCTCTCCCCA |
| SEQ ID NO: 274 | c.-32-175_-155 | TCCTTCTGGCCCTCTCCCCAG |
| SEQ ID NO: 275 | c.-32-174_-154 | CCTTCTGGCCCTCTCCCCAGT |
| SEQ ID NO: 276 | c.-32-173_-153 | CTTCTGGCCCTCTCCCCAGTC |
| SEQ ID NO: 277 | c.-32-172_-152 | TTCTGGCCCTCTCCCCAGTCT |
| SEQ ID NO: 278 | c.-32-171_-151 | TCTGGCCCTCTCCCCAGTCTA |
| SEQ ID NO: 279 | c.-32-170_-150 | CTGGCCCTCTCCCCAGTCTAG |
| SEQ ID NO: 280 | c.-32-169_-149 | TGGCCCTCTCCCCAGTCTAGA |
| SEQ ID NO: 281 | c.-32-168_-148 | GGCCCTCTCCCCAGTCTAGAC |
| SEQ ID NO: 282 | c.-32-167_-147 | GCCCTCTCCCCAGTCTAGACA |
| SEQ ID NO: 283 | c.-32-166_-146 | CCCTCTCCCCAGTCTAGACAG |
| SEQ ID NO: 284 | c.-32-165_-145 | CCTCTCCCCAGTCTAGACAGC |
| SEQ ID NO: 285 | c.-32-164_-144 | CTCTCCCCAGTCTAGACAGCA |
| SEQ ID NO: 286 | c.-32-163_-143 | TCTCCCCAGTCTAGACAGCAG |
| SEQ ID NO: 287 | c.-32-162_-142 | CTCCCCAGTCTAGACAGCAGG |
| SEQ ID NO: 288 | c.-32-161_-141 | TCCCCAGTCTAGACAGCAGGG |
| SEQ ID NO: 289 | c.-32-160_-140 | CCCCAGTCTAGACAGCAGGGC |
| SEQ ID NO: 290 | c.-32-159_-139 | CCCAGTCTAGACAGCAGGGCA |
| SEQ ID NO: 291 | c.-32-158_-138 | CCAGTCTAGACAGCAGGGCAA |
| SEQ ID NO: 292 | c.-32-157_-137 | CAGTCTAGACAGCAGGGCAAC |
| SEQ ID NO: 293 | c.-32-156_-136 | AGTCTAGACAGCAGGGCAACA |
| SEQ ID NO: 294 | c.-32-155_-135 | GTCTAGACAGCAGGGCAACAC |

TABLE 6

| | | 18 bp TARGET sequence 5' → 3'. |
|---|---|---|
| SEQ ID NO: 295 | c.-32-205_-188 | GCACTCCCCTGCTGGAGC |
| SEQ ID NO: 296 | c.-32-204_-187 | CACTCCCCTGCTGGAGCT |
| SEQ ID NO: 297 | c.-32-203_-186 | ACTCCCCTGCTGGAGCTT |
| SEQ ID NO: 298 | c.-32-202_-185 | CTCCCCTGCTGGAGCTTT |
| SEQ ID NO: 299 | c.-32-201_-184 | TCCCCTGCTGGAGCTTTT |
| SEQ ID NO: 300 | c.-32-200_-183 | CCCCTGCTGGAGCTTTTC |
| SEQ ID NO: 301 | c.-32-199_-182 | CCCTGCTGGAGCTTTTCT |
| SEQ ID NO: 302 | c.-32-198_-181 | CCTGCTGGAGCTTTTCTC |
| SEQ ID NO: 303 | c.-32-197_-180 | CTGCTGGAGCTTTTCTCG |
| SEQ ID NO: 304 | c.-32-196_-179 | TGCTGGAGCTTTTCTCGC |
| SEQ ID NO: 305 | c.-32-195_-178 | GCTGGAGCTTTTCTCGCC |
| SEQ ID NO: 306 | c.-32-194_-177 | CTGGAGCTTTTCTCGCCC |
| SEQ ID NO: 307 | c.-32-193_-176 | TGGAGCTTTTCTCGCCCT |
| SEQ ID NO: 308 | c.-32-192_-175 | GGAGCTTTTCTCGCCCTT |
| SEQ ID NO: 309 | c.-32-191_-174 | GAGCTTTTCTCGCCCTTC |
| SEQ ID NO: 310 | c.-32-190_-173 | AGCTTTTCTCGCCCTTCC |
| SEQ ID NO: 311 | c.-32-189_-172 | GCTTTTCTCGCCCTTCCT |
| SEQ ID NO: 312 | c.-32-188_-171 | CTTTTCTCGCCCTTCCTT |
| SEQ ID NO: 313 | c.-32-187_-170 | TTTTCTCGCCCTTCCTTC |
| SEQ ID NO: 314 | c.-32-186_-169 | TTTCTCGCCCTTCCTTCT |
| SEQ ID NO: 315 | c.-32-185_-168 | TTCTCGCCCTTCCTTCTG |
| SEQ ID NO: 316 | c.-32-184_-167 | TCTCGCCCTTCCTTCTGG |
| SEQ ID NO: 317 | c.-32-183_-166 | CTCGCCCTTCCTTCTGGC |
| SEQ ID NO: 318 | c.-32-182_-165 | TCGCCCTTCCTTCTGGCC |
| SEQ ID NO: 319 | c.-32-181_-164 | CGCCCTTCCTTCTGGCCC |
| SEQ ID NO: 320 | c.-32-180_-163 | GCCCTTCCTTCTGGCCCT |
| SEQ ID NO: 321 | c.-32-179_-162 | CCCTTCCTTCTGGCCCTC |
| SEQ ID NO: 322 | c.-32-178_-161 | CCTTCCTTCTGGCCCTCT |
| SEQ ID NO: 323 | c.-32-177_-160 | CTTCCTTCTGGCCCTCTC |
| SEQ ID NO: 324 | c.-32-176_-159 | TTCCTTCTGGCCCTCTCC |
| SEQ ID NO: 325 | c.-32-175_-158 | TCCTTCTGGCCCTCTCCC |
| SEQ ID NO: 326 | c.-32-174_-157 | CCTTCTGGCCCTCTCCCC |
| SEQ ID NO: 327 | c.-32-173_-156 | CTTCTGGCCCTCTCCCCA |
| SEQ ID NO: 328 | c.-32-172_-155 | TTCTGGCCCTCTCCCCAG |
| SEQ ID NO: 329 | c.-32-171_-154 | TCTGGCCCTCTCCCCAGT |
| SEQ ID NO: 330 | c.-32-170_-153 | CTGGCCCTCTCCCCAGTC |
| SEQ ID NO: 331 | c.-32-169_-152 | TGGCCCTCTCCCCAGTCT |
| SEQ ID NO: 332 | c.-32-168_-151 | GGCCCTCTCCCCAGTCTA |
| SEQ ID NO: 333 | c.-32-167_-150 | GCCCTCTCCCCAGTCTAG |
| SEQ ID NO: 334 | c.-32-166_-149 | CCCTCTCCCCAGTCTAGA |
| SEQ ID NO: 335 | c.-32-165_-148 | CCTCTCCCCAGTCTAGAC |
| SEQ ID NO: 336 | c.-32-164_-147 | CTCTCCCCAGTCTAGACA |
| SEQ ID NO: 337 | c.-32-163_-146 | TCTCCCCAGTCTAGACAG |
| SEQ ID NO: 338 | c.-32-162_-145 | CTCCCCAGTCTAGACAGC |
| SEQ ID NO: 339 | c.-32-161_-144 | TCCCCAGTCTAGACAGCA |
| SEQ ID NO: 340 | c.-32-160_-143 | CCCCAGTCTAGACAGCAG |
| SEQ ID NO: 341 | c.-32-159_-142 | CCCAGTCTAGACAGCAGG |
| SEQ ID NO: 342 | c.-32-158_-141 | CCAGTCTAGACAGCAGGG |
| SEQ ID NO: 343 | c.-32-157_-140 | CAGTCTAGACAGCAGGGC |
| SEQ ID NO: 344 | c.-32-156_-139 | AGTCTAGACAGCAGGGCA |
| SEQ ID NO: 345 | c.-32-155_-138 | GTCTAGACAGCAGGGCAA |

The nomenclature identifies the location of the natural cryptic splice site. It is understood that the antisense oligomeric compound targets the location of the natural cryptic splice site. The antisense oligomeric compound may also be targeted to a sequence comprising nucleotides upstream and nucleotides downstream of the location of the splice site. Suitably the antisense oligomeric compound targets a sequence comprising 2-50 nucleotides upstream, and/or 2-50 nucleotides downstream of the location of the splice site, more suitably the antisense oligomeric compound target a sequence comprising 3-45 nucleotides upstream, and/or 3-45 nucleotides downstream of the location of the splice site, more suitably the antisense oligomeric compound target a sequence comprising 5-40 nucleotides upstream, and/or 5-40 nucleotides downstream of the location of the splice site, more suitably the antisense oligomeric compound target a sequence comprising 6-35 nucleotides upstream, and/or 6-35 nucleotides downstream of the location of the splice site, more suitably the antisense oligomeric compound target a sequence comprising 7-33 nucleotides upstream, and/or 7-33 nucleotides downstream of the location of the splice site, more suitably the antisense oligomeric compound target a sequence comprising 8-30 nucleotides upstream, and/or 8-30 nucleotides downstream of the location of the splice site, more suitably the antisense oligomeric compound target a sequence comprising 9-28 nucleotides upstream, and/or 9-28 nucleotides downstream of the location of the splice site, more suitably the antisense oligomeric compound target a sequence comprising 10-25 nucleotides upstream, and/or 10-25 nucleotides downstream of the location of the splice site, more suitably the antisense oligomeric compound target a sequence comprising 11-22 nucleotides upstream, and/or 11-22 nucleotides downstream of the location of the splice site, more suitably the antisense oligomeric compound target a sequence comprising 12-20 nucleotides upstream, and/or 12-20 nucleotides downstream of the location of the splice site, more suitably the antisense oligomeric compound target a sequence comprising 13-18 nucleotides upstream, and/or 13-18 nucleotides downstream of the location of the splice site, more suitably the antisense oligomeric compound target a sequence comprising 14-16 nucleotides upstream, and/or 14-16 nucleotides downstream of the location of the splice site.

The nomenclature is well known to a skilled person and can be found in Dunnen and Antonarakis Human mutation 15:7-12(2000) and Antonarakis S E, the Nomenclature Working Group. 1998. Recommendations for a nomenclature system for human gene mutations. Hum Mutat 11:1-3 and on the website (http://www.dmd.nl/mutnomen.html. Genomic positions may also be found on www.pompecenter.nl. All of these are incorporated by reference.

Preferably the genomic nucleic acid sequence is pre-mRNA.

These antisense oligomeric compounds are useful in the treatment of glycogen storage disease type II/Pompe disease.

Preferably the target sequence is the sequence of SEQ ID NO:1: 5'-GTCTCAGAGCTGCTTTGAGAGAGCCCCGTGAGTGCCGCCCCTCCCGCCTCCC-3' more preferably SEQ ID NO: 5 or 16. Antisense oligomeric compounds targeting SEQ ID NO: 1 and in particular targeting SEQ ID NO: 2-90 as one part of the pair of antisense oligomeric compounds and antisense oligomeric compounds targeting SEQ ID NO: 180 and in particular targeting SEQ ID NO: 181-345 as the other part of the pair of antisense oligonucleotide compounds are very suitable to treat Pompe patients. Exemplary antisense oligomeric compounds targeting SEQ ID NO: 1-90 are SEQ ID NO: 91-179 provided below and in particular SEQ ID NO: 93, 104, 110 and 116 (FIG. 11). Exemplary antisense oligomeric compounds targeting SEQ ID NO: 180-345 are SEQ ID NO: 346-508 are also provided below. However the invention is not limited to these sequences. A skilled person is capable of designing antisense oligomeric compounds against target sequence SEQ ID NO: 1-90 and/or target sequence SEQ ID NO: 180-345. The antisense oligomeric compounds against target sequences SEQ ID NO: 1-90 and/or target sequences SEQ ID NO: 180-345 may have length of 10 to 100 nucleotides, preferably 11 to 75 nucleotides, preferably 12 to 73 nucleotides, preferably 13 to 70 nucleotides, preferably 14 to 65 nucleotides, preferably 15 to 60 nucleotides, preferably 16 to 55 nucleotides, preferably 17 to 50 nucleotides, preferably 18 to 45 nucleotides, preferably 19 to 40 nucleotides, preferably 20 to 38 nucleotides, preferably 21 to 35 nucleotides, preferably 22 to 33 nucleotides, preferably 23 to 30 nucleotides, preferably 24 to 29 nucleotides, preferably 25 to 28 nucleotides, preferably 25 nucleotides.

Further preferred targeting sequences are SEQ ID NO: 2-27 and SEQ ID NO: 196-216.

Hereunder exemplary antisense oligomeric compounds targeting SEQ ID NO: 1-90 are given in Table 7.

TABLE 7

AON sequences targeting SEQ ID 1-90

| Seq ID | Sequence in cDNA to which AON anneals* | sequence of AON (5' → 3'): |
|---|---|---|
| 91 | c.-32-77_-53 | GGGGCTCTCAAAGCAGCTCTGAGAC |
| 92 | c.-32-76_-52 | CGGGGCTCTCAAAGCAGCTCTGAGA |
| 93 | c.-32-75_-51 | ACGGGGCTCTCAAAGCAGCTCTGAG |
| 94 | c.-32-74_-50 | CACGGGGCTCTCAAAGCAGCTCTGA |
| 95 | c.-32-73_-49 | TCACGGGGCTCTCAAAGCAGCTCTG |
| 96 | c.-32-72_-48 | CTCACGGGGCTCTCAAAGCAGCTCT |
| 97 | c.-32-71_-47 | ACTCACGGGGCTCTCAAAGCAGCTC |

TABLE 7-continued

AON sequences targeting SEQ ID 1-90

| Seq ID | Sequence in cDNA to which AON anneals* | sequence of AON (5' → 3'): |
|---|---|---|
| 98 | c.-32-70_-46 | CACTCACGGGGCTCTCAAAGCAGCT |
| 99 | c.-32-69_-45 | GCACTCACGGGGCTCTCAAAGCAGC |
| 100 | c.-32-68_-44 | GGCACTCACGGGGCTCTCAAAGCAG |
| 101 | c.-32-67_-43 | CGGCACTCACGGGGCTCTCAAAGCA |
| 102 | c.-32-66_-42 | GCGGCACTCACGGGGCTCTCAAAGC |
| 103 | c.-32-65_-41 | GGCGGCACTCACGGGGCTCTCAAAG |
| 104 | c.-32-64_-40 | GGGCGGCACTCACGGGGCTCTCAAA |
| 105 | c.-32-63_-39 | GGGGCGGCACTCACGGGGCTCTCAA |
| 106 | c.-32-62_-38 | AGGGGCGGCACTCACGGGGCTCTCA |
| 107 | c.-32-61_-37 | GAGGGGCGGCACTCACGGGGCTCTC |
| 108 | c.-32-60_-36 | GGAGGGGCGGCACTCACGGGGCTCT |
| 109 | c.-32-59_-35 | GGGAGGGGCGGCACTCACGGGGCTC |
| 110 | c.-32-58_-34 | CGGGAGGGGCGGCACTCACGGGGCT |
| 111 | c.-32-57_-33 | GCGGGAGGGGCGGCACTCACGGGGC |
| 112 | c.-32-56_-32 | GGCGGGAGGGGCGGCACTCACGGGG |
| 113 | c.-32-55_-31 | AGGCGGGAGGGGCGGCACTCACGGG |
| 114 | c.-32-54_-30 | GAGGCGGGAGGGGCGGCACTCACGG |
| 115 | c.-32-53_-29 | GGAGGCGGGAGGGGCGGCACTCACG |
| 116 | c.-32-52_-28 | GGGAGGCGGGAGGGGCGGCACTCAC |
| 117 | c.-32-77_-57 | CTCTCAAAGCAGCTCTGAGAC |
| 118 | c.-32-76_-56 | GCTCTCAAAGCAGCTCTGAGA |
| 119 | c.-32-75_-55 | GGCTCTCAAAGCAGCTCTGAG |
| 120 | c.-32-74_-54 | GGGCTCTCAAAGCAGCTCTGA |
| 121 | c.-32-73_-53 | GGGGCTCTCAAAGCAGCTCTG |
| 122 | c.-32-72_-52 | CGGGGCTCTCAAAGCAGCTCT |
| 123 | c.-32-71_-51 | ACGGGGCTCTCAAAGCAGCTC |
| 124 | c.-32-70_-50 | CACGGGGCTCTCAAAGCAGCT |
| 125 | c.-32-69_-49 | TCACGGGGCTCTCAAAGCAGC |
| 126 | c.-32-68_-48 | CTCACGGGGCTCTCAAAGCAG |
| 127 | c.-32-67_-47 | ACTCACGGGGCTCTCAAAGCA |
| 128 | c.-32-66_-46 | CACTCACGGGGCTCTCAAAGC |
| 129 | c.-32-65_-45 | GCACTCACGGGGCTCTCAAAG |
| 130 | c.-32-64_-44 | GGCACTCACGGGGCTCTCAAA |
| 131 | c.-32-63_-43 | CGGCACTCACGGGGCTCTCAA |
| 132 | c.-32-62_-42 | GCGGCACTCACGGGGCTCTCA |
| 133 | c.-32-61_-41 | GGCGGCACTCACGGGGCTCTC |
| 134 | c.-32-60_-40 | GGGCGGCACTCACGGGGCTCT |

TABLE 7-continued

AON sequences targeting SEQ ID 1-90

| Seq ID | Sequence in cDNA to which AON anneals* | sequence of AON (5' → 3'): |
|---|---|---|
| 135 | c.-32-59_-39 | GGGGCGGCACTCACGGGGCTC |
| 136 | c.-32-58_-38 | AGGGGCGGCACTCACGGGGCT |
| 137 | c.-32-57_-37 | GAGGGGCGGCACTCACGGGGC |
| 138 | c.-32-56_-36 | GGAGGGGCGGCACTCACGGGG |
| 139 | c.-32-55_-35 | GGGAGGGGCGGCACTCACGGG |
| 140 | c.-32-54_-34 | CGGGAGGGGCGGCACTCACGG |
| 141 | c.-32-53_-33 | GCGGGAGGGGCGGCACTCACG |
| 142 | c.-32-52_-32 | GGCGGGAGGGGCGGCACTCAC |
| 143 | c.-32-51_-31 | AGGCGGGAGGGGCGGCACTCA |
| 144 | c.-32-50_-30 | GAGGCGGGAGGGGCGGCACTC |
| 145 | c.-32-49_-29 | GGAGGCGGGAGGGGCGGCACT |
| 146 | c.-32-48_-28 | GGGAGGCGGGAGGGGCGGCAC |
| 147 | c.-32-77_-60 | TCAAAGCAGCTCTGAGAC |
| 148 | c.-32-76_-59 | CTCAAAGCAGCTCTGAGA |
| 149 | c.-32-75_-58 | TCTCAAAGCAGCTCTGAG |
| 150 | c.-32-74_-57 | CTCTCAAAGCAGCTCTGA |
| 151 | c.-32-73_-56 | GCTCTCAAAGCAGCTCTG |
| 152 | c.-32-72_-55 | GGCTCTCAAAGCAGCTCT |
| 153 | c.-32-71_-54 | GGGCTCTCAAAGCAGCTC |
| 154 | c.-32-70_-53 | GGGGCTCTCAAAGCAGCT |
| 155 | c.-32-69_-52 | CGGGGCTCTCAAAGCAGC |
| 156 | c.-32-68_-51 | ACGGGGCTCTCAAAGCAG |
| 157 | c.-32-67_-50 | CACGGGGCTCTCAAAGCA |
| 158 | c.-32-66_-49 | TCACGGGGCTCTCAAAGC |
| 159 | c.-32-65_-48 | CTCACGGGGCTCTCAAAG |
| 160 | c.-32-64_-47 | ACTCACGGGGCTCTCAAA |
| 161 | c.-32-63_-46 | CACTCACGGGGCTCTCAA |
| 162 | c.-32-62_-45 | GCACTCACGGGGCTCTCA |
| 163 | c.-32-61_-44 | GGCACTCACGGGGCTCTC |
| 164 | c.-32-60_-43 | CGGCACTCACGGGGCTCT |
| 165 | c.-32-59_-42 | GCGGCACTCACGGGGCTC |
| 166 | c.-32-58_-41 | GGCGGCACTCACGGGGCT |
| 167 | c.-32-57_-40 | GGGCGGCACTCACGGGGC |
| 168 | c.-32-56_-39 | GGGGCGGCACTCACGGGG |
| 169 | c.-32-55_-38 | AGGGGCGGCACTCACGGG |
| 170 | c.-32-54_-37 | GAGGGGCGGCACTCACGG |
| 171 | c.-32-53_-36 | GGAGGGGCGGCACTCACG |
| 172 | c.-32-52_-35 | GGGAGGGGCGGCACTCAC |
| 173 | c.-32-51_-34 | CGGGAGGGGCGGCACTCA |
| 174 | c.-32-50_-33 | GCGGGAGGGGCGGCACTC |
| 175 | c.-32-49_-32 | GGCGGGAGGGGCGGCACT |
| 176 | c.-32-48_-31 | AGGCGGGAGGGGCGGCAC |
| 177 | c.-32-47_-30 | GAGGCGGGAGGGGCGGCA |
| 178 | c.-32-46_-29 | GGAGGCGGGAGGGGCGGC |
| 179 | c.-32-45_-28 | GGGAGGCGGGAGGGGCGG |

Hereunder exemplary antisense oligomeric compounds targeting SEQ ID NO: 180-345 are given in Table 8.

TABLE 8

AON sequences targeting SEQ ID NO: 180-345.

| Seq ID | Sequence in cDNA to which AON anneals* | sequence of AON (5' → 3'): |
|---|---|---|
| 346 | c.-32-212_-188 | GCTCCAGCAGGGGAGTGCAGAGCAC |
| 347 | c.-32-211_-187 | AGCTCCAGCAGGGGAGTGCAGAGCA |
| 348 | c.-32-210_-186 | AAGCTCCAGCAGGGGAGTGCAGAGC |
| 349 | c.-32-209_-185 | AAAGCTCCAGCAGGGGAGTGCAGAG |
| 350 | c.-32-208_-184 | AAAAGCTCCAGCAGGGGAGTGCAGA |
| 351 | c.-32-207_-183 | GAAAAGCTCCAGCAGGGGAGTGCAG |
| 352 | c.-32-206_-182 | AGAAAAGCTCCAGCAGGGGAGTGCA |
| 353 | c.-32-205_-181 | GAGAAAAGCTCCAGCAGGGGAGTGC |
| 354 | c.-32-204_-180 | CGAGAAAAGCTCCAGCAGGGGAGTG |
| 355 | c.-32-203_-179 | GCGAGAAAAGCTCCAGCAGGGGAGT |
| 356 | c.-32-202_-178 | GGCGAGAAAAGCTCCAGCAGGGGAG |
| 357 | c.-32-201_-177 | GGGCGAGAAAAGCTCCAGCAGGGGA |
| 358 | c.-32-200_-176 | AGGGCGAGAAAAGCTCCAGCAGGGG |
| 359 | c.-32-199_-175 | AAGGGCGAGAAAAGCTCCAGCAGGG |
| 360 | c.-32-198_-174 | GAAGGGCGAGAAAAGCTCCAGCAGG |
| 361 | c.-32-197_-173 | GGAAGGGCGAGAAAAGCTCCAGCAG |
| 362 | c.-32-196_-172 | AGGAAGGGCGAGAAAAGCTCCAGCA |
| 363 | c.-32-195_-171 | AAGGAAGGGCGAGAAAAGCTCCAGC |
| 364 | c.-32-194_-170 | GAAGGAAGGGCGAGAAAAGCTCCAG |
| 365 | c.-32-193_-169 | AGAAGGAAGGGCGAGAAAAGCTCCA |
| 366 | c.-32-192_-168 | CAGAAGGAAGGGCGAGAAAAGCTCC |
| 367 | c.-32-191_-167 | CCAGAAGGAAGGGCGAGAAAAGCTC |

TABLE 8-continued

AON sequences targeting SEQ ID NO: 180-345.

| Seq ID | Sequence in cDNA to which AON anneals* | sequence of AON (5' → 3'): |
|---|---|---|
| 368 | c.-32-190_-166 | GCCAGAAGGAAGGGCGAGAAAAGCT |
| 369 | c.-32-189_-165 | GGCCAGAAGGAAGGGCGAGAAAAGC |
| 370 | c.-32-188_-164 | GGGCCAGAAGGAAGGGCGAGAAAAG |
| 371 | c.-32-187_-163 | AGGGCCAGAAGGAAGGGCGAGAAAA |
| 372 | c.-32-186_-162 | GAGGGCCAGAAGGAAGGGCGAGAAA |
| 373 | c.-32-185_-161 | AGAGGGCCAGAAGGAAGGGCGAGAA |
| 374 | c.-32-184_-160 | GAGAGGGCCAGAAGGAAGGGCGAGA |
| 375 | c.-32-183_-159 | GGAGAGGGCCAGAAGGAAGGGCGAG |
| 376 | c.-32-182_-158 | GGGAGAGGGCCAGAAGGAAGGGCGA |
| 377 | c.-32-181_-157 | GGGGAGAGGGCCAGAAGGAAGGGCG |
| 378 | c.-32-180_-156 | TGGGGAGAGGGCCAGAAGGAAGGGC |
| 379 | c.-32-179_-155 | CTGGGGAGAGGGCCAGAAGGAAGGG |
| 380 | c.-32-178_-154 | ACTGGGGAGAGGGCCAGAAGGAAGG |
| 381 | c.-32-177_-153 | GACTGGGGAGAGGGCCAGAAGGAAG |
| 382 | c.-32-176_-152 | AGACTGGGGAGAGGGCCAGAAGGAA |
| 383 | c.-32-175_-151 | TAGACTGGGGAGAGGGCCAGAAGGA |
| 384 | c.-32-174_-150 | CTAGACTGGGGAGAGGGCCAGAAGG |
| 385 | c.-32-173_-149 | TCTAGACTGGGGAGAGGGCCAGAAG |
| 386 | c.-32-172_-148 | GTCTAGACTGGGGAGAGGGCCAGAA |
| 387 | c.-32-171_-147 | TGTCTAGACTGGGGAGAGGGCCAGA |
| 388 | c.-32-170_-146 | CTGTCTAGACTGGGGAGAGGGCCAG |
| 389 | c.-32-169_-145 | GCTGTCTAGACTGGGGAGAGGGCCA |
| 390 | c.-32-168_-144 | TGCTGTCTAGACTGGGGAGAGGGCC |
| 391 | c.-32-167_-143 | CTGCTGTCTAGACTGGGGAGAGGGC |
| 392 | c.-32-166_-142 | CCTGCTGTCTAGACTGGGGAGAGGG |
| 393 | c.-32-165_-141 | CCCTGCTGTCTAGACTGGGGAGAGG |
| 394 | c.-32-164_-140 | GCCCTGCTGTCTAGACTGGGGAGAG |
| 395 | c.-32-163_-139 | TGCCCTGCTGTCTAGACTGGGGAGA |
| 396 | c.-32-162_-138 | TTGCCCTGCTGTCTAGACTGGGGAG |
| 397 | c.-32-161_-137 | GTTGCCCTGCTGTCTAGACTGGGGA |
| 398 | c.-32-160_-136 | TGTTGCCCTGCTGTCTAGACTGGGG |
| 399 | c.-32-159_-135 | GTGTTGCCCTGCTGTCTAGACTGGG |
| 400 | c.-32-158_-134 | GGTGTTGCCCTGCTGTCTAGACTGG |
| 401 | c.-32-157_-133 | GGGTGTTGCCCTGCTGTCTAGACTG |
| 402 | c.-32-156_-132 | TGGGTGTTGCCCTGCTGTCTAGACT |
| 403 | c.-32-155_-131 | GTGGGTGTTGCCCTGCTGTCTAGAC |
| 404 | c.-32-208_-188 | GCTCCAGCAGGGGAGTGCAGA |
| 405 | c.-32-207_-187 | AGCTCCAGCAGGGGAGTGCAG |
| 406 | c.-32-206_-186 | AAGCTCCAGCAGGGGAGTGCA |
| 407 | c.-32-205_-185 | AAAGCTCCAGCAGGGGAGTGC |
| 408 | c.-32-204_-184 | AAAAGCTCCAGCAGGGGAGTG |
| 409 | c.-32-203_-183 | GAAAAGCTCCAGCAGGGGAGT |
| 410 | c.-32-202_-182 | AGAAAAGCTCCAGCAGGGGAG |
| 411 | c.-32-201_-181 | GAGAAAAGCTCCAGCAGGGGA |
| 412 | c.-32-200_-180 | CGAGAAAAGCTCCAGCAGGGG |
| 413 | c.-32-199_-179 | GCGAGAAAAGCTCCAGCAGGG |
| 414 | c.-32-198_-178 | GGCGAGAAAAGCTCCAGCAGG |
| 415 | c.-32-197_-177 | GGGCGAGAAAAGCTCCAGCAG |
| 416 | c.-32-196_-176 | AGGGCGAGAAAAGCTCCAGCA |
| 417 | c.-32-195_-175 | AAGGGCGAGAAAAGCTCCAGC |
| 418 | c.-32-194_-174 | GAAGGGCGAGAAAAGCTCCAG |
| 419 | c.-32-193_-173 | GGAAGGGCGAGAAAAGCTCCA |
| 420 | c.-32-192_-172 | AGGAAGGGCGAGAAAAGCTCC |
| 421 | c.-32-191_-171 | AAGGAAGGGCGAGAAAAGCTC |
| 422 | c.-32-190_-170 | GAAGGAAGGGCGAGAAAAGCT |
| 423 | c.-32-189_-169 | AGAAGGAAGGGCGAGAAAAGC |
| 424 | c.-32-188_-168 | CAGAAGGAAGGGCGAGAAAAG |
| 425 | c.-32-187_-167 | CCAGAAGGAAGGGCGAGAAAA |
| 426 | c.-32-186_-166 | GCCAGAAGGAAGGGCGAGAAA |
| 427 | c.-32-185_-165 | GGCCAGAAGGAAGGGCGAGAA |
| 428 | c.-32-184_-164 | GGGCCAGAAGGAAGGGCGAGA |
| 429 | c.-32-183_-163 | AGGGCCAGAAGGAAGGGCGAG |
| 430 | c.-32-182_-162 | GAGGGCCAGAAGGAAGGGCGA |
| 431 | c.-32-181_-161 | AGAGGGCCAGAAGGAAGGGCG |
| 432 | c.-32-180_-160 | GAGAGGGCCAGAAGGAAGGGC |
| 433 | c.-32-179_-159 | GGAGAGGGCCAGAAGGAAGGG |
| 434 | c.-32-178_-158 | GGGAGAGGGCCAGAAGGAAGG |
| 435 | c.-32-177_-157 | GGGGAGAGGGCCAGAAGGAAG |
| 436 | c.-32-176_-156 | TGGGGAGAGGGCCAGAAGGAA |
| 437 | c.-32-175_-155 | CTGGGGAGAGGGCCAGAAGGA |
| 438 | c.-32-174_-154 | ACTGGGGAGAGGGCCAGAAGG |
| 439 | c.-32-173_-153 | GACTGGGGAGAGGGCCAGAAG |
| 440 | c.-32-172_-152 | AGACTGGGGAGAGGGCCAGAA |
| 441 | c.-32-171_-151 | TAGACTGGGGAGAGGGCCAGA |

TABLE 8-continued

AON sequences targeting SEQ ID NO: 180-345.

| Seq ID | Sequence in cDNA to which AON anneals* | sequence of AON (5' → 3'): |
|---|---|---|
| 442 | c.-32-170_-150 | CTAGACTGGGGAGAGGGCCAG |
| 443 | c.-32-169_-149 | TCTAGACTGGGGAGAGGGCCA |
| 444 | c.-32-168_-148 | GTCTAGACTGGGGAGAGGGCC |
| 445 | c.-32-167_-147 | TGTCTAGACTGGGGAGAGGGC |
| 446 | c.-32-166_-146 | CTGTCTAGACTGGGGAGAGGG |
| 447 | c.-32-165_-145 | GCTGTCTAGACTGGGGAGAGG |
| 448 | c.-32-164_-144 | TGCTGTCTAGACTGGGGAGAG |
| 449 | c.-32-163_-143 | CTGCTGTCTAGACTGGGGAGA |
| 450 | c.-32-162_-142 | CCTGCTGTCTAGACTGGGGAG |
| 451 | c.-32-161_-141 | CCCTGCTGTCTAGACTGGGGA |
| 452 | c.-32-160_-140 | GCCCTGCTGTCTAGACTGGGG |
| 453 | c.-32-159_-139 | TGCCCTGCTGTCTAGACTGGG |
| 454 | c.-32-158_-138 | TTGCCCTGCTGTCTAGACTGG |
| 455 | c.-32-157_-137 | GTTGCCCTGCTGTCTAGACTG |
| 456 | c.-32-156_-136 | TGTTGCCCTGCTGTCTAGACT |
| 457 | c.-32-155_-135 | GTGTTGCCCTGCTGTCTAGAC |
| 458 | c.-32-205_-188 | GCTCCAGCAGGGGAGTGC |
| 459 | c.-32-204_-187 | AGCTCCAGCAGGGGAGTG |
| 460 | c.-32-203_-186 | AAGCTCCAGCAGGGGAGT |
| 461 | c.-32-202_-185 | AAAGCTCCAGCAGGGGAG |
| 462 | c.-32-201_-184 | AAAAGCTCCAGCAGGGGA |
| 463 | c.-32-200_-183 | GAAAAGCTCCAGCAGGGG |
| 464 | c.-32-199_-182 | AGAAAAGCTCCAGCAGGG |
| 465 | c.-32-198_-181 | GAGAAAAGCTCCAGCAGG |
| 466 | c.-32-197_-180 | CGAGAAAAGCTCCAGCAG |
| 467 | c.-32-196_-179 | GCGAGAAAAGCTCCAGCA |
| 468 | c.-32-195_-178 | GGCGAGAAAAGCTCCAGC |
| 469 | c.-32-194_-177 | GGGCGAGAAAAGCTCCAG |
| 470 | c.-32-193_-176 | AGGGCGAGAAAAGCTCCA |
| 471 | c.-32-192_-175 | AAGGGCGAGAAAAGCTCC |
| 472 | c.-32-191_-174 | GAAGGGCGAGAAAAGCTC |
| 473 | c.-32-190_-173 | GGAAGGGCGAGAAAAGCT |
| 474 | c.-32-189_-172 | AGGAAGGGCGAGAAAAGC |
| 475 | c.-32-188_-171 | AAGGAAGGGCGAGAAAAG |
| 476 | c.-32-187_-170 | GAAGGAAGGGCGAGAAAA |
| 477 | c.-32-186_-169 | AGAAGGAAGGGCGAGAAA |
| 478 | c.-32-185_-168 | CAGAAGGAAGGGCGAGAA |
| 479 | c.-32-184_-167 | CCAGAAGGAAGGGCGAGA |
| 480 | c.-32-183_-166 | GCCAGAAGGAAGGGCGAG |
| 481 | c.-32-182_-165 | GGCCAGAAGGAAGGGCGA |
| 482 | c.-32-181_-164 | GGGCCAGAAGGAAGGGCG |
| 483 | c.-32-180_-163 | AGGGCCAGAAGGAAGGGC |
| 484 | c.-32-179_-162 | GAGGGCCAGAAGGAAGGG |
| 485 | c.-32-178_-161 | AGAGGGCCAGAAGGAAGG |
| 486 | c.-32-177_-160 | GAGAGGGCCAGAAGGAAG |
| 487 | c.-32-176_-159 | GGAGAGGGCCAGAAGGAA |
| 488 | c.-32-175_-158 | GGGAGAGGGCCAGAAGGA |
| 489 | c.-32-174_-157 | GGGGAGAGGGCCAGAAGG |
| 490 | c.-32-173_-156 | TGGGGAGAGGGCCAGAAG |
| 491 | c.-32-172_-155 | CTGGGGAGAGGGCCAGAA |
| 492 | c.-32-171_-154 | ACTGGGGAGAGGGCCAGA |
| 493 | c.-32-170_-153 | GACTGGGGAGAGGGCCAG |
| 494 | c.-32-169_-152 | AGACTGGGGAGAGGGCCA |
| 495 | c.-32-168_-151 | TAGACTGGGGAGAGGGCC |
| 496 | c.-32-167_-150 | CTAGACTGGGGAGAGGGC |
| 497 | c.-32-166_-149 | TCTAGACTGGGGAGAGGG |
| 498 | c.-32-165_-148 | GTCTAGACTGGGGAGAGG |
| 499 | c.-32-164_-147 | TGTCTAGACTGGGGAGAG |
| 500 | c.-32-163_-146 | CTGTCTAGACTGGGGAGA |
| 501 | c.-32-162_-145 | GCTGTCTAGACTGGGGAG |
| 502 | c.-32-161_-144 | TGCTGTCTAGACTGGGGA |
| 503 | c.-32-160_-143 | CTGCTGTCTAGACTGGGG |
| 504 | c.-32-159_-142 | CCTGCTGTCTAGACTGGG |
| 505 | c.-32-158_-141 | CCCTGCTGTCTAGACTGG |
| 506 | c.-32-157_-140 | GCCCTGCTGTCTAGACTG |
| 507 | c.-32-156_-139 | TGCCCTGCTGTCTAGACT |
| 508 | c.-32-155_-138 | TTGCCCTGCTGTCTAGAC |

In the above examples the sequences are 18, 21 and 25 nucleotides long however longer derivatives or shorter fragment are also envisioned. In a preferred embodiment of the invention and/or embodiments thereof of the present invention and/or embodiments thereof the antisense oligomeric compounds are selected from the group of SEQ ID NO: 91-179, preferably selected from the group of SEQ ID NO: 91-116 and/or from the group of SEQ ID NO: 346-508, preferably selected from the group of SEQ ID NO: 360-380 and fragments and derivatives thereof having at least 80% sequence identity. In a preferred embodiment of the invention and/or embodiments thereof of the present invention and/or embodiments thereof the antisense oligomeric compounds are selected from the group of SEQ ID NO: 91-179, preferably selected from the group of SEQ ID NO: 91-116 and/or from the group of SEQ ID NO: 346-508, preferably selected from the group of SEQ ID NO: 360-380 and fragments and derivatives thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 91-179 and/or SEQ ID NO: 346-508.

Accordingly, preferred are sequences that are at least 80% identical to SEQ ID NO: 91-179 and/or SEQ ID NO: 346-508, more preferably at least 85% identical to SEQ ID NO: 91-179 and/or SEQ ID NO: 346-508, more preferably at least 88% identical to SEQ ID NO: 91-179 and/or SEQ ID NO: 346-508, more preferably at least 90% identical to SEQ ID NO: 91-179 and/or SEQ ID NO: 346-508, more preferably at least 91% identical to SEQ ID NO: 91-179 and/or SEQ ID NO: 346-508, more preferably at least 92% identical to SEQ ID NO: 91-179 and/or SEQ ID NO: 346-508, more preferably at least 93% identical to SEQ ID NO: 91-179 and/or SEQ ID NO: 346-508, more preferably at least 94% identical to SEQ ID NO: 91-179 and/or SEQ ID NO: 346-508, more preferably at least 95% identical to SEQ ID NO: 91-179 and/or SEQ ID NO: 346-508, more preferably at least 96% identical to SEQ ID NO: 91-179 and/or SEQ ID NO: 346-508, more preferably at least 97% identical to SEQ ID NO: 91-179 and/or SEQ ID NO: 346-508, more preferably at least 98% identical to SEQ ID NO: 91-179 and/or SEQ ID NO: 346-508, more preferably at least 99% identical to SEQ ID NO: 91-179 and/or SEQ ID NO: 346-508.

In a preferred embodiment of the invention and/or embodiments thereof of the present invention and/or embodiments thereof the antisense oligomeric compounds are selected from the group of fragments SEQ ID NO: 91-179, preferably selected from the group of SEQ ID NO: 91-116 and/or SEQ ID NO: 346-508, preferably selected from the group of SEQ ID NO: 360-380 wherein the fragment is 16, 17, 18, 19, 20, 21, 22, 23, or 24 nucleotides long. In a preferred embodiment of the invention and/or embodiments thereof of the present invention and/or embodiments thereof the antisense oligomeric compounds are selected from the group of fragments SEQ ID NO: 91-179, preferably selected from the group of SEQ ID NO: 91-116 and/or SEQ ID NO: 346-508, preferably selected from the group of SEQ ID NO: 360-380, wherein the fragment is 17, 18, 19, 20, 21, or 22 nucleotides long. In a preferred embodiment of the invention and/or embodiments thereof of the present invention and/or embodiments thereof the antisense oligomeric compounds are selected from the group of fragments SEQ ID NO: 91-179, preferably selected from the group of SEQ ID NO: 91-116 and/or SEQ ID NO: 346-508, preferably selected from the group of SEQ ID NO: 360-380, wherein the fragment is 19, 20, or 21 nucleotides long.

It should further be understood that for the above mentioned sequences of SEQ ID NO: 91-179 preferably selected from the group of SEQ ID NO: 91-116 and SEQ ID NO: 346-508, preferably selected from the group of SEQ ID NO: 360-380 also alternative sequences in which one or more of the thymine (T) residues have been replaced by uracil (U) may be used, since such a change would not affect the binding capacity of these sequences to the target sequences of SEQ ID NO: 1-90 and SEQ ID NO: 180-345, respectively.

It is also possible to provide AONs to the branchpoint of the natural pseudo-exon. In this case, an AON targeting the branchpoint may be combined with an AON targeting the acceptor site, an AON targeting the donor site or both.

Most preferred for forming a first part of the pair of antisense oligomeric compounds according to the invention are antisense oligomeric compounds that are complementary to a genomic nucleic acid sequence of GAA gene targeting SEQ ID NO: 1. GTCTCAGAGCTGCTTTGAGAGC-CCCGTGAGTGCCGCCCCTCCCGCCTCCC—(SEQ ID NO: 1). Most preferred for forming a second part of the pair of antisense oligomeric compounds according to the invention are antisense oligomeric compounds that are complementary to a genomic nucleic acid sequence of GAA gene targeting GTGCTCTGCACTCCCCTGCTG-GAGCTTTTCTCGCCCTTCCTTCTGGCCCTCTC-CCCAGTCTAGACAGCAGGGCAACACCCAC (SEQ ID NO: 180).

In a preferred embodiment of the invention and/or embodiments thereof, the antisense oligomeric compound are 8 to 80 nucleotides in length, 9 to 50 nucleotides in length, 10 to 30 nucleotides in length, 12 to 30 nucleotides in length, 15 to 25 nucleotides in length or about 20 nucleotides in length. One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 80 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 50 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleotides.

In one embodiment of the invention and/or embodiments thereof, the antisense compounds comprise 13 to 30 nucleotides. One having ordinary skill in the art will appreciate that this embodies antisense compounds of 13, 14, 15, 16, 17, 18, 19, 20, 21, 22, 23, 24, 25, 26, 27, 28, 29 or 30 nucleotides.

In one embodiment of the invention and/or embodiments thereof, the antisense compounds comprise 20 to 30 nucleotides. One having ordinary skill in the art will appreciate that this embodies antisense compounds of 20, 21, 22, 23, 24, 25, 26, 27, 28, 29, or 30 nucleotides.

In one embodiment of the invention and/or embodiments thereof, the antisense compounds comprise 15 to 25 nucleotides. One having ordinary skill in the art will appreciate that this embodies antisense compounds of 15, 16, 17, 18, 19, 20, 21, 22, 23, 24 or 25.

In one embodiment of the invention and/or embodiments thereof, the antisense compounds comprise 20 nucleotides.

In one embodiment of the invention and/or embodiments thereof, the antisense compounds comprise 19 nucleotides.

In one embodiment of the invention and/or embodiments thereof, the antisense compounds comprise 18 nucleotides.

In one embodiment of the invention and/or embodiments thereof, the antisense compounds comprise 17 nucleotides.

In one embodiment of the invention and/or embodiments thereof, the antisense compounds comprise 16 nucleotides.

In one embodiment of the invention and/or embodiments thereof, the antisense compounds comprise 15 nucleotides.

In one embodiment of the invention and/or embodiments thereof, the antisense compounds comprise 14 nucleotides.

In one embodiment of the invention and/or embodiments thereof, the antisense compounds comprise 13 nucleotides.

In one embodiment of the invention and/or embodiments thereof, compounds include oligonucleotide sequences that comprise at least 8 consecutive nucleotides from one of the antisense compounds as claimed, preferably at least 9 consecutive nucleotides from one of the antisense compounds as claimed, more preferably at least 10 consecutive nucleotides from one of the antisense compounds as claimed, more preferably at least 11 consecutive nucleotides from one of the antisense compounds as claimed, more preferably at least 12 consecutive nucleotides from one of the antisense compounds as claimed, more preferably at least 13 consecutive nucleotides from one of the antisense compounds as claimed, more preferably at least 14 consecutive nucleotides from one of the antisense compounds as claimed, more preferably at least 15 consecutive nucleotides from one of the antisense compounds as claimed, more preferably at least 16 consecutive nucleotides from one of the antisense compounds as claimed, more preferably at least 17 consecutive nucleotides from one of the antisense compounds as claimed, more preferably at least 18 consecutive nucleotides from one of the antisense compounds as claimed, more preferably at least 19 consecutive nucleotides from one of the antisense compounds as claimed, more preferably at least 20 consecutive nucleotides from one of the antisense compounds as claimed.

Any remaining nucleotides from the oligonucleotides may be oligonucleotides that improve resistance to Rnase H, cell-targeting sequences, cell penetrating sequences, marker sequences or any other sequences.

One having skill in the art armed with the antisense compounds disclosed herein will be able, without undue experimentation, to identify further antisense compounds.

In order for an antisense oligonucleotide to achieve therapeutic success, oligonucleotide chemistry must allow for adequate cellular uptake (Kurreck, J. (2003) Eur. J. Biochem. 270:1628-1644). Splicing oligonucleotides have traditionally been comprised of uniform modifications that render the oligonucleotide RNA-like, and thus resistant to cleavage by RNase H, which is critical to achieve modulation of splicing. Provided herein are (pairs of) antisense compounds for modulation of splicing.

In a preferred embodiment of the invention and/or embodiments thereof, the antisense compounds are chimeric, with regions of RNA-like and DNA-like chemistry. Despite regions of DNA-like chemistry, the chimeric compounds are preferably RNase H-resistant and effectively modulate splicing of target mRNA in vitro and in vivo. In another preferred embodiment the disclosed antisense oligomeric compounds show enhanced cellular uptake and greater pharmacologic activity compared with uniformly modified oligonucleotides.

One skilled in the art recognizes that the inclusion of mismatches is possible without eliminating the activity of the antisense compound. Compounds provided herein are therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

It is known by a skilled person that hybridization to a target mRNA depends on the conditions. "Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Antisense compounds, or a portion thereof, may have a defined percent identity to a SEQ ID NO. As used herein, a sequence is identical to the sequence disclosed herein if it has the same nucleobase pairing ability. For example, an RNA which contains uracil in place of thymidine in the disclosed sequences would be considered identical as they both pair with adenine. This identity may be over the entire length of the oligomeric compound, or in a portion of the antisense compound (e.g., nucleotides 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed throughout the oligonucleotide, or both.

For example, a 16-mer having the same sequence as nucleotides 2-17 of a 20-mer is 80% identical to the 20-mer. Alternatively, a 20-mer containing four nucleotides not identical to the 20-mer is also 80% identical to the 20-mer. A 14-mer having the same sequence as nucleotides 1-14 of an 18-mer is 78% identical to the 18-mer. Such calculations are well within the ability of those skilled in the art.

The percent identity is based on the percent of nucleotides in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. In a preferred embodiment of the invention and/or embodiments thereof, the oligonucleotides are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7310, 1992, incorporated herein by reference), a series of antisense oligomeric compounds of 13-25 nucleotides in length were tested for their ability to induce cleavage of a target RNA. Antisense oligomeric compounds of 25 nucleotides in length with 8 or 11 mismatch bases near the ends of the antisense oligomeric compounds were able to direct specific cleavage of the target mRNA, albeit to a lesser extent than the antisense oligomeric compounds that contained no mismatches. Similarly, target specific cleavage was achieved using a 13 nucleobase antisense oligomeric compounds, including those with 1 or 3 mismatches. Maher and Dolnick (Nuc. Acid. Res. 16:3341-3358, 1988, incorporated herein by reference) tested a series of tandem 14 nucleobase antisense oligomeric compounds, and a 28 and 42 nucleobase antisense oligomeric compounds comprised of the sequence of two or three of the tandem antisense oligomeric compounds, respectively, for their ability to arrest translation of human DHFR in a rabbit reticulocyte assay. Each of the three 14 nucleobase antisense oligomeric compounds alone were able to inhibit translation, albeit at a more modest level than the 28 or 42 nucleobase antisense oligomeric compounds. It is understood that antisense compounds can vary in length and percent complementarity to the target provided that they maintain the desired activity. Methods to determine desired activity are disclosed herein and well known to those skilled in the art. In a preferred embodiment of the invention and/or embodiments thereof, the antisense oligomeric compounds have at least 80% complementarity to the target mRNA, more preferably at least 85% complementarity to the target mRNA, more preferably at least 90% complementarity to the target mRNA, more preferably at least 95% complementarity to the target mRNA, more preferably at least 96% complementarity to the target mRNA, more preferably at least 97% complementarity to the target mRNA, more preferably at least 98% complementarity to the target mRNA, more preferably at least 99% complementarity to the target mRNA, more preferably at least 100% complementarity to the target mRNA.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetic of the oligonucleotide. The use of chemistries that increase the affinity of an oligonucleotide for its target can allow for the use of shorter oligonucleotide compounds.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R1)(R2) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-$(CH_2)_2$—O-2' bridge); and substituted sugars, especially 2'-substituted sugars having a 2'-F, 2'-OCH$_2$ or a 2'-O$(CH_2)_2$—OCH$_3$ substituent group. Sugars can also be replaced with sugar mimetic groups among others. Methods for the preparations of modified sugars are well known to those skilled in the art. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O$((CH_2)_nO)_mCH_3$, O$(CH_2)_nOCH_3$, O$(CH_2)_nNH_2$, O$(CH_2)_nCH_3$, O$(CH_2)_nONH_2$, and O(CH2)nON((CH2)nCH3)2, where n and m are from 1 to about 10. Other oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504), i.e., an alkoxyalkoxy group. A further modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O)—(CH$_2$)$_2$—O—(CH$_2$)$_2$—N(CH$_3$)$_2$. Other modifications include 2'-methoxy (2'-O—CH$_3$), 2'-aminopropoxy (2'-OCH$_2$CH$_2$CH$_2$NH$_2$), 2'-allyl (2'-CH$_2$—CH—CH$_2$), 2'-O-allyl (2'-O—CH$_2$—CH—CH$_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

In one aspect of the present invention oligomeric compounds include nucleosides modified to induce a 3'-endo sugar conformation. A nucleoside can incorporate modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

In the present invention there is a preference for an RNA type duplex (A form helix, predominantly 3'-endo) as they are RNase H resistant. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, one or more nucleosides may be modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

Preferred modification of the sugar are selected from the group consisting of 2'-O-methyl 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methyl or 2'-O-methoxyethyl.

Oligomeric compounds can also include nucleobase (often referred to in the art as heterocyclic base or simply as "base") modifications or substitutions. As used herein, "unmodified" or "natural" nucleotides include the purine bases adenine (A) and guanine (G), and the pyrimidine bases thymine (T), cytosine (C) and uracil (U). A "substitution" is the replacement of an unmodified or natural base with another unmodified or natural base. "Modified" nucleotides mean other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C[identical to]C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleotides include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleotides may also include those in which the purine or pyrimidine base is replaced with other heterocycles, for example 7-deaza-adenine, 7-deazaguanosine, 2-aminopyridine and 2-pyridone. Further nucleotides include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleotides are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleotides as well as other modified nucleotides include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763,588; 6,005,096; 5,681,941; and 5,750,692.

Oligomeric compounds of the present invention may also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., Nucleosides and Nucleotides, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 2003/0207804 and 2003/0175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. (Chem. Soc. 1998, 120, 8531-8532). Binding studies demonstrated that a single incorporation could enhance the binding affinity of a model oligonucleotide to its complementary target DNA or RNA with a ΔTm of up to 18° C. relative to 5-methyl cytosine, which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified internucleoside linkages, compared to natural phosphodiester linkages, can be used to alter, typically increase, nuclease resistance of the antisense compound. Internucleoside linkages having a chiral atom may be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

Suitable modified internucleoside linking groups are for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al., Nucleic Acids Research, 2003, 31(14), 4109-4118 and Dellinger et al., J. Am. Chem. Soc., 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., J. Am. Chem. Soc., 1994, 116, 3143-3144). N3'-P5'-phosphoramidates have been studied with some success in vivo to specifically down regulate the expression of the c-myc gene (Skorski et al., Proc. Natl. Acad. Sci., 1997, 94, 3966-3971; and Faira et al., Nat. Biotechnol., 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_2$)—CH$_2$—, —CH$_2$—N(CH$_2$)—N(CH$_3$)—CH$_2$— and —O—N(CH$_3$)—CH$_2$—CH$_2$— (wherein the native phosphodiester internucleotide linkage is represented as —O—P(—O)(OH)—O—CH$_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In a preferred embodiment of the invention and/or embodiments thereof the internucleoside linkage is phosphorothioate, or phosphorodiamidate It is further intended that multiple modifications can be made to one or more of the oligomeric compounds of the invention at multiple sites of one or more monomeric subunits (nucleosides are suitable) and/or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

In a preferred embodiment of the invention and/or embodiments thereof, the oligomeric compounds of the present invention are morpholino phosphorothioates, or phosphorodiamidate morpholino.

Another group of oligomeric compounds includes oligonucleotide mimetics. As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art. The heterocyclic base moiety or a modified heterocyclic base moiety is preferably maintained for hybridization with an appropriate target nucleic acid.

The compounds described herein may contain one or more asymmetric centers and thus give rise to enantiomers, diastereomers, and other stereoisomeric configurations that may be defined, in terms of absolute stereochemistry, as (R) or (S), [alpha] or [beta], or as (D) or (L) such as for amino acids et al. The present disclosure is meant to include all such possible isomers, as well as their racemic and optically pure forms.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleotides are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule. A polyarginine tail may be a suitable for enhancing cell penetration.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(—O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids ((CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—$CH_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10[deg.]C.), stability towards 3'-exonucleolytic degradation and good solubility properties. LNAs are commercially available from ProLigo (Paris, France and Boulder, Colo., USA).

An isomer of LNA that has also been studied is alpha-L-LNA which has been shown to have superior stability against a 3'-exonuclease. The alpha-L-LNAs were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp.LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sc U.S.A., 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-alpha-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim. Acta, 1997, 80, 2426-2439; Steffens et al., J. Am. Chem. Soc., 1999, 121, 3249-3255; Renneberg et al., J. Am. Chem. Soc., 2002, 124, 5993-6002; and Renneberg et al., Nucleic acids res., 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

In certain embodiments, oligomeric compounds, may be conjugated with a wide variety of different positively charged polymers. Examples of positively charged polymers include peptides, such as argine rich peptides (Examples of positively charged peptides that may be used in the practice of the invention include $R_9F_2C$; $(RXR)_4XB$ (where X can be any amino acid); $R_5F_2R_4C$; $(RFF)_3$; Tat proteins, such as TAT sequence CYGRKKRRQRRR; and $(RFF)_3R$, cationic polymers, such as dendrimeric octaguanindine polymer, and other positively charged molecules as known in the art for conjugation to antisense oligonucleotide compounds. In one embodiment of the invention and/or embodiments thereof, the antisense oligonucleotides are conjugated with positively charged polymer comprising a polymer having a molecular weight that is from about 1,000 to 20,000 Daltons, and preferably from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

In a preferred embodiment of the invention and/or embodiments thereof the oligomeric compounds are modified with cell penetrating sequences. Suitable cell penetrating sequences include cell penetrating peptides, such as TAT peptide, MPG, Pep-1, MAP, fusogenic, antimicrobial peptides (AMPs), bacteriocidal peptides, fungicidal peptides, virucidal peptides, Cell-penetrating peptides (CPPs) are short peptides that facilitate cellular uptake of the particles of the invention. The particle of the invention is associated with the CPP peptides either through chemical linkage via covalent bonds or through non-covalent interactions. The function of the CPPs are to deliver the particles into cells, a process that commonly occurs through endocytosis with the cargo delivered to the endosomes of living mammalian cells. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake.

An exemplary cell penetrating peptide is the trans-activating transcriptional activator (Tat) from Human Immunodeficiency Virus 1 (HIV-1) that can be efficiently taken up from the surrounding media by numerous cell types in culture. Other cell penetrating peptides are MPG, Pep-1, transportan, penetratin, CADY, TP, TP10, arginine octamer. polyarginine sequences, Arg8, VP22 HSV-1 structural protein, SAP Proline-rich motifs, Vectocell® peptides, hCT (9-32), SynB, Pvec, and PPTG1. Cell penetrating peptides may be cationic, essentially containing clusters of polyarginine in their primary sequence or amphipathic. CPPs are generally peptides of less than 30 amino acids, derived from natural or unnatural protein or chimeric sequences.

In suitable embodiments, the oligomeric compounds are incorporated or otherwise associated with nanoparticles. Nanoparticles may suitably modified for targeting specific cells and optimised for penetrating cells. A skilled person is aware of methods to employ nanoparticles for oligomeric compounds delivery to cells.

In suitable embodiments of the present invention, the oligomeric compounds are modified with an endosomal escape agent moiety. The endocytic pathway is a major uptake mechanism of cells. Compounds taken up by the endocytic pathway become entrapped in endosomes and may be degraded by specific enzymes in the lysosome. This may be desired or not desired depending on the purpose. If uptake by the endosomes is not desired, an endosomal escape agent may be used. Suitable endosomal escape agents may be chloroquine, TAT peptide.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytityl-2'-deoxy-N4-benzoyl-5-methylcytidine penultimate intermediate for 5-methyl dC amidite, (5'-O-(4,4'-Dimethoxytriphenylmethyl)-2'-deoxy-N4-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N<4>-benzoyl-5-methylcytidine penultimate intermediate, (5'-O-(4,4'-Dimethoxytriphenylmethyl)-2'-O-(2-methoxyethyl)-N<4>-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N<6>-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N<4>-isobutyrylguanosin-3'-O-yl)-2-cyanoethyl-N, N-diisopropylphosphoramidite (MOE G amidite), 2'-O-

(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O<2>-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(4,4'-dimethoxytrityl) guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., Nucleic Acids Research, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., J. Med. Chem., 1993, 36, 831-841) and U.S. Pat. No. 5,670,633.

2'-O-Methoxyethyl-substituted nucleoside amidites can be prepared routinely as per the methods of Martin, P., Helvetica Chimica Acta, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P—S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or 5,366,878.

Alkylphosphonothioate oligonucleotides can be prepared as described in published PCT applications WO 94/17093 and WO 94/02499.

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-Thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P—O or P—S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, 5,719,262, 6,559,279 and 6,762,281.

Oligomeric compounds can incorporate at least one 2'-O-protected nucleoside prepared according to methods routine in the art. After incorporation and appropriate deprotection the 2'-O-protected nucleoside will be converted to a ribonucleoside at the position of incorporation. The number and position of the 2-ribonucleoside units in the final oligomeric compound may vary from one at any site or the strategy can be used to prepare up to a full 2'-OH modified oligomeric compound.

The main RNA synthesis strategies that are presently being used commercially include 5'-[beta]-DMT-2'-O-t-butyldimethylsilyl (TBDMS), 5'-O-DMT-2'-[1 (2-fluorophenyl)-4-methoxypiperidin-4-yl] (FPMP), 2'-O-[(triisopropylsilyl)oxy]methyl (2'-O—CH$_2$—O—Si(iPr)3 (TOM), and the 5'-O-silyl ether-2'-ACE (5'-O-bis(trimethylsiloxy)cyclododecyloxysilyl ether (DOD)-2'-O-bis(2-acetoxyethoxy) methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

Chimeric oligonucleotides, chimeric oligonucleosides and mixed chimeric oligonucleotides/oligonucleosides can be synthesized according to U.S. Pat. No. 5,623,065.

Chimeric oligomeric compounds exhibiting enhanced cellular uptake and greater pharmacologic activity may be made in accordance to U.S. Pat. No. 8,501,703.

Another form of oligomeric compounds comprise tricyclo-DNA (tc-DNA) antisense oligonucleotides. Tricyclo- DNA nucleotides are nucleotides modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Antisense oligomeric compound that contains between 6-22 tricyclo nucleotides in length, in particular between 8-20 tricyclo nucleotides, more particularly between 10 and 18 or between 11 and 18 tricyclo nucleotides are suitable. See e.g. WO2010115993 for examples of tricyclo-DNA (tc-DNA) antisense oligonucleotides. For the present invention this means that any sequence of 8-20, preferably 10-18, more preferably 11-18, more preferably 12, 13, 14, 15, 16 or 17 nucleotides as depicted in any of the above Tables may be useful when such a sequence is in tc-DNA form.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

In a preferred embodiment of the invention and/or embodiments thereof, the antisense compounds provided herein are resistant to RNase H degradation.

In one embodiment of the invention and/or embodiments thereof, the antisense compounds comprise at least one modified nucleotide. In another embodiment, the antisense compounds comprise a modified nucleotide at each position. In yet another embodiment, the antisense compounds are uniformly modified at each position.

Modulation of splicing can be assayed in a variety of ways known in the art. Target mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by a target mRNA can be quantitated in a variety of ways well known in the art, such as immunoprecipitation, Western blot analysis (immunoblotting), ELISA or fluorescence-activated cell sorting (FACS). Antibodies directed to a protein encoded by a target mRNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

The effect of the oligomeric compounds of the present invention may be analysed by RT PCT, qPCR, flanking exon PCR and/or a method comprising flanking exon PCR on each internal exon corresponding to the mRNA to obtain one or more flanking exon amplification products, and detecting the presence and length of the said flanking exon amplification products, and further quantifying of each protein encoding exon of said mRNA.

The oligomeric compounds provided herein may be utilized for therapeutics or research. Furthermore, antisense compounds, which are able to inhibit gene expression or modulate splicing with specificity, may be used to elucidate the function of particular genes or gene products or to distinguish between functions of various members of a biological pathway. In a preferred embodiment of the invention and/or embodiments thereof the oligomeric compounds are used for the treatment of Pompe disease. In a preferred embodiment of the invention and/or embodiments thereof the oligomeric compounds are used in research of the function of the GAA gene.

Compounds described herein can be used to modulate splicing of a target mRNA in metazoans, preferably mammals, more preferably human. In one non-limiting embodiment of the invention and/or embodiments thereof, the methods comprise the step of administering to said animal an effective amount of an antisense compound that modulates splicing of a target mRNA.

For example, modulation of splicing of a target mRNA can be measured by determining levels of mRNA splicing products in a bodily fluid, tissue, organ of cells of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues, organs or cells include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, connective tissue, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues, organs and cells can be routinely obtained by biopsy. In some alternative situations, samples of tissues or organs can be recovered from an animal after death. In a preferred embodiment of the invention and/or embodiments thereof modulation of splicing is measured in fibroblast, preferably primary fibroblasts, preferably primary fibroblasts from patients suffering from Pompe disease.

Next to use of a single oligomeric compound as herein described, or a pair of AONs targeted to the (cryptic) splice sites of one and the same pseudo-exon, it is also possible to use combinations of an AON or a pair of AONs as described above with any other AON targeted to a different area of the gene or even another gene for therapy against a different aberrant splicing variant. Accordingly, the AONs of the present invention may be readily combined with one or more AONs that are directed against another splice mutation of Pompe disease, such as AONs directed against one or more of the following mutations c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15_17AAA, c.17C>T, c.19_21AAA, c.26_28AAA, c.33_35AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T. AONs against these mutations have been disclosed in co-pending application WO 2015/190922, more specifically SEQ ID NOs 2-33, 37-40 and 41-540 as disclosed therein.

It is further envisaged that the mutations listed in Table A and mutations in the neighbourhood of these mutations also are accompanied by the introduction of a natural pseudo-exon. These then can be dealt with in the same manner as discussed above.

TABLE A mutations that lead to the inclusion of a pseudo-exon.

c.546G > A
c.546G > T
c.546G > C
c.546+1G > T
c.546+2T > C
c.546+2_5deltggg
c.546+5G > T
c.546+24G > A
c.546+45G > C
c.547-67C > G
c.547-39T > G Advantageously AONs that prevent pseudo-exon expression for the mutations listed in Table A may be combined with the AONs or pairs of AONs of the invention.

It is further preferred to combine the AONs or pairs of AONs according to the present invention with the compounds mentioned in e.g. WO 2015/035231 (especially the tricycle-phosphorothiate compounds described therein) or described in WO 2015/036451.

It can also be imagined that different genes are targeted with AONs for the same disease. For example, Genzyme has published AONs to reduce levels of glycogen synthase (Clayton, N. P. et al., 2014, Mol. Ther. Nucleic Acids. October 28; 3:e206. doi: 10.1038/mtna.2014.57). They hope to reduce synthesis of cytoplasmic glycogen in this way, and this should be a so-called substrate reduction therapy The AONs of the present invention may be suitably combined with these.

Further therapy based on the AONs of the present invention may be readily combined with enzymatic replacement therapy (ERT) to improve the treatment of Pompe Disease. Compounds for ERT are generally known and used an may be the compounds mentioned in co-pending application PCT/NL2015/050849 such as GAA, Myozyme®, Lumizyme®, neoGAA, Gilt GAA (BMN-701), or oxyrane optionally in combination with genistein, deoxynojirimycin-HCl, N-butyl-deoxynojirimycin, $C_{10}H_{19}NO_4$, $C_{12}H_{23}NO_4$ (as disclosed in this co-pending application), a combination of rituximab and methotrexate. All ERT schedules mentioned in PCT/NL2015/050849 in combination with the AONs of the present invention may be used in the dosage schemes and amounts as have been mentioned therein.

The effects of treatment with the oligomeric compounds can be assessed by measuring biomarkers associated with modulation of splicing of a target mRNA in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine, creatinine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes. In a preferred embodiment of the invention and/or embodiments thereof the biomarker is glycogen.

The compounds disclosed herein can be utilized in pharmaceutical compositions by adding an effective amount of a compound to a suitable pharmaceutically acceptable diluent or carrier. The compounds can also be used in the manufacture of a medicament for the treatment of diseases and disorders related to alterations in splicing. In a preferred embodiment of the invention and/or embodiments thereof, the disease is Pompe disease.

Methods whereby bodily fluids, organs or tissues are contacted with an effective amount of one or more of the antisense compounds or compositions of the disclosure are also contemplated. Bodily fluids, organs or tissues can be contacted with one or more of the compounds of the disclosure resulting in modulation of splicing of target mRNA in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

A sufficient amount of an antisense oligomeric compound to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). The amount may also vary according to the method of administration such as systemically or locally.

Typical dosage amounts of the antisense oligonucleotide molecules in pharmaceutical formulations may range from about 0.05 to 1000 mg/kg body weight, and in particular from about 5 to 500 mg/kg body weight. In one embodiment of the invention and/or embodiments thereof, the dosage amount is from about 50 to 300 mg/kg body weight once in 2 weeks, or once or twice a week, or any frequency required to achieve therapeutic effect. Suitably amounts are from 3-50 mg/kg, more suitably 10-40 mg/kg, more suitably 15-25 mg/kg.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment of the invention and/or embodiments thereof, dosage forms (compositions) of the inventive pharmaceutical composition may contain about 1 microgram to 50,000 micrograms of active ingredient per unit, and in particular, from about 10 to 10,000 micrograms of active ingredient per unit. (if here a unit means a vial or one package for one injection, then it will be much higher, up to 15 g if the weight of a patient is 50 kg) For intravenous delivery, a unit dose of the pharmaceutical formulation will generally contain from 0.5 to 500 micrograms per kg body weight and preferably will contain from 5 to 300 micrograms, in particular 10, 15, 20, 30, 40, 50, 100, 200, or 300 micrograms per kg body weight ([mu]g/kg body weight) of the antisense oligonucleotide molecule. Preferred intravenous dosage ranges from 10 ng to 2000 µg, preferably 3 to 300 µg, more preferably 10 to 100 µg of compound per kg of body weight. Alternatively the unit dose may contain from 2 to 20 milligrams of the antisense oligonucleotide molecule and be administered in multiples, if desired, to give the preceding daily dose. In these pharmaceutical compositions, the antisense oligonucleotide molecule will ordinarily be present in an amount of about 0.5-95% by weight based on the total weight of the composition.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

Preferably the compounds are administered daily, once every 2 days, once every 3 days, once a week, once every two weeks, or once every month.

In another preferred embodiment the administration is only one time, e.g. when using a viral vector.

If a viral-based delivery of antisense oligomeric compounds is chosen, suitable doses will depend on different factors such as the viral strain that is employed, the route of delivery (intramuscular, intravenous, intra-arterial or other), Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the antisense oligomeric compounds of the invention will likely be administered on multiple occasions, that may be, depending on the results obtained, several days apart, several weeks apart, or several months apart, or even several years apart.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein. In preferred embodiment the functionality of the GAA protein is measured. This is suitably performed with an enzymatic activity assays as is well known to a skilled person.

In a particular embodiment of the invention and/or embodiments thereof, antisense oligonucleotides of the invention may be delivered in vivo alone or in association with a vector. In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA or DNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Preferred viral vectors according to the invention include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100) passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al, 1989. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected intramuscular, or intravenous. It may also be administered into the epidermis or a mucosal surface using a gene-gun. The plasmids may be given in an aqueous solution, dried onto gold particles or in association with another DNA delivery system including but not limited to liposomes, dendrimers, cochleates and micro-encapsulation.

In a preferred embodiment of the invention and/or embodiments thereof, the antisense oligonucleotide nucleic acid sequence is under the control of a heterologous regulatory region, e.g., a heterologous promoter. The promoter can also be, e.g., a viral promoter, such as CMV promoter or any synthetic promoters.

In a preferred embodiment of the invention and/or embodiments thereof, the vector may code for more than one antisense oligomeric compound. Each antisense oligomeric compound is directed to different targets.

Pharmaceutical compositions comprising the antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleotides that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment of the invention and/or embodiments thereof, sodium salts of dsRNA compounds are also provided.

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. In a preferred embodiment of the invention and/or embodiments thereof, administration is intramuscular or intravenous.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment of the invention and/or embodiments thereof, the pharmaceutical formulations are prepared for intramuscular administration in an appropriate solvent, e.g., water or normal saline, possibly in a sterile formulation, with carriers or other agents.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Compositions provided herein may contain two or more antisense compounds. In another related embodiment, compositions may contain one or more antisense compounds, particularly oligonucleotides, targeted to SEQ ID NO: 1 and/or targeted to SEQ ID NO: 180 and one or more additional antisense compounds targeted to a further nucleic acid target, which may relevant to the patient to be treated. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

The antisense oligomeric compound described herein may be in admixture with excipients suitable for the manufacture of aqueous suspensions. Such excipients are suspending agents, for example polyvinylpyrrolidone, sodium carboxymethylcellulose, methylcellulose, hydropropylmethylcellulose, sodium alginate, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives. antisense oligomeric compound compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes antisense oligomeric compound compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxy ethylene sorbitan monooleate.

The antisense oligomeric compound of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus the antisense oligomeric compound of the present disclosure may be administered in any form, for example intramuscular or by local, systemic, or intrathecal injection.

This disclosure also features the use of antisense oligomeric compound compositions comprising surface-modified liposomes containing poly(ethylene glycol) lipids (PEG-modified, or long-circulating liposomes or stealth liposomes). These formulations offer a method for increasing the accumulation of antisense oligomeric compound in target tissues. This class of drug carriers resists opsonization and elimination by the mononuclear phagocytic system (MPS or RES), thereby enabling longer blood circulation times and enhanced tissue exposure for the encapsulated antisense oligomeric compound (Lasic et al, Chem. Rev. 95:2601-2627 (1995) and Ishiwata et al, Chem. Pharm. Bull. 43:1005-1011 (1995). Long-circulating liposomes enhance the pharmacokinetics and pharmacodynamics of antisense oligomeric compound, particularly compared to conventional cationic liposomes which are known to accumulate in tissues of the MPS (Liu et al, J. Biol. Chem. 42:24864-24870 (1995); Choi et al, PCT Publication No. WO 96/10391; Ansell et al, PCT Publication No. WO 96/10390; Holland et al, PCT Publication No. WO 96/10392). Long-circulating liposomes are also likely to protect antisense oligomeric compound from nuclease degradation to a greater extent compared to cationic liposomes, based on their ability to avoid accumulation in metabolically aggressive MPS tissues such as the liver and spleen.

Following administration of the antisense oligomeric compound compositions according to the formulations and methods of this disclosure, test subjects will exhibit about a 10% up to about a 99% reduction in one or more symptoms associated with the disease or disorder being treated, as compared to placebo-treated or other suitable control subjects.

Examples

Materials & Methods
Generation of Induced Pluripotent Stem Cells
Dermal fibroblasts from control 1 and two patients (1 and 2) with Pompe disease were obtained via skin biopsy with informed consent. The Institutional Review Board approved the study protocol. All patient and control primary cell lines were negative for HIV, hepatitis B, hepatitis C as tested by quantitative PCR analysis at the diagnostic department of Virology of the Erasmus MC Rotterdam, The Netherlands. Both patient cell lines contain the IVS1 mutation on one allele. The second allele was c.525delT for patient 1, and c.923A>C (his>pro) for patient 2, which both are established pathogenic GAA variants (www.pompecenter.nl). Primary fibroblasts were reprogrammed into iPS cells using a polycistronic lentiviral vector of Oct4, Sox2, Klf4, and c-Myc as described54. iPS control 2 cell line was a gift from Christian Freund and Christine Mummery and has been characterized previously26. iPS cells were cultured on γ-irradiated mouse embryonic feeder (MEF) cells. The culture medium consisted of DMEM/F12 medium (Invitrogen), 20% knock-out serum replacement (Invitrogen), 1% non-essential amino acids (Gibco), 1% penicillin/streptomycin/L-glutamine (100×, Gibco), 2 mM ß-mercaptoethanol (Invitrogen) and 20 ng/ml basic fibroblast growth factor (Peprotech).

Immunofluorescence
Cells were fixed with 4% paraformaldehyde (Merck) in PBS for 10 minutes at room temperature, washed with PBS and permeabilized for 5 minutes with 0.1% Triton X-100 (AppliChem) in PBS. Blocking was performed for 45 minutes at room temperature with blocking solution containing PBS-T (0.1% Tween, Sigma) with 3% BSA (Sigma). Primary antibodies (Supplementary Table 1) were diluted into 0.2% BSA in PBS-T and incubated either 1 hour at room temperature or overnight at 4° C. After incubation wells were washed three times for 5 minutes with PBS-T and incubated with the secondary antibodies (1:500, Alexa-Fluor-594-α-goat, Alexa-Fluor-488-α-mouse, Invitrogen) in PBS-T for 30 minutes at room temperature. The wells were subsequently washed two times for 5 minutes with PBS and incubated for 15 minutes with Hoechst (Thermo Scientific). Afterwards cells were embedded in Vectashield Mounting Medium (Vector).

Microarray Analysis
RNA samples to be analyzed by microarrays were prepared using RNeasy columns with on-column DNA digestion (Qiagen). 300 ng of total RNA per sample was used as input into a linear amplification protocol (Ambion), which involved synthesis of T7-linked double-stranded cDNA and 12 hours of in vitro transcription incorporating biotin-labelled nucleotides. Purified and labeled cRNA was then hybridized for 18 h onto HumanHT-12 v4 expression Bead-Chips (Illumina) following the manufacturer's instructions. After recommended washing, chips were stained with streptavidin-Cy3 (GE Healthcare) and scanned using the iScan reader (Illumina) and accompanying software. Samples were exclusively hybridized as biological replicates. The bead intensities were mapped to gene information using BeadStudio 3.2 (Illumina). Background correction was performed using the Affymetrix Robust Multi-array Analysis (RMA) background correction model 55. Variance stabilization was performed using the log 2 scaling and gene expression normalization was calculated with the method implemented in the lumi package of R-Bioconductor. Data post-processing and graphics was performed with in-house developed functions in Matlab. Hierarchical clustering of genes and samples was performed with one minus correlation metric and the unweighted average distance (UPGMA) (also known as group average) linkage method. The microarray data have been deposited with accession number (in progress).

In Vitro Differentiation iPS colonies were washed once with PBS and treated for 45 minutes with 1 mg/ml collagenases IV (Invitrogen) at 37° C., scraped and centrifuged for 15 seconds at 800 rpm. The pellet was slowly dissolved into EB medium (iPS medium without FGF2) with 10 µM Y-27632 dihydrochloride (Ascent Scientific) and plated on low binding plates (Cyto one). For the endoderm condition 10 µM SB 431542 (Ascent Scientific) was added to the EB medium. Six days later EBs were plated in 12 wells coated with 0.1% gelatin (Sigma) for endoderm and mesoderm differentiation or with matrigel-coated plates for ectoderm differentiation in endo/meso/ectoderm medium. Cells were fixed after 14 days of differentiation with 4% paraformaldehyde (Merck) in PBS for 5 minutes at room temperature and processed for immunofluorescence.

Karyotype Analysis iPS or myogenic progenitors were detached with TrypLe (Gibco) for 5 minutes at 37° C. The pellet was incubated with 10 µg/ml colcemid (Gibco) for 30 minutes at room temperature. Cells were then centrifuged for 10 minutes at 1100 rpm and resuspended into prewarmed 0.075 M KCL and incubated for 10 minutes at 37° C. After incubation cells were five times washed with fixation solution (3:1 methanol: acetic acid) and spread onto glass slides. Hoechst staining was performed as described above.

Differentiation of iPS Cells to Myogenic Progenitor Cells

Differentiation of iPS cells to myogenic progenitors cells was modified from Borchin et al. 5. Briefly, 0.6 mm large iPS colonies cultured in 10 cm dishes on MEF feeders were treated for 5 days with 3.5 µM CHIR99021 (Axon Medchem) in myogenic differentiation medium (DMEM/F12, 1×ITS-X and Penicillin/Streptomycin-Glutamine, all Gibco). After 5 days, CHIR99021 was removed and cells were cultured in myogenic differentiation medium containing 20 ng/ml FGF2 (Prepotech) for 14 days and switched for an additional 14 days to myogenic differentiation medium only. Fusion index represent the % of nuclei inside myofibers relative to the total number of nuclei. Five random fields at 20× magnification were counted.

FACS Sorting

Cells were washed once with PBS, detached for 5 minutes with TrypLe (Gibco) at 37° C., and filtered through a 0.45 µM FACS strainer (Falcon). Cells were stained with HNK-1-FITC (1:100, Aviva Systems Biology) and C-MET-APC (1:50, R&D Systems) for 30 minutes on ice in myogenic differentiation medium and washed three times with ice-cold 0.1% BSA in PBS before FACS sorting. Hoechst (33258, Life Technology) was used as viability marker.

Expansion of Myogenic Progenitor Cells

Hoechst/C-MET-positive cells were plated at 40,000 cells/well on ECM (Sigma Aldrich)-coated 48 wells plates in iPS-myogenic progenitor proliferation medium containing DMEM high glucose (Gibco) supplemented with 100 U/ml Penicillin/Streptomycin/Glutamine (Life Technology), 10% Fetal bovine serum (Hyclone, Thermo Scientific), 100 ng/ml FGF2 (Prepotech), and 1× RevitaCell™ Supplement (Gibco). Cells were passaged using 2× diluted TrypLe. For differentiation to skeletal muscle cells, myogenic progenitors were grown to 90% confluence and the medium was then replaced with myogenic differentiation medium (see above).

Modification of the U7 snRNA Vector for Intermediate Throughput Cloning of AON Sequences The U7 snRNA gene and promoter were amplified by PCR from female mouse genomic DNA using Fw-ms-U7snRNA-PstI and Rv-ms-U7snRNA-SalI primers, which included PstI and SalI overhang restriction sites. The PCR fragment (425 bp) was cloned into a pCRII-TOPO vector according to the manufacture's manual (Invitrogen). SMopt and NsiI sites were generated by site-directed mutagenesis according to an inner and outer primer design with Fw- and Rv-U7snRNA-SMopt or Fw- and Rv-U7snRNA-NsiI as inner primers and with Fw-M13 and Rv-M13 as outer primers (Table 9), and subcloned using the PstI and SalI sites in front of the polypurine tract fragment of the lentiviral vector used for reprogramming from which OSKM and the SF promoter were removed.

Cloning of AONs into the U7 snRNA Vector

AONs were inserted via PCR amplification using an forward primer that contained the desired antisense sequence and the unique NsiI restriction site and the reverse primer Rv-ms-U7snRNA-SalI. The amplified PCR product was purified by agarose gel electrophorese, extracted (gel extraction kit, Qiagen), digested with NsiI and SalI, purified (PCR purification kit, Qiagen), and cloned into the NsiI and SalI sites of the U7 snRNA vector. Clones were verified by sequencing with the Fw-ms-U7snRNA-PstI (Supplementary Table 3) and restriction enzyme digestion.

Cell Culture

HEK293T cells or human primary fibroblasts were cultured in Dulbecco's Modified Eagle's Medium (DMEM) high glucose (Gibco) supplemented with 100 U/ml Penicillin/Streptomycin/Glutamine (Gibco) and 10% Fetal bovine serum (Hyclone, Thermo Scientific). Cells were passaged after reaching 80/90% confluence with TrypLE (Gibco). Human ES lines H1 and H9 were obtained from Wicell Research Institute, Madison, Wis., USA. The identity of cell lines used in this study was confirmed by DNA sequence and microarray analyses. All cell lines were routinely tested for *Mycoplasma* infection using the MycoAlert™ *Mycoplasma* Detection Kit (Lonza) and were found negative.

Virus Production

Lentiviruses were produced by co-transfecting HEK293T cells at 80% confluency in a 10 cm culture dish with the lentivirus transfer vector (3 µg SF-OSKM or SF-U7snRNA vectors) and packaging plasmids (2 µg psPAX2 and 1 µg pVSV vectors) using Fugene 6 transfection according to manufacturer's protocol (Promega). Lentiviruses were harvested from the medium after 72 hours of transfection and filtered using a 0.45 μm PDFV filter (Milipore). After filtering lentiviruses were concentrated by high speed centrifugation for 2 hours at 20000 rpm in a Beckman Coulter Ultracentrifuge with SW32 Ti rotor at 4° C. The supernatant was removed and the pellet was dissolved in 25 μl Dulbecco's Modified Eagle's medium Low Glucose (Invitrogen) per plate and stored in aliquots at −80° C.

P24 ELISA

Viral titers were determined with the HIV-1 p24 antigen ELISA kit (Retrotek) according to manufacturer's manual. Each virus was diluted 1:40000 and 1:100000 and the OD450 nm was measured with a varioskan (Thermos Scientific) reader.

Transduction of U7 snRNA Vectors

One day before infection $6 \times 10^4$ cells per single well of a 12 wells plate of patient 1-derived primary fibroblasts were seeded. One day later the cells were infected with 200 ng virus containing the SF-U7snRNA constructs, and after 24 hours cells were washed three times with PBS before adding fresh medium. After 4 days cells were washed with PBS and harvested with RLT buffer of the RNAeasy kit for RNA isolation (Qiagen). For GAA enzyme activity assay cells were harvested after 12 days.

Morpholino Transfections

Human fibroblasts or myogenic progenitors (day −1 or 0 of differentiation) were transfected with morpholino AONs using Endoporter reagent (Gene-Tools, LLC). Cells were plated out and grown to 90% confluency before transfection. Endoporter was used at a concentration of 4.5 μl per ml of medium. Morpholino was dissolved in sterile water to a concentration of 1 mM and the appropriate volume was added to each culture well. Cells were harvested after 3 to 5 days in culture.

In Vitro Enzyme Replacement Therapy

Culturing media for culturing for iPSC-derived myotubes was supplemented with 3 mM PIPES (Sigma) and Myozyme® (Sanofi Genzyme) 1 day before harvesting the cells. Activity of Myozyme was determined before addition to the media as described below. Myozyme® was added at concentrations that give activities between 100 and 1000 nmol 4 MU/hr/ml medium.

RNA Isolation and cDNA Synthesis

RNA was extracted with the RNeasy mini kit with Dnase treatment (Qiagen) and was stored at −80° C. in RNase-free water. cDNA was synthesized from 500 ng RNA using iScript cDNA synthesis kit (Bio-Rad).

qPCR cDNA was diluted five, ten or twenty times and used with 7.5 μl iTaq Universersal SYBR Green Supermix (Bio-Rad) and 10 pmol/μl forward and reverse primers (Table 9) in a CFX96 real-time system (Bio-Rad). Ct values were related to amounts using standard curves of 4-6 dilutions. Quantification of expression was calculated relative to ß-Actin expression in experiments where primary fibroblasts used, to expression of four markers (Myog, MyoD, LAMP1 and LAMP2) in experiments where myotubes were used, and to RNA input in experiments were multiple tissues (fibroblasts, myogenic progenitors and myotubes) were compared.

Flanking Exon RT-PCR

Ten times diluted cDNA with GC GAA Exon 1-3 fw and GC GAA Exon 1-3 rv primers were used for RT-PCR with the Advantage GC 2 PCR kit (Clontech) and a GC-melt concentration of 0.5 M according to manufacturer's protocol. The whole GC-PCR reaction was analyzed on a 1.5% agarose gel containing 0.5 μg/ml ethidium bromide (Sigma).

GAA Enzyme Activity Assay

Cells were harvested with ice cold lysis buffer (50 mM Tris (pH 7.5), 100 mM NaCl, 50 mM NaF, 1% Triton X-100 and one tablet Protease Inhibitor Cocktail (cOmplete, with EDTA, Roche) and incubated for 10 minutes on ice. Samples were centrifuged at 14000 rpm for 10 minutes at 4° C. GAA enzyme activity was measured using 4-methylumbelliferyl α-D-glucopyranoside (Sigma) as substrate as described 21. Total protein concentration was determined using a BCA protein assay kit (Pierce, Thermo Scientific).

Statistical Analysis

All data represent mean+/−SD, and p-values refer to two-sided t-tests. Bonferroni multiple testing correction was applied where necessary. A p-value <0.05 was considered to be significant. Data showed normal variance. There was no power calculation in any of the experiments. No randomization method was used. No samples were excluded from the analyses. Experiments on expansion of iPS-derived muscle progenitors, differentiation into myotubes, and AON treatment have been performed at least two times. Investigators were not blinded to the identity of the samples.

TABLE 9

| Primer target | Sequence (5'-3') | Used for |
|---|---|---|
| β-Actin fw | AACCGCGAGAAGATGACCC | qPCR/RT-PCR |
| β-Actin rv | GCCAGAGGCGTACAGGGATAG | qPCR/RT-PCR |
| GAA Exon 1-2 fw | AAACTGAGGCACGGAGCG | qPCR |
| GAA Exon 1-2 rv | GAGTGCAGCGGTTGCCAA | qPCR |
| GAA Cryptic Exon 2 fw | GGCACGGAGCGGGACA | qPCR |
| GAA Cryptic Exon 2 rv | CTGTTAGCTGGATCTTTGATCGTG | qPCR |
| GAA Full Skip Exon 2 fw | AGGCACGGAGCGGATCA | qPCR |
| GAA Full Skip Exon 2 rv | TCGGAGAACTCCACGCTGTA | qPCR |
| GAA Pseudo Exon fw | AAACTGAGGCACGGAGCG | qPCR |
| GAA Pseudo Exon rv | GCAGCTCTGAGACATCAACCG | qPCR |

Primers used for qRT-PCR, RT-PC, cloning and sequencing

TABLE 9-continued

Primers used for qRT-PCR,
RT-PC, cloning and sequencing

| Primer target | Sequence (5'-3') | Used for |
|---|---|---|
| α-Actinin fw | GAGACAGCGGCTAACAGGAT | qPCR |
| α-Actinin fw | ATTCCAAAAGCTCACTCGCT | qPCR |
| Six1 fw | GTCCAGAACCTCCCCTACTCC | qPCR |
| Six1 rv | CGAAAACCGGAGTCGGAACTT | qPCR |
| Six4 fw | CCATGCTGCTGGCTGTGGGAT | qPCR |
| Six4 rv | AGCAGTACAACACAGGTGCTCTTGC | qPCR |
| FGF2 fw | CAAAAACGGGGCTTCTTCC | qPCR |
| FGF2 rv | GCCAGGTAACGGTTAGCACA | qPCR |
| Sox1 fw | GAGCTGCAACTTGGCCACGAC | qPCR |
| Sox1 rv | GAGACGGAGAGGAATTCAGAC | qPCR |
| MyoD fw | CACTCCGGTCCCAAATGTAG | qPCR |
| MyoD rv | TTCCCTGTAGCACCACACAC | qPCR |
| Myog fw | CACTCCCTCACCTCCATCGT | qPCR |
| Myog rv | CATCTGGGAAGGCCACAGA | qPCR |
| LAMP1 fw | GTGTTAGTGGCACCCAGGTC | qPCR |
| LAMP1 rv | GGAAGGCCTGTCTTGTTCAC | qPCR |
| LAMP2 fw | CCTGGATTGCGAATTTTACC | qPCR |
| LAMP2 rv | ATGGAATTCTGATGGCCAAA | qPCR |
| Fw-U7snRNA-smOPT | GCTCTTTTAGAATTTTGGAGCAGGTTTTCTGACTTCG | Cloning |
| Rv-U7snRNA-smOPT | CGAAGTCAGAAAACCTGCTCCAAAAATTCTAAAAGAGC | Cloning |
| Fw-U7snRNA-NsiI | CCTGGCTCGCTACAGATGCATAGGAGGACGGAGGACG | Cloning |
| Rv-U7snRNA-NsiI | CGTCCTCCGTCCTCCTATGCATCTGTAGCGAGCCAGG | Cloning |
| M13 fw | GTAAAACGACGGGCCAG | Sequencing |
| M13 rv | CAGGAAACAGCTATGAC | Sequencing |
| GAA Exon1-3 fw | AGGTTCTCCTCGTCCGCCCGTTGTTCA | RT-PCR |
| GAA Exon1-3 rv | TCCAAGGGCACCTCGTAGCGCCTGTTA | RT-PCR |
| Fw-ms-U7snRNA-PstI | GCGCCTGCAGTAACAACATAGGAGCTGTG | Cloning |
| Rv-ms-U7snRNA-SalI | GCGCGTCGACCAGATACGCGTTTCCTAGGA | Cloning |

Results

Figure 6A:
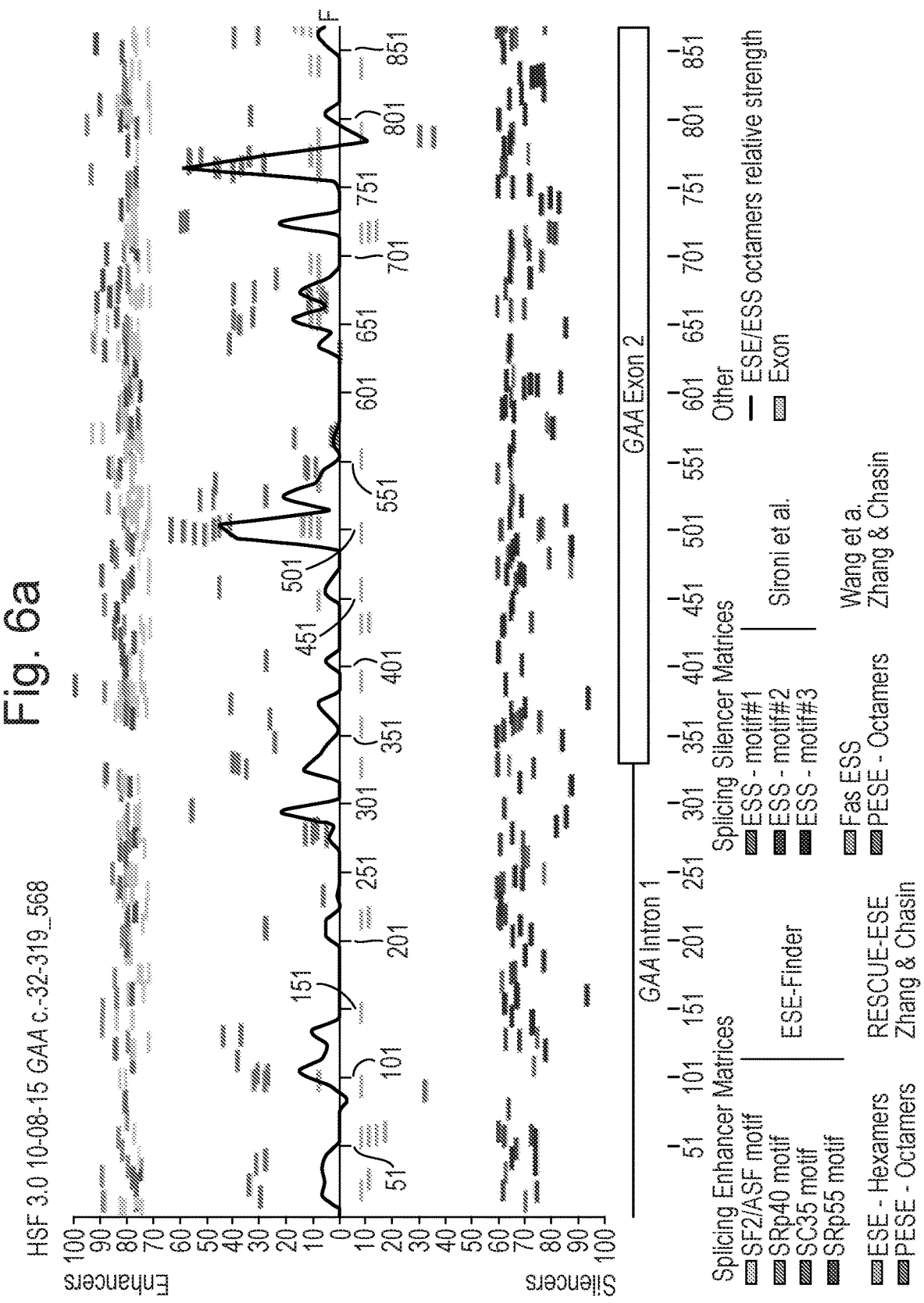

Our purpose was to promote exon 2 inclusion in cells from IVS1 patients to restore wild type GAA splicing. Primary fibroblasts from such patients show partial and complete skipping of exon 2 (FIG. 1a), as reported previously[23, 24, 25]. We aimed to block a splicing repressor sequence using AONs. However, no splicing silencer sequences have been described so far for GAA. To identify silencers of exon 2 splicing, in silico prediction analysis was performed using Human Splicing Finder (http://www.um-d.be/HSF/) (FIG. 6a). This yielded many possible hits that failed to overlap between different prediction algorithms, and it was unclear which hits should be used to design and synthesize rather expensive chemically stable AONs. This indicated the need to screen the GAA pre-mRNA for possible splicing regulatory motifs (FIG. 1b) in a functional and cost-effective assay.

Figure 6B:
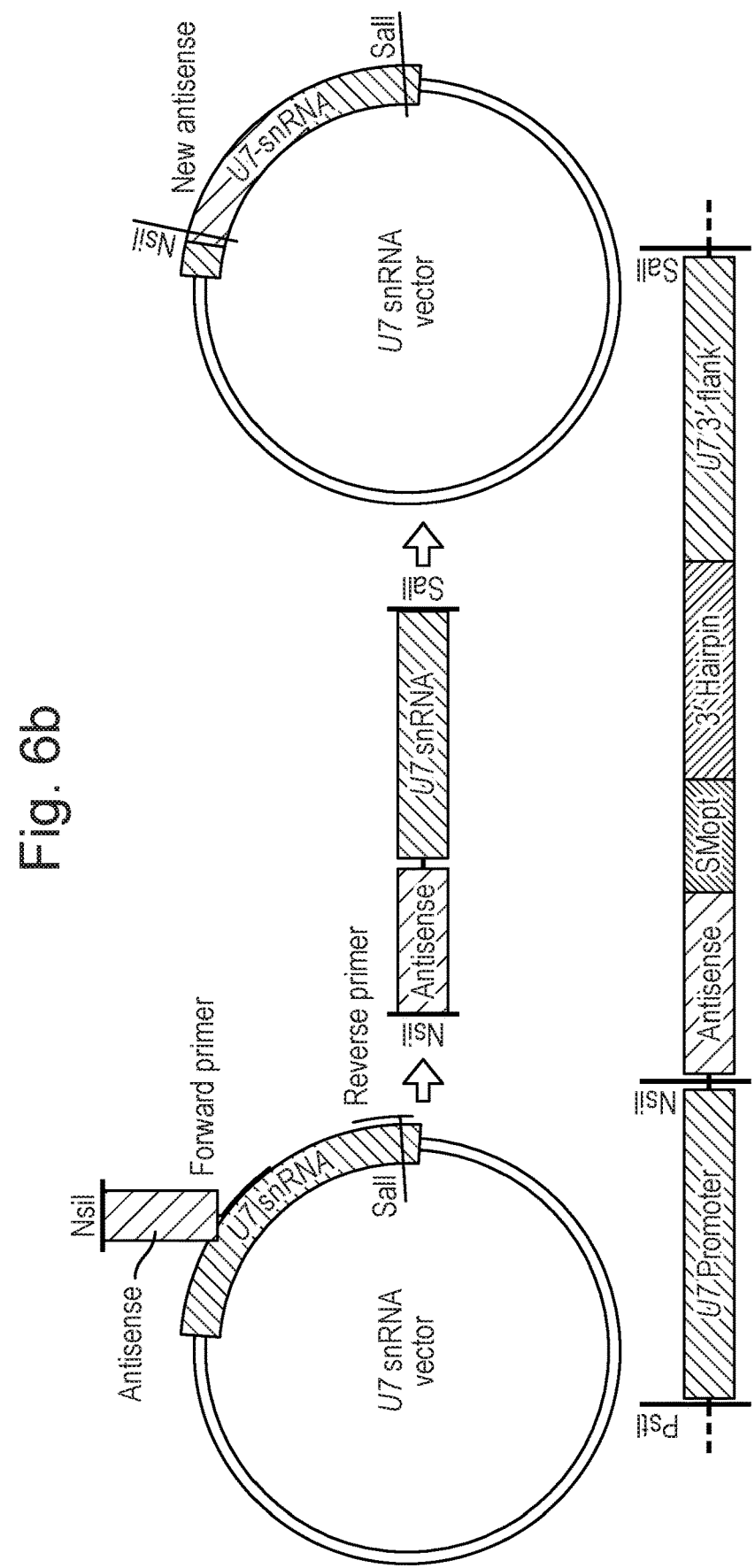
Figure 6C:
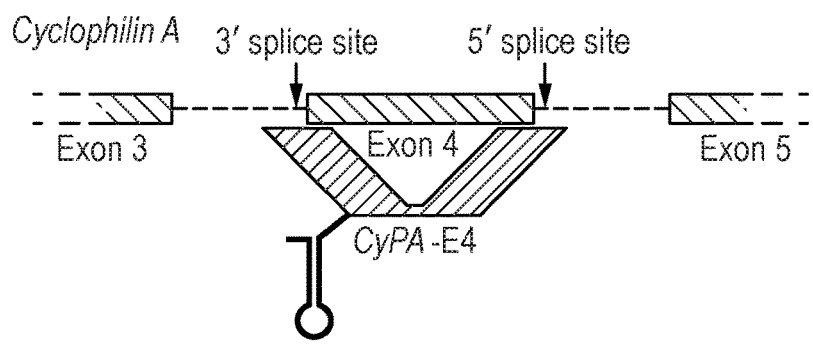
Figure 6D:
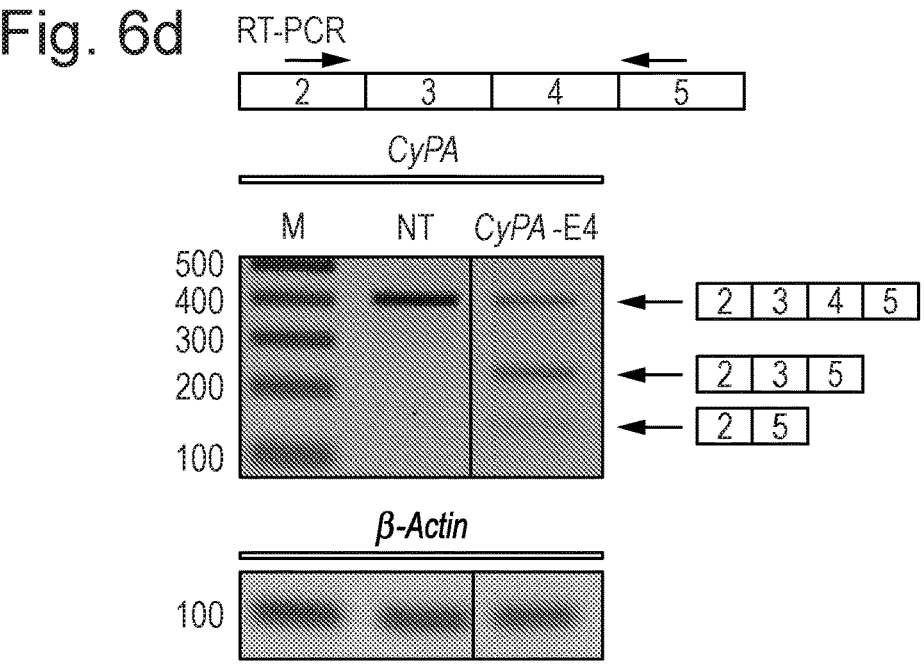
Figure 6E:
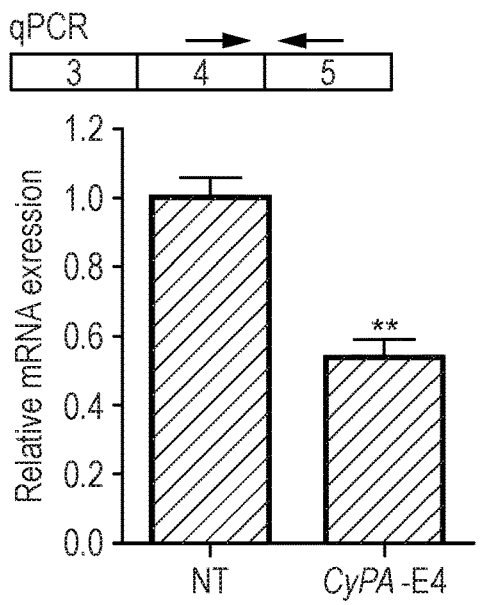

We used modified U7 snRNA to express AONs as shown previously[40, 41]. This enables the expression of AONs in the nucleus that are stabilized by a stem loop that is provided by the snRNA (FIG. 1b, FIG. 6c). We aimed to test endogenous GAA splicing in primary cells, as these would be the closest to splicing regulation in vivo. Patient-derived primary fibroblasts, obtained via a skin biopsy, are routinely used for biochemical diagnosis of Pompe disease. GAA enzymatic activities of 1-20% of healthy control values indicate childhood/adult onset Pompe disease. Transfection of U7 snRNA expression constructs in primary cells was inefficient, preventing efficient modulation of endogenous splicing (data not shown). We therefore cloned the U7 snRNA cassette in a lentivirus and used lentiviral transduction, which resulted in ~100% transduction efficiency of primary fibroblasts. This vector was then modified by introduction of a NsiI site to allow 1-step cloning of AONs, introduced via a forward PCR primer, with a cloning success rate of >95% (FIG. 6b). We validated the lentiviral U7 snRNA system by promoting exon skipping of a control gene, cyclophilin A (CypA)42 in primary fibroblasts (FIG. 6c-e). We conclude that AONs expressed as U7 snRNAs using a lentivirus provides a fast and cheap method to screen putative target sites for splice-switching AONs in primary cells.

Figure 6F:
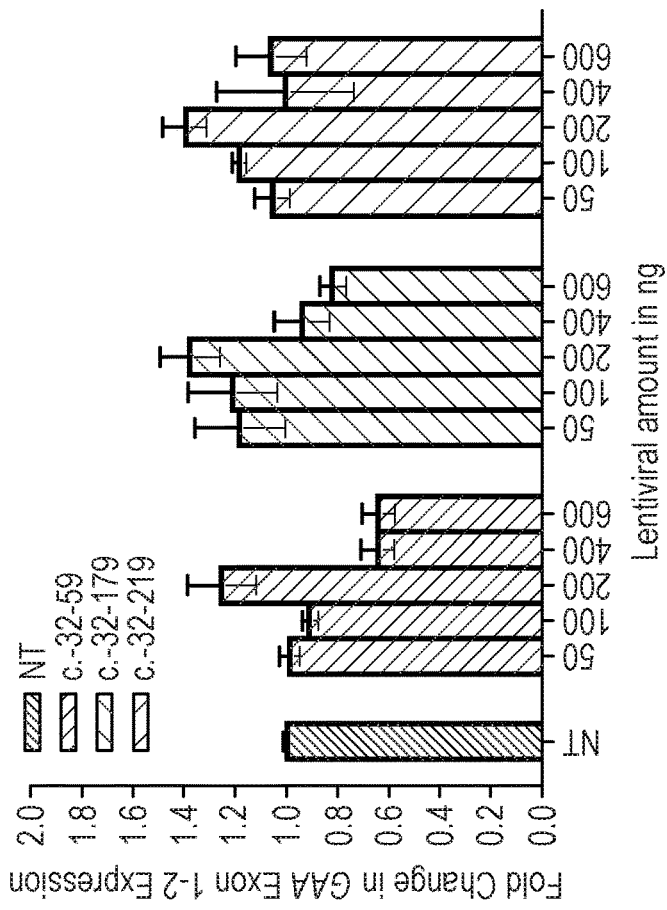
Figure 6G:
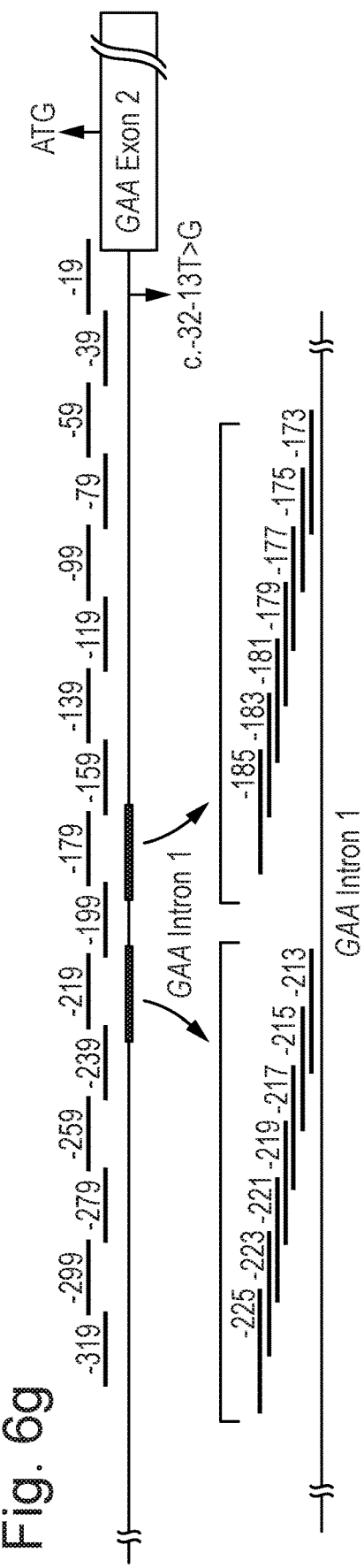
Figure 6H:
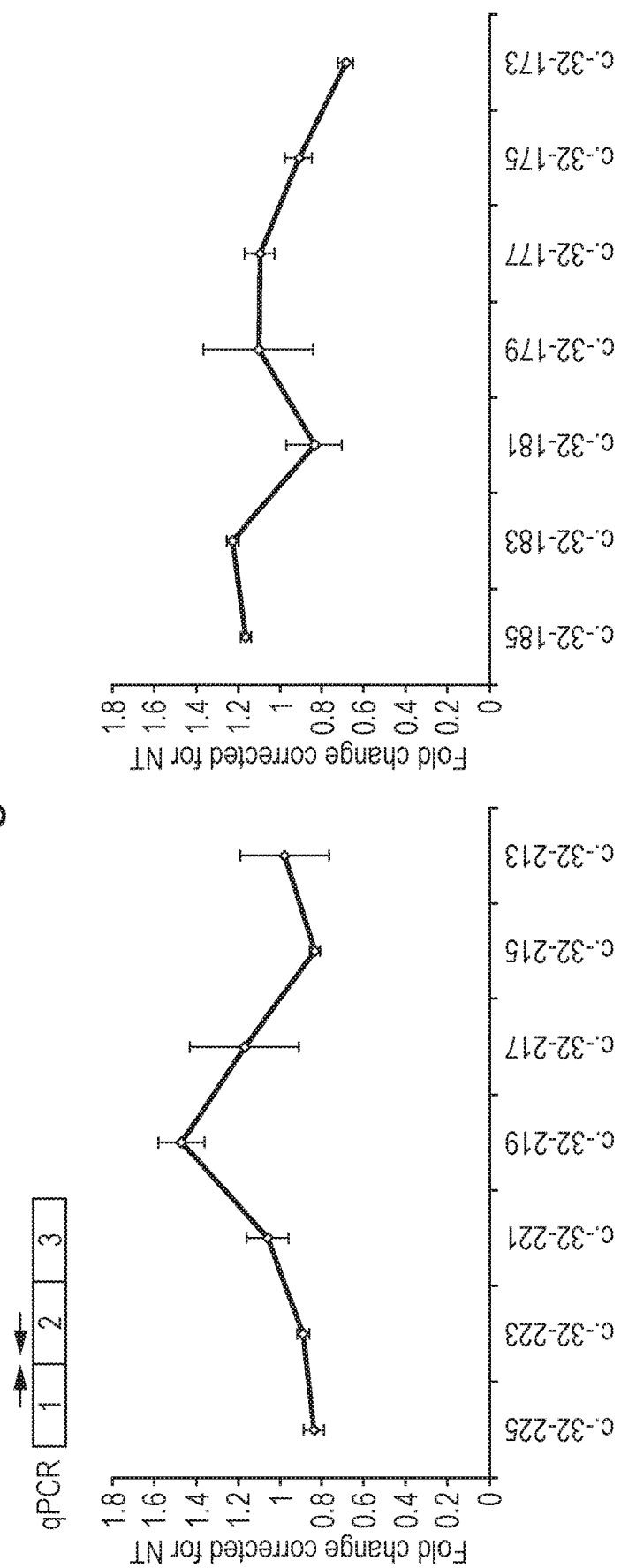

A screen was then performed in Pompe patient-derived fibroblasts in which AONs targeted the GAA pre-mRNA surrounding the IVS1 variant in a non-overlapping tiling arrangement, from c.-32-319 to c.530 (FIG. 1c). Three read outs were used: GAA mRNA expression by RT-qPCR and flanking exon PCR, and GAA enzyme activity (FIG. 1d,e). This resulted in the identification of two regions in intron 1 (c.-32-219 and c.-32-179) that acted as splicing silencer sequences and whose repression by AONs promoted exon 2 inclusion and GAA enzyme activity. Lentiviral-mediated U7 snRNA expression appeared to have a small window in which splicing modulation could be investigated, due to toxicity at high virus titers (FIG. 6f). We then performed a miniscreen around these targets using AONs that shifted 2 nt each, and this defined c.-32-179 and c.-32-179 as the peaks of the regions that acted as silencers of GAA exon 2 splicing (FIG. 6g-i).

To explore the possibility for the development of AONs that could be used in a clinical setting, we used phosphorodiamidate morpholino oligomer (PMO)-based AONs. In a validation experiment, exon 4 of CypA was efficiently skipped using AONs CypA 1 and CypA 2 that targeted the splice acceptor (FIG. 7a-d). No signs of toxicity were observed. This confirmed that PMO-based AONs are suitable for the modulation of splicing in primary fibroblasts, in agreement with previous reports[43, 44].

Figures 7A, 7B:
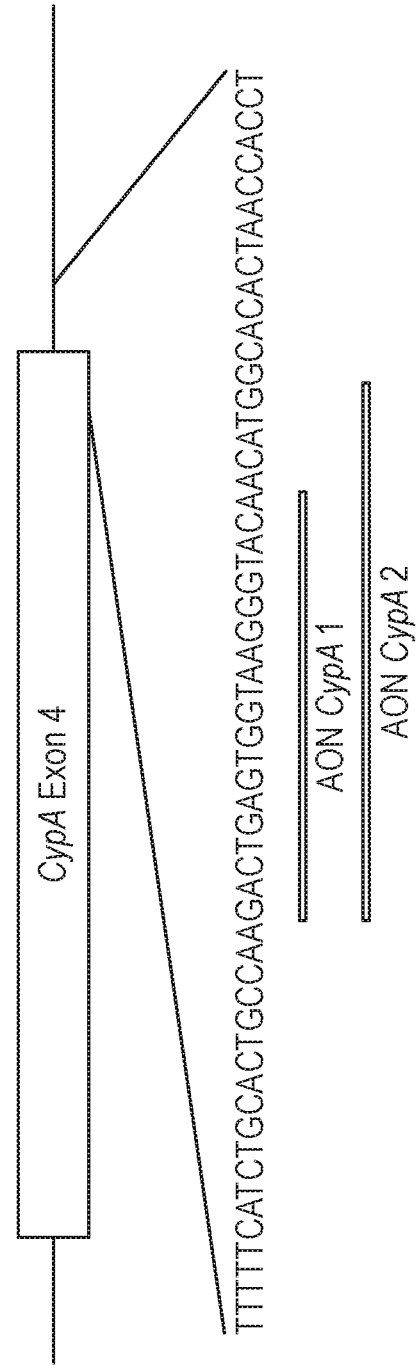
Figure 7C:
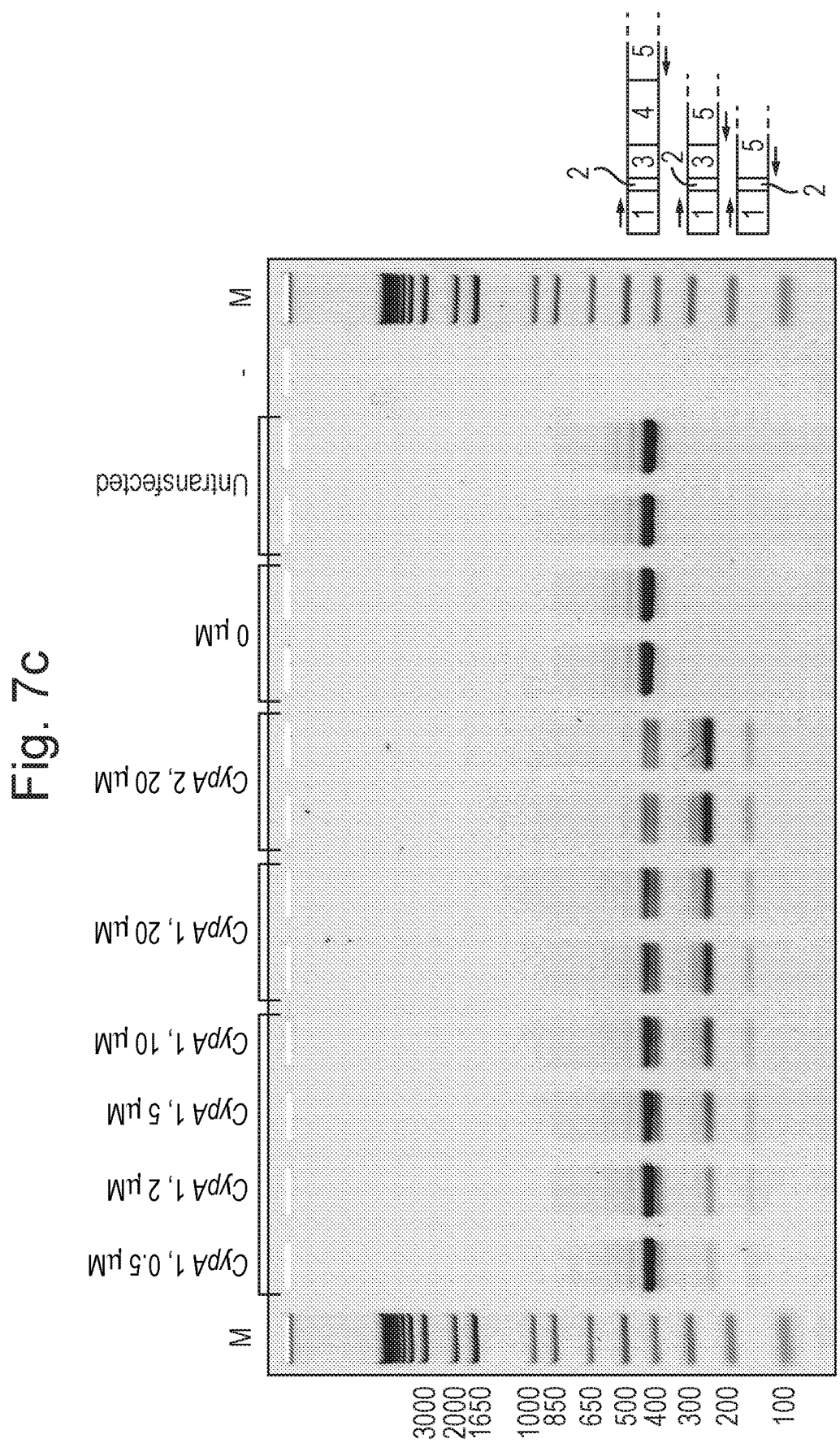
Figure 7D:
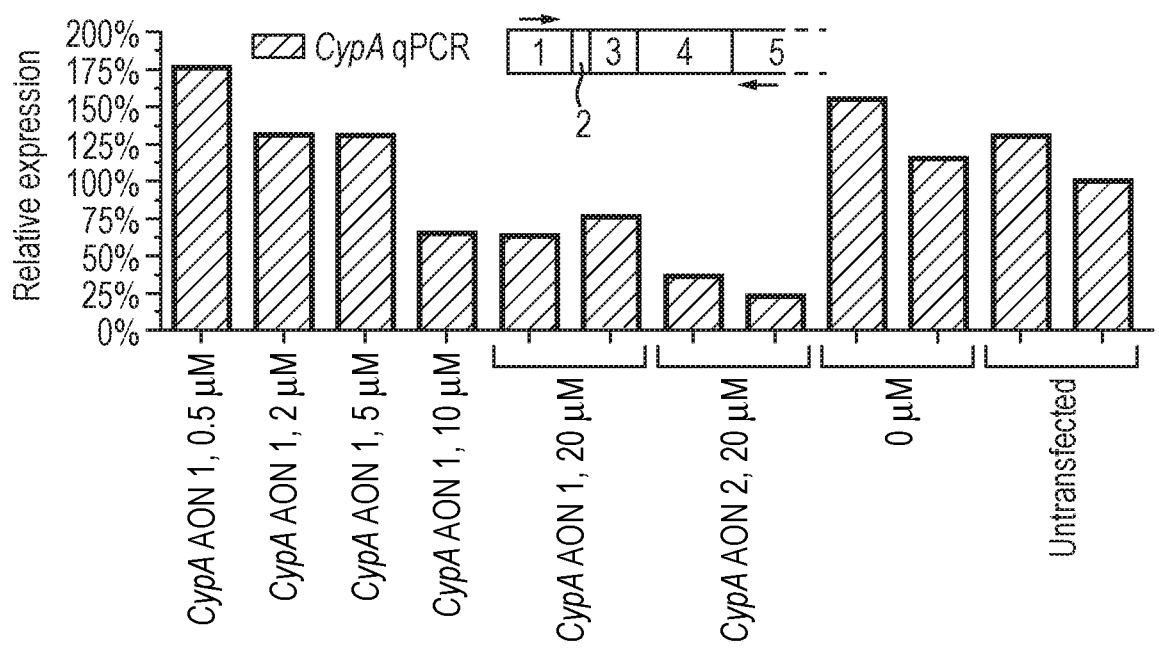
Figure 7E:
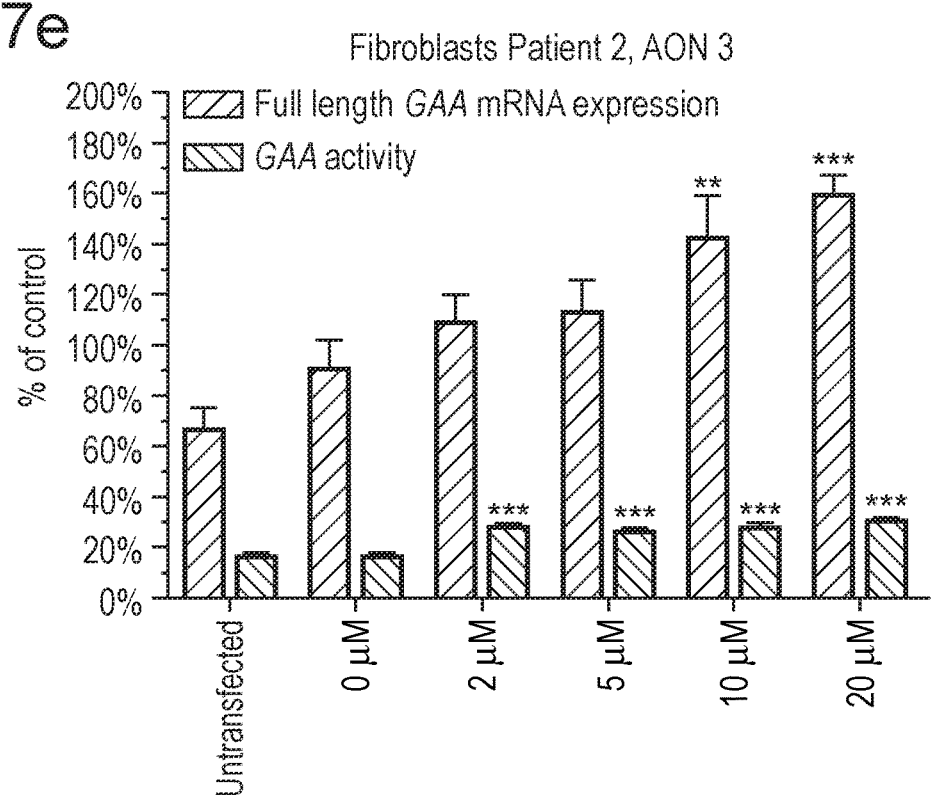
Figure 7F:
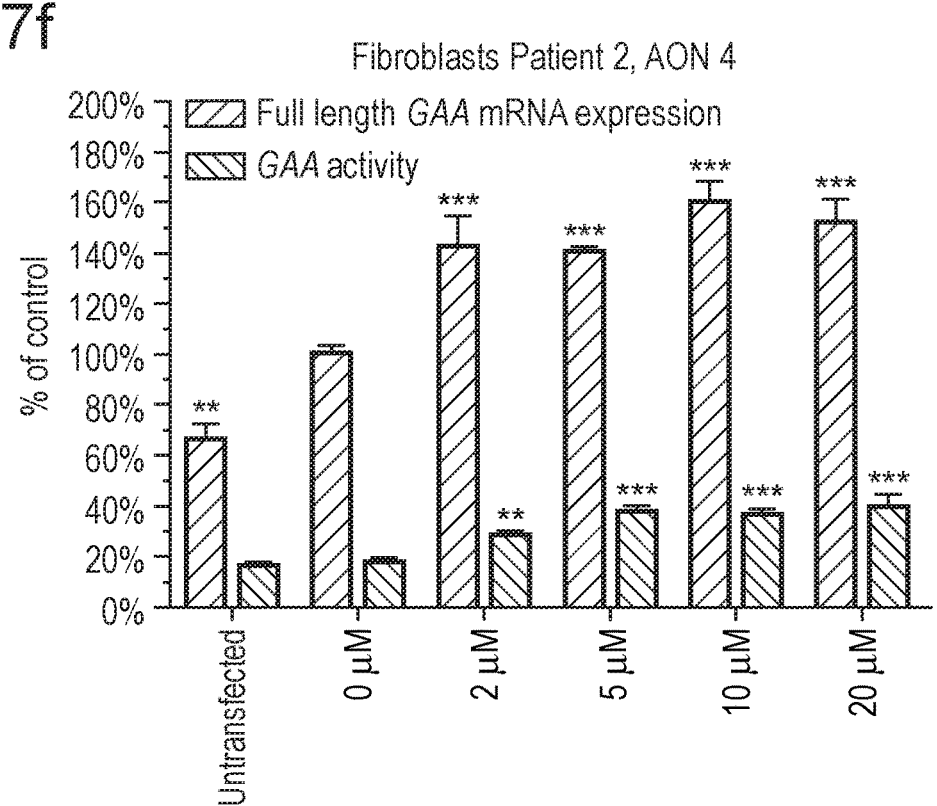

Next, we designed PMO AONs based on the results of the U7 snRNA screen, and tested these in fibroblasts derived from Pompe patient 1 (genotype IVS1, c.525delT; the second allele is not expressed) for promoting GAA exon 2 inclusion (FIG. 2a, FIG. 7a). The putative splicing silencer sequences at c.-32-219 and c.-32-179 were targeted using PMO-based AONs (FIG. 2a). Blocking of c.-32-179 using AONs 3 or 4 resulted in promotion of exon 2 inclusion and enhancement of GAA enzymatic activity, while AONs 1 and 2 that targeted c.-32-219 were inactive (FIG. 2b-e). It is likely that blocking of c.-32-219 may require further optimization of PMO-AON sequences. AONs 3 and 4 also promoted exon inclusion and GAA enzymatic activity in fibroblasts from patient 2 (genotype IVS1, c.923A>C; the second allele is expressed)(FIG. 7e,f). The maximal possible enhancement of GAA enzyme activity using this approach is ~3.5-5 fold: patients with the IVS1 allele have ~10-15% leaky wild type splicing, and full restoration of this allele will amount to a maximum of 50% of healthy controls. AONs 3 and 4 promoted GAA exon 2 inclusion and GAA activity in fibroblasts with ~2.5 fold, indicating that these corrected 50-70% of exon 2 splicing.

Figure 2E:
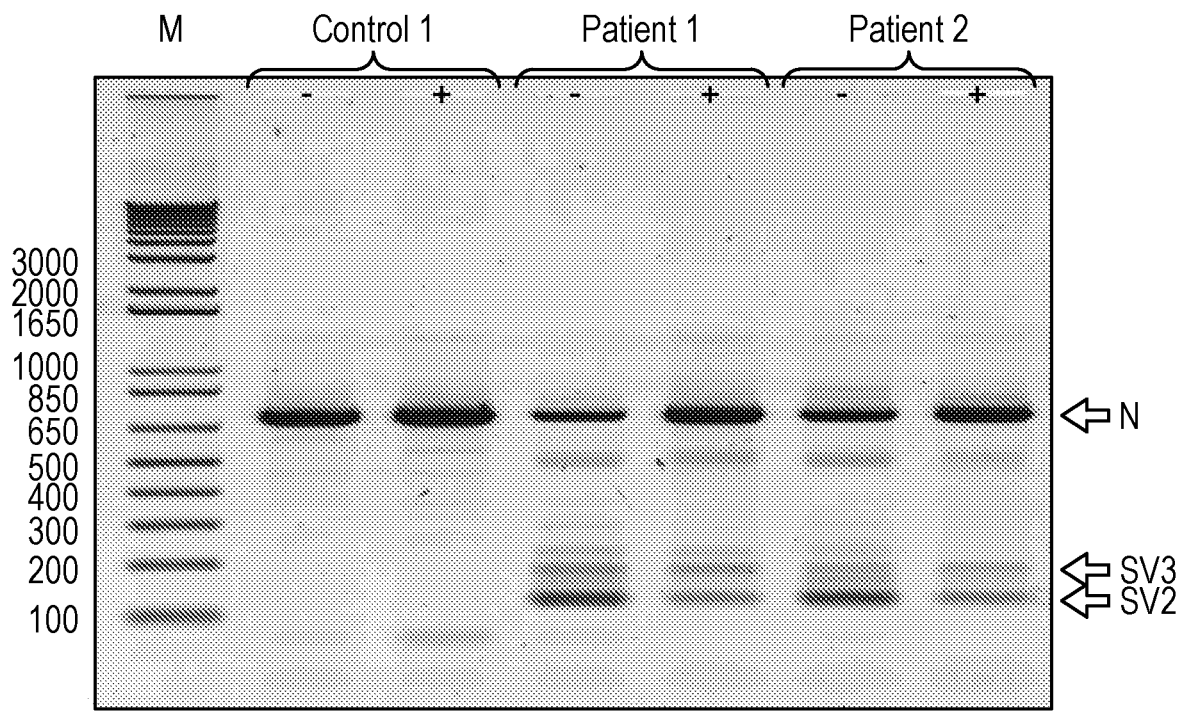
Figure 2F:
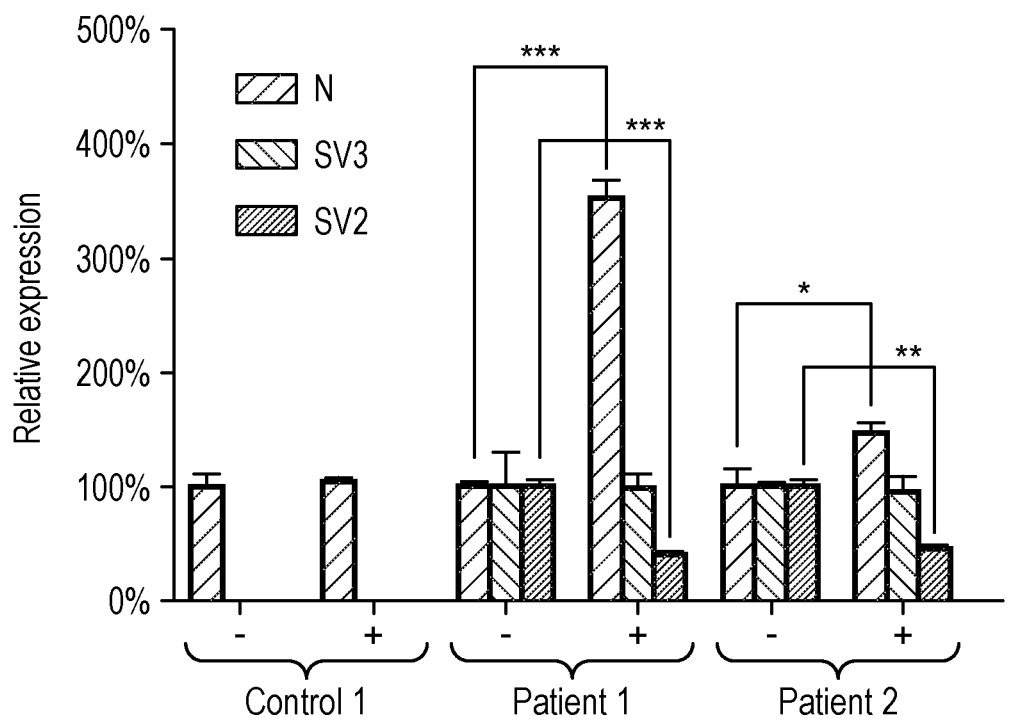
Figure 2F:
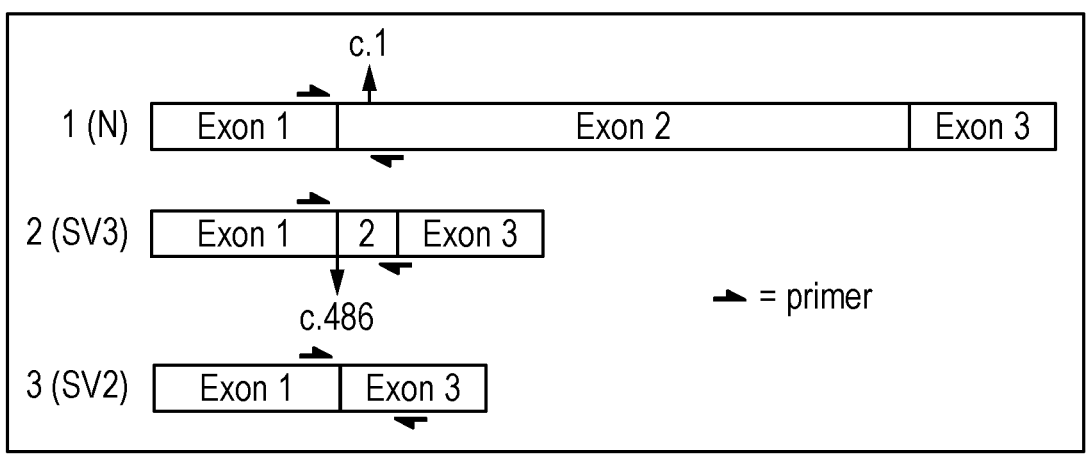

To confirm that AONs acted by modulating splicing rather than total GAA mRNA expression, splicing product-specific RT-qPCR analysis was performed. This showed that AONs 4 enhanced expression of wild type GAA mRNA while it repressed expression of aberrant splicing products SV2 and SV3 (FIG. 2e,f). In addition, AON 4 was ineffective in fibroblasts from a healthy control (FIG. 2e,f). Taken together, PMO AONs 3 and 4 were identified to promote exon 2 inclusion with 50-70% efficiency in fibroblasts from patients with the IVS1 GAA variant.

Splicing can occur in a tissue-specific manner, and it was unknown how the IVS1 variant and the putative splicing silencer would operate in differentiated skeletal muscle cells, which are affected in Pompe disease. To test this, we first used primary myoblasts derived from healthy controls and Pompe patients. However, these showed limited and heterogeneous capacity to proliferate and differentiate into multinucleated myotubes, which hindered the use of myoblasts for quantitative analysis of AONs (data not shown). A similar reduction of proliferation and differentiation capacity upon passaging of primary myoblasts has been reported previously[45].

Figure 8A:
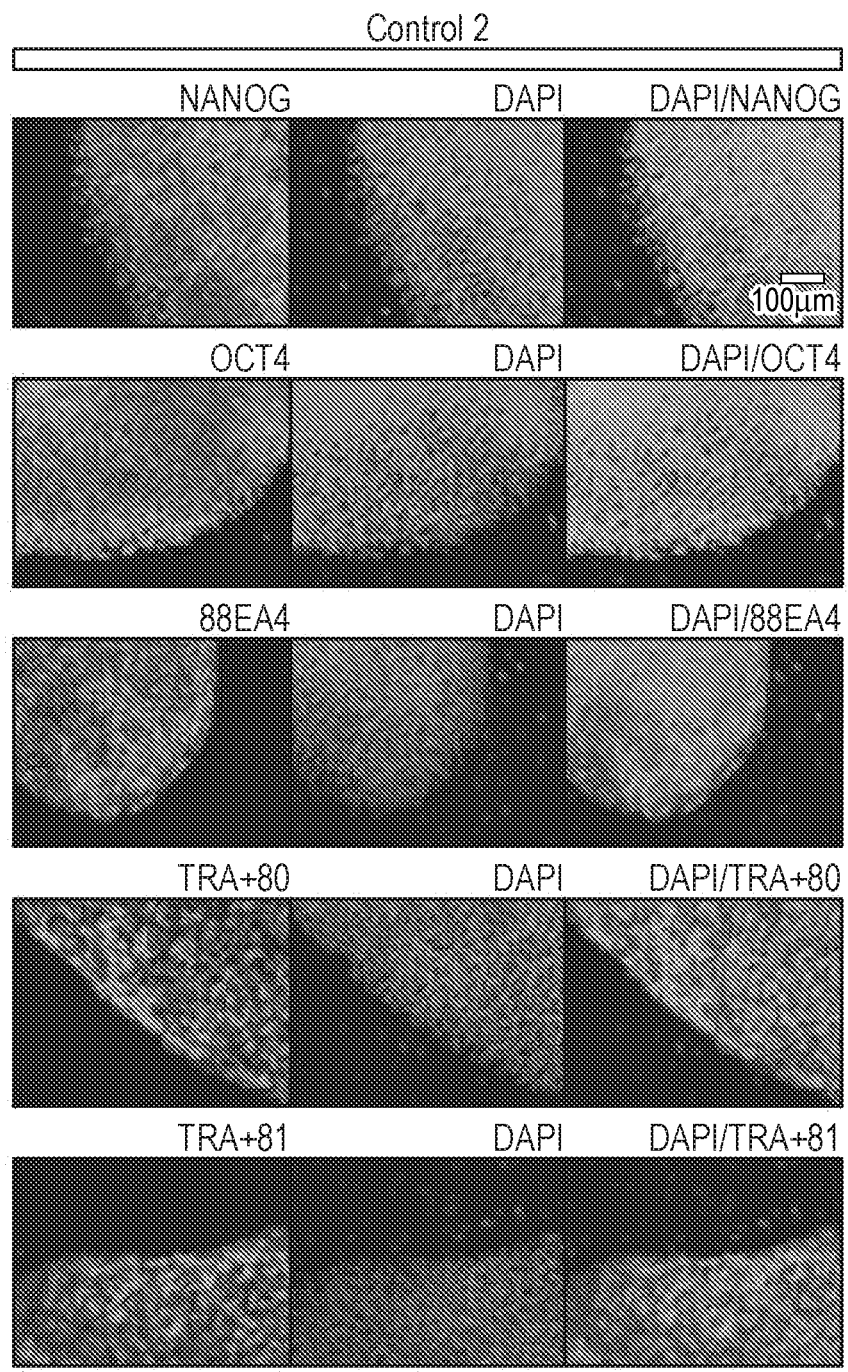
Figure 8B:
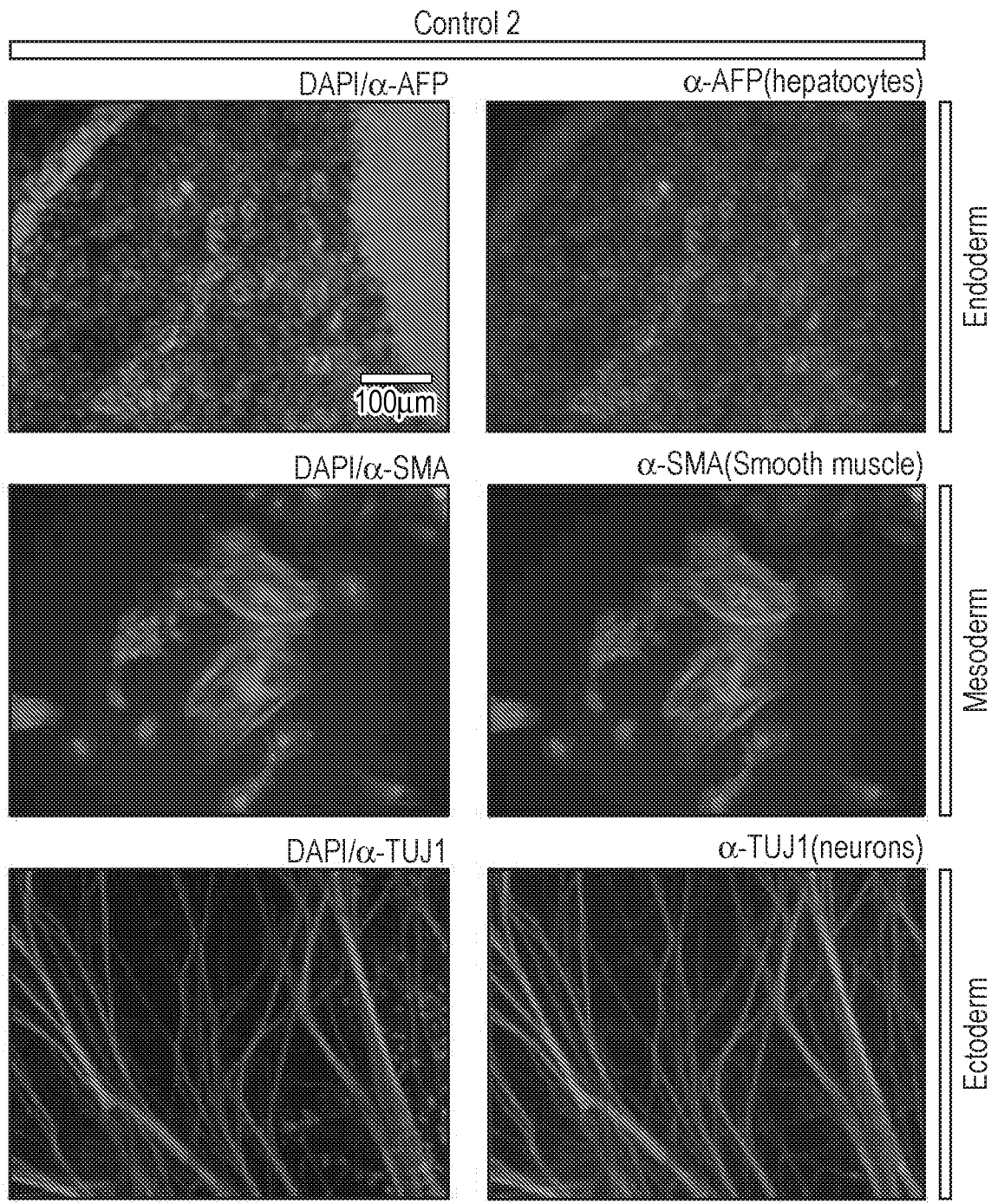
Figure 8D:
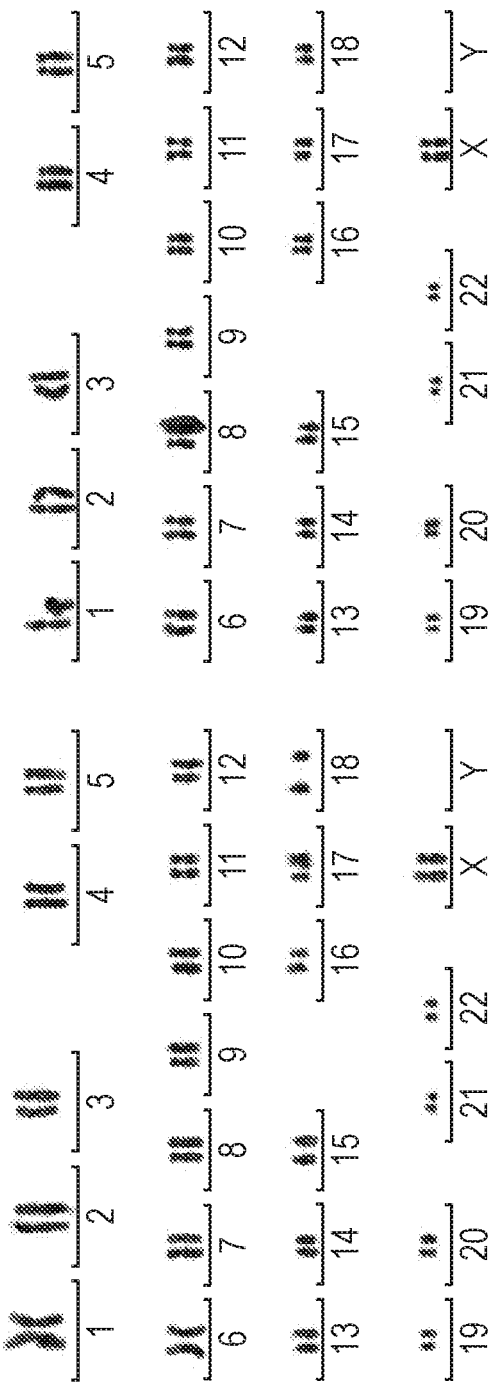
Figure 8E:
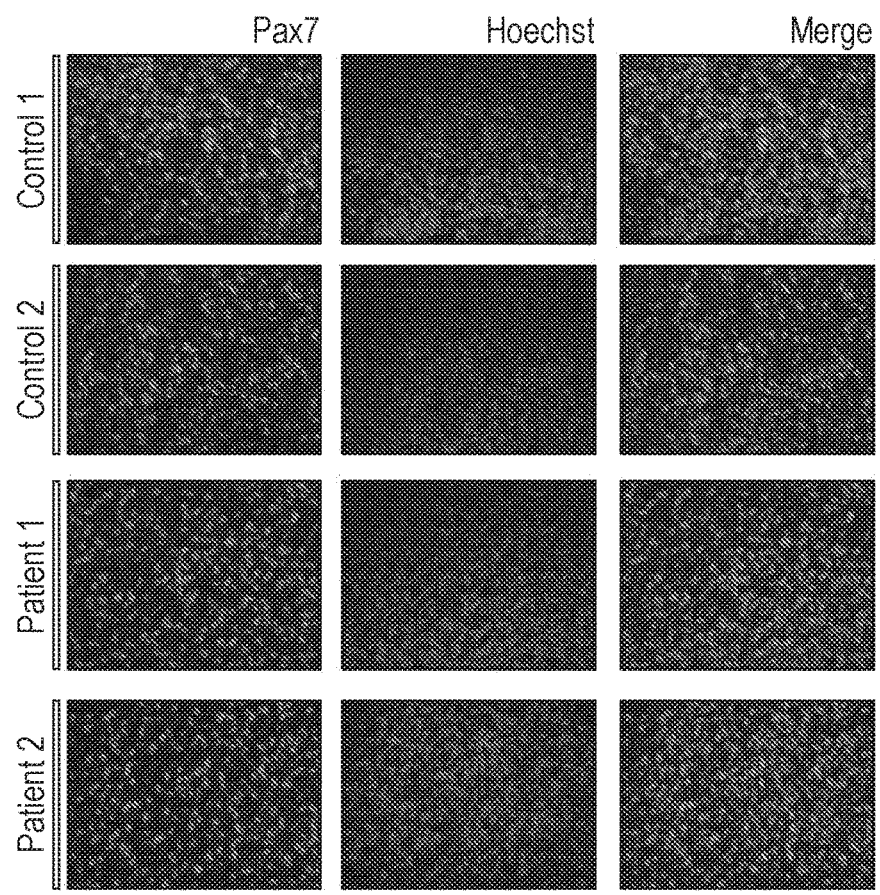
Figure 8F:
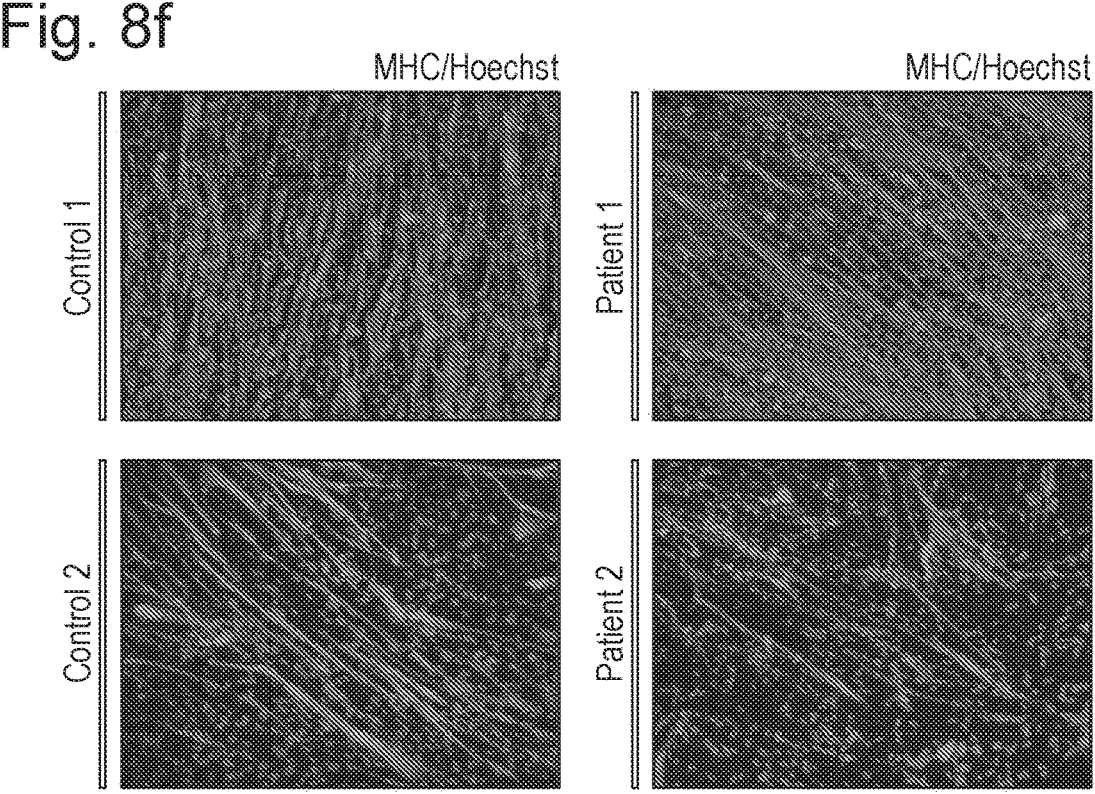
Figure 8H:
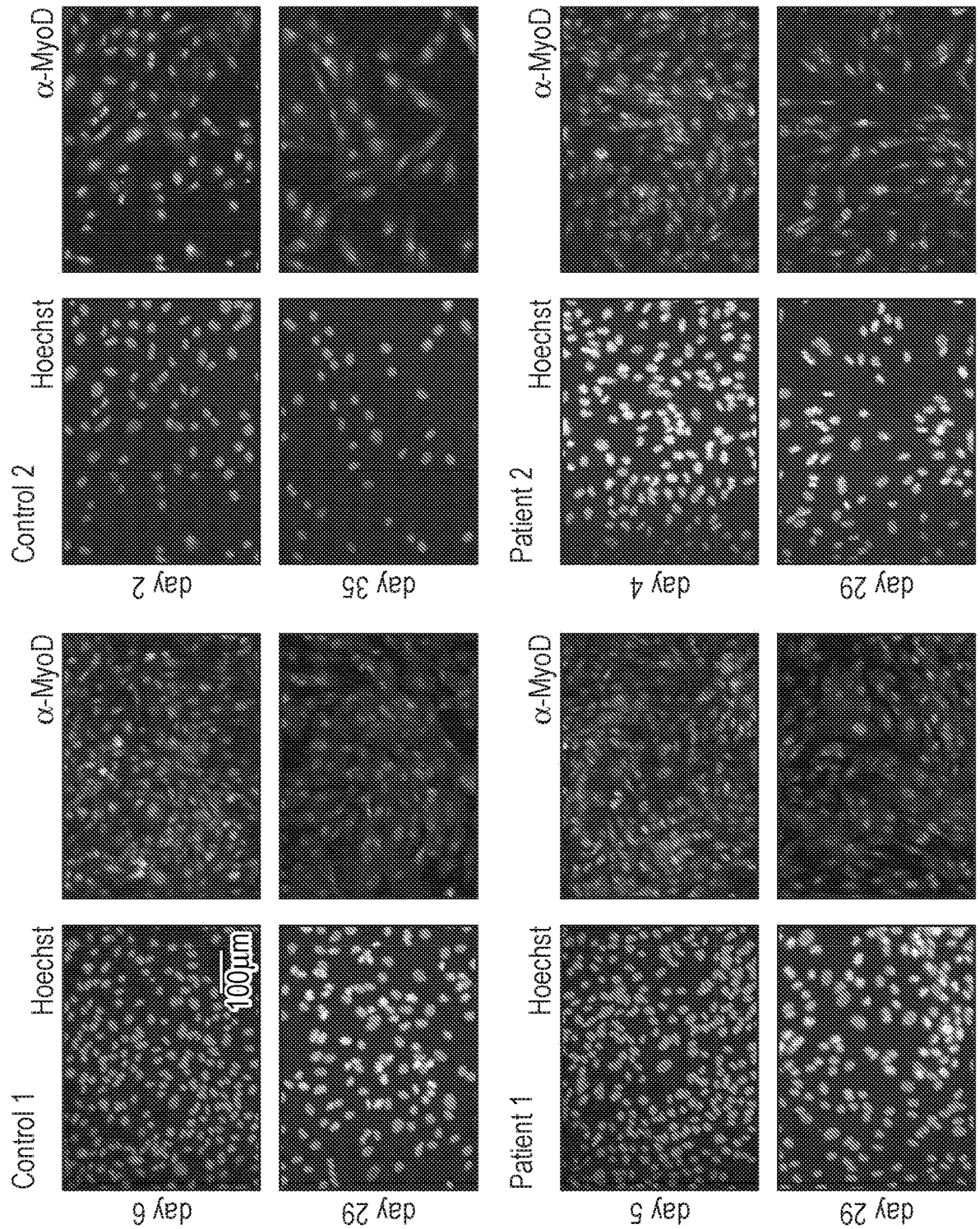

We therefore developed an in vitro model for childhood/adult Pompe disease using iPS cells (see also co-pending patent application NL 2017078). Reprogramming of fibroblasts and characterization of iPS cells are described in FIG. 8a-d. iPS cells from two patients and two healthy controls were differentiated into myogenic progenitors using a transgene-free protocol modified from Borchin et al.[37]. While this method yielded purified Pax7+ myogenic progenitors after a 35-day protocol (FIG. 8e), the recovery after FACS sorting was low. Between 50,000 and 500,000 cells could be purified starting from a full 10 cm dish of iPS cells, yielding only a few wells in a tissue culture dish that could be used for testing AONs. In addition, the capacity to differentiate into multinucleated myotubes varied largely between individual purifications (FIG. 8f). It was therefore not possible to reproducibly test the effect of AONs on splicing in freshly isolated iPS-derived myogenic progenitors.

Figure 3A:
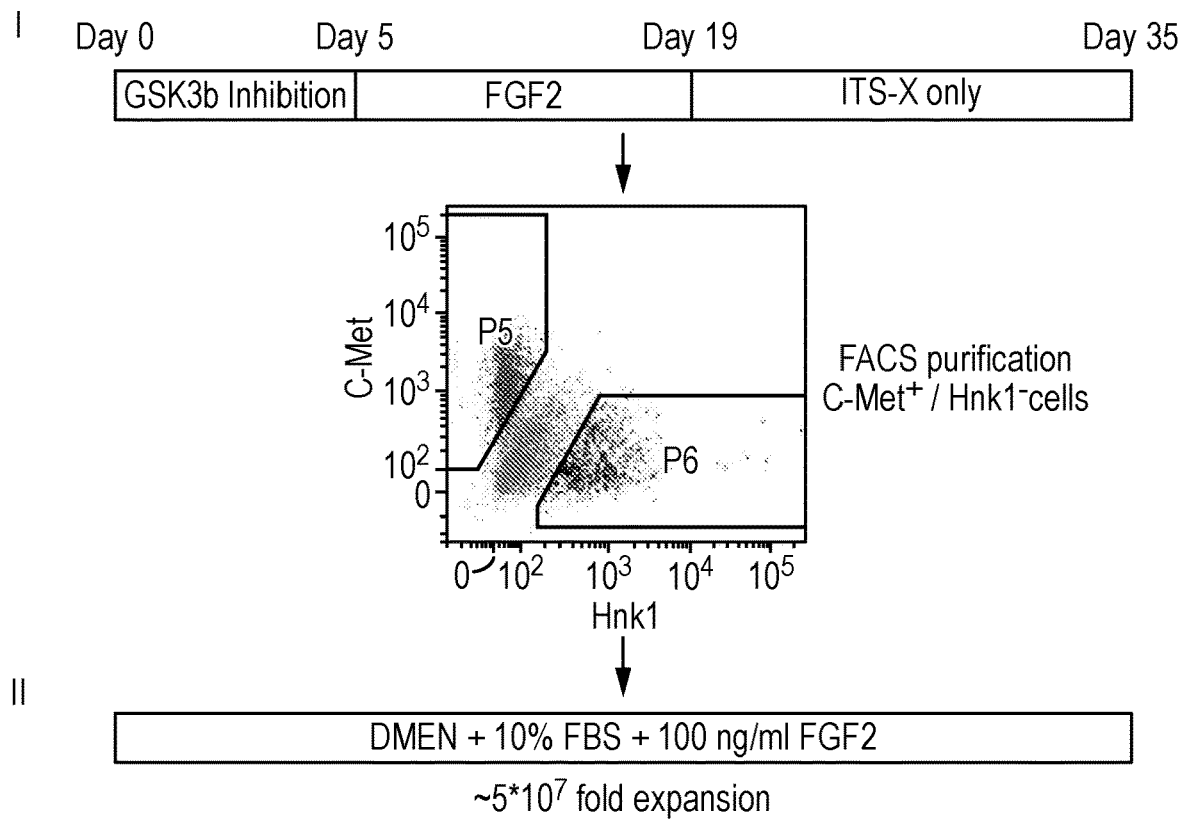
Figure 3B:
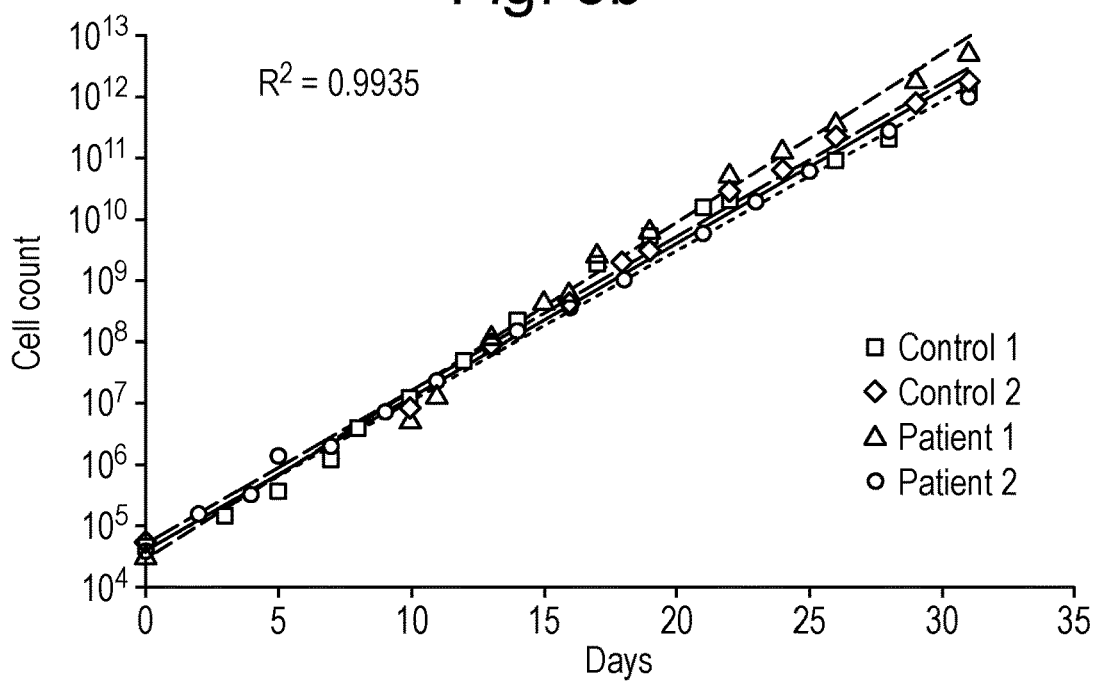
Figure 3C:
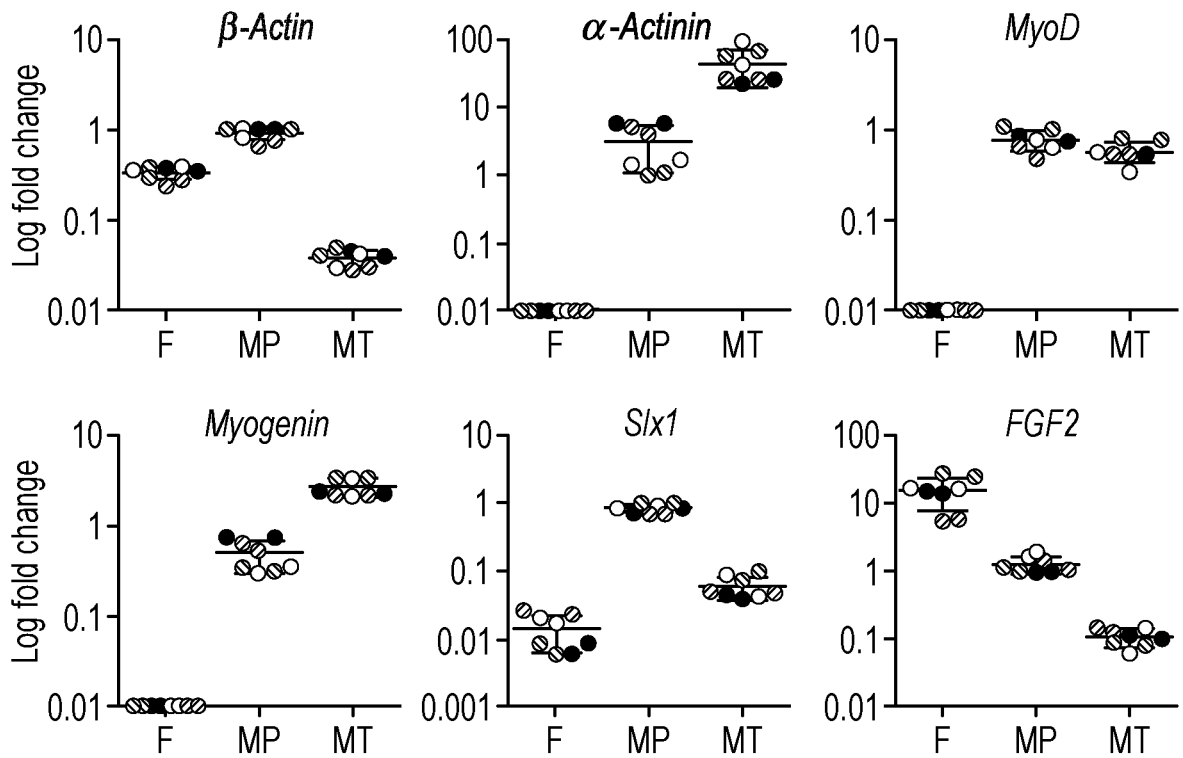
Figure 3D:
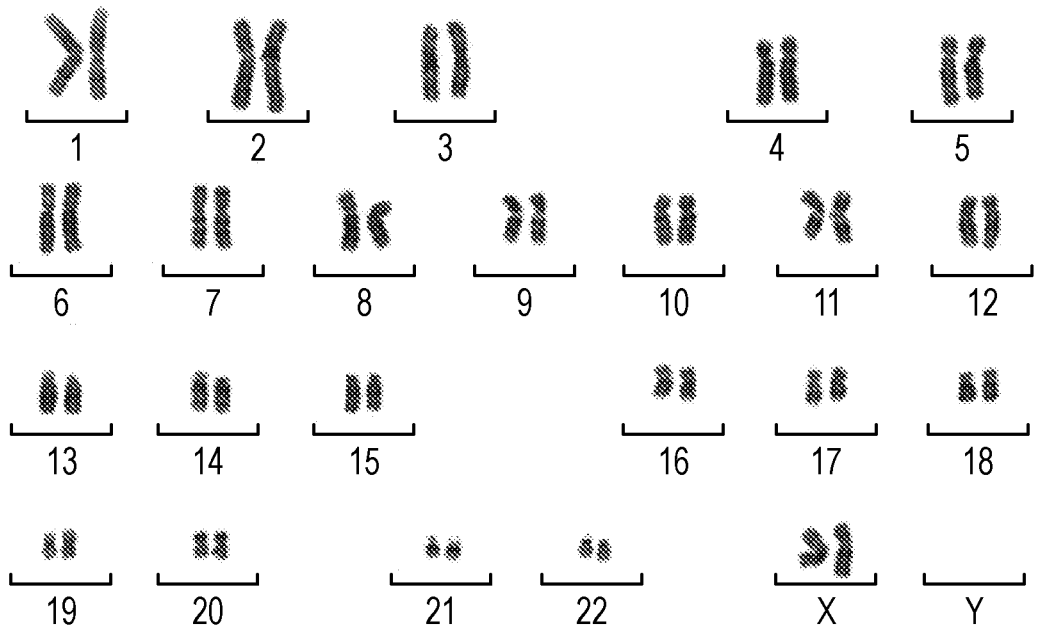
Figure 8I:
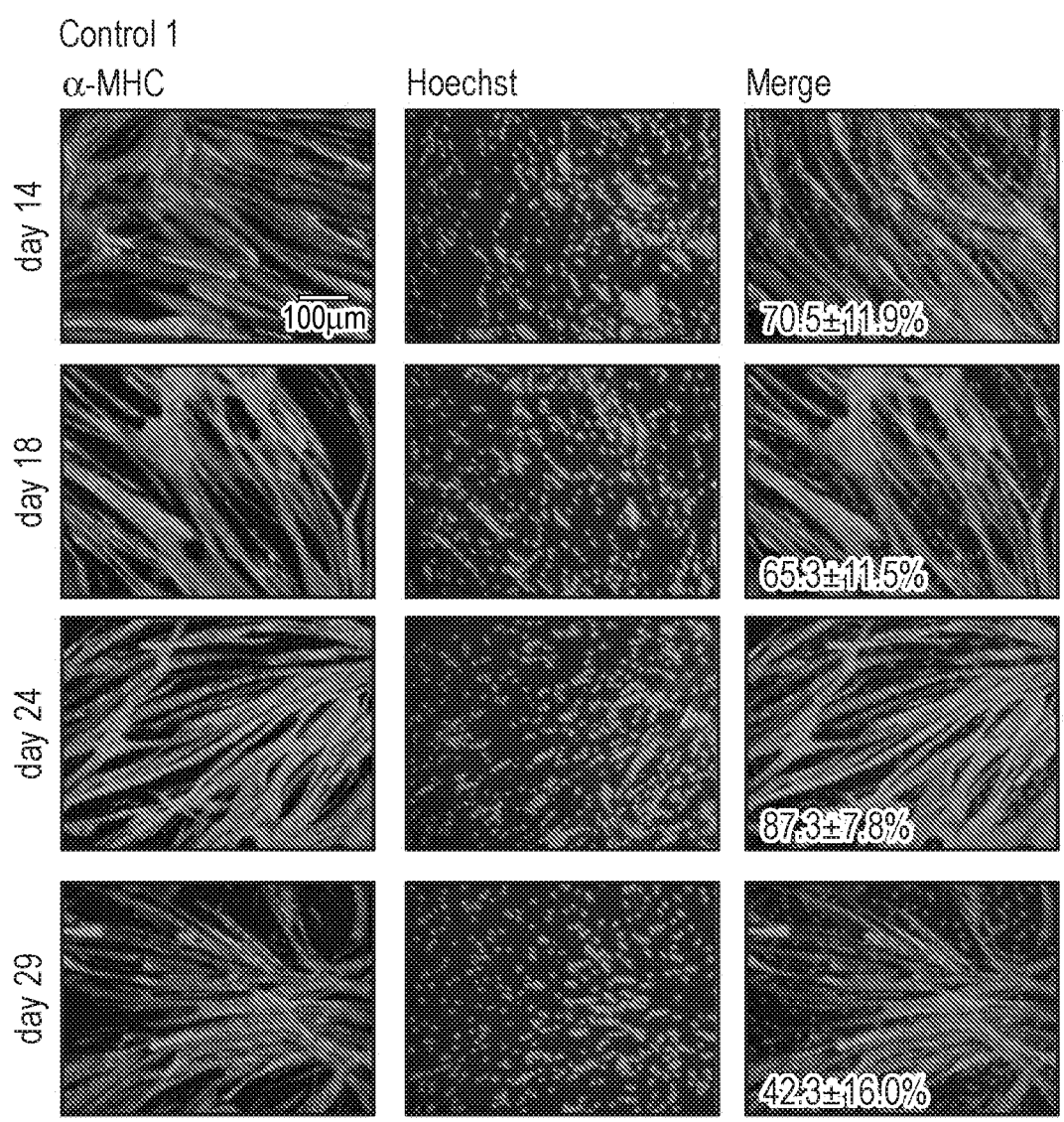

To address this, we tested cell culture conditions aiming to expand purified Pax7+ cells while maintaining proliferative and differentiation capacity. Out of 5 media tested medium 5 supported prolonged proliferation of myogenic cells (FIG. 3a). Critical components included DMEM as basal medium and FGF2, which supports proliferation. All 4 lines (2 Pompe patients, 2 healthy controls) could be expanded with nearly identical proliferation rates at an average of 29.4±1.3 hrs/cell cycle with at least $5\times10^7$ fold to yield at least $1\times10^{12}$ cells (FIG. 3b). At several time points during the expansion phase, cells could be frozen in viable state and used for subsequent expansion. Proliferating myogenic progenitors were characterized by high expression of the myogenic markers MyoD, Myogenin, Six1, and Six4, moderately high expression of the myogenic differentiation marker α-actinin and of FGF2, while the neural crest marker Sox1 was not expressed (FIG. 3c, FIG. 8g,h). Upon expansion, the karyotype remained normal (FIG. 3d). In addition, at any stage of expansion, cells could be differentiated into multinucleated myotubes in a highly reproducible manner (tested in >500 differentiations performed to date) (FIG. 3e, FIG. 8i). Multinucleated myotubes showed high expression of the myogenic differentiation markers Myosin Heavy Chain (MHC) (FIG. 3e) and α-actinin (FIG. 3c). The lysosomal markers LAMP1 and LAMP2 were expressed at similar levels in myogenic progenitors and myotubes from healthy controls and patients (FIG. 8g). This suggests that Pompe disease pathology, which includes enlarged lysosomes and elevated expression of LAMP1/2 in a subset of skeletal muscle fibers in patients[46], has not advanced to critical levels that affect lysosomal size and numbers in vitro, which is consistent with the late-onset phenotype of childhood/adult onset Pompe disease. We conclude that the expansion protocol reproducibly provided the amounts of purified iPS-derived myotubes that were required for the quantitative analysis of AONs on splicing.

Figure 4A:
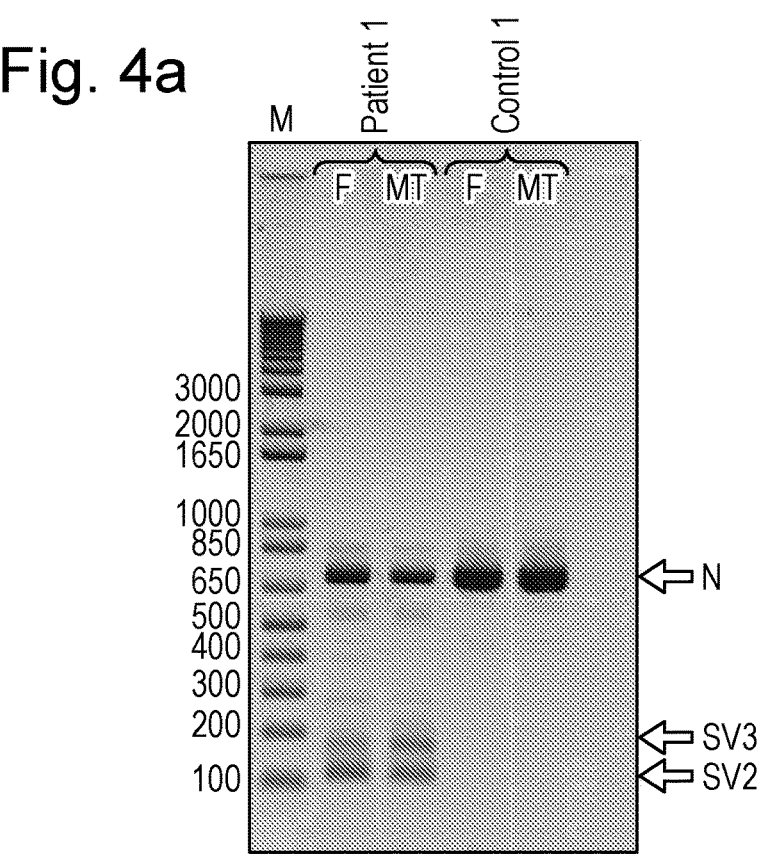
Figure 4B:
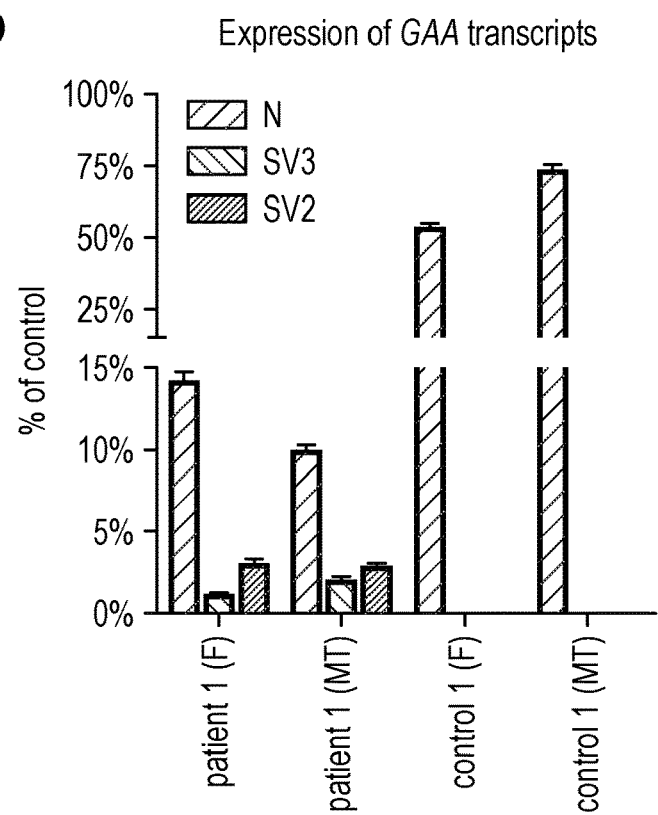

We expanded myogenic progenitors, differentiated them in a four-day protocol into multinucleated myotubes, and analyzed GAA splicing by flanking exon RT-PCR and quantitative RT-qPCR of splicing products. This showed leaky wild type splicing, and partial and complete skipping of exon 2 in patient-derived myotubes, but not in myotubes from healthy controls, similar to primary fibroblasts (FIG. 4a,b). This confirmed that the IVS1 variant caused aberrant splicing of exon 2 in skeletal muscle cells.

Figure 4C:
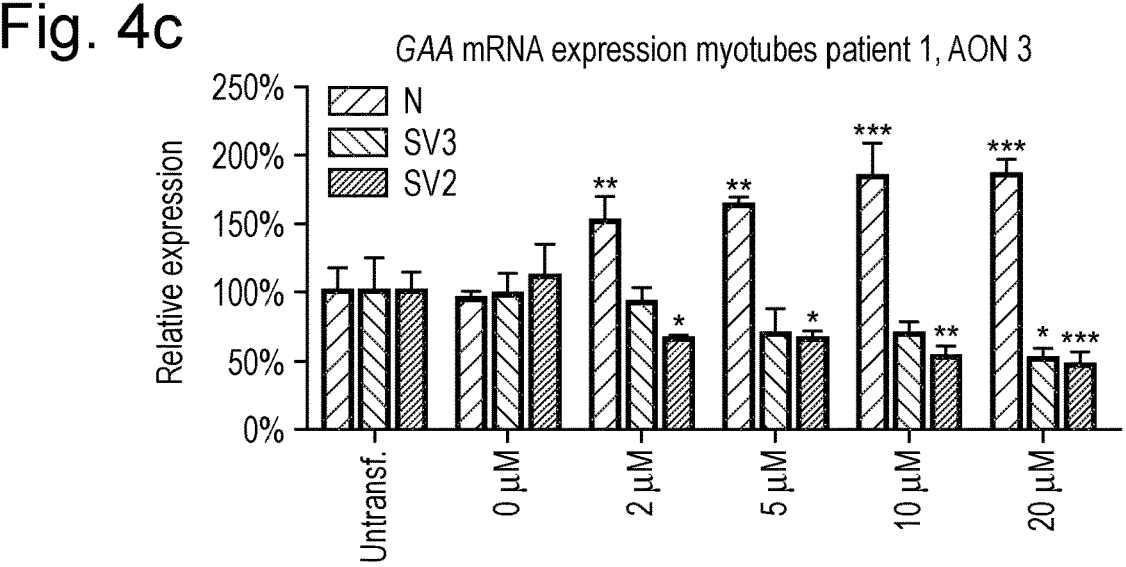
Figure 4D:
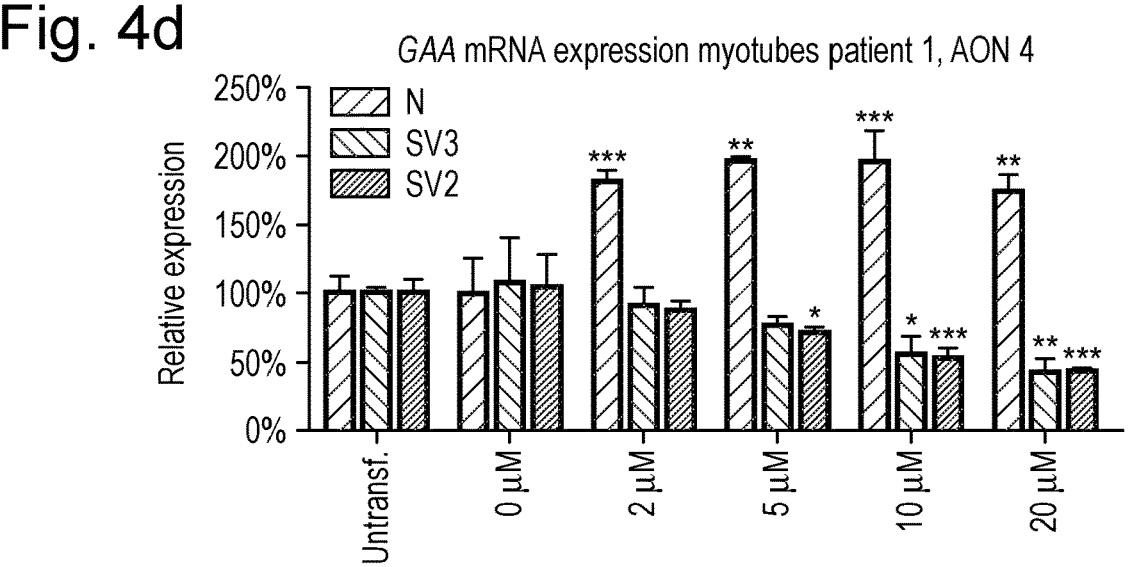
Figure 4E:
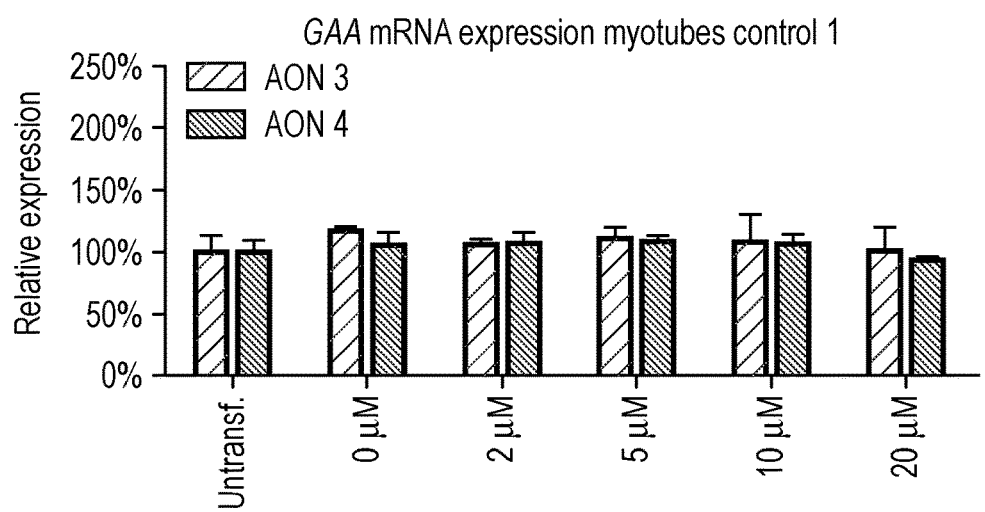
Figure 4F:
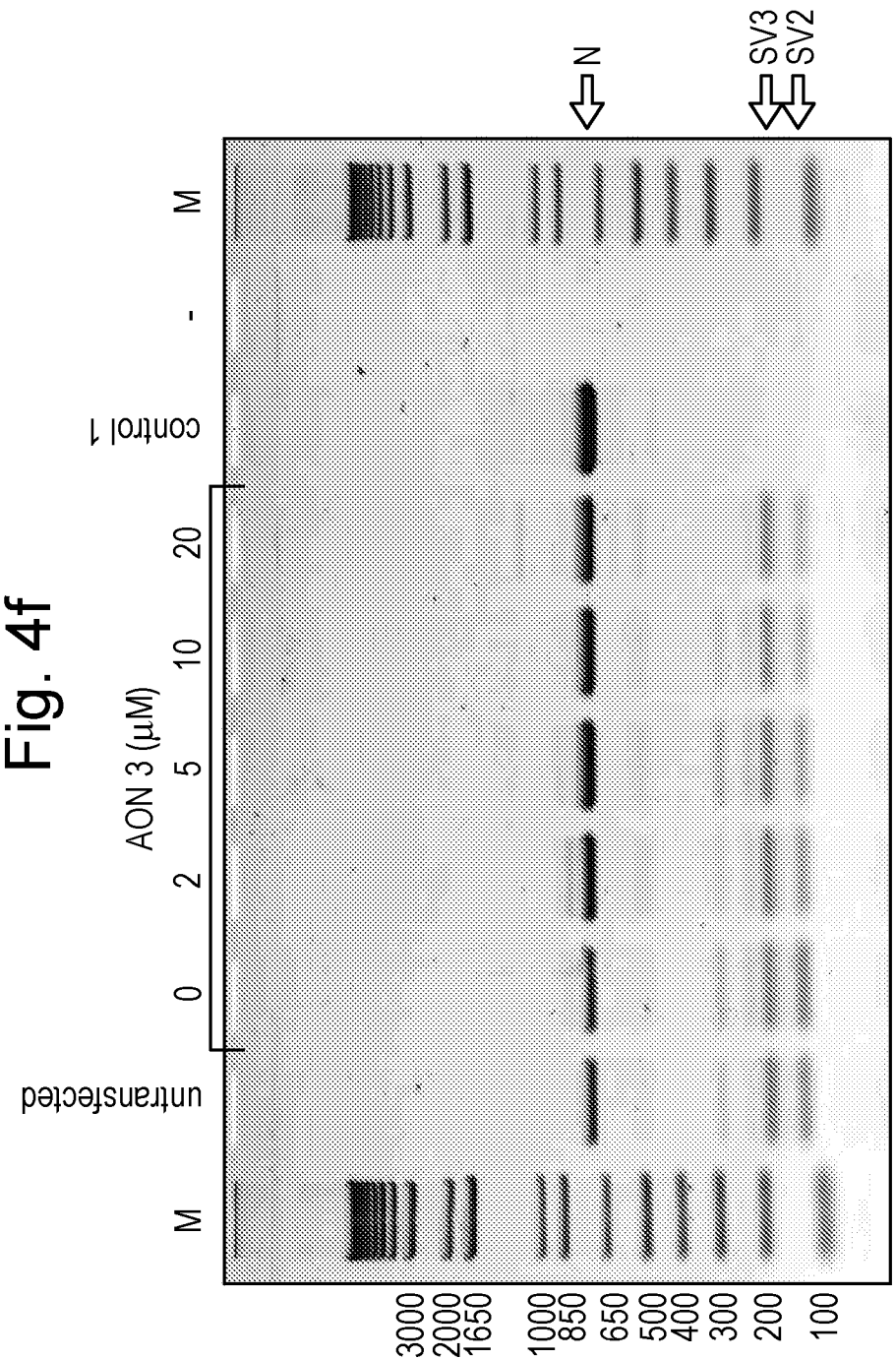
Figure 4G:
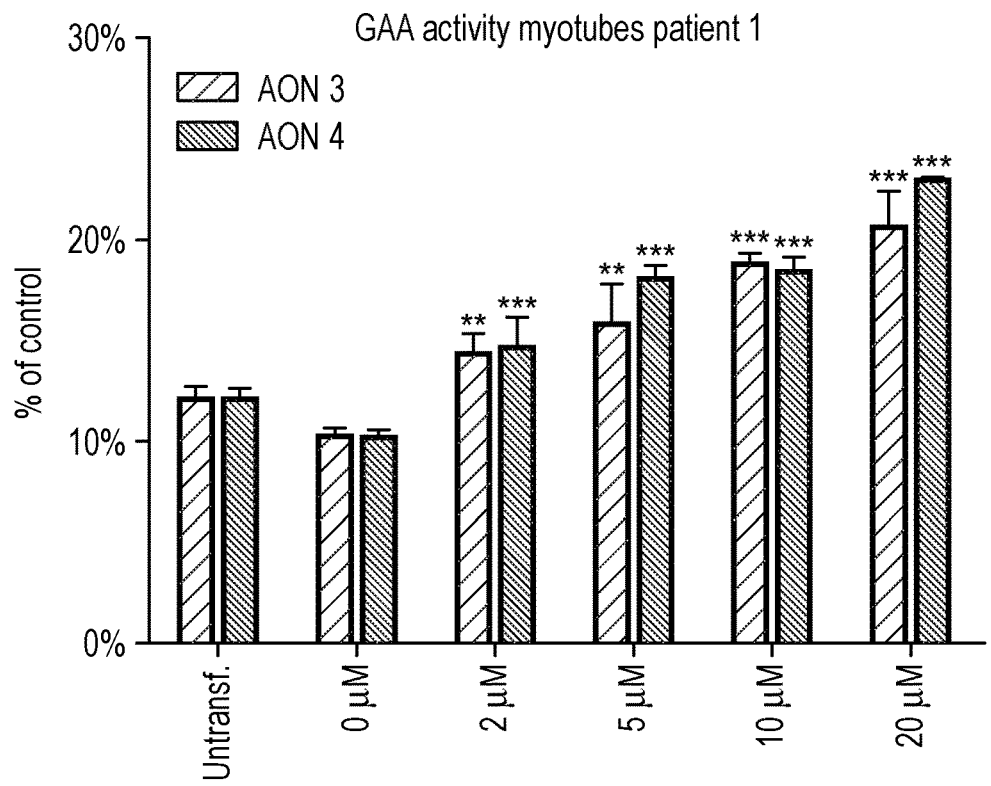
Figure 4H:
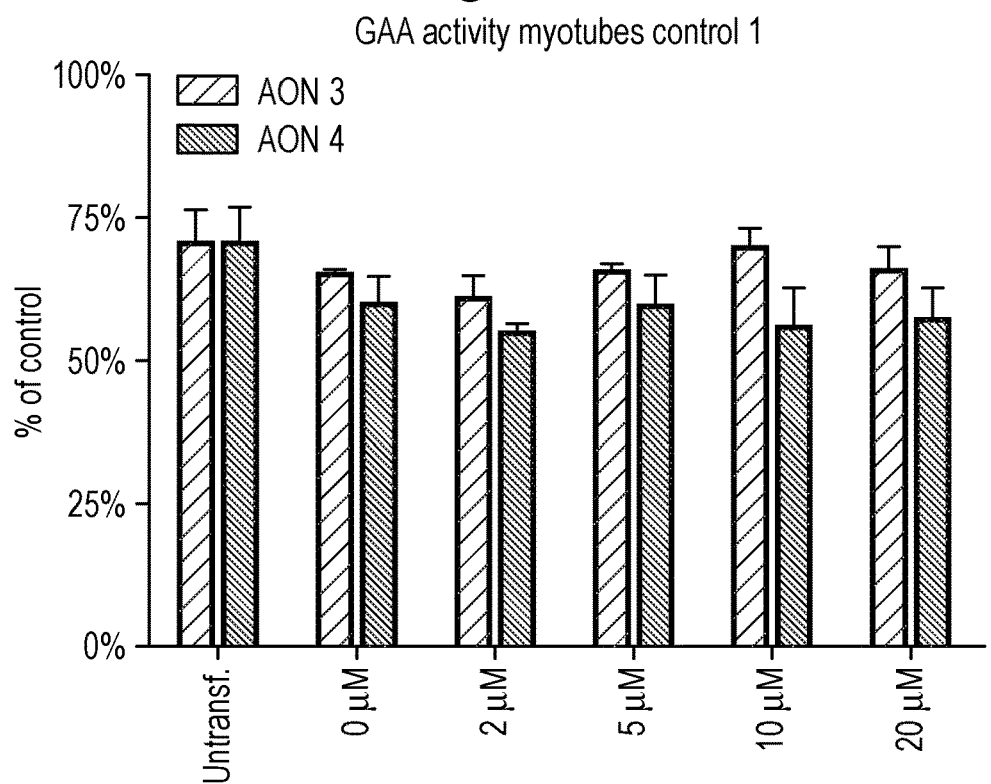
Figure 4I:
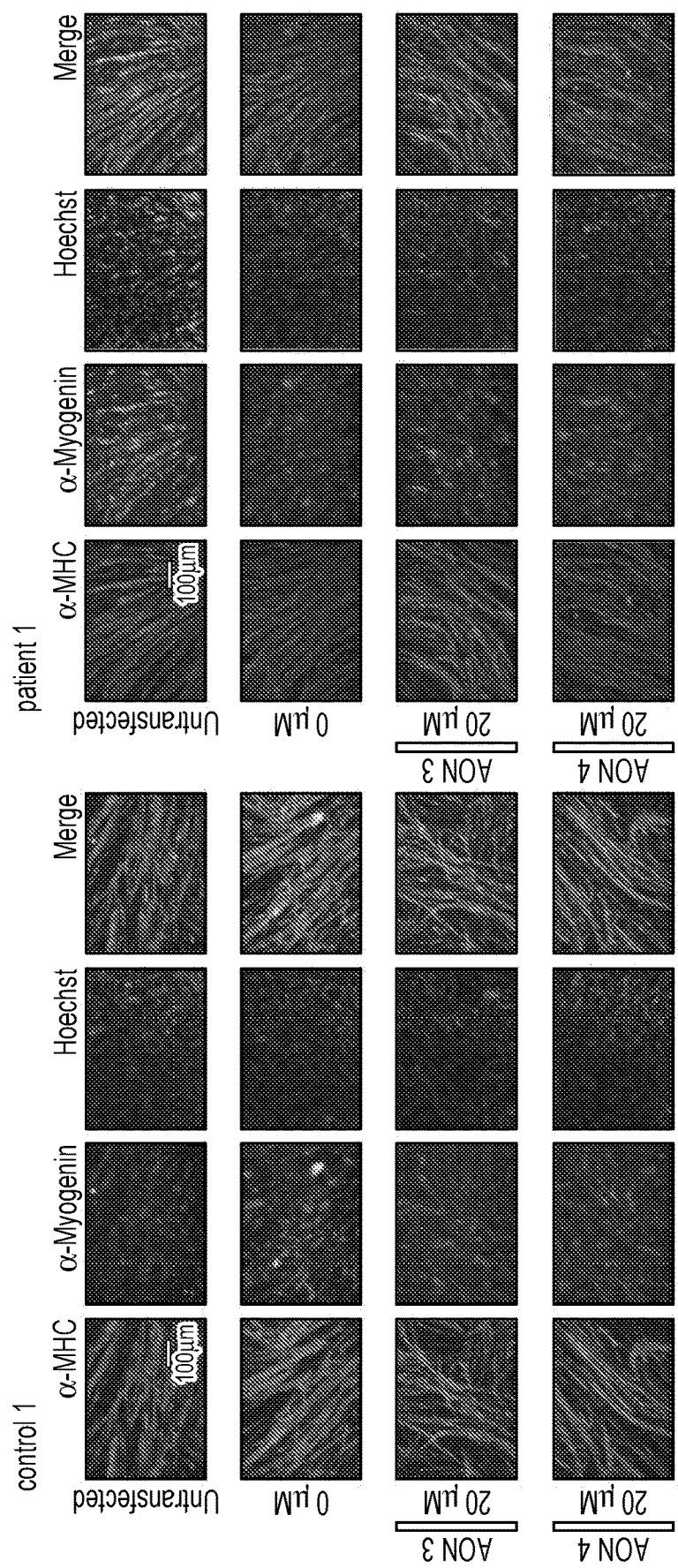
Figure 9A:
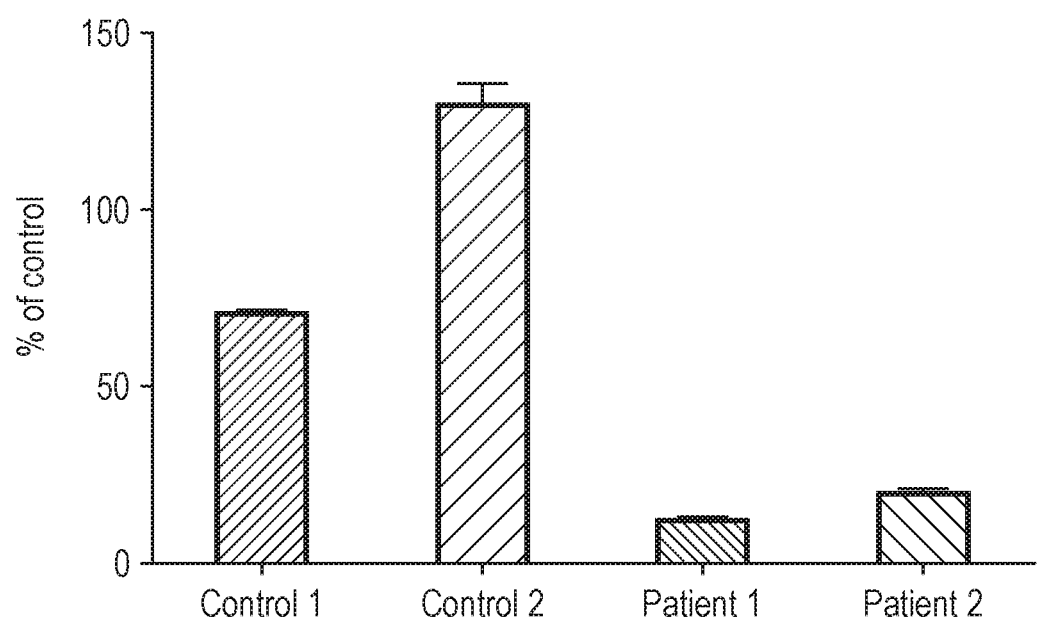
Figure 9B:
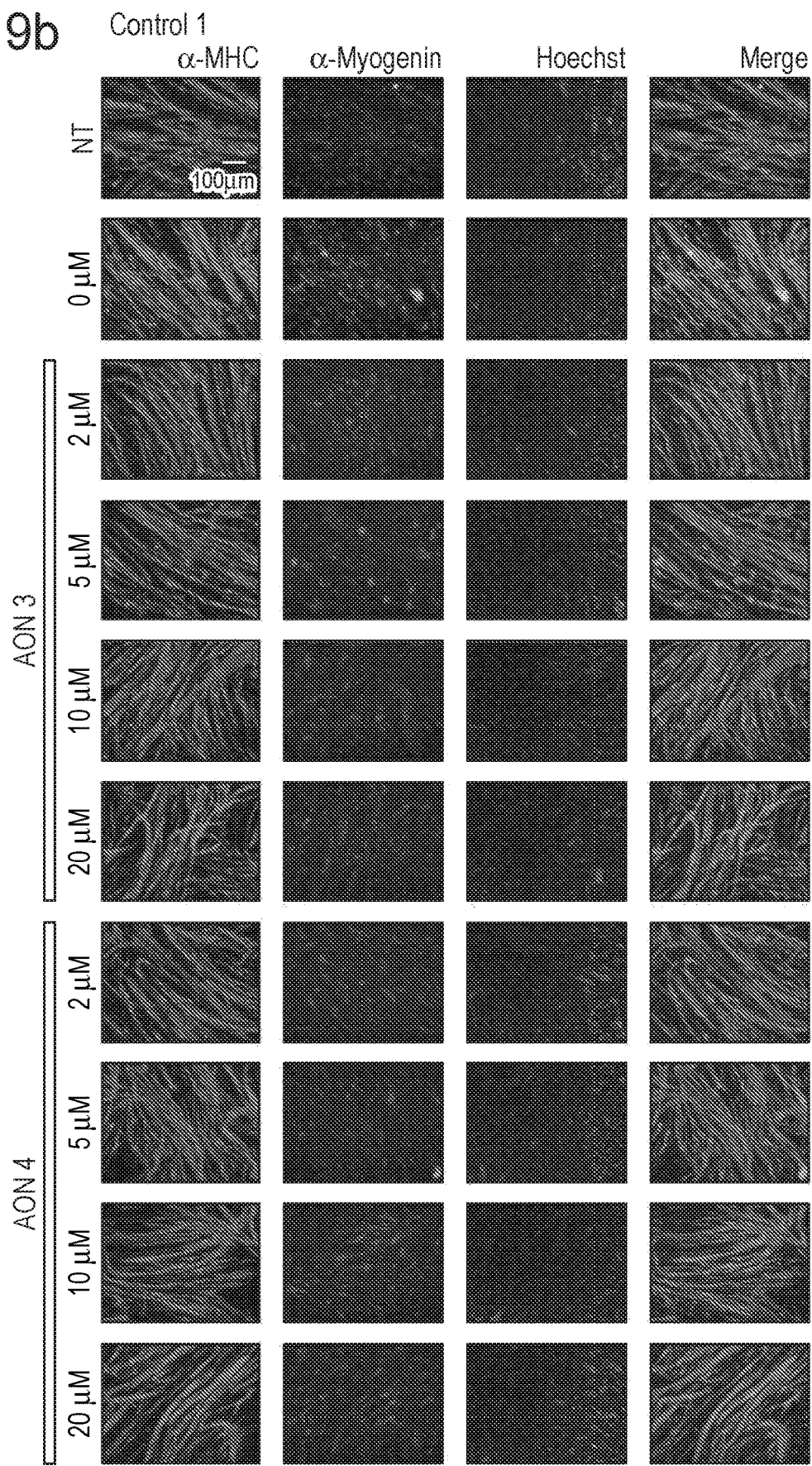
Figure 9B:
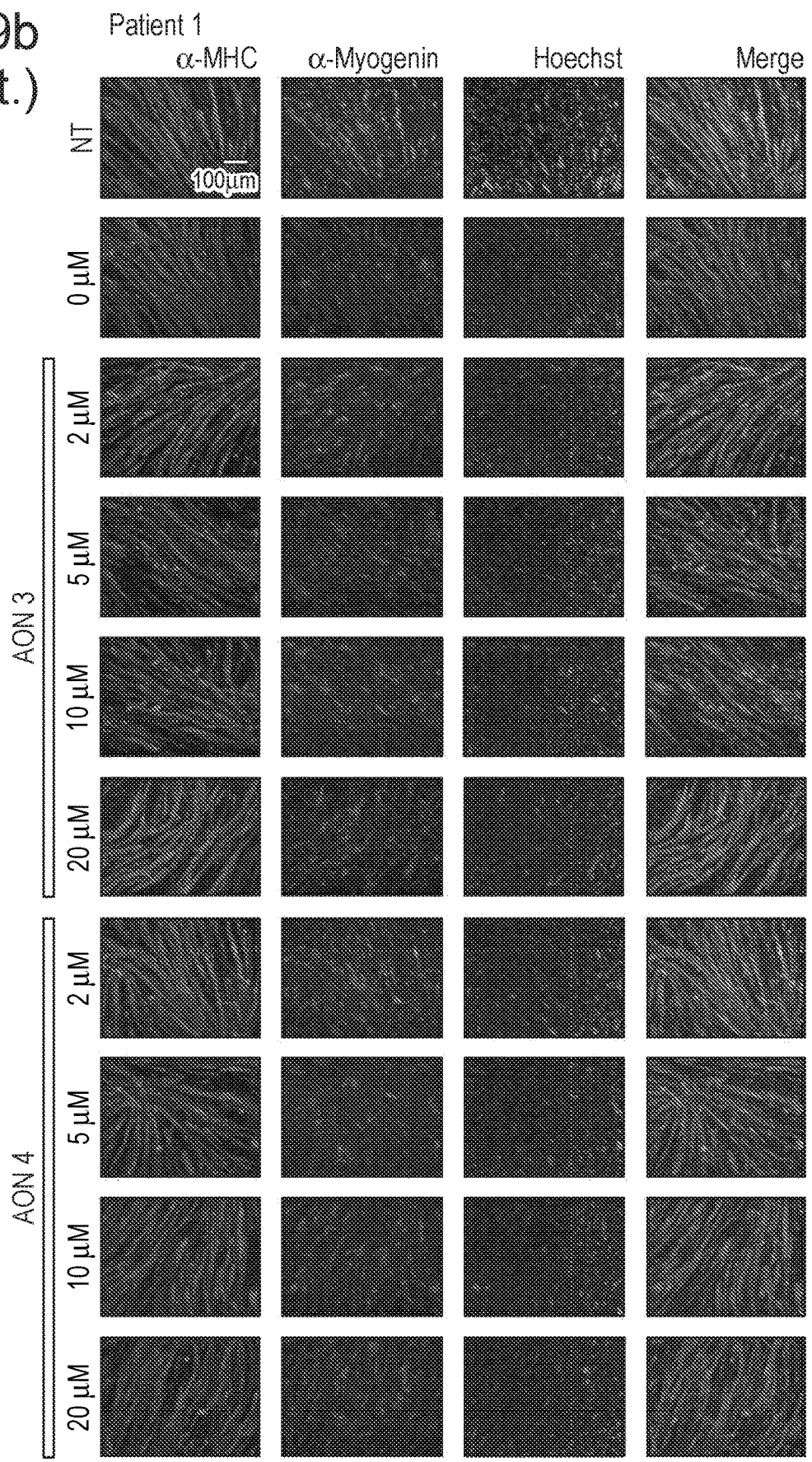
Figure 9C:
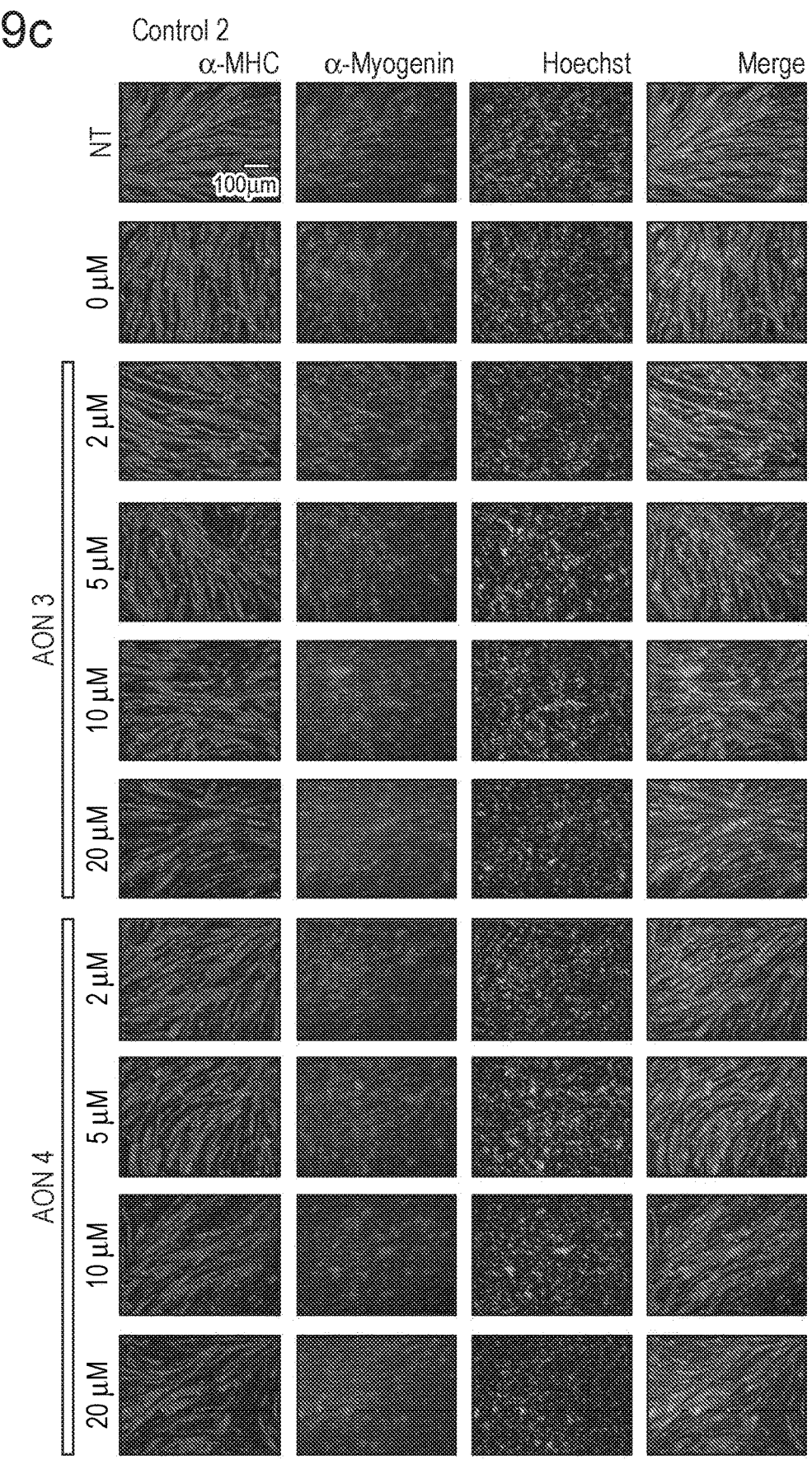
Figure 9C:
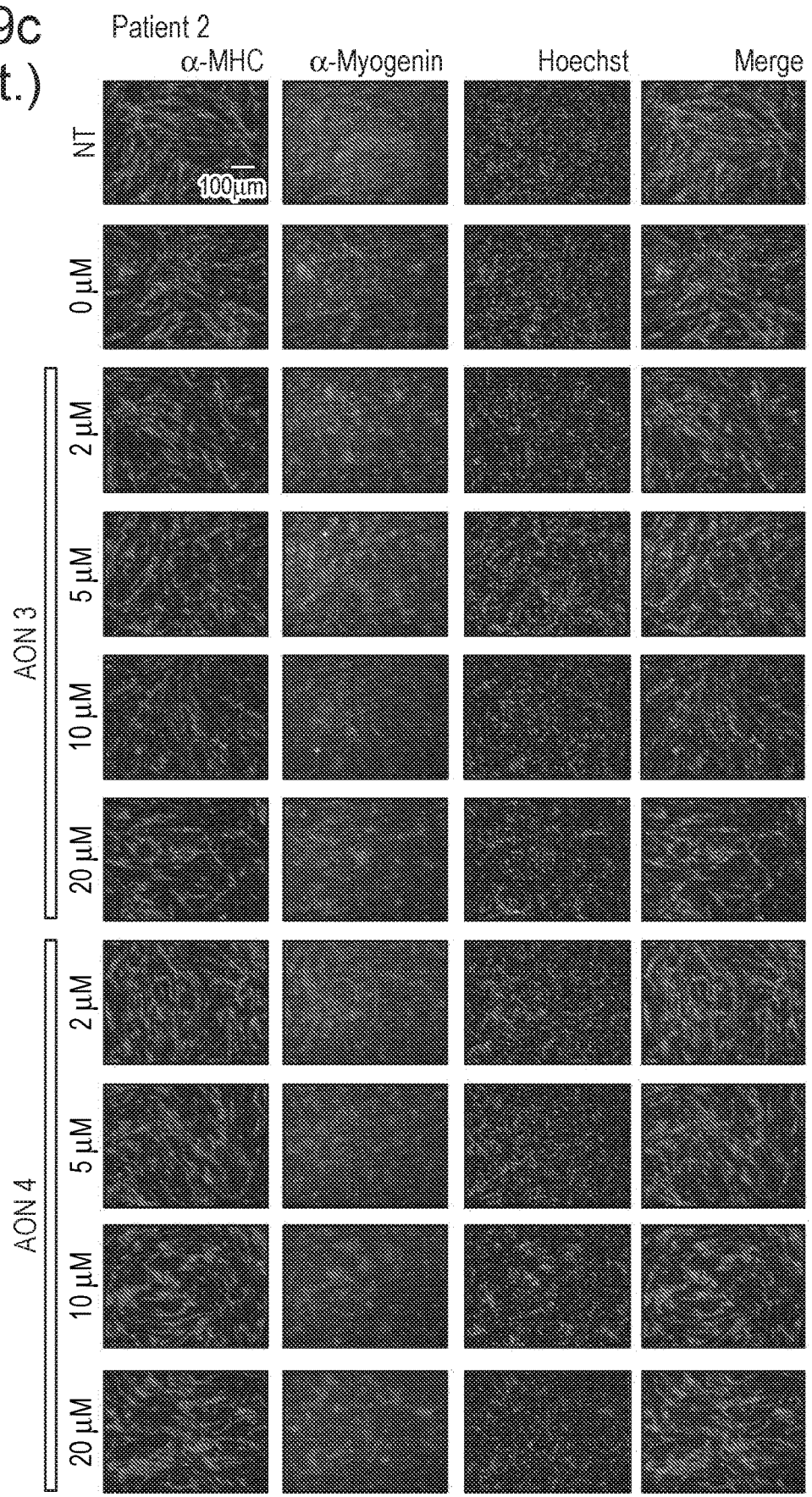
Figure 9D:
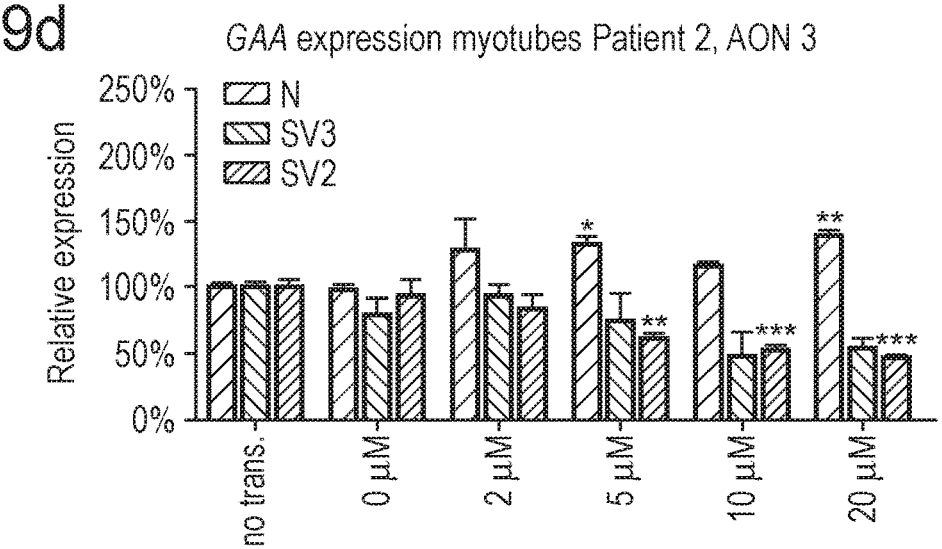
Figure 9E:
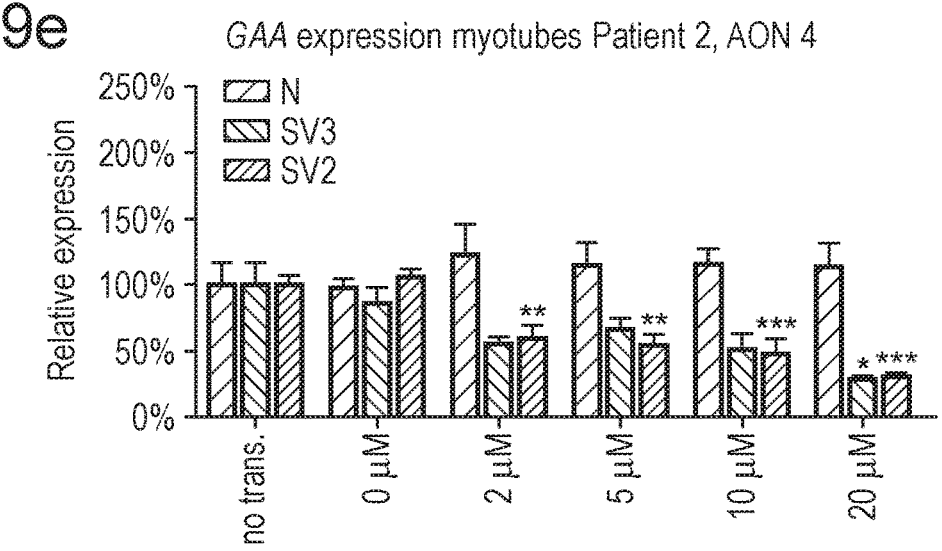
Figure 9F:
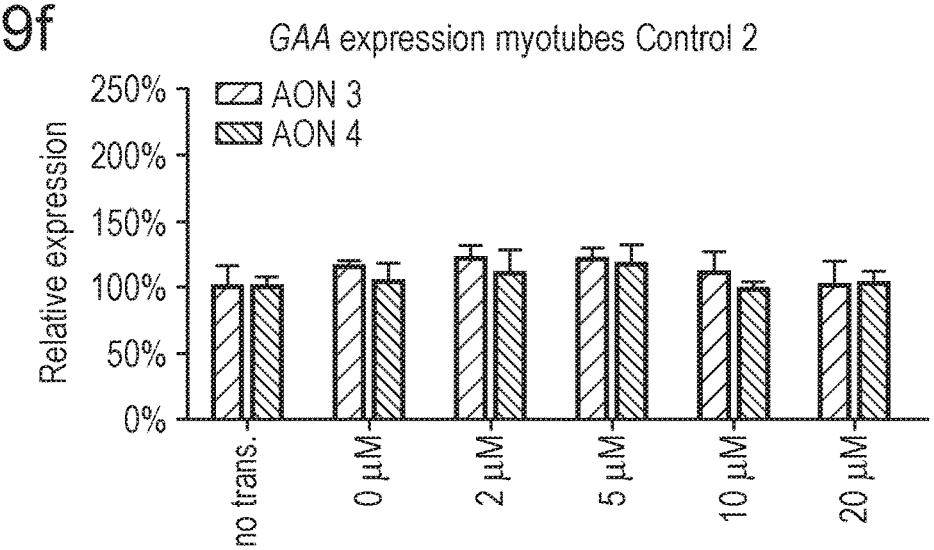
Figure 9G:
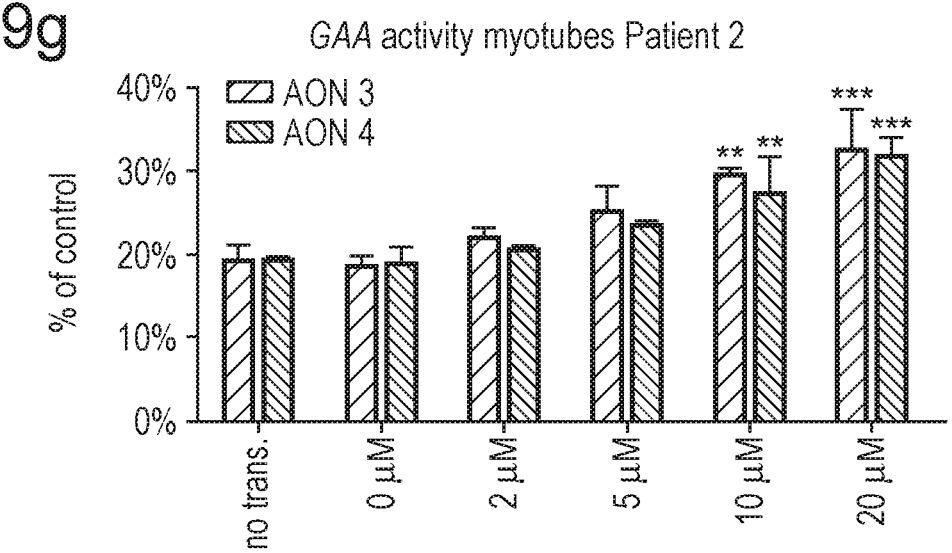
Figure 9H:
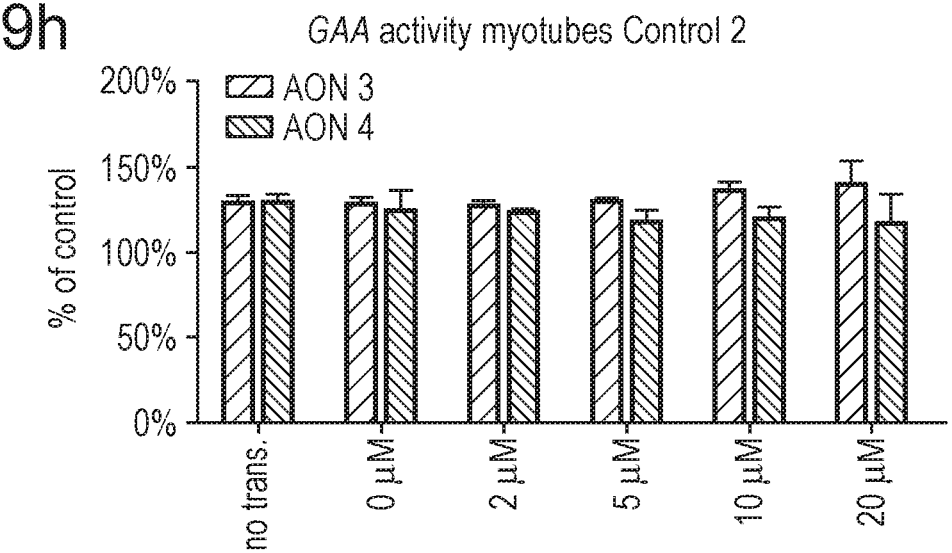
Figure 9I:
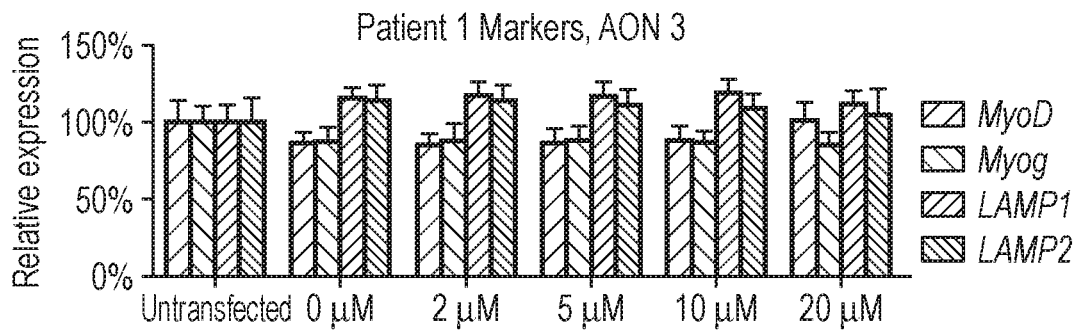
Figure 9I:
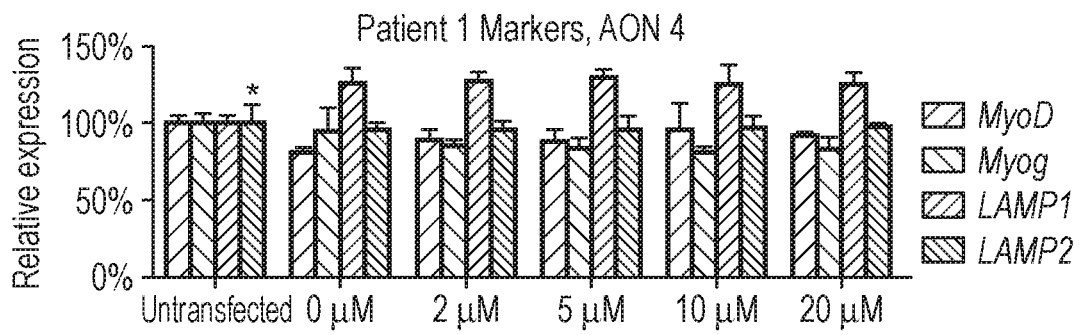
Figure 9I:
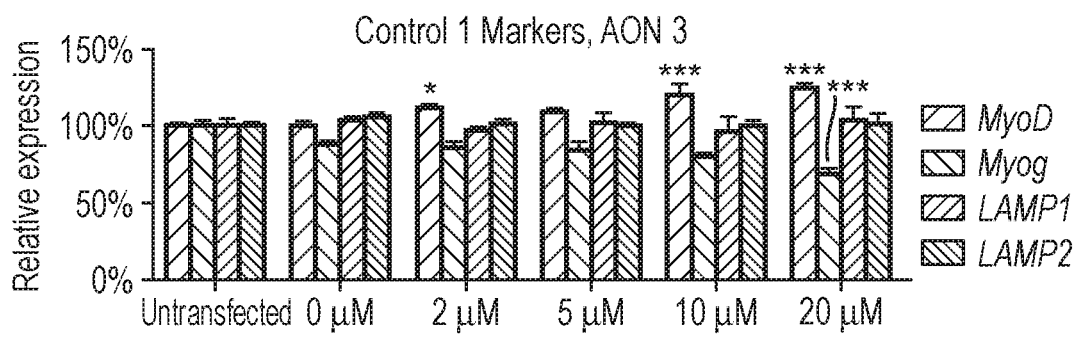
Figure 9I:
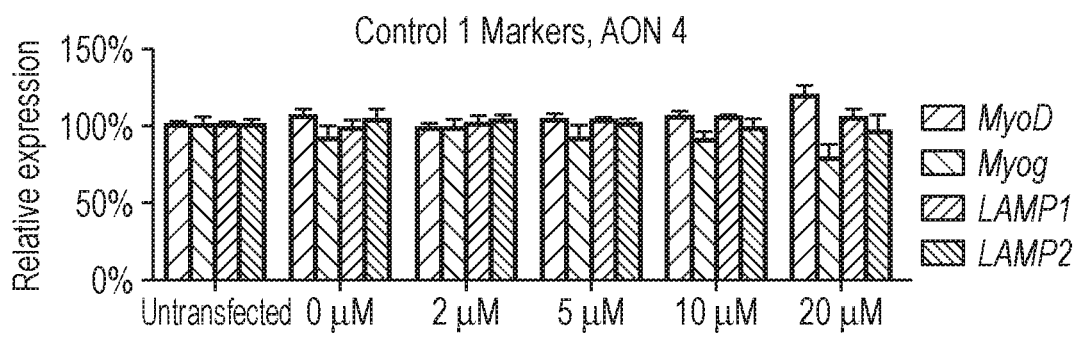
Figure 9I:
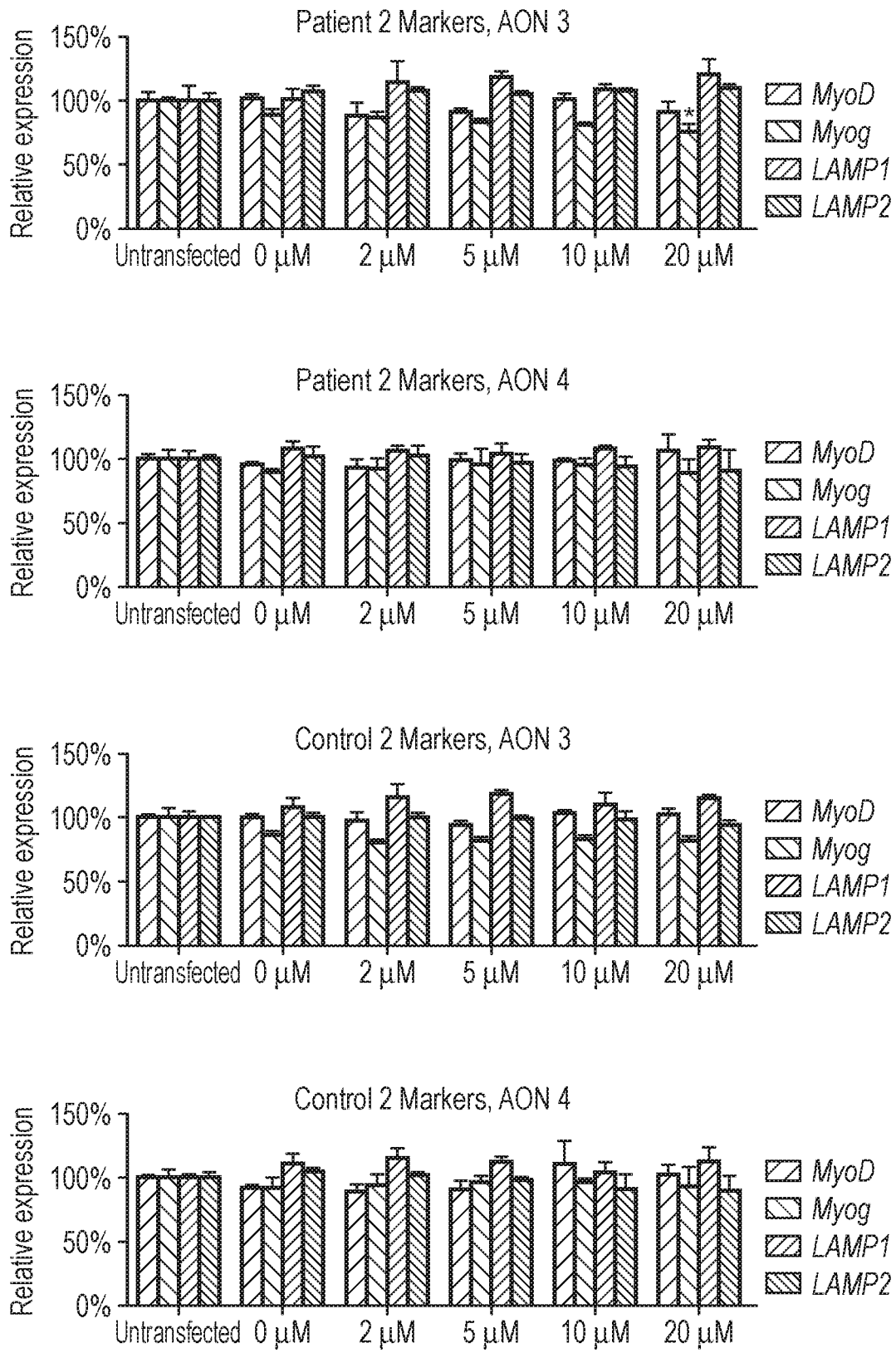

Next, we tested the effect of AONs 3 and 4 on exon 2 inclusion in myotubes (FIG. 4c, FIG. 9a,b). Treatment of patient-derived myotubes resulted in a concentration-dependent increase in wild type GAA splicing and a concomitant decrease in expression of aberrant splicing products SV2 and SV3, as shown by quantitative analysis of individual splicing products using RT-qPCR (FIG. 4c,d, i, FIG. 9c,d). In myotubes from healthy controls, AONs 3 and 4 did not affect GAA exon 2 splicing (FIG. 4e, FIG. 9e), indicating that these only restored normal splicing in the context of the IVS1 variant without promoting additional effects on GAA mRNA expression. This was confirmed by flanking exon RT-PCR analysis of exon 2 (FIG. 4f). Importantly, treatment of patient-derived myotubes with AONs 3 or 4 resulted in elevation of GAA enzyme activity above the disease threshold of 20% of healthy control levels (FIG. 4g, FIG. 9f), suggesting that these AONs are capable of restoring GAA enzyme levels to those present in healthy individuals. Treatment of myotubes from healthy controls did not affect (GAA enzyme activity (FIG. 4h, FIG. 9g). We conclude that the splicing silencer sequence at c.-32-179 operates in skeletal muscle cells and that its inhibition by AONs can restore splicing in cells from Pompe patients carrying the IVS1 variant.

Figure 5A:
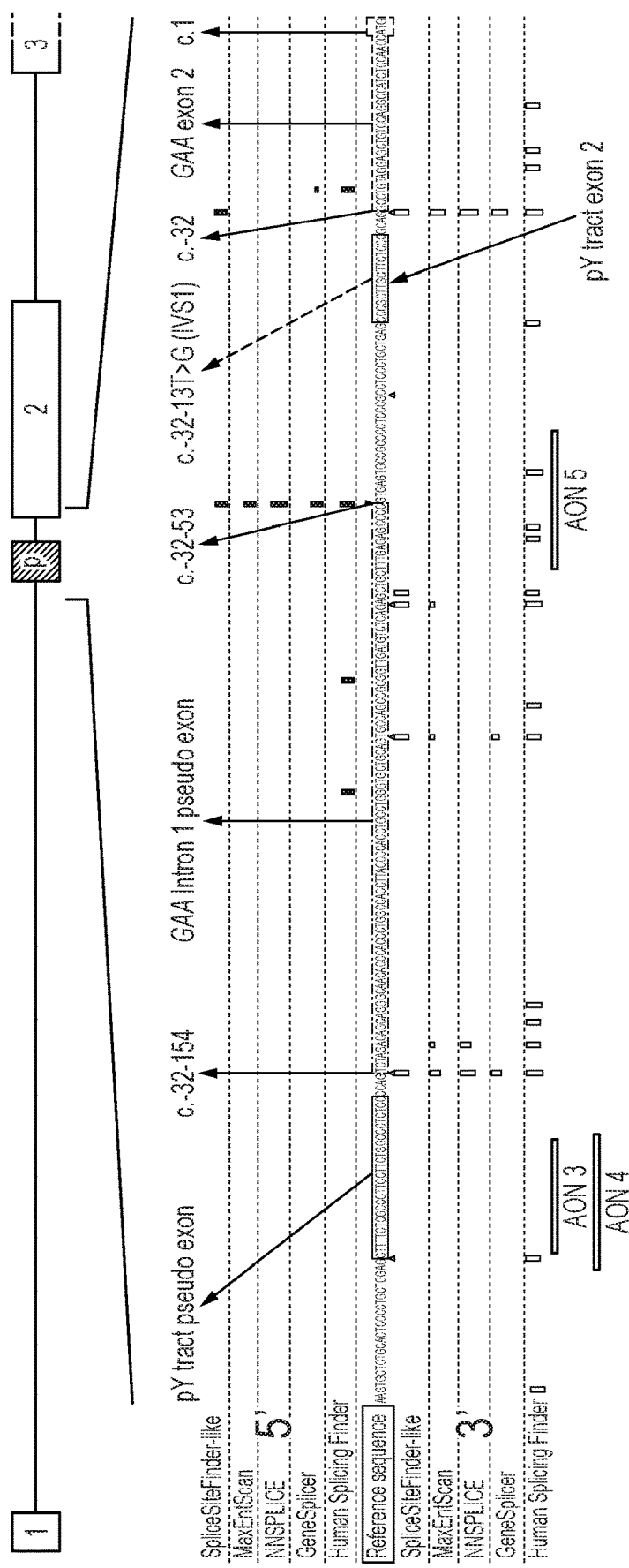
Figure 10C:
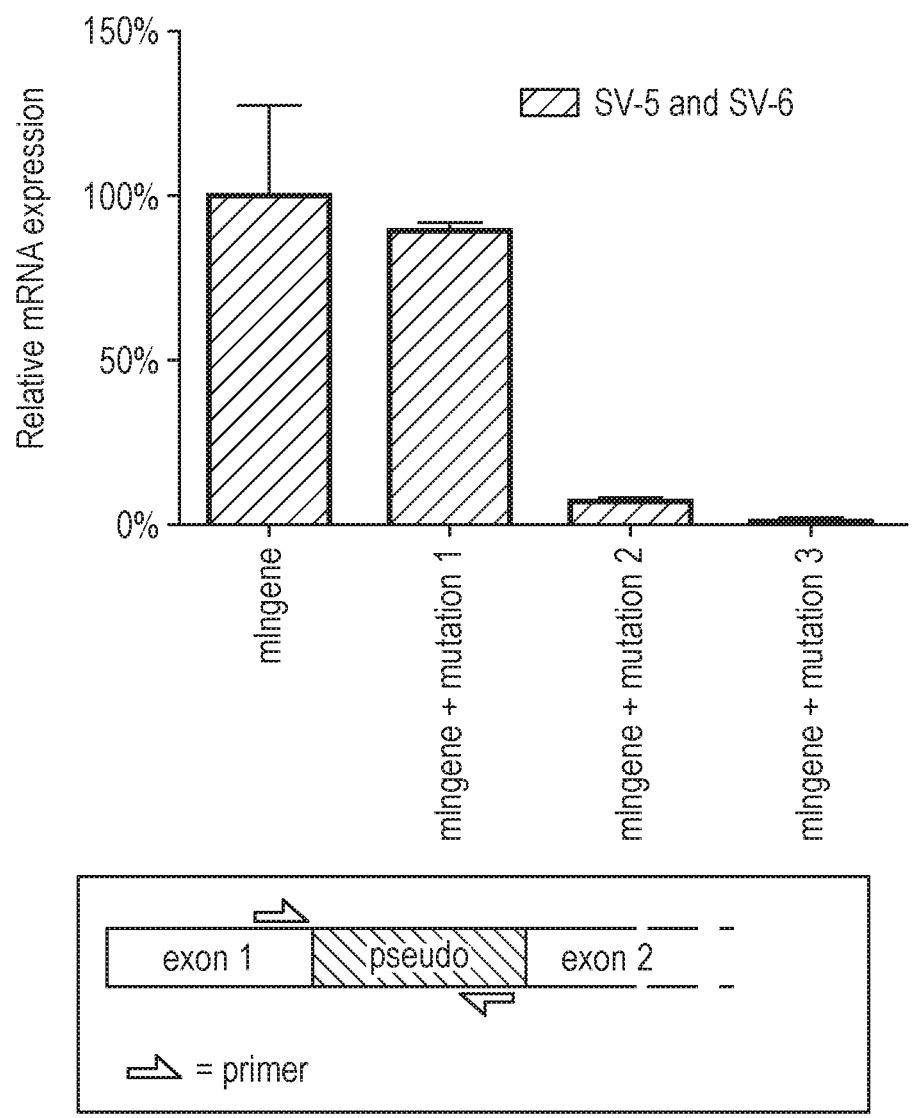
Figure 10D:
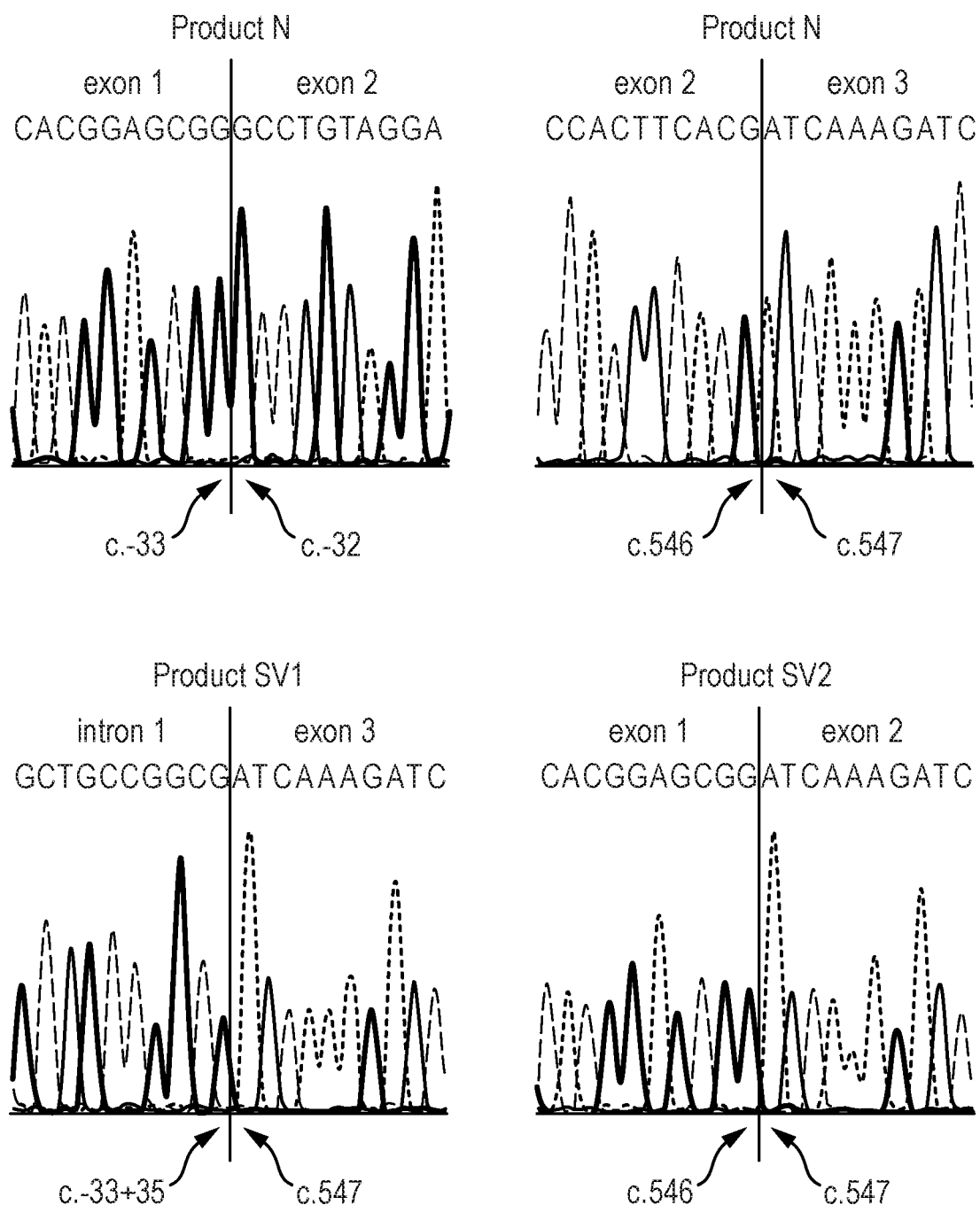

As it was unclear how AONs 3 and 4 restored exon 2 inclusion, we were interested to investigate their mechanism of action. We noted that the target sequence of these AONs showed similarity to a pY tract, which is usually present between 5-40 nucleotides upstream of a splice acceptor. We then performed in silico analysis of splice sites, and this predicted a strong natural cryptic splice acceptor site 12 nt downstream of the binding site for AONs 3 and 4 (FIG. 5a). One hundred and three nt further downstream, a strong natural cryptic splice donor was predicted. Together, these cryptic splice sites defined a hypothetical natural pseudo exon. Mutation of the predicted splice sites abolished inclusion of the pseudo exon in a minigene construct (FIG. 10c-e). This suggested the possibility that AONs 3 and 4 may act by inhibiting cryptic splicing rather than by repressing a putative ISS.

Figure 5B:
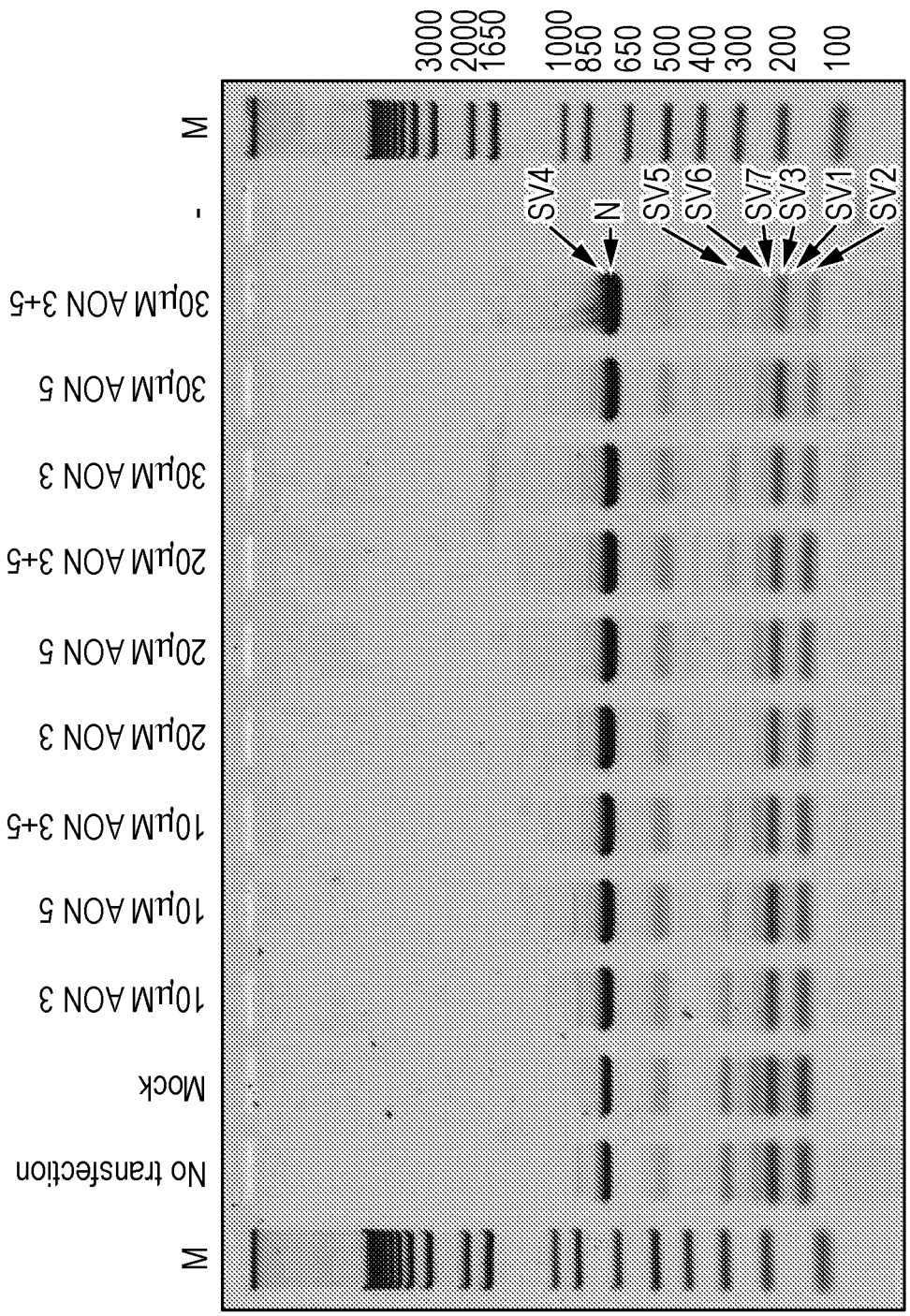

To test this, we first analyzed whether splice products comprising the pseudo exon exist in cells from Pompe patients. To this end, mRNA isolated from patient-derived myotubes was analyzed by flanking exon RT-PCR of exon 2, and PCR products were cloned in a TOPO vector. One hundred clones were analyzed by Sanger sequencing, and this resulted in the identification of 8 splice variants (FIG. 5b,c, Table 6, FIG. 10a). The predicted pseudo exon was indeed detected in two splice products, in which exon 2 was fully (SV6) or partially (SV5) skipped. Both products were likely subject to mRNA degradation due to the lack of the translation start codon, explaining their low abundance. Nevertheless, these could be identified on agarose gels following flanking exon PCR of exon 2 (FIG. 5b). Other low abundant splice products (SV1, SV4, and SV7) utilized a previously described cryptic splice donor nearby exon 123.

However, these never contained the pseudo exon. We conclude that the predicted pseudo exon indeed exists in vivo and that it is preferentially included in splice products in which exon 2 is partially or fully skipped due to the IVS1 variant.

Short introns are unfavorable for successful splicing and have a typical minimum length of 70-80 nt. The length of the intron between the pseudo exon and exon 2 is 52 nt, which violates this rule. This suggested the possibility that inclusion of the pseudo exon competes with exon 2 inclusion, which is in agreement with the mutually exclusive inclusion of the pseudo exon or exon 2 in splice products. Such scenario explains why AONs 3 and 4 promote exon 2 inclusion, namely by repression of inclusion of the pseudo exon via interfering with the pY tract of the cryptic splice acceptor site. We hypothesized that repression of the cryptic splice donor would likewise promote exon 2 inclusion. To test this, AON 5 was designed to target the cryptic splice donor site of the pseudo exon (FIG. 5a, FIG. 7a). In patient-derived myotubes, AON 5 promoted exon 2 inclusion (product N) and repressed inclusion of the pseudo exon (products SV5 and SV6), as shown by flanking exon RT-PCR and splicing product-specific RT-qPCR (FIG. 5b,d, and Supplementary FIG. 5b). AON 5 was equally effective in splicing correction compared to AON 3, in agreement with the idea that both AONs prevent utilization of the pseudo exon. GAA enzyme activity was enhanced by AON 5 to similar levels compared to AON 3 (FIG. 5e) and myotube differentiation was not altered by the AON treatment (FIG. 5f). These results suggest that the pseudo exon competes with exon 2 splicing and that pseudo exon skipping by AONs promotes exon 2 inclusion.

Figure 5C:
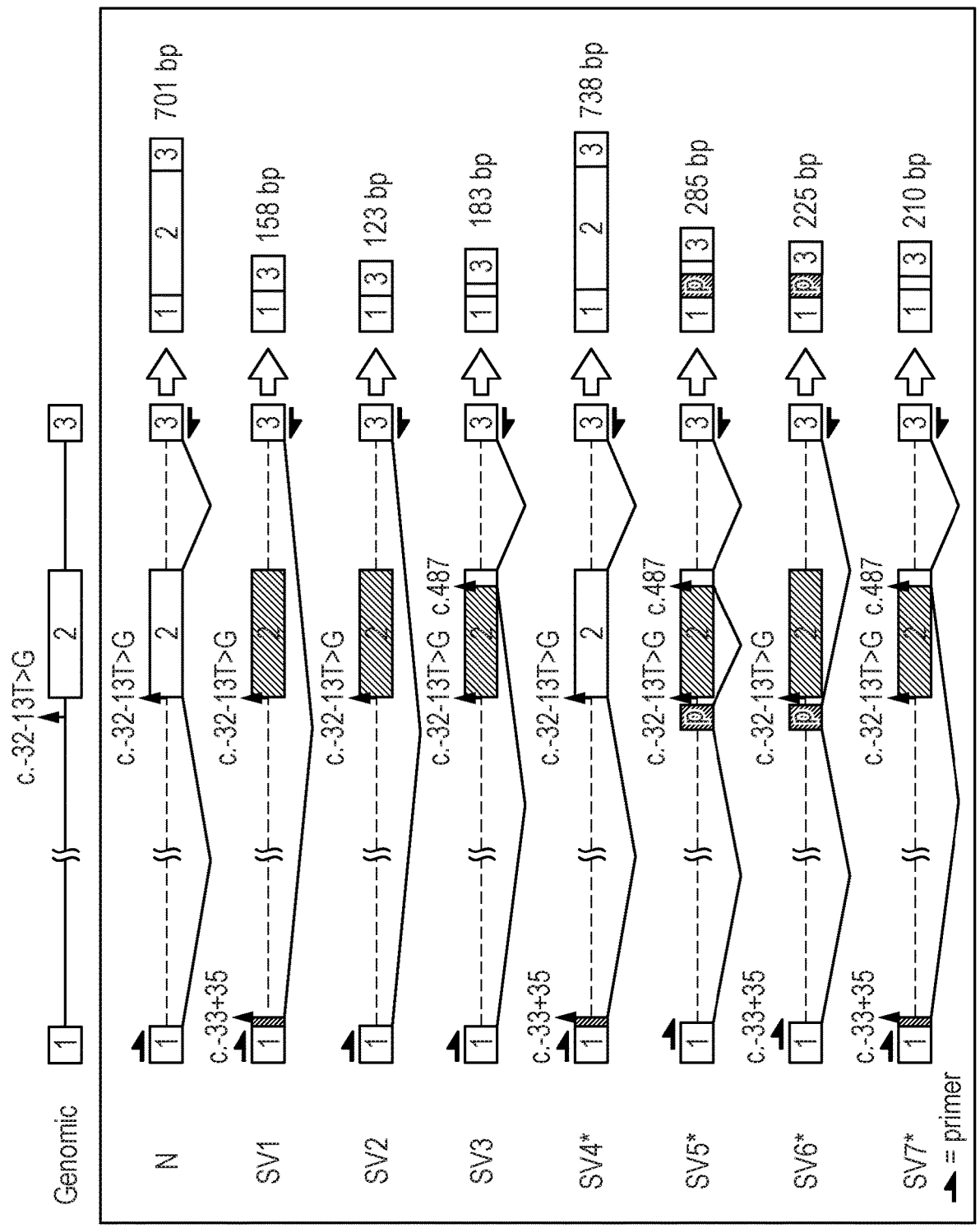
Figure 5D:
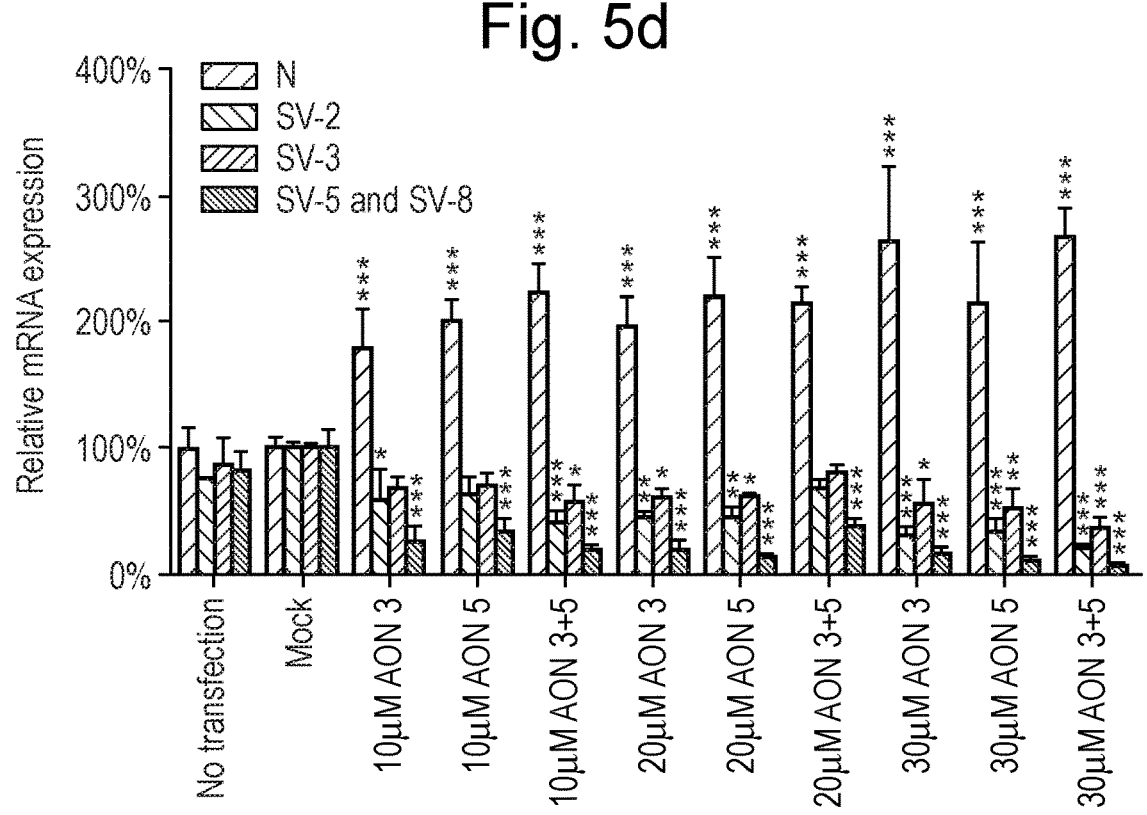

The identification of the pseudo exon offered an additional option for splicing correction, namely by the simultaneous targeting of the cryptic splice acceptor and donor sites. To test this, a combination of AON3 plus AON 5 was tested in patient-derived myotubes. At the same total AON concentrations, the combination of AON 3 plus AON 5 showed higher efficacy than single AONs in promoting exon 2 inclusion and repressing aberrant exon 2 splicing (FIG. 5c,d).

Figure 5E:
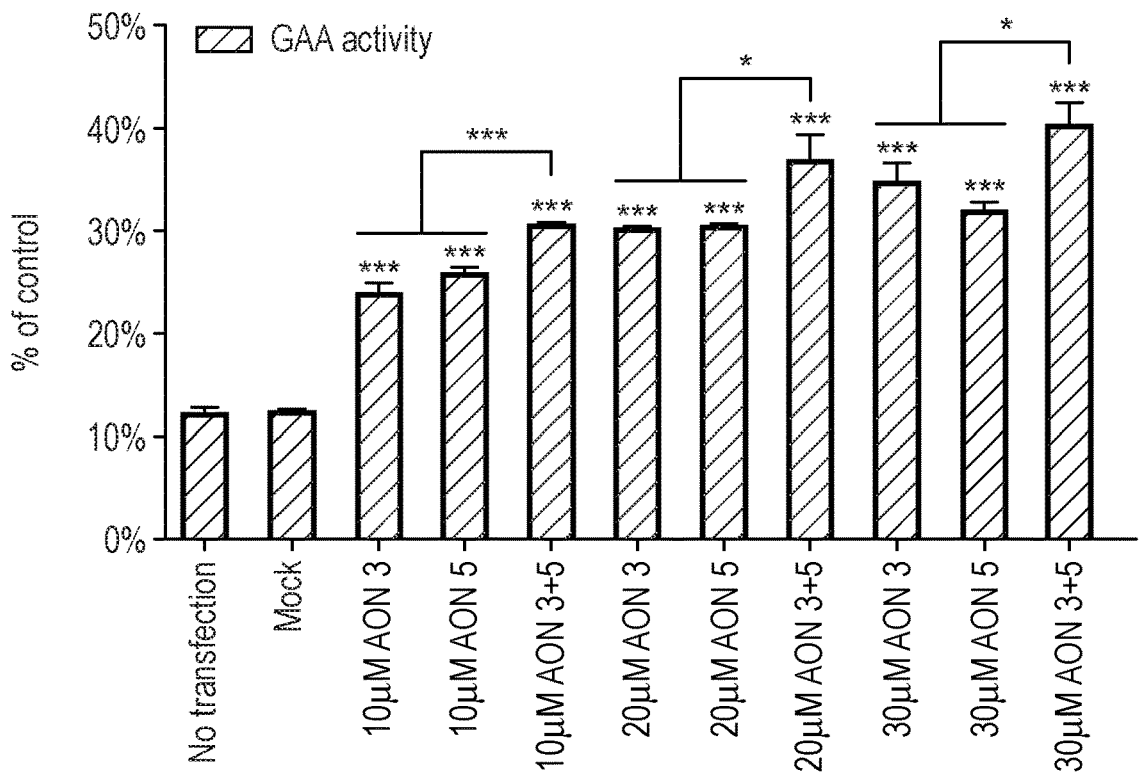

We used TOPO cloning as above to analyze all products that arise from treatment with AON 3 plus AON 5 (Table 10). No additional products besides the 8 known splicing products were identified. Compared to mock treated cells, cells treated with AON 1+5 showed an increase in the number of clones with a wild type exon 2 insert from 14 to 45 (3.2 fold), while the number of clones that contained the pseudo exon was reduced 6 fold from 6 to 1 (Table 10). GAA enzymatic activity was elevated by AONs 3 plus AON 5 up to 3.3 fold (FIG. 5e). Following the calculation outlined above, this amounts to a highly efficient splicing correction of the IVS1 allele of 66-99%. We conclude that the simultaneous inhibition of the cryptic splice donor and acceptor sites of the pseudo exon is the most efficient way to promote exon 2 inclusion and is able to restore the majority of GAA enzymatic activity in patient-derived skeletal muscle cells towards healthy control levels.

TABLE 10 splice variants observed.

| Splice variant | colony count mock transfection | colony count transfection of 15 µM AON 3 and 5 |
| --- | --- | --- |
| N | 14 | 45 |
| SV1 | 3 | 3 |
| SV2 | 44 | 16 |

TABLE 10-continued splice variants observed.

| Splice variant | colony count mock transfection | colony count transfection of 15 μM AON 3 and 5 |
|---|---|---|
| SV3 | 24 | 23 |
| SV4 | 0 | 2 |
| SV5 | 4 | 1 |
| SV6 | 2 | 0 |
| SV7 | 2 | 0 |
| total | 93 | 90 |

To better define the region for AON targeting of the splice acceptor and splice donor sites of the pseudo exon, a screen was performed. For each target, five AONs were designed that together cover a large part of the target regions (FIG. 11A and Table 11).

First, AONs targeting the splice acceptor of the pseudo exon were transfected in cultured myotubes derived from iPSCs that were generated from primary fibroblasts of an IVS1 Pompe patient. Results indicate that transfection of AON 3 leads to a 2.9 fold increase in GAA activity due to promotion of GAA exon 2 inclusion (FIG. 11B). AONs 2, 4 and 5 lead to slightly less increases in GAA enzyme activity (2.2, 1.9 and 1.5 fold, respectively), and AON 1 does not lead to an increase in GAA enzyme activity. The optimal target region seems to be within the region marked at the 5' boundary by AON 1, and at the 3' boundary by AON 5. Therefore, the optimal target region for targeting the pseudo exon splice acceptor is within c.-32-198 to c.-32-154.

The same experiment was performed with AONs 6 to 10 to determine the optimal target region for targeting the pseudo exon splice donor site. Results indicate that AON 3 is the most optimal AON with a 4.1 fold increase of GAA activity (FIG. 11C). AON 7 also leads to a significant increase (4.0 fold) in GAA activity. With a 2.6 fold and 1.7 fold increase in GAA activity, AONs 9 and 10 are less efficacious, but still promote GAA exon 2 inclusion. AON 6 has a slightly negative effect on exon 2 inclusion and leads to a 1.4 fold decrease in GAA activity. These results lead to the definition of the target region for the pseudo exon splice donor site within c.-32-77 to c.-32-28.

Furthermore, we tested whether the combination of AONs for targeting both splice donor and acceptor sites could be beneficial in combination with enzyme replacement therapy (ERT). To this end, we treated iPSC-derived myotubes of an IVS1 patient in vitro with ERT. The myotubes were transfected with either a single AON targeting the pseudo exon splice donor site (SEQ ID NO: 104), or with two AONs targeting both the splice acceptor and splice donor site of the pseudo exon (SEQ ID NO: 104 and 368). Results show that ERT with mock transfection leads to a maximum of 55% of GAA activity compared to average healthy control levels (FIG. 12). Treatment of the cells with both ERT and a single AON leads to a maximum of 71%, and with double targeting, 79% of GAA activity is reached. Importantly, the presence of a plateau phase after addition of 600, 800 or 1000 nmol 4-MU/hr/ml medium indicates that ERT treatment of myotubes will only lead to a maximum increase of GAA activity to 55% compared to healthy control levels. However, combined treatment of ERT with AONs can lead to further increase of GAA activity: Poor cellular uptake of exogenously administered ERT is one of the limitations of ERT and a likely reason why the clinical response is heterogeneous. By showing that skeletal muscle cells have a surprisingly low plateau phase for uptake of ERT, we provide new molecular evidence that may explain the variable response of ERT in patients. Our finding that additional treatment with AONs stimulate intracellular GAA activity to higher levels on compared to the maximum level reached with ERT suggest that skeletal muscle cells that are insufficiently corrected by ERT may still benefit from treatment with AONs.

TABLE 11

AONs used for the experiments described in FIG. 11.

| AON nr. | AON name and target location | AON sequence (5' to 3') | SeqID |
|---|---|---|---|
| 1 | GAA_c.-32-199_-175 | AAGGGCGAGAAAAGCTCCAGCAGGG | 195 (target), 359 |
| 2 | GAA_c.-32-195_-171 | AAGGAAGGGCGAGAAAAGCTCCAGC | 199 (target), 363 |
| 3 | GAA_c.-32-190_-166 | GCCAGAAGGAAGGGCGAGAAAAGCT | 204 (target), 368 |
| 4 | GAA_c.-32-183_-159 | GGAGAGGGCCAGAAGGAAGGGCGAG | 211 (target), 375 |
| 5 | GAA_c.-32-178_-154 | ACTGGGGAGAGGGCCAGAAGGAAGG | 216 (target), 380 |
| 6 | GAA_c.-32-86_-62 | AAAGCAGCTCTGAGACATCAACCGC | — |
| 7 | GAA_c.-32-75_-51 | ACGGGGCTCTCAAAGCAGCTCTGAG | 5 (target), 93 |
| 8 | GAA_c.-32-64_-40 | GGGCGGCACTCACGGGGCTCTCAAA | 16 (target), 104 |
| 9 | GAA_c.-32-58_-34 | CGGGAGGGGCGGCACTCACGGGGCT | 21 (target), 110 |
| 10 | GAA_c.-32-52_-28 | GGGAGGCGGGAGGGGCGGCACTCAC | 27 (target), 116 |

REFERENCES

1. Kaplan J C, Hamroun D. The 2015 version of the gene table of monogenic neuromuscular disorders (nuclear genome). Neuromuscul Disord 24, 1123-1153 (2014).

2. van der Ploeg A T, Reuser A J. Pompe's disease. Lancet 372, 1342-1353 (2008).

3. Kishnani P S, Beckemeyer A A. New therapeutic approaches for Pompe disease: enzyme replacement therapy and beyond. Pediatr Endocrinol Rev 12 Suppl 1, 114-124 (2014).
4. Schoser B, et al. Survival and long-term outcomes in late-onset Pompe disease following alglucosidase alfa treatment: a systematic review and meta-analysis. J Neurol, (2016).
5. Van den Hout H, Reuser A J, Vulto A G, Loonen M C, Cromme-Dijkhuis A, Van der Ploeg A T. Recombinant human alpha-glucosidase from rabbit milk in Pompe patients. Lancet 356, 397-398 (2000).
6. van der Ploeg A T, et al, A randomized study of alglucosidase alfa in late-onset Pompe's disease. N Engl J Med 362, 1396-1406 (2010).
7. Gungor D, et al. Impact of enzyme replacement therapy on survival in adults with Pompe disease: results from a prospective international observational study. Orphanet J Rare Dis 8, 49 (2013).
8. van der Ploeg A T, et al. Open-label extension study following the Late-Onset Treatment Study (LOTS) of alglucosidase alfa. Mol Genet Metab 107, 456-461 (2012).
9. Bembi B, et al. Long-term observational, non-randomized study of enzyme replacement therapy in late-onset glycogenosis type II. J Inherit Metab Dis 33, 727-735 (2010).
10. Orlikowski D, et al. Recombinant human acid alpha-glucosidase (rhGAA) in adult patients with severe respiratory failure due to Pompe disease. Neuromuscul Disord 21, 477-482 (2011).
11. Strothotte S, et al. Enzyme replacement therapy with alglucosidase alfa in 44 patients with late-onset glycogen storage disease type 2: 12-month results of an observational clinical trial. J Neurol 257, 91-97 (2010).
12. Angelini C, et al. Observational clinical study in juvenile-adult glycogenosis type 2 patients undergoing enzyme replacement therapy for up to 4 years. J Neurol 259, 952-958 (2012).
13. Regnery C, et al. 36 months observational clinical study of 38 adult Pompe disease patients under alglucosidase alfa enzyme replacement therapy. J Inherit Metab Dis 35, 837-845 (2012).
14. Anderson L J, et al. Effectiveness of enzyme replacement therapy in adults with late-onset Pompe disease: results from the NCS-LSD cohort study. J Inherit Metab Dis 37, 945-952 (2014).
15. de Vries J M, et al. Effect of enzyme therapy and prognostic factors in 69 adults with Pompe disease: an open-label single-center study. Orphanet J Rare Dis 7, 73 (2012).
16. de Vries J M, et al. High antibody titer in an adult with Pompe disease affects treatment with alglucosidase alfa. Mol Genet Metab 101, 338-345 (2010).
17. de Vries J M, et al, Pompe disease in adulthood: effects of antibody formation on enzyme replacement therapy. Genet Med. (2016).
18. Patel T T, Banugaria S G, Case L E, Wenninger S, Schoser B, Kishnani P S. The impact of antibodies in late-onset Pompe disease: a case series and literature review. Mol Genet Metab 106, 301-309 (2012).
19. Cardone M, et al. Abnormal mannose-6-phosphate receptor trafficking impairs recombinant alpha-glucosidase uptake in Pompe disease fibroblasts. Pathogenetics 1, 6 (2008).
20. Settembre C, Fraldi A. Rubinsztein D C, Ballabio A. Lysosomal storage diseases as disorders of autophagy. Autophagy 4, 113-114 (2008).
21. Fukuda T, et al. Autophagy and lysosomes in Pompe disease. Autophagy 2, 318-320 (2006).
22. Huie M L, et al. Aberrant splicing in adult onset glycogen storage disease type II (GSDII): molecular identification of an IVS1 (−13T→G) mutation in a majority of patients and a novel IVS10 (+1GT→CT) mutation. Hum Mol Genet 3, 2231-2236 (1994).
23. Boerkoel C F, et al. Leaky splicing mutation in the acid maltase gene is associated with delayed onset of glycogenosis type II. Am J Hum Genet 56, 887-897 (1995).
24. Dardis A, et al. Functional characterization of the common c.-32-13T>G mutation of GAA gene: identification of potential therapeutic agents. Nucleic Acids Res 42, 1291-1302 (2014).
25. Bergsma A J, Kroos M, Hoogeveen-Westerveld M. Halley D, van der Ploeg A T, Pijnappel W W. Identification and characterization of aberrant GAA pre-mRNA splicing in pompe disease using a generic approach. Hum Mutat 36, 57-68 (2015).
26. McClorey G, Wood M J. An overview of the clinical application of antisense oligonucleotides for RNA-targeting therapies. Curr Opin Pharmacol 24, 52-58 (2015).
27. Jirka S, Aartsma-Rus A. An update on RNA-targeting therapies for neuromuscular disorders. Curr Opin Neurol 28, 515-521 (2015).
28. Rigo F, Seth P P, Bennett C F. Antisense oligonucleotide-based therapies for diseases caused by pre-mRNA processing defects. Adv Exp Med Biol 825, 303-352 (2014).
29. Havens M A, Hastings M L. Splice-switching antisense oligonucleotides as therapeutic drugs. Nucleic Acids Res. (2016).
30. Hua Y, Vickers T A, Okunola H L, Bennett C F, Krainer A R. Antisense masking of an hnRNP A1/A2 intronic splicing silencer corrects SMN2 splicing in transgenic mice. Am J Hum Genet 82, 834-848 (2008).
31. Lorson C L, Androphy E J. An exonic enhancer is required for inclusion of an essential exon in the SMA-determining gene SMN. Hum Mol Genet 9, 259-265 (2000).
32. Singh N K, Singh N N, Androphy E J, Singh R N. Splicing of a critical exon of human Survival Motor Neuron is regulated by a unique silencer element located in the last intron. Mol Cell Biol 26, 1333-1346 (2006).
33. Singh N N, Shishimorova M, Cao L C, Gangwani L, Singh R N. A short antisense oligonucleotide masking a unique intronic motif prevents skipping of a critical exon in spinal muscular atrophy. RNA Biol 6, 341-350 (2009).
34. Lee Y, Rio D C. Mechanisms and Regulation of Alternative Pre-mRNA Splicing. Annu Rev Biochem 84, 291-323 (2015).
35. Merkin J, Russell C, Chen P, Burge C B. Evolutionary dynamics of gene and isoform regulation in Mammalian tissues. Science 338, 1593-1599 (2012).
36. Nehlin J O, Just M, Rustan A C, Gaster M. Human myotubes from myoblast cultures undergoing senescence exhibit defects in glucose and lipid metabolism. Biogerontology 12, 349-365 (2011).
37. Borchin B, Chen J, Barberi T. Derivation and FACS-mediated purification of PAX3+/PAX7+ skeletal muscle precursors from human pluripotent stem cells. Stem Cell Reports 1, 620-631 (2013).
38. Shelton M, Kocharyan A, Liu J, Skerjanc I S. Stanford W L. Robust generation and expansion of skeletal muscle progenitors and myocytes from human pluripotent stem cells. Methods 101, 73-84 (2016).

39. Chal J, et al. Differentiation of pluripotent stem cells to muscle fiber to model Duchenne muscular dystrophy. Nat Biotechnol 33, 962-969 (2015).
40. Gorman L, Suter D, Emerick V, Schumperli D, Kole R. Stable alteration of pre-mRNA splicing patterns by modified U7 small nuclear RNAs. Proc Natl Acad Sci USA 95, 4929-4934 (1998).
41. Nlend R N, Schumperli D. Antisense genes to induce exon inclusion. Methods Mol Biol 867, 325-347 (2012).
42. Liu S. Asparuhova M, Brondani V, Ziekau I, Klimkait T, Schumperli D. Inhibition of HIV-1 multiplication by antisense U7 snRNAs and siRNAs targeting cyclophilin A. Nucleic Acids Res 32, 3752-3759 (2004).
43. Perez B, et al. Pseudoexon exclusion by antisense therapy in methylmalonic aciduria (MMAuria). Hum Mutat 30, 1676-1682 (2009).
44. Kollberg G, Holme E. Antisense oligonucleotide therapeutics for iron-sulphur cluster deficiency myopathy. Neuromuscul Disord 19, 833-836 (2009).
45. Bigot A, et al. Replicative aging down-regulates the myogenic regulatory factors in human myoblasts. Biol Cell 100, 189-199 (2008),
46. Drost M R, et al. Both type 1 and type 2a muscle fibers can respond to enzyme therapy in Pompe disease. Muscle Nerve 37, 251-255 (2008).
47. Droge C, Schaal H, Engelmann G, Wenning D, Haussinger D, Kubitz R. Exon-skipping and mRNA decay in human liver tissue: molecular consequences of pathogenic bile salt export pump mutations. Sci Rep 6, 24827 (2016).
48. Xue Y, et al. Exome Sequencing Identified a Splice Site Mutation in FHL1 that Causes Uruguay Syndrome, an X-Linked Disorder With Skeletal Muscle Hypertrophy and Premature Cardiac Death. Circ Cardiovasc Genet 9, 130-135 (2016).
49. Iida K, et al. A novel heterozygous splice site OPA1 mutation causes exon 10 skipping in Japanese patients with dominant optic atrophy. Ophthalmic Genet, 37, 354-356 (2016).
50. Heilker R, Traub S, Reinhardt P, Scholer H R, Sterneckert J. iPS cell derived neuronal cells for drug discovery. Trends Pharmacol Sci 35, 510-579 (2014).
51. Takahashi K, et al. Induction of pluripotent stem cells from adult human fibroblasts by defined factors. Cell 131, 861-872 (2007).
52. Ebert A D, Liang P, Wu J C. Induced pluripotent stem cells as a disease modeling and drug screening platform. J Cardiovasc Pharmacol 60, 408-416 (2012).
53. Choi I Y, et al. Concordant but Varied Phenotypes among Duchenne Muscular Dystrophy Patient-Specific Myoblasts Derived using a Human iPSC-Based Model. Cell Rep 15, 2301-2312 (2016).
54. Warlich E, et al. Lentiviral vector design and imaging approaches to visualize the early stages of cellular reprogramming. Mol Ther 19, 782-789 (2011).
55. Irizarry R A, Bolstad B M, Collin F, Cope L M, Hobbs B, Speed T P. Summaries of Affymetrix GeneChip probe level data. Nucleic Acids Res 31, e15 (2003).
56. Gao K, Masuda A, Matsuura T, Ohno K. Human branch point consensus sequence is yUnAy. Nucleic Acids Res 36, 2257-2267 (2008).

The invention claimed is:

1. A method for repairing aberrant splicing wherein such aberrant splicing causes Pompe disease and results from acid α-glucosidase (GAA) mutation c.-32-13T>G, mutation c.-32-3C>G or mutation c.-32-3C>A, wherein such aberrant splicing is caused by the expression of a natural pseudo exon, comprising blocking of both the natural cryptic 3' splice site and the natural cryptic 5' splice site of said natural pseudo exon with AONs.

2. The method according to claim 1, comprising providing a pair of AONs, in which the first AON is directed to the natural cryptic 3' acceptor splice site of said natural pseudo exon and wherein the second AON is directed to the natural cryptic 5' donor splice site of said natural pseudo exon, wherein the application of said pair of AONs provides for a silencing of the expression of the natural pseudo exon, and promotes canonical splicing.

3. The method according to claim 1, wherein said natural pseudo exon is comprised in an intron of a gene.

4. The method according to claim 1, wherein the AON is directed against the natural cryptic donor splice site comprising SEQ ID NO: 1.

5. The method according to claim 1, wherein the AON is directed against the natural cryptic acceptor site comprising SEQ ID NO: 180.

6. The method according to claim 1, wherein the AON is chosen from the sequences of SEQ ID NOS: 91-179 or sequences that have an identity of 80% with said sequences.

7. The method according to claim 1, wherein the AON is chosen from the sequences of SEQ ID NOS: 346-508 or sequences that have an identity of 80% with said sequences.

8. The method according to claim 2, wherein the pair of AONs is formed by selecting a first AON from the sequences of SEQ ID NOS: 91-179 or sequences that have an identity of 80% with said sequences and a second AON from the sequences of SEQ ID NOS: 346-508 or sequences that have an identity of 80% with said sequences.

9. The method according to claim 8, wherein the pair of AONs comprises a first AON chosen from SEQ ID NOS: 93, 104 and 110 and a second AON chosen from SEQ ID NOS: 363, 368, 375, 380 and 425.

10. The method according to claim 4, wherein the natural cryptic donor splice site further comprises SEQ ID NOS: 2-90.

11. The method according to claim 5, wherein the natural cryptic acceptor site further comprises SEQ ID NOS: 181-345.

* * * * *

SEQUENCE LISTING

```
<160> NUMBER OF SEQ ID NOS: 569

<210> SEQ ID NO 1
<211> LENGTH: 50
<212> TYPE: DNA
<213> ORGANISM: Artificial Sequence
<220> FEATURE:
<223> OTHER INFORMATION: target for AONs

<400> SEQUENCE: 1
gtctcagagc tgctttgaga gccccgtgag tgccgcccct cccgcctccc         50

<210> SEQ ID NO 2
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 2
tgagagcccc gtgagtgccg ccsct                                    25

<210> SEQ ID NO 3
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 3
gtctcagagc tgctttgaga gcccc                                    25

<210> SEQ ID NO 4
```

```
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 4
tctcagagct gctttgagag ccccg                                              25

<210> SEQ ID NO 5
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 5
ctcagagctg ctttgagagc cccgt                                              25

<210> SEQ ID NO 6
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 6
tcagagctgc tttgagagcc ccgtg                                              25

<210> SEQ ID NO 7
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 7
cagagctgct ttgagagccc cgtga                                              25

<210> SEQ ID NO 8
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 8
agagctgctt tgagagcccc gtgag                                              25

<210> SEQ ID NO 9
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 9
gagctgcttt gagagccccg tgagt                                              25

<210> SEQ ID NO 10
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 10
```
agctgctttg agagccccgt gagtg                                    25

<210> SEQ ID NO 11
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 11
gctgctttga gagccccgtg agtgc                                    25

<210> SEQ ID NO 12
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 12
ctgctttgag agccccgtga gtgcc                                    25

<210> SEQ ID NO 13
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 13
tgctttgaga gccccgtgag tgccg                                    25

<210> SEQ ID NO 14
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 14
gctttgagag ccccgtgagt gccgc                                    25

<210> SEQ ID NO 15
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 15
ctttgagagc cccgtgagtg ccgcc                                    25

<210> SEQ ID NO 16
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 16
tttgagagcc ccgtgagtgc cgccc                                    25

<210> SEQ ID NO 17
<211> LENGTH: 25
<212> TYPE: DNA

```
<213> ORGANISM: Artificial Sequence
<220> FEATURE:
<223> OTHER INFORMATION: 25 bp TARGET sequence 5' -> 3'

<400> SEQUENCE: 17
ttgagagccc cgtgagtgcc gcccc                                              25

<210> SEQ ID NO 18
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 18
tgagagcccc gtgagtgccg cccct                                              25

<210> SEQ ID NO 19
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 19
gagagccccg tgagtgccgc ccctc                                              25

<210> SEQ ID NO 20
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 20
agagccccgt gagtgccgcc cctcc                                              25

<210> SEQ ID NO 21
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 21
gagccccgtg agtgccgccc ctccc                                              25

<210> SEQ ID NO 22
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 22
agccccgtga gtgccgcccc tcccg                                              25

<210> SEQ ID NO 23
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 23
gccccgtgag tgccgcccct cccgc                                              25
```

<210> SEQ ID NO 24
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 24
ccccgtgagt gccgcccctc ccgcc                                    25

<210> SEQ ID NO 25
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 25
cccgtgagtg ccgcccctcc cgcct                                    25

<210> SEQ ID NO 26
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 26
ccgtgagtgc cgcccctccc gcctc                                    25

<210> SEQ ID NO 27
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 27
cgtgagtgcc gcccctcccg cctcc                                    25

<210> SEQ ID NO 28
<211> LENGTH: 25
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 28
gtgagtgccg ccctcccgc ctccc                                     25

<210> SEQ ID NO 29
<211> LENGTH: 42
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 29
tctcagagct gctttgagag cgtctcagag ctgctttgag ag                 42

<210> SEQ ID NO 30
<211> LENGTH: 21
<212> TYPE: DNA
<213> ORGANISM: Artificial Sequence
<220> FEATURE:

<223> OTHER INFORMATION: 21 bp TARGET sequence 5' -> 3'.

<400> SEQUENCE: 30
ctcagagctg ctttgagagc c                                              21

<210> SEQ ID NO 31
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 31
tcagagctgc tttgagagcc c                                              21

<210> SEQ ID NO 32
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 32
cagagctgct ttgagagccc c                                              21

<210> SEQ ID NO 33
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 33
agagctgctt tgagagcccc g                                              21

<210> SEQ ID NO 34
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 34
gagctgcttt gagagccccg t                                              21

<210> SEQ ID NO 35
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 35
agctgctttg agagccccgt g                                              21

<210> SEQ ID NO 36
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 36
gctgctttga gagccccgtg a                                              21

```
<210> SEQ ID NO 37
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 37
ctgctttgag agccccgtga g                                      21

<210> SEQ ID NO 38
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 38
tgctttgaga gccccgtgag t                                      21

<210> SEQ ID NO 39
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 39
gctttgagag ccccgtgagt g                                      21

<210> SEQ ID NO 40
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 40
ctttgagagc cccgtgagtg c                                      21

<210> SEQ ID NO 41
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 41
tttgagagcc ccgtgagtgc c                                      21

<210> SEQ ID NO 42
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 42
ttgagagccc cgtgagtgcc g                                      21

<210> SEQ ID NO 43
<211> LENGTH: 21
<212> TYPE: DNA
<213> ORGANISM: Artificial Sequence
<220> FEATURE:
<223> OTHER INFORMATION: 21 bp TARGET sequence 5' -> 3'.
```

<400> SEQUENCE: 43
tgagagcccc gtgagtgccg c                                    21

<210> SEQ ID NO 44
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 44
gagagccccg tgagtgccgc c                                    21

<210> SEQ ID NO 45
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 45
agagccccgt gagtgccgcc c                                    21

<210> SEQ ID NO 46
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 46
gagccccgtg agtgccgccc c                                    21

<210> SEQ ID NO 47
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 47
agccccgtga gtgccgcccc t                                    21

<210> SEQ ID NO 48
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 48
gccccgtgag tgccgccct c                                     21

<210> SEQ ID NO 49
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 49
ccccgtgagt gccgccctc c                                     21

<210> SEQ ID NO 50
<211> LENGTH: 21

```
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 50
cccgtgagtg ccgcccctcc c                                               21

<210> SEQ ID NO 51
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 51
ccgtgagtgc cgcccctccc g                                               21

<210> SEQ ID NO 52
<211> LENGTH: 42
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 52
cgtgagtgcc gcccctcccg cggtactcca gaaggcaggg ct                        42

<210> SEQ ID NO 53
<211> LENGTH: 42
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 53
gtgagtgccg ccctcccgc cgtactccag aaggcagggc tc                         42

<210> SEQ ID NO 54
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 54
tgagtgccgc ccctcccgcc t                                               21

<210> SEQ ID NO 55
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 55
gagtgccgcc cctcccgcct c                                               21

<210> SEQ ID NO 56
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 56
```
agtgccgccc ctcccgcctc c                                              21

<210> SEQ ID NO 57
<211> LENGTH: 21
<212> TYPE: DNA
<213> ORGANISM: Artificial Sequence
<220> FEATURE:
<223> OTHER INFORMATION: 21 bp TARGET sequence 5' -> 3'.

<400> SEQUENCE: 57
gtgccgcccc tcccgcctcc c                                              21

<210> SEQ ID NO 58
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 58
gtctcagagc tgctttga                                                  18

<210> SEQ ID NO 59
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 59
tctcagagct gctttgag                                                  18

<210> SEQ ID NO 60
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 60
ctcagagctg ctttgaga                                                  18

<210> SEQ ID NO 61
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 61
tcagagctgc tttgagag                                                  18

<210> SEQ ID NO 62
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 62
cagagctgct ttgagagc                                                  18

<210> SEQ ID NO 63
<211> LENGTH: 18
<212> TYPE: DNA
<213> ORGANISM: Artificial Sequence

```
<220> FEATURE:
<223> OTHER INFORMATION: 18 bp TARGET sequence 5' -> 3'.

<400> SEQUENCE: 63
agagctgctt tgagagcc                                                 18

<210> SEQ ID NO 64
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 64
gagctgcttt gagagccc                                                 18

<210> SEQ ID NO 65
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 65
agctgctttg agagcccc                                                 18

<210> SEQ ID NO 66
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 66
gctgctttga gagccccg                                                 18

<210> SEQ ID NO 67
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 67
ctgctttgag agccccgt                                                 18

<210> SEQ ID NO 68
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 68
tgctttgaga gccccgtg                                                 18

<210> SEQ ID NO 69
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 69
gctttgagag ccccgtga                                                 18
```

```
<210> SEQ ID NO 70
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 70
ctttgagagc cccgtgag                                                  18

<210> SEQ ID NO 71
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 71
tttgagagcc ccgtgagt                                                  18

<210> SEQ ID NO 72
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 72
ttgagagccc cgtgagtg                                                  18

<210> SEQ ID NO 73
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 73
tgagagcccc gtgagtgc                                                  18

<210> SEQ ID NO 74
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 74
gagagccccg tgagtgcc                                                  18

<210> SEQ ID NO 75
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 75
agagccccgt gagtgccg                                                  18

<210> SEQ ID NO 76
<211> LENGTH: 18
<212> TYPE: DNA
<213> ORGANISM: Artificial Sequence
<220> FEATURE:
<223> OTHER INFORMATION: 18 bp TARGET sequence 5' -> 3'.
```

```
<400> SEQUENCE: 76
gagccccgtg agtgccgc                                                 18

<210> SEQ ID NO 77
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 77
agccccgtga gtgccgcc                                                 18

<210> SEQ ID NO 78
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 78
gccccgtgag tgccgccc                                                 18

<210> SEQ ID NO 79
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 79
ccccgtgagt gccgcccc                                                 18

<210> SEQ ID NO 80
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 80
cccgtgagtg ccgcccct                                                 18

<210> SEQ ID NO 81
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 81
ccgtgagtgc cgcccctc                                                 18

<210> SEQ ID NO 82
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 82
cgtgagtgcc gcccctcc                                                 18

<210> SEQ ID NO 83
```

-continued

```
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 83
gtgagtgccg ccctccc                                                  18

<210> SEQ ID NO 84
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 84
tgagtgccgc cctcccg                                                  18

<210> SEQ ID NO 85
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 85
gagtgccgcc cctcccgc                                                 18

<210> SEQ ID NO 86
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 86
agtgccgccc ctcccgcc                                                 18

<210> SEQ ID NO 87
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 87
gtgccgcccc tcccgcct                                                 18

<210> SEQ ID NO 88
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 88
tgccgcccct cccgcctc                                                 18

<210> SEQ ID NO 89
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 89
```
gccgcccctc ccgcctcc                                                 18

<210> SEQ ID NO 90
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 90
ccgcccctcc cgcctccc                                                 18

<210> SEQ ID NO 91
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 91
ggggctctca aagcagctct gagac                                         25

<210> SEQ ID NO 92
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 92
cggggctctc aaagcagctc tgaga                                         25

<210> SEQ ID NO 93
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 93
acggggctct caaagcagct ctgag                                         25

<210> SEQ ID NO 94
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 94
cacggggctc tcaaagcagc tctga                                         25

<210> SEQ ID NO 95
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 95
tcacggggct ctcaaagcag ctctg                                         25

<210> SEQ ID NO 96
<211> LENGTH: 25
<212> TYPE: DNA

```
<213> ORGANISM: Artificial Sequence
<220> FEATURE:
<223> OTHER INFORMATION: sequence of AON (5'-> 3')

<400> SEQUENCE: 96
ctcacggggc tctcaaagca gctct                                            25

<210> SEQ ID NO 97
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 97
actcacgggg ctctcaaagc agctc                                            25

<210> SEQ ID NO 98
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 98
cactcacggg gctctcaaag cagct                                            25

<210> SEQ ID NO 99
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 99
gcactcacgg ggctctcaaa gcagc                                            25

<210> SEQ ID NO 100
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 100
ggcactcacg gggctctcaa agcag                                            25

<210> SEQ ID NO 101
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 101
cggcactcac ggggctctca aagca                                            25

<210> SEQ ID NO 102
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 102
gcggcactca cggggctctc aaagc                                            25
```

<210> SEQ ID NO 103
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 103
ggcggcactc acggggctct caaag                                             25

<210> SEQ ID NO 104
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 104
gggcggcact cacggggctc tcaaa                                             25

<210> SEQ ID NO 105
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 105
ggggcggcac tcacggggct ctcaa                                             25

<210> SEQ ID NO 106
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 106
aggggcggca ctcacggggc tctca                                             25

<210> SEQ ID NO 107
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 107
gaggggcggc actcacgggg ctctc                                             25

<210> SEQ ID NO 108
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 108
ggaggggcgg cactcacggg gctct                                             25

<210> SEQ ID NO 109
<211> LENGTH: 25
<212> TYPE: DNA
<213> ORGANISM: Artificial Sequence
<220> FEATURE:

```
<223> OTHER INFORMATION: sequence of AON (5'-> 3')

<400> SEQUENCE: 109
gggaggggcg gcactcacgg ggctc                                              25

<210> SEQ ID NO 110
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 110
cgggaggggc ggcactcacg gggct                                              25

<210> SEQ ID NO 111
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 111
gcgggagggg cggcactcac ggggc                                              25

<210> SEQ ID NO 112
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 112
ggcgggaggg gcggcactca cgggg                                              25

<210> SEQ ID NO 113
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 113
aggcgggagg ggcggcactc acggg                                              25

<210> SEQ ID NO 114
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 114
gaggcgggag gggcggcact cacgg                                              25

<210> SEQ ID NO 115
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 115
ggaggcggga ggggcggcac tcacg                                              25
```

```
<210> SEQ ID NO 116
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 116
gggaggcggg aggggcggca ctcac                                     25

<210> SEQ ID NO 117
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 117
ctctcaaagc agctctgaga c                                         21

<210> SEQ ID NO 118
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 118
gctctcaaag cagctctgag a                                         21

<210> SEQ ID NO 119
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 119
ggctctcaaa gcagctctga g                                         21

<210> SEQ ID NO 120
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 120
gggctctcaa agcagctctg a                                         21

<210> SEQ ID NO 121
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 121
ggggctctca aagcagctct g                                         21

<210> SEQ ID NO 122
<211> LENGTH: 21
<212> TYPE: DNA
<213> ORGANISM: Artificial Sequence
<220> FEATURE:
<223> OTHER INFORMATION: sequence of AON (5'-> 3')
```

```
<400> SEQUENCE: 122
cggggctctc aaagcagctc t                                              21

<210> SEQ ID NO 123
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 123
acggggctct caaagcagct c                                              21

<210> SEQ ID NO 124
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 124
cacggggctc tcaaagcagc t                                              21

<210> SEQ ID NO 125
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 125
tcacggggct ctcaaagcag c                                              21

<210> SEQ ID NO 126
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 126
ctcacggggc tctcaaagca g                                              21

<210> SEQ ID NO 127
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 127
actcacgggg ctctcaaagc a                                              21

<210> SEQ ID NO 128
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 128
cactcacggg gctctcaaag c                                              21

<210> SEQ ID NO 129
<211> LENGTH: 21
```

```
<212> TYPE: DNA
<213> ORGANISM: Artificial Sequence
<220> FEATURE:
<223> OTHER INFORMATION: sequence of AON (5'-> 3')

<400> SEQUENCE: 129
gcactcacgg ggctctcaaa g                                              21

<210> SEQ ID NO 130
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 130
ggcactcacg gggctctcaa a                                              21

<210> SEQ ID NO 131
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 131
cggcactcac ggggctctca a                                              21

<210> SEQ ID NO 132
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 132
gcggcactca cggggctctc a                                              21

<210> SEQ ID NO 133
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 133
ggcggcactc acggggctct c                                              21

<210> SEQ ID NO 134
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 134
gggcggcact cacggggctc t                                              21

<210> SEQ ID NO 135
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 135
```
ggggcggcac tcacggggct c                                              21

<210> SEQ ID NO 136
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 136
aggggcggca ctcacggggc t                                              21

<210> SEQ ID NO 137
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 137
gaggggcggc actcacgggg c                                              21

<210> SEQ ID NO 138
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 138
ggaggggcgg cactcacggg g                                              21

<210> SEQ ID NO 139
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 139
gggaggggcg gcactcacgg g                                              21

<210> SEQ ID NO 140
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 140
cgggaggggc ggcactcacg g                                              21

<210> SEQ ID NO 141
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 141
gcgggagggg cggcactcac g                                              21

<210> SEQ ID NO 142
<211> LENGTH: 21
<212> TYPE: DNA
<213> ORGANISM: Artificial Sequence

```
<220> FEATURE:
<223> OTHER INFORMATION: sequence of AON (5'-> 3')

<400> SEQUENCE: 142
ggcgggaggg gcggcactca c                                              21

<210> SEQ ID NO 143
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 143
aggcgggagg ggcggcactc a                                              21

<210> SEQ ID NO 144
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 144
gaggcgggag gggcggcact c                                              21

<210> SEQ ID NO 145
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 145
ggaggcggga ggggcggcac t                                              21

<210> SEQ ID NO 146
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 146
gggaggcggg aggggcggca c                                              21

<210> SEQ ID NO 147
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 147
tcaaagcagc tctgagac                                                  18

<210> SEQ ID NO 148
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 148
ctcaaagcag ctctgaga                                                  18
```

<210> SEQ ID NO 149
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 149
tctcaaagca gctctgag                                                  18

<210> SEQ ID NO 150
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 150
ctctcaaagc agctctga                                                  18

<210> SEQ ID NO 151
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 151
gctctcaaag cagctctg                                                  18

<210> SEQ ID NO 152
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 152
ggctctcaaa gcagctct                                                  18

<210> SEQ ID NO 153
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 153
gggctctcaa agcagctc                                                  18

<210> SEQ ID NO 154
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 154
ggggctctca aagcagct                                                  18

<210> SEQ ID NO 155
<211> LENGTH: 18
<212> TYPE: DNA
<213> ORGANISM: Artificial Sequence
<220> FEATURE:
<223> OTHER INFORMATION: sequence of AON (5'-> 3')

```
<400> SEQUENCE: 155
cggggctctc aaagcagc                                                 18

<210> SEQ ID NO 156
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 156
acggggctct caaagcag                                                 18

<210> SEQ ID NO 157
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 157
cacggggctc tcaaagca                                                 18

<210> SEQ ID NO 158
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 158
tcacggggct ctcaaagc                                                 18

<210> SEQ ID NO 159
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 159
ctcacggggc tctcaaag                                                 18

<210> SEQ ID NO 160
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 160
actcacgggg ctctcaaa                                                 18

<210> SEQ ID NO 161
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 161
cactcacggg gctctcaa                                                 18

<210> SEQ ID NO 162
```

```
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 162
gcactcacgg ggctctca                                          18

<210> SEQ ID NO 163
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 163
ggcactcacg gggctctc                                          18

<210> SEQ ID NO 164
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 164
cggcactcac ggggctct                                          18

<210> SEQ ID NO 165
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 165
gcggcactca cggggctc                                          18

<210> SEQ ID NO 166
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 166
ggcggcactc acggggct                                          18

<210> SEQ ID NO 167
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 167
gggcggcact cacggggc                                          18

<210> SEQ ID NO 168
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 168
```

```
ggggcggcac tcacgggg                                              18

<210> SEQ ID NO 169
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 169
aggggcggca ctcacggg                                              18

<210> SEQ ID NO 170
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 170
gaggggcggc actcacgg                                              18

<210> SEQ ID NO 171
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 171
ggaggggcgg cactcacg                                              18

<210> SEQ ID NO 172
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 172
gggaggggcg gcactcac                                              18

<210> SEQ ID NO 173
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 173
cgggaggggc ggcactca                                              18

<210> SEQ ID NO 174
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 174
gcgggagggg cggcactc                                              18

<210> SEQ ID NO 175
<211> LENGTH: 18
<212> TYPE: DNA
```

```
<213> ORGANISM: Artificial Sequence
<220> FEATURE:
<223> OTHER INFORMATION: sequence of AON (5'-> 3')

<400> SEQUENCE: 175
ggcgggaggg gcggcact                                                    18

<210> SEQ ID NO 176
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 176
aggcgggagg ggcggcac                                                    18

<210> SEQ ID NO 177
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 177
gaggcgggag gggcggca                                                    18

<210> SEQ ID NO 178
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 178
ggaggcggga ggggcggc                                                    18

<210> SEQ ID NO 179
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 179
gggaggcggg aggggcgg                                                    18

<210> SEQ ID NO 180
<211> LENGTH: 82
<212> TYPE: DNA
<213> ORGANISM: Artificial Sequence
<220> FEATURE:
<223> OTHER INFORMATION: GAA gene targeting

<400> SEQUENCE: 180
gtgctctgca ctcccctgct ggagcttttc tcgcccttcc ttctggccct ctccccagtc      60
tagacagcag ggcaacaccc ac                                               82

<210> SEQ ID NO 181
<211> LENGTH: 32
<212> TYPE: DNA
<213> ORGANISM: Artificial Sequence
<220> FEATURE:
<223> OTHER INFORMATION: GAA gene targeting

<400> SEQUENCE: 181
```
cttttctcgc ccttccttct ggccctctcc cc					32

<210> SEQ ID NO 182
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 182
gtgctctgca ctcccctgct ggagc					25

<210> SEQ ID NO 183
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 183
tgctctgcac tccctgctg gagct					25

<210> SEQ ID NO 184
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 184
gctctgcact ccctgctgg agctt					25

<210> SEQ ID NO 185
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 185
ctctgcactc ccctgctgga gcttt					25

<210> SEQ ID NO 186
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 186
tctgcactcc cctgctggag ctttt					25

<210> SEQ ID NO 187
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 187
ctgcactccc ctgctggagc ttttc					25

<210> SEQ ID NO 188
<211> LENGTH: 25
<212> TYPE: DNA

```
<213> ORGANISM: Artificial Sequence
<220> FEATURE:
<223> OTHER INFORMATION: 25 bp TARGET sequence 5' -> 3'

<400> SEQUENCE: 188
tgcactcccc tgctggagct tttct                                         25

<210> SEQ ID NO 189
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 189
gcactcccct gctggagctt ttctc                                         25

<210> SEQ ID NO 190
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 190
cactcccctg ctggagcttt tctcg                                         25

<210> SEQ ID NO 191
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 191
actcccctgc tggagctttt ctcgc                                         25

<210> SEQ ID NO 192
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 192
ctcccctgct ggagcttttc tcgcc                                         25

<210> SEQ ID NO 193
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 193
tcccctgctg gagcttttct cgccc                                         25

<210> SEQ ID NO 194
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 194
cccctgctgg agcttttctc gccct                                         25
```

<210> SEQ ID NO 195
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 195
ccctgctgga gcttttctcg ccctt                                    25

<210> SEQ ID NO 196
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 196
cctgctggag cttttctcgc ccttc                                    25

<210> SEQ ID NO 197
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 197
ctgctggagc ttttctcgcc cttcc                                    25

<210> SEQ ID NO 198
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 198
tgctggagct tttctcgccc ttcct                                    25

<210> SEQ ID NO 199
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 199
gctggagctt ttctcgccct tcctt                                    25

<210> SEQ ID NO 200
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 200
ctggagcttt tctcgccctt ccttc                                    25

<210> SEQ ID NO 201
<211> LENGTH: 25
<212> TYPE: DNA
<213> ORGANISM: Artificial Sequence
<220> FEATURE:

<223> OTHER INFORMATION: 25 bp TARGET sequence 5' -> 3'

<400> SEQUENCE: 201
tggagctttt ctcgcccttc cttct                                              25

<210> SEQ ID NO 202
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 202
ggagcttttc tcgcccttcc ttctg                                              25

<210> SEQ ID NO 203
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 203
gagcttttct cgcccttcct tctgg                                              25

<210> SEQ ID NO 204
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 204
agcttttctc gcccttcctt ctggc                                              25

<210> SEQ ID NO 205
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 205
gcttttctcg cccttccttc tggcc                                              25

<210> SEQ ID NO 206
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 206
cttttctcgc ccttccttct ggccc                                              25

<210> SEQ ID NO 207
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 207
ttttctcgcc cttccttctg gccct                                              25

```
<210> SEQ ID NO 208
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 208
tttctcgccc ttccttctgg ccctc                                    25

<210> SEQ ID NO 209
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 209
ttctcgccct tccttctggc cctct                                    25

<210> SEQ ID NO 210
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 210
tctcgccctt ccttctggcc ctctc                                    25

<210> SEQ ID NO 211
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 211
ctcgcccttc cttctggccc tctcc                                    25

<210> SEQ ID NO 212
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 212
tcgcccttcc ttctggccct ctccc                                    25

<210> SEQ ID NO 213
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 213
cgcccttcct tctggccctc tcccc                                    25

<210> SEQ ID NO 214
<211> LENGTH: 25
<212> TYPE: DNA
<213> ORGANISM: Artificial Sequence
<220> FEATURE:
<223> OTHER INFORMATION: 25 bp TARGET sequence 5' -> 3'
```

-continued

<400> SEQUENCE: 214
gcccttcctt ctggccctct cccca                                          25

<210> SEQ ID NO 215
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 215
cccttccttc tggccctctc cccag                                          25

<210> SEQ ID NO 216
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 216
ccttccttct ggccctctcc ccagt                                          25

<210> SEQ ID NO 217
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 217
cttccttctg gccctctccc cagtc                                          25

<210> SEQ ID NO 218
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 218
ttccttctgg ccctctcccc agtct                                          25

<210> SEQ ID NO 219
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 219
tccttctggc cctctcccca gtcta                                          25

<210> SEQ ID NO 220
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 220
ccttctggcc ctctccccag tctag                                          25

<210> SEQ ID NO 221
<211> LENGTH: 25

```
<212> TYPE: DNA
<213> ORGANISM: Artificial Sequence
<220> FEATURE:
<223> OTHER INFORMATION: 25 bp TARGET sequence 5' -> 3'

<400> SEQUENCE: 221
cttctggccc tctccccagt ctaga                                    25

<210> SEQ ID NO 222
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 222
ttctggccct ctccccagtc tagac                                    25

<210> SEQ ID NO 223
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 223
tctggccctc tccccagtct agaca                                    25

<210> SEQ ID NO 224
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 224
ctggccctct ccccagtcta gacag                                    25

<210> SEQ ID NO 225
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 225
tggccctctc cccagtctag acagc                                    25

<210> SEQ ID NO 226
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 226
ggccctctcc ccagtctaga cagca                                    25

<210> SEQ ID NO 227
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 227
```
gccctctccc cagtctagac agcag                                         25

<210> SEQ ID NO 228
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 228
ccctctcccc agtctagaca gcagg                                         25

<210> SEQ ID NO 229
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 229
cctctcccca gtctagacag caggg                                         25

<210> SEQ ID NO 230
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 230
ctctccccag tctagacagc agggc                                         25

<210> SEQ ID NO 231
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 231
tctccccagt ctagacagca gggca                                         25

<210> SEQ ID NO 232
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 232
ctccccagtc tagacagcag ggcaa                                         25

<210> SEQ ID NO 233
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 233
tccccagtct agacagcagg gcaac                                         25

<210> SEQ ID NO 234
<211> LENGTH: 25
<212> TYPE: DNA
<213> ORGANISM: Artificial Sequence

```
<220> FEATURE:
<223> OTHER INFORMATION: 25 bp TARGET sequence 5' -> 3'

<400> SEQUENCE: 234
ccccagtcta gacagcaggg caaca                                          25

<210> SEQ ID NO 235
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 235
cccagtctag acagcagggc aacac                                          25

<210> SEQ ID NO 236
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 236
ccagtctaga cagcagggca acacc                                          25

<210> SEQ ID NO 237
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 237
cagtctagac agcagggcaa caccc                                          25

<210> SEQ ID NO 238
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 238
agtctagaca gcagggcaac accca                                          25

<210> SEQ ID NO 239
<211> LENGTH: 25
<212> TYPE: DNA
<213> ORGANISM: Artificial Sequence
<220> FEATURE:
<223> OTHER INFORMATION: 25 bp TARGET sequence 5' -> 3'

<400> SEQUENCE: 239
gtctagacag cagggcaaca cccac                                          25

<210> SEQ ID NO 240
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 240
tctgcactcc cctgctggag c                                              21
```

<210> SEQ ID NO 241
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 241
ctgcactccc ctgctggagc t                                      21

<210> SEQ ID NO 242
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 242
tgcactcccc tgctggagct t                                      21

<210> SEQ ID NO 243
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 243
gcactcccct gctggagctt t                                      21

<210> SEQ ID NO 244
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 244
cactcccctg ctggagcttt t                                      21

<210> SEQ ID NO 245
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 245
actcccctgc tggagctttt c                                      21

<210> SEQ ID NO 246
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 246
ctcccctgct ggagcttttc t                                      21

<210> SEQ ID NO 247
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 247
tcccctgctg gagcttttct c					21

<210> SEQ ID NO 248
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 248 ccctgctgg agcttttctc g					21

<210> SEQ ID NO 249
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 249
ccctgctgga gcttttctcg c					21

<210> SEQ ID NO 250
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 250
cctgctggag cttttctcgc c					21

<210> SEQ ID NO 251
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 251
ctgctggagc ttttctcgcc c					21

<210> SEQ ID NO 252
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 252
tgctggagct tttctcgccc t					21

<210> SEQ ID NO 253
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 253
gctggagctt ttctcgccct t					21

<210> SEQ ID NO 254

```
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 254
ctggagcttt tctcgccctt c                                              21

<210> SEQ ID NO 255
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 255
tggagctttt ctcgcccttc c                                              21

<210> SEQ ID NO 256
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 256
ggagcttttc tcgcccttcc t                                              21

<210> SEQ ID NO 257
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 257
gagcttttct cgcccttcct t                                              21

<210> SEQ ID NO 258
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 258
agcttttctc gcccttcctt c                                              21

<210> SEQ ID NO 259
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 259
gcttttctcg cccttccttc t                                              21

<210> SEQ ID NO 260
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 260
```
cttttctcgc ccttccttct g                                        21

<210> SEQ ID NO 261
<211> LENGTH: 22
<212> TYPE: DNA
<213> ORGANISM: Artificial Sequence
<220> FEATURE:
<223> OTHER INFORMATION: fake sequence to correct numbering

<400> SEQUENCE: 261
aaaaaaaaaa aaaaaaaaaa aa                                       22

<210> SEQ ID NO 262
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 262
ttttctcgcc cttccttctg g                                        21

<210> SEQ ID NO 263
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 263
tttctcgccc ttccttctgg c                                        21

<210> SEQ ID NO 264
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 264
ttctcgccct tccttctggc c                                        21

<210> SEQ ID NO 265
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 265
tctcgccctt ccttctggcc c                                        21

<210> SEQ ID NO 266
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 266
ctcgcccttc cttctggccc t                                        21

<210> SEQ ID NO 267
<211> LENGTH: 21
<212> TYPE: DNA

```
<213> ORGANISM: Artificial Sequence
<220> FEATURE:
<223> OTHER INFORMATION: 21 bp TARGET sequence 5' -> 3'

<400> SEQUENCE: 267
tcgcccttcc ttctggccct c                                              21

<210> SEQ ID NO 268
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 268
cgcccttcct tctggccctc t                                              21

<210> SEQ ID NO 269
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 269
gcccttcctt ctggccctct c                                              21

<210> SEQ ID NO 270
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 270
cccttccttc tggccctctc c                                              21

<210> SEQ ID NO 271
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 271
ccttccttct ggccctctcc c                                              21

<210> SEQ ID NO 272
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 272
cttccttctg gccctctccc c                                              21

<210> SEQ ID NO 273
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 273
ttccttctgg ccctctcccc a                                              21
```

<210> SEQ ID NO 274
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 274
tccttctggc cctctcccca g                                              21

<210> SEQ ID NO 275
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 275
ccttctggcc ctctccccag t                                              21

<210> SEQ ID NO 276
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 276
cttctggccc tctccccagt c                                              21

<210> SEQ ID NO 277
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 277
ttctggccct ctccccagtc t                                              21

<210> SEQ ID NO 278
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 278
tctggccctc tccccagtct a                                              21

<210> SEQ ID NO 279
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 279
ctggccctct ccccagtcta g                                              21

<210> SEQ ID NO 280
<211> LENGTH: 21
<212> TYPE: DNA
<213> ORGANISM: Artificial Sequence
<220> FEATURE:

<223> OTHER INFORMATION: 21 bp TARGET sequence 5' -> 3'

<400> SEQUENCE: 280
tggccctctc cccagtctag a                                             21

<210> SEQ ID NO 281
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 281
ggccctctcc ccagtctaga c                                             21

<210> SEQ ID NO 282
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 282
gccctctccc cagtctagac a                                             21

<210> SEQ ID NO 283
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 283
ccctctcccc agtctagaca g                                             21

<210> SEQ ID NO 284
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 284
cctctcccca gtctagacag c                                             21

<210> SEQ ID NO 285
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 285
ctctccccag tctagacagc a                                             21

<210> SEQ ID NO 286
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 286
tctccccagt ctagacagca g                                             21

```
<210> SEQ ID NO 287
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 287
ctccccagtc tagacagcag g                                              21

<210> SEQ ID NO 288
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 288
tccccagtct agacagcagg g                                              21

<210> SEQ ID NO 289
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 289
ccccagtcta gacagcaggg c                                              21

<210> SEQ ID NO 290
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 290
cccagtctag acagcagggc a                                              21

<210> SEQ ID NO 291
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 291
ccagtctaga cagcagggca a                                              21

<210> SEQ ID NO 292
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 292
cagtctagac agcagggcaa c                                              21

<210> SEQ ID NO 293
<211> LENGTH: 21
<212> TYPE: DNA
<213> ORGANISM: Artificial Sequence
<220> FEATURE:
<223> OTHER INFORMATION: 21 bp TARGET sequence 5' -> 3'
```

```
<400> SEQUENCE: 293
agtctagaca gcagggcaac a                                              21

<210> SEQ ID NO 294
<211> LENGTH: 21
<212> TYPE: DNA
<213> ORGANISM: Artificial Sequence
<220> FEATURE:
<223> OTHER INFORMATION: 21 bp TARGET sequence 5' -> 3'

<400> SEQUENCE: 294
gtctagacag cagggcaaca c                                              21

<210> SEQ ID NO 295
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 295
gcactcccct gctggagc                                                  18

<210> SEQ ID NO 296
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 296
cactcccctg ctggagct                                                  18

<210> SEQ ID NO 297
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 297
actcccctgc tggagctt                                                  18

<210> SEQ ID NO 298
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 298
ctcccctgct ggagcttt                                                  18

<210> SEQ ID NO 299
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 299
tcccctgctg gagctttt                                                  18

<210> SEQ ID NO 300
<211> LENGTH: 18
```

```
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 300
cccctgctgg agcttttc                                                 18

<210> SEQ ID NO 301
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 301
ccctgctgga gcttttct                                                 18

<210> SEQ ID NO 302
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 302
cctgctggag cttttctc                                                 18

<210> SEQ ID NO 303
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 303
ctgctggagc ttttctcg                                                 18

<210> SEQ ID NO 304
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 304
tgctggagct tttctcgc                                                 18

<210> SEQ ID NO 305
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 305
gctggagctt ttctcgcc                                                 18

<210> SEQ ID NO 306
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 306
```

```
ctggagcttt tctcgccc                                                18

<210> SEQ ID NO 307
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 307
tggagctttt ctcgccct                                                18

<210> SEQ ID NO 308
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 308
ggagcttttc tcgccctt                                                18

<210> SEQ ID NO 309
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 309
gagcttttct cgcccttc                                                18

<210> SEQ ID NO 310
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 310
agcttttctc gcccttcc                                                18

<210> SEQ ID NO 311
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 311
gcttttctcg cccttcct                                                18

<210> SEQ ID NO 312
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 312
cttttctcgc ccttcctt                                                18

<210> SEQ ID NO 313
<211> LENGTH: 18
<212> TYPE: DNA
<213> ORGANISM: Artificial Sequence
```

```
<220> FEATURE:
<223> OTHER INFORMATION: 18 bp TARGET sequence 5' -> 3'.

<400> SEQUENCE: 313
ttttctcgcc cttccttc                                                 18

<210> SEQ ID NO 314
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 314
tttctcgccc ttccttct                                                 18

<210> SEQ ID NO 315
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 315
ttctcgccct tccttctg                                                 18

<210> SEQ ID NO 316
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 316
tctcgccctt ccttctgg                                                 18

<210> SEQ ID NO 317
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 317
ctcgcccttc cttctggc                                                 18

<210> SEQ ID NO 318
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 318
tcgcccttcc ttctggcc                                                 18

<210> SEQ ID NO 319
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 319
cgcccttcct tctggccc                                                 18
```

<210> SEQ ID NO 320
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 320
gcccttcctt ctggccct                                          18

<210> SEQ ID NO 321
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 321
cccttccttc tggccctc                                          18

<210> SEQ ID NO 322
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 322
ccttccttct ggccctct                                          18

<210> SEQ ID NO 323
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 323
cttccttctg gccctctc                                          18

<210> SEQ ID NO 324
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 324
ttccttctgg ccctctcc                                          18

<210> SEQ ID NO 325
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 325
tccttctggc cctctccc                                          18

<210> SEQ ID NO 326
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

```
<400> SEQUENCE: 326
ccttctggcc ctctcccc                                                 18

<210> SEQ ID NO 327
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 327
cttctggccc tctccca                                                  18

<210> SEQ ID NO 328
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 328
ttctggccct ctccccag                                                 18

<210> SEQ ID NO 329
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 329
tctggccctc tccccagt                                                 18

<210> SEQ ID NO 330
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 330
ctggccctct ccccagtc                                                 18

<210> SEQ ID NO 331
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 331
tggccctctc cccagtct                                                 18

<210> SEQ ID NO 332
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 332
ggccctctcc ccagtcta                                                 18

<210> SEQ ID NO 333
```

```
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 333
gccctctccc cagtctag                                                  18

<210> SEQ ID NO 334
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 334
ccctctcccc agtctaga                                                  18

<210> SEQ ID NO 335
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 335
cctctcccca gtctagac                                                  18

<210> SEQ ID NO 336
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 336
ctctccccag tctagaca                                                  18

<210> SEQ ID NO 337
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 337
tctccccagt ctagacag                                                  18

<210> SEQ ID NO 338
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 338
ctccccagtc tagacagc                                                  18

<210> SEQ ID NO 339
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 339
```

| | |
|---|---|
| tccccagtct agacagca | 18 |

<210> SEQ ID NO 340
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 340

| | |
|---|---|
| ccccagtcta gacagcag | 18 |

<210> SEQ ID NO 341
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 341

| | |
|---|---|
| cccagtctag acagcagg | 18 |

<210> SEQ ID NO 342
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 342

| | |
|---|---|
| ccagtctaga cagcaggg | 18 |

<210> SEQ ID NO 343
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 343

| | |
|---|---|
| cagtctagac agcagggc | 18 |

<210> SEQ ID NO 344
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 344

| | |
|---|---|
| agtctagaca gcagggca | 18 |

<210> SEQ ID NO 345
<211> LENGTH: 18
<212> TYPE: DNA
<213> ORGANISM: Artificial Sequence
<220> FEATURE:
<223> OTHER INFORMATION: 18 bp TARGET sequence 5' -> 3'.

<400> SEQUENCE: 345

| | |
|---|---|
| gtctagacag cagggcaa | 18 |

<210> SEQ ID NO 346
<211> LENGTH: 25
<212> TYPE: DNA

```
<213> ORGANISM: Artificial Sequence
<220> FEATURE:
<223> OTHER INFORMATION: sequence of AON (5'-> 3')

<400> SEQUENCE: 346
gctccagcag gggagtgcag agcac                                      25

<210> SEQ ID NO 347
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 347
agctccagca ggggagtgca gagca                                      25

<210> SEQ ID NO 348
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 348
aagctccagc aggggagtgc agagc                                      25

<210> SEQ ID NO 349
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 349
aaagctccag caggggagtg cagag                                      25

<210> SEQ ID NO 350
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 350
aaaagctcca gcaggggagt gcaga                                      25

<210> SEQ ID NO 351
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 351
gaaaagctcc agcaggggag tgcag                                      25

<210> SEQ ID NO 352
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 352
agaaaagctc cagcagggga gtgca                                      25
```

<210> SEQ ID NO 353
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 353
gagaaaagct ccagcagggg agtgc                                    25

<210> SEQ ID NO 354
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 354
cgagaaaagc tccagcaggg gagtg                                    25

<210> SEQ ID NO 355
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 355
gcgagaaaag ctccagcagg ggagt                                    25

<210> SEQ ID NO 356
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 356
ggcgagaaaa gctccagcag gggag                                    25

<210> SEQ ID NO 357
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 357
gggcgagaaa agctccagca gggga                                    25

<210> SEQ ID NO 358
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 358
agggcgagaa aagctccagc agggg                                    25

<210> SEQ ID NO 359
<211> LENGTH: 25
<212> TYPE: DNA
<213> ORGANISM: Artificial Sequence
<220> FEATURE:

<223> OTHER INFORMATION: sequence of AON (5'-> 3')

<400> SEQUENCE: 359
aagggcgaga aaagctccag caggg                                              25

<210> SEQ ID NO 360
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 360
gaagggcgag aaaagctcca gcagg                                              25

<210> SEQ ID NO 361
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 361
ggaagggcga gaaaagctcc agcag                                              25

<210> SEQ ID NO 362
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 362
aggaagggcg agaaaagctc cagca                                              25

<210> SEQ ID NO 363
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 363
aaggaagggc gagaaaagct ccagc                                              25

<210> SEQ ID NO 364
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 364
gaaggaaggg cgagaaaagc tccag                                              25

<210> SEQ ID NO 365
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 365
agaaggaagg gcgagaaaag ctcca                                              25

```
<210> SEQ ID NO 366
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 366
cagaaggaag ggcgagaaaa gctcc                                25

<210> SEQ ID NO 367
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 367
ccagaaggaa gggcgagaaa agctc                                25

<210> SEQ ID NO 368
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 368
gccagaagga agggcgagaa aagct                                25

<210> SEQ ID NO 369
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 369
ggccagaagg aagggcgaga aaagc                                25

<210> SEQ ID NO 370
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 370
gggccagaag gaagggcgag aaaag                                25

<210> SEQ ID NO 371
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 371
agggccagaa ggaagggcga gaaaa                                25

<210> SEQ ID NO 372
<211> LENGTH: 25
<212> TYPE: DNA
<213> ORGANISM: Artificial Sequence
<220> FEATURE:
<223> OTHER INFORMATION: sequence of AON (5'-> 3')
```

-continued

<400> SEQUENCE: 372
gagggccaga aggaagggcg agaaa                                              25

<210> SEQ ID NO 373
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 373
agagggccag aaggaagggc gagaa                                              25

<210> SEQ ID NO 374
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 374
gagagggcca gaaggaaggg cgaga                                              25

<210> SEQ ID NO 375
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 375
ggagagggcc agaaggaagg gcgag                                              25

<210> SEQ ID NO 376
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 376
gggagagggc cagaaggaag ggcga                                              25

<210> SEQ ID NO 377
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 377
ggggagaggg ccagaaggaa gggcg                                              25

<210> SEQ ID NO 378
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 378
tggggagagg gccagaagga agggc                                              25

<210> SEQ ID NO 379
<211> LENGTH: 25

```
<212> TYPE: DNA
<213> ORGANISM: Artificial Sequence
<220> FEATURE:
<223> OTHER INFORMATION: sequence of AON (5'-> 3')

<400> SEQUENCE: 379
ctggggagag ggccagaagg aaggg                                              25

<210> SEQ ID NO 380
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 380
actggggaga gggccagaag gaagg                                              25

<210> SEQ ID NO 381
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 381
gactggggag agggccagaa ggaag                                              25

<210> SEQ ID NO 382
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 382
agactgggga gagggccaga aggaa                                              25

<210> SEQ ID NO 383
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 383
tagactgggg agagggccag aagga                                              25

<210> SEQ ID NO 384
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 384
ctagactggg gagagggcca gaagg                                              25

<210> SEQ ID NO 385
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 385
```
tctagactgg ggagagggcc agaag                                          25

<210> SEQ ID NO 386
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 386
gtctagactg gggagagggc cagaa                                          25

<210> SEQ ID NO 387
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 387
tgtctagact ggggagaggg ccaga                                          25

<210> SEQ ID NO 388
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 388
ctgtctagac tggggagagg gccag                                          25

<210> SEQ ID NO 389
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 389
gctgtctaga ctggggagag ggcca                                          25

<210> SEQ ID NO 390
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 390
tgctgtctag actggggaga gggcc                                          25

<210> SEQ ID NO 391
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 391
ctgctgtcta gactggggag agggc                                          25

<210> SEQ ID NO 392
<211> LENGTH: 25
<212> TYPE: DNA
<213> ORGANISM: Artificial Sequence

```
<220> FEATURE:
<223> OTHER INFORMATION: sequence of AON (5'-> 3')

<400> SEQUENCE: 392
cctgctgtct agactgggga gaggg                                              25

<210> SEQ ID NO 393
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 393
ccctgctgtc tagactgggg agagg                                              25

<210> SEQ ID NO 394
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 394
gccctgctgt ctagactggg gagag                                              25

<210> SEQ ID NO 395
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 395
tgccctgctg tctagactgg ggaga                                              25

<210> SEQ ID NO 396
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 396
ttgccctgct gtctagactg gggag                                              25

<210> SEQ ID NO 397
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 397
gttgccctgc tgtctagact gggga                                              25

<210> SEQ ID NO 398
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 398
tgttgccctg ctgtctagac tgggg                                              25
```

```
<210> SEQ ID NO 399
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 399
gtgttgccct gctgtctaga ctggg                                               25

<210> SEQ ID NO 400
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 400
ggtgttgccc tgctgtctag actgg                                               25

<210> SEQ ID NO 401
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 401
gggtgttgcc ctgctgtcta gactg                                               25

<210> SEQ ID NO 402
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 402
tgggtgttgc cctgctgtct agact                                               25

<210> SEQ ID NO 403
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 403
gtgggtgttg ccctgctgtc tagac                                               25

<210> SEQ ID NO 404
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 404
gctccagcag gggagtgcag a                                                   21

<210> SEQ ID NO 405
<211> LENGTH: 21
<212> TYPE: DNA
<213> ORGANISM: Artificial Sequence
<220> FEATURE:
<223> OTHER INFORMATION: sequence of AON (5'-> 3')
```

```
<400> SEQUENCE: 405
agctccagca ggggagtgca g                                              21

<210> SEQ ID NO 406
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 406
aagctccagc aggggagtgc a                                              21

<210> SEQ ID NO 407
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 407
aaagctccag caggggagtg c                                              21

<210> SEQ ID NO 408
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 408
aaaagctcca gcaggggagt g                                              21

<210> SEQ ID NO 409
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 409
gaaaagctcc agcaggggag t                                              21

<210> SEQ ID NO 410
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 410
agaaaagctc cagcagggga g                                              21

<210> SEQ ID NO 411
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 411
gagaaaagct ccagcagggg a                                              21

<210> SEQ ID NO 412
```

```
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 412
cgagaaaagc tccagcaggg g                                              21

<210> SEQ ID NO 413
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 413
gcgagaaaag ctccagcagg g                                              21

<210> SEQ ID NO 414
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 414
ggcgagaaaa gctccagcag g                                              21

<210> SEQ ID NO 415
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 415
gggcgagaaa agctccagca g                                              21

<210> SEQ ID NO 416
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 416
agggcgagaa aagctccagc a                                              21

<210> SEQ ID NO 417
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 417
aagggcgaga aaagctccag c                                              21

<210> SEQ ID NO 418
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 418
```
gaagggcgag aaaagctcca g					21

<210> SEQ ID NO 419
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 419
ggaagggcga gaaaagctcc a					21

<210> SEQ ID NO 420
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 420
aggaagggcg agaaaagctc c					21

<210> SEQ ID NO 421
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 421
aaggaagggc gagaaaagct c					21

<210> SEQ ID NO 422
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 422
gaaggaaggg cgagaaaagc t					21

<210> SEQ ID NO 423
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 423
agaaggaagg gcgagaaaag c					21

<210> SEQ ID NO 424
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 424
cagaaggaag ggcgagaaaa g					21

<210> SEQ ID NO 425
<211> LENGTH: 21
<212> TYPE: DNA

```
<213> ORGANISM: Artificial Sequence
<220> FEATURE:
<223> OTHER INFORMATION: sequence of AON (5'-> 3')

<400> SEQUENCE: 425
ccagaaggaa gggcgagaaa a                                              21

<210> SEQ ID NO 426
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 426
gccagaagga agggcgagaa a                                              21

<210> SEQ ID NO 427
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 427
ggccagaagg aagggcgaga a                                              21

<210> SEQ ID NO 428
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 428
gggccagaag gaagggcgag a                                              21

<210> SEQ ID NO 429
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 429
agggccagaa ggaagggcga g                                              21

<210> SEQ ID NO 430
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 430
gagggccaga aggaagggcg a                                              21

<210> SEQ ID NO 431
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 431
agagggccag aaggaagggc g                                              21
```

<210> SEQ ID NO 432
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 432
gagagggcca gaaggaaggg c                                              21

<210> SEQ ID NO 433
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 433
ggagagggcc agaaggaagg g                                              21

<210> SEQ ID NO 434
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 434
gggagagggc cagaaggaag g                                              21

<210> SEQ ID NO 435
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 435
ggggagaggg ccagaaggaa g                                              21

<210> SEQ ID NO 436
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 436
tggggagagg gccagaagga a                                              21

<210> SEQ ID NO 437
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 437
ctggggagag ggccagaagg a                                              21

<210> SEQ ID NO 438
<211> LENGTH: 21
<212> TYPE: DNA
<213> ORGANISM: Artificial Sequence
<220> FEATURE:

```
<223> OTHER INFORMATION: sequence of AON (5'-> 3')

<400> SEQUENCE: 438
actggggaga gggccagaag g                                              21

<210> SEQ ID NO 439
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 439
gactggggag agggccagaa g                                              21

<210> SEQ ID NO 440
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 440
agactgggga gagggccaga a                                              21

<210> SEQ ID NO 441
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 441
tagactgggg agagggccag a                                              21

<210> SEQ ID NO 442
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 442
ctagactggg gagagggcca g                                              21

<210> SEQ ID NO 443
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 443
tctagactgg ggagagggcc a                                              21

<210> SEQ ID NO 444
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 444
gtctagactg gggagagggc c                                              21
```

<210> SEQ ID NO 445
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 445
tgtctagact ggggagaggg c                                    21

<210> SEQ ID NO 446
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 446
ctgtctagac tggggagagg g                                    21

<210> SEQ ID NO 447
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 447
gctgtctaga ctggggagag g                                    21

<210> SEQ ID NO 448
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 448
tgctgtctag actggggaga g                                    21

<210> SEQ ID NO 449
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 449
ctgctgtcta gactggggag a                                    21

<210> SEQ ID NO 450
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 450
cctgctgtct agactgggga g                                    21

<210> SEQ ID NO 451
<211> LENGTH: 21
<212> TYPE: DNA
<213> ORGANISM: Artificial Sequence
<220> FEATURE:
<223> OTHER INFORMATION: sequence of AON (5'-> 3')

-continued

<400> SEQUENCE: 451
ccctgctgtc tagactgggg a                                              21

<210> SEQ ID NO 452
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 452
gccctgctgt ctagactggg g                                              21

<210> SEQ ID NO 453
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 453
tgccctgctg tctagactgg g                                              21

<210> SEQ ID NO 454
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 454
ttgccctgct gtctagactg g                                              21

<210> SEQ ID NO 455
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 455
gttgccctgc tgtctagact g                                              21

<210> SEQ ID NO 456
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 456
tgttgccctg ctgtctagac t                                              21

<210> SEQ ID NO 457
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 457
gtgttgccct gctgtctaga c                                              21

<210> SEQ ID NO 458
<211> LENGTH: 18

```
<212> TYPE: DNA
<213> ORGANISM: Artificial Sequence
<220> FEATURE:
<223> OTHER INFORMATION: sequence of AON (5'-> 3')

<400> SEQUENCE: 458
gctccagcag gggagtgc                                                 18

<210> SEQ ID NO 459
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 459
agctccagca ggggagtg                                                 18

<210> SEQ ID NO 460
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 460
aagctccagc aggggagt                                                 18

<210> SEQ ID NO 461
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 461
aaagctccag caggggag                                                 18

<210> SEQ ID NO 462
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 462
aaaagctcca gcagggga                                                 18

<210> SEQ ID NO 463
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 463
gaaaagctcc agcagggg                                                 18

<210> SEQ ID NO 464
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 464
```
agaaaagctc cagcaggg                                               18

<210> SEQ ID NO 465
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 465
gagaaaagct ccagcagg                                               18

<210> SEQ ID NO 466
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 466
cgagaaaagc tccagcag                                               18

<210> SEQ ID NO 467
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 467
gcgagaaaag ctccagca                                               18

<210> SEQ ID NO 468
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 468
ggcgagaaaa gctccagc                                               18

<210> SEQ ID NO 469
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 469
gggcgagaaa agctccag                                               18

<210> SEQ ID NO 470
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 470
agggcgagaa aagctcca                                               18

<210> SEQ ID NO 471
<211> LENGTH: 18
<212> TYPE: DNA
<213> ORGANISM: Artificial Sequence

```
<220> FEATURE:
<223> OTHER INFORMATION: sequence of AON (5'-> 3')

<400> SEQUENCE: 471
aagggcgaga aaagctcc                                                     18

<210> SEQ ID NO 472
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 472
gaagggcgag aaaagctc                                                     18

<210> SEQ ID NO 473
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 473
ggaagggcga gaaaagct                                                     18

<210> SEQ ID NO 474
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 474
aggaagggcg agaaaagc                                                     18

<210> SEQ ID NO 475
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 475
aaggaagggc gagaaaag                                                     18

<210> SEQ ID NO 476
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 476
gaaggaaggg cgagaaaa                                                     18

<210> SEQ ID NO 477
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 477
agaaggaagg gcgagaaa                                                     18
```

```
<210> SEQ ID NO 478
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 478
cagaaggaag ggcgagaa                                                 18

<210> SEQ ID NO 479
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 479
ccagaaggaa gggcgaga                                                 18

<210> SEQ ID NO 480
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 480
gccagaagga agggcgag                                                 18

<210> SEQ ID NO 481
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 481
ggccagaagg aagggcga                                                 18

<210> SEQ ID NO 482
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 482
gggccagaag gaagggcg                                                 18

<210> SEQ ID NO 483
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 483
agggccagaa ggaagggc                                                 18

<210> SEQ ID NO 484
<211> LENGTH: 18
<212> TYPE: DNA
<213> ORGANISM: Artificial Sequence
<220> FEATURE:
<223> OTHER INFORMATION: sequence of AON (5'-> 3')
```

<400> SEQUENCE: 484
gagggccaga aggaaggg                                               18

<210> SEQ ID NO 485
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 485
agagggccag aaggaagg                                               18

<210> SEQ ID NO 486
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 486
gagagggcca gaaggaag                                               18

<210> SEQ ID NO 487
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 487
ggagagggcc agaaggaa                                               18

<210> SEQ ID NO 488
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 488
gggagagggc cagaagga                                               18

<210> SEQ ID NO 489
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 489
ggggagaggg ccagaagg                                               18

<210> SEQ ID NO 490
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 490
tggggagagg gccagaag                                               18

<210> SEQ ID NO 491

```
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 491
ctggggagag ggccagaa                                                 18

<210> SEQ ID NO 492
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 492
actggggaga gggccaga                                                 18

<210> SEQ ID NO 493
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 493
gactggggag agggccag                                                 18

<210> SEQ ID NO 494
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 494
agactgggga gagggcca                                                 18

<210> SEQ ID NO 495
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 495
tagactgggg agagggcc                                                 18

<210> SEQ ID NO 496
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 496
ctagactggg gagagggc                                                 18

<210> SEQ ID NO 497
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 497
```
tctagactgg ggagaggg                          18

<210> SEQ ID NO 498
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 498
gtctagactg gggagagg                          18

<210> SEQ ID NO 499
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 499
tgtctagact ggggagag                          18

<210> SEQ ID NO 500
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 500
ctgtctagac tggggaga                          18

<210> SEQ ID NO 501
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 501
gctgtctaga ctggggag                          18

<210> SEQ ID NO 502
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 502
tgctgtctag actggga                           18

<210> SEQ ID NO 503
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 503
ctgctgtcta gactgggg                          18

<210> SEQ ID NO 504
<211> LENGTH: 18
<212> TYPE: DNA

```
<213> ORGANISM: Artificial Sequence
<220> FEATURE:
<223> OTHER INFORMATION: sequence of AON (5'-> 3')

<400> SEQUENCE: 504
cctgctgtct agactggg                                                 18

<210> SEQ ID NO 505
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 505
ccctgctgtc tagactgg                                                 18

<210> SEQ ID NO 506
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 506
gccctgctgt ctagactg                                                 18

<210> SEQ ID NO 507
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 507
tgccctgctg tctagact                                                 18

<210> SEQ ID NO 508
<211> LENGTH: 18
<212> TYPE: DNA
<213> ORGANISM: Artificial Sequence
<220> FEATURE:
<223> OTHER INFORMATION: sequence of AON (5'-> 3')

<400> SEQUENCE: 508
ttgccctgct gtctagac                                                 18

<210> SEQ ID NO 509
<211> LENGTH: 13
<212> TYPE: PRT
<213> ORGANISM: Artificial Sequence
<220> FEATURE:
<223> OTHER INFORMATION: positively charged peptide

<400> SEQUENCE: 509

Arg Arg Arg Arg Arg Arg Arg Arg Arg Phe Phe Cys Cys
1               5                   10

<210> SEQ ID NO 510
<211> LENGTH: 14
<212> TYPE: PRT
<213> ORGANISM: Artificial Sequence
<220> FEATURE:
<223> OTHER INFORMATION: positively charged peptide
<220> FEATURE:
<221> NAME/KEY: misc_feature
<222> LOCATION: (2)..(2)
```

```
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 510

Arg Xaa Arg Arg Xaa Arg Arg Xaa Arg Arg Xaa Arg Xaa Asx
1               5                   10

<210> SEQ ID NO 511
<211> LENGTH: 12
<212> TYPE: PRT
<213> ORGANISM: Artificial Sequence
<220> FEATURE:
<223> OTHER INFORMATION: positively charged peptide

<400> SEQUENCE: 511

Arg Arg Arg Arg Arg Phe Phe Arg Arg Arg Arg Cys
1               5                   10

<210> SEQ ID NO 512
<211> LENGTH: 12
<212> TYPE: PRT
<213> ORGANISM: Artificial Sequence
<220> FEATURE:
<223> OTHER INFORMATION: positively charged peptide

<400> SEQUENCE: 512

Cys Tyr Gly Arg Lys Lys Arg Arg Gln Arg Arg Arg
1               5                   10

<210> SEQ ID NO 513
<211> LENGTH: 10
<212> TYPE: PRT
<213> ORGANISM: Artificial Sequence
<220> FEATURE:
<223> OTHER INFORMATION: positively charged peptide

<400> SEQUENCE: 513

Arg Phe Phe Arg Phe Phe Arg Phe Phe Arg
1               5                   10

<210> SEQ ID NO 514
<211> LENGTH: 19
<212> TYPE: DNA
<213> ORGANISM: Artificial Sequence
<220> FEATURE:
<223> OTHER INFORMATION: primer

<400> SEQUENCE: 514
aaccgcgaga agatgaccc                                                 19

<210> SEQ ID NO 515
<211> LENGTH: 21
<212> TYPE: DNA
<213> ORGANISM: Artificial Sequence
```

```
<220> FEATURE:
<223> OTHER INFORMATION: primer

<400> SEQUENCE: 515
gccagaggcg tacagggata g                                              21

<210> SEQ ID NO 516
<211> LENGTH: 18
<212> TYPE: DNA
<213> ORGANISM: Artificial Sequence
<220> FEATURE:
<223> OTHER INFORMATION: primer

<400> SEQUENCE: 516
aaactgaggc acggagcg                                                  18

<210> SEQ ID NO 517
<211> LENGTH: 18
<212> TYPE: DNA
<213> ORGANISM: Artificial Sequence
<220> FEATURE:
<223> OTHER INFORMATION: primer

<400> SEQUENCE: 517
gagtgcagcg gttgccaa                                                  18

<210> SEQ ID NO 518
<211> LENGTH: 16
<212> TYPE: DNA
<213> ORGANISM: Artificial Sequence
<220> FEATURE:
<223> OTHER INFORMATION: primer

<400> SEQUENCE: 518
ggcacggagc gggaca                                                    16

<210> SEQ ID NO 519
<211> LENGTH: 24
<212> TYPE: DNA
<213> ORGANISM: Artificial Sequence
<220> FEATURE:
<223> OTHER INFORMATION: primer

<400> SEQUENCE: 519
ctgttagctg gatctttgat cgtg                                           24

<210> SEQ ID NO 520
<211> LENGTH: 17
<212> TYPE: DNA
<213> ORGANISM: Artificial Sequence
<220> FEATURE:
<223> OTHER INFORMATION: primer

<400> SEQUENCE: 520
aggcacggag cggatca                                                   17

<210> SEQ ID NO 521
<211> LENGTH: 20
<212> TYPE: DNA
<213> ORGANISM: Artificial Sequence
<220> FEATURE:
<223> OTHER INFORMATION: primer

<400> SEQUENCE: 521
tcggagaact ccacgctgta                                                20
```

```
<210> SEQ ID NO 522
<211> LENGTH: 18
<212> TYPE: DNA
<213> ORGANISM: Artificial Sequence
<220> FEATURE:
<223> OTHER INFORMATION: primer

<400> SEQUENCE: 522
aaactgaggc acggagcg                                                    18

<210> SEQ ID NO 523
<211> LENGTH: 21
<212> TYPE: DNA
<213> ORGANISM: Artificial Sequence
<220> FEATURE:
<223> OTHER INFORMATION: primer

<400> SEQUENCE: 523
gcagctctga gacatcaacc g                                                21

<210> SEQ ID NO 524
<211> LENGTH: 20
<212> TYPE: DNA
<213> ORGANISM: Artificial Sequence
<220> FEATURE:
<223> OTHER INFORMATION: primer

<400> SEQUENCE: 524
gagacagcgg ctaacaggat                                                  20

<210> SEQ ID NO 525
<211> LENGTH: 20
<212> TYPE: DNA
<213> ORGANISM: Artificial Sequence
<220> FEATURE:
<223> OTHER INFORMATION: primer

<400> SEQUENCE: 525
attccaaaag ctcactcgct                                                  20

<210> SEQ ID NO 526
<211> LENGTH: 21
<212> TYPE: DNA
<213> ORGANISM: Artificial Sequence
<220> FEATURE:
<223> OTHER INFORMATION: primer

<400> SEQUENCE: 526
gtccagaacc tccctactc c                                                 21

<210> SEQ ID NO 527
<211> LENGTH: 21
<212> TYPE: DNA
<213> ORGANISM: Artificial Sequence
<220> FEATURE:
<223> OTHER INFORMATION: primer

<400> SEQUENCE: 527
cgaaaaccgg agtcggaact t                                                21

<210> SEQ ID NO 528
<211> LENGTH: 21
<212> TYPE: DNA
<213> ORGANISM: Artificial Sequence
<220> FEATURE:
<223> OTHER INFORMATION: primer
```

-continued

```
<400> SEQUENCE: 528
ccatgctgct ggctgtggga t                                              21

<210> SEQ ID NO 529
<211> LENGTH: 25
<212> TYPE: DNA
<213> ORGANISM: Artificial Sequence
<220> FEATURE:
<223> OTHER INFORMATION: primer

<400> SEQUENCE: 529
agcagtacaa cacaggtgct cttgc                                          25

<210> SEQ ID NO 530
<211> LENGTH: 20
<212> TYPE: DNA
<213> ORGANISM: Artificial Sequence
<220> FEATURE:
<223> OTHER INFORMATION: primer

<400> SEQUENCE: 530
caaaaacggg ggcttcttcc                                                20

<210> SEQ ID NO 531
<211> LENGTH: 20
<212> TYPE: DNA
<213> ORGANISM: Artificial Sequence
<220> FEATURE:
<223> OTHER INFORMATION: primer

<400> SEQUENCE: 531
gccaggtaac ggttagcaca                                                20

<210> SEQ ID NO 532
<211> LENGTH: 21
<212> TYPE: DNA
<213> ORGANISM: Artificial Sequence
<220> FEATURE:
<223> OTHER INFORMATION: primer

<400> SEQUENCE: 532
gagctgcaac ttggccacga c                                              21

<210> SEQ ID NO 533
<211> LENGTH: 21
<212> TYPE: DNA
<213> ORGANISM: Artificial Sequence
<220> FEATURE:
<223> OTHER INFORMATION: primer

<400> SEQUENCE: 533
gagacggaga ggaattcaga c                                              21

<210> SEQ ID NO 534
<211> LENGTH: 20
<212> TYPE: DNA
<213> ORGANISM: Artificial Sequence
<220> FEATURE:
<223> OTHER INFORMATION: primer

<400> SEQUENCE: 534
cactccggtc ccaaatgtag                                                20

<210> SEQ ID NO 535
```

```
<211> LENGTH: 20
<212> TYPE: DNA
<213> ORGANISM: Artificial Sequence
<220> FEATURE:
<223> OTHER INFORMATION: primer

<400> SEQUENCE: 535
ttccctgtag caccacacac                                                 20

<210> SEQ ID NO 536
<211> LENGTH: 20
<212> TYPE: DNA
<213> ORGANISM: Artificial Sequence
<220> FEATURE:
<223> OTHER INFORMATION: primer

<400> SEQUENCE: 536
cactccctca cctccatcgt                                                 20

<210> SEQ ID NO 537
<211> LENGTH: 19
<212> TYPE: DNA
<213> ORGANISM: Artificial Sequence
<220> FEATURE:
<223> OTHER INFORMATION: primer

<400> SEQUENCE: 537
catctgggaa ggccacaga                                                  19

<210> SEQ ID NO 538
<211> LENGTH: 20
<212> TYPE: DNA
<213> ORGANISM: Artificial Sequence
<220> FEATURE:
<223> OTHER INFORMATION: primer

<400> SEQUENCE: 538
gtgttagtgg cacccaggtc                                                 20

<210> SEQ ID NO 539
<211> LENGTH: 20
<212> TYPE: DNA
<213> ORGANISM: Artificial Sequence
<220> FEATURE:
<223> OTHER INFORMATION: primer

<400> SEQUENCE: 539
ggaaggcctg tcttgttcac                                                 20

<210> SEQ ID NO 540
<211> LENGTH: 20
<212> TYPE: DNA
<213> ORGANISM: Artificial Sequence
<220> FEATURE:
<223> OTHER INFORMATION: primer

<400> SEQUENCE: 540
cctggattgc gaattttacc                                                 20

<210> SEQ ID NO 541
<211> LENGTH: 20
<212> TYPE: DNA
<213> ORGANISM: Artificial Sequence
<220> FEATURE:
<223> OTHER INFORMATION: primer

<400> SEQUENCE: 541
```
atggaattct gatggccaaa                                                  20

<210> SEQ ID NO 542
<211> LENGTH: 38
<212> TYPE: DNA
<213> ORGANISM: Artificial Sequence
<220> FEATURE:
<223> OTHER INFORMATION: primer

<400> SEQUENCE: 542
gctcttttag aattttggga gcaggttttc tgacttcg                              38

<210> SEQ ID NO 543
<211> LENGTH: 38
<212> TYPE: DNA
<213> ORGANISM: Artificial Sequence
<220> FEATURE:
<223> OTHER INFORMATION: primer

<400> SEQUENCE: 543
cgaagtcaga aacctgctcc aaaaattct aaaagagc                               38

<210> SEQ ID NO 544
<211> LENGTH: 37
<212> TYPE: DNA
<213> ORGANISM: Artificial Sequence
<220> FEATURE:
<223> OTHER INFORMATION: primer

<400> SEQUENCE: 544
cctggctcgc tacagatgca taggaggacg gaggacg                               37

<210> SEQ ID NO 545
<211> LENGTH: 37
<212> TYPE: DNA
<213> ORGANISM: Artificial Sequence
<220> FEATURE:
<223> OTHER INFORMATION: primer

<400> SEQUENCE: 545
cgtcctccgt cctcctatgc atctgtagcg agccagg                               37

<210> SEQ ID NO 546
<211> LENGTH: 17
<212> TYPE: DNA
<213> ORGANISM: Artificial Sequence
<220> FEATURE:
<223> OTHER INFORMATION: primer

<400> SEQUENCE: 546
gtaaaacgac gggccag                                                     17

<210> SEQ ID NO 547
<211> LENGTH: 17
<212> TYPE: DNA
<213> ORGANISM: Artificial Sequence
<220> FEATURE:
<223> OTHER INFORMATION: primer

<400> SEQUENCE: 547
caggaaacag ctatgac                                                     17

<210> SEQ ID NO 548
<211> LENGTH: 27
<212> TYPE: DNA

-continued

```
<213> ORGANISM: Artificial Sequence
<220> FEATURE:
<223> OTHER INFORMATION: primer

<400> SEQUENCE: 548
aggttctcct cgtccgcccg ttgttca                                    27

<210> SEQ ID NO 549
<211> LENGTH: 27
<212> TYPE: DNA
<213> ORGANISM: Artificial Sequence
<220> FEATURE:
<223> OTHER INFORMATION: primer

<400> SEQUENCE: 549
tccaagggca cctcgtagcg cctgtta                                    27

<210> SEQ ID NO 550
<211> LENGTH: 29
<212> TYPE: DNA
<213> ORGANISM: Artificial Sequence
<220> FEATURE:
<223> OTHER INFORMATION: primer

<400> SEQUENCE: 550
gcgcctgcag taacaacata ggagctgtg                                  29

<210> SEQ ID NO 551
<211> LENGTH: 30
<212> TYPE: DNA
<213> ORGANISM: Artificial Sequence
<220> FEATURE:
<223> OTHER INFORMATION: primer

<400> SEQUENCE: 551
gcgcgtcgac cagatacgcg tttcctagga                                 30

<210> SEQ ID NO 552
<211> LENGTH: 20
<212> TYPE: DNA
<213> ORGANISM: Artificial Sequence
<220> FEATURE:
<223> OTHER INFORMATION: target for aon's

<400> SEQUENCE: 552
tgtaccctta ccactcagtc                                            20

<210> SEQ ID NO 553
<211> LENGTH: 25
<212> TYPE: DNA
<213> ORGANISM: Artificial Sequence
<220> FEATURE:
<223> OTHER INFORMATION: target for AON's

<400> SEQUENCE: 553
catgttgtac ccttaccact cagtc                                      25

<210> SEQ ID NO 554
<211> LENGTH: 20
<212> TYPE: DNA
<213> ORGANISM: Artificial Sequence
<220> FEATURE:
<223> OTHER INFORMATION: target for AON's

<400> SEQUENCE: 554
gagtgcagag cacttgcaca                                            20
```

```
<210> SEQ ID NO 555
<211> LENGTH: 25
<212> TYPE: DNA
<213> ORGANISM: Artificial Sequence
<220> FEATURE:
<223> OTHER INFORMATION: target for AON's

<400> SEQUENCE: 555
gagtgcagag cacttgcaca gtctg                                       25

<210> SEQ ID NO 556
<211> LENGTH: 21
<212> TYPE: DNA
<213> ORGANISM: Artificial Sequence
<220> FEATURE:
<223> OTHER INFORMATION: target for AON's

<400> SEQUENCE: 556
ccagaaggaa gggcgagaaa a                                           21

<210> SEQ ID NO 557
<211> LENGTH: 25
<212> TYPE: DNA
<213> ORGANISM: Artificial Sequence
<220> FEATURE:
<223> OTHER INFORMATION: target for AON's

<400> SEQUENCE: 557
gccagaagga agggcgagaa aagct                                       25

<210> SEQ ID NO 558
<211> LENGTH: 25
<212> TYPE: DNA
<213> ORGANISM: Artificial Sequence
<220> FEATURE:
<223> OTHER INFORMATION: target for AON's

<400> SEQUENCE: 558
tttgagagcc ccgtgagtgc cgccc                                       25

<210> SEQ ID NO 559
<211> LENGTH: 60
<212> TYPE: DNA
<213> ORGANISM: Artificial Sequence
<220> FEATURE:
<223> OTHER INFORMATION: target for AON's

<400> SEQUENCE: 559
tttttcatct gcactgccaa gactgagtgg taagggtaca acatggcaca ctaaccacct    60

<210> SEQ ID NO 560
<211> LENGTH: 20
<212> TYPE: DNA
<213> ORGANISM: Artificial Sequence
<220> FEATURE:
<223> OTHER INFORMATION: product N

<400> SEQUENCE: 560
cacggagcgg gcctgtagga                                             20

<210> SEQ ID NO 561
<211> LENGTH: 20
<212> TYPE: DNA
<213> ORGANISM: Artificial Sequence
<220> FEATURE:
```

<223> OTHER INFORMATION: Product N

<400> SEQUENCE: 561
ccacttcacg atcaaagatc                                       20

<210> SEQ ID NO 562
<211> LENGTH: 20
<212> TYPE: DNA
<213> ORGANISM: Artificial Sequence
<220> FEATURE:
<223> OTHER INFORMATION: Product SV1

<400> SEQUENCE: 562
gctgccggcg atcaaagatc                                       20

<210> SEQ ID NO 563
<211> LENGTH: 20
<212> TYPE: DNA
<213> ORGANISM: Artificial Sequence
<220> FEATURE:
<223> OTHER INFORMATION: Product SV2

<400> SEQUENCE: 563
cacggagcgg atcaaagatc                                       20

<210> SEQ ID NO 564
<211> LENGTH: 20
<212> TYPE: DNA
<213> ORGANISM: Artificial Sequence
<220> FEATURE:
<223> OTHER INFORMATION: Product SV3

<400> SEQUENCE: 564
cacggagcgg gacatcctga                                       20

<210> SEQ ID NO 565
<211> LENGTH: 20
<212> TYPE: DNA
<213> ORGANISM: Artificial Sequence
<220> FEATURE:
<223> OTHER INFORMATION: Product SV4

<400> SEQUENCE: 565
gctgccggcg gcctgtagga                                       20

<210> SEQ ID NO 566
<211> LENGTH: 20
<212> TYPE: DNA
<213> ORGANISM: Artificial Sequence
<220> FEATURE:
<223> OTHER INFORMATION: Product SV5

<400> SEQUENCE: 566
cacggagcgg tctagacagc                                       20

<210> SEQ ID NO 567
<211> LENGTH: 20
<212> TYPE: DNA
<213> ORGANISM: Artificial Sequence
<220> FEATURE:
<223> OTHER INFORMATION: Product SV5

<400> SEQUENCE: 567
tgagagcccc gacatcctga                                       20

```
<210> SEQ ID NO 568
<211> LENGTH: 20
<212> TYPE: DNA
<213> ORGANISM: Artificial Sequence
<220> FEATURE:
<223> OTHER INFORMATION: Product SV6

<400> SEQUENCE: 568
tgagagcccc atcaaagatc                                                    20

<210> SEQ ID NO 569
<211> LENGTH: 20
<212> TYPE: DNA
<213> ORGANISM: Artificial Sequence
<220> FEATURE:
<223> OTHER INFORMATION: Product SV7

<400> SEQUENCE: 569
gctgccggcg gacatcctga                                                    20
```